United States Patent
Cook et al.

(10) Patent No.: US 10,870,696 B2
(45) Date of Patent: *Dec. 22, 2020

(54) TREATMENT OF FIBROSIS WITH INTERLEUKIN-11 ANTIBODY

(71) Applicants: Singapore Health Services PTE LTD., Singapore (SG); National University of Singapore, Singapore (SG)

(72) Inventors: Stuart Alexander Cook, Singapore (SG); Sebastian Schaefer, Singapore (SG)

(73) Assignees: Singapore Health Services PTE LTD., Singapore (SG); National University of Singapore, Singapore (SG)

(*) Notice: Subject to any disclaimer, the term of this patent is extended or adjusted under 35 U.S.C. 154(b) by 62 days.

This patent is subject to a terminal disclaimer.

(21) Appl. No.: 16/055,245

(22) Filed: Aug. 6, 2018

(65) Prior Publication Data

US 2018/0362633 A1   Dec. 20, 2018

Related U.S. Application Data

(60) Continuation of application No. 15/988,463, filed on May 24, 2018, now Pat. No. 10,106,603, which is a division of application No. 15/381,622, filed on Dec. 16, 2016, now Pat. No. 10,035,852.

(30) Foreign Application Priority Data

Dec. 16, 2015   (GB) .................................. 1522186.4

(51) Int. Cl.
| | | |
|---|---|---|
| A61K 39/395 | (2006.01) | |
| C07K 16/24 | (2006.01) | |
| C07K 16/28 | (2006.01) | |
| C07K 14/54 | (2006.01) | |
| C07K 14/715 | (2006.01) | |
| C12N 15/113 | (2010.01) | |
| A61K 39/00 | (2006.01) | |

(52) U.S. Cl.
CPC ........ C07K 16/244 (2013.01); C07K 14/5428 (2013.01); C07K 14/7155 (2013.01); C07K 16/2866 (2013.01); C12N 15/1136 (2013.01); C12N 15/1138 (2013.01); *A61K 2039/505* (2013.01); *A61K 2039/54* (2013.01); *C07K 2317/20* (2013.01); *C07K 2317/21* (2013.01); *C07K 2317/73* (2013.01); *C07K 2317/76* (2013.01); *C07K 2319/00* (2013.01); *C07K 2319/32* (2013.01); *C07K 2319/43* (2013.01); *C12N 2310/14* (2013.01)

(58) Field of Classification Search
CPC ........................................... A61K 2039/55527
See application file for complete search history.

(56) References Cited

U.S. PATENT DOCUMENTS

| | | |
|---|---|---|
| 5,679,339 A | 10/1997 | Keith et al. |
| 5,843,509 A | 12/1998 | Salve et al. |
| 6,126,933 A | 10/2000 | Warne et al. |
| 6,270,759 B1 | 8/2001 | Keith et al. |
| 6,540,993 B1 | 4/2003 | Warne et al. |
| 6,649,192 B2 | 11/2003 | Maria Jose et al. |
| 6,846,907 B1 | 1/2005 | Shaughnessy et al. |
| 6,953,777 B2 | 10/2005 | Keith et al. |
| 6,998,123 B1 | 2/2006 | Shaughnessy et al. |
| 7,993,637 B2 | 8/2011 | Baca |
| 8,182,814 B2 | 5/2012 | Baca et al. |
| 8,361,966 B2 | 1/2013 | Azuma et al. |
| 8,518,888 B2 | 8/2013 | Jenkins et al. |
| 8,540,977 B2 | 9/2013 | Baca |
| 9,340,618 B2 | 5/2016 | Edwards et al. |
| 10,035,852 B2 * | 7/2018 | Cook ................. C07K 16/244 |
| 10,106,603 B2 | 10/2018 | Cook et al. |
| 2003/0147849 A1 | 8/2003 | Warne et al. |
| 2004/0126358 A1 | 7/2004 | Warne et al. |
| 2004/0142871 A1 | 7/2004 | Shaughnessy et al. |
| 2006/0062760 A1 | 3/2006 | Keith et al. |
| 2007/0160577 A1 | 7/2007 | Damle et al. |
| 2009/0191147 A1 | 7/2009 | Keith et al. |
| 2009/0202533 A1 | 8/2009 | Baca et al. |
| 2010/0062058 A1 | 3/2010 | Warne et al. |
| 2010/0093976 A1 | 4/2010 | Azuma et al. |
| 2010/0183544 A1 | 7/2010 | Jenkins et al. |
| 2013/0302277 A1 | 11/2013 | Jenkins et al. |
| 2014/0219919 A1 | 8/2014 | Edwards et al. |

(Continued)

FOREIGN PATENT DOCUMENTS

| | | |
|---|---|---|
| CN | 105497893 A | 4/2016 |
| EP | 1630232 A2 | 3/2006 |

(Continued)

OTHER PUBLICATIONS

PGR2019-00053, Exhibit # 1003, Declaration of Dr. Peter Bowers, date reviewed 3.*
PGR2019-00053, Exhibit # 1004, Declaration of Dr. Stephen Ledbetter, date reviewed Mar. 14, 2020.*
PGR2019-00053, Exhibit # 1004, Victoria A. Barton et al., Interleukin-11 Signals through the Formation of a Hexameric Receptor Complex, 275 The J. of Biological Chemistry 36197 (2000), date reviewed Mar. 14, 2020.*
PGR2019-00053 Reviewed Petition for Post Grant Review of U.S. Pat. No. 10,106,603, date reviewed Mar. 14, 2020.*

(Continued)

*Primary Examiner* — Prema M Mertz
(74) *Attorney, Agent, or Firm* — Wolf, Greenfield & Sacks, P.C.

(57) ABSTRACT

Aspects of the disclosure relate to the treatment, prevention or alleviation of conditions such as fibrosis in a subject. In some embodiments, the treatment, prevention or alleviation of fibrosis in a subject through the administration of an agent capable of inhibiting the action of Interleukin 11 (IL-11) is disclosed.

12 Claims, 66 Drawing Sheets

Specification includes a Sequence Listing.

(56) References Cited

U.S. PATENT DOCUMENTS

| | | |
|---|---|---|
| 2016/0031999 A1 | 2/2016 | Edwards et al. |
| 2017/0174759 A1 | 6/2017 | Cook et al. |
| 2018/0186871 A1 | 7/2018 | Cook et al. |
| 2018/0186872 A1 | 7/2018 | Cook et al. |
| 2018/0265579 A1 | 9/2018 | Cook et al. |
| 2018/0362634 A1 | 12/2018 | Cook et al. |
| 2018/0362635 A1 | 12/2018 | Cook et al. |
| 2018/0362636 A1 | 12/2018 | Cook et al. |
| 2018/0362637 A1 | 12/2018 | Cook et al. |
| 2018/0362638 A1 | 12/2018 | Cook et al. |
| 2018/0362639 A1 | 12/2018 | Cook et al. |
| 2018/0362640 A1 | 12/2018 | Cook et al. |
| 2018/0362641 A1 | 12/2018 | Cook et al. |
| 2018/0371077 A1 | 12/2018 | Cook et al. |
| 2018/0371078 A1 | 12/2018 | Cook et al. |
| 2019/0002553 A1 | 1/2019 | Cook et al. |
| 2019/0241637 A1 | 8/2019 | Cook et al. |
| 2019/0389957 A1 | 12/2019 | Cook et al. |
| 2020/0031918 A1 | 1/2020 | Cook et al. |
| 2020/0199218 A1 | 6/2020 | Cook et al. |
| 2020/0207847 A1 | 7/2020 | Cook et al. |

FOREIGN PATENT DOCUMENTS

| | | |
|---|---|---|
| KR | 20110047179 A | 6/2011 |
| RU | 2016 125 115 A | 12/2017 |
| RU | 2016 151 730 A | 6/2018 |
| WO | WO 1991/019813 A1 | 12/1991 |
| WO | WO 1996/019574 A1 | 6/1996 |
| WO | WO 1997/001353 A1 | 1/1997 |
| WO | WO 1998/36061 A2 | 6/1998 |
| WO | WO 1999/020755 A2 | 4/1999 |
| WO | WO 1999/032619 A1 | 7/1999 |
| WO | WO 1999/059608 A2 | 11/1999 |
| WO | WO 2000/078336 A1 | 12/2000 |
| WO | WO 2001/029058 A1 | 4/2001 |
| WO | WO 2002/020609 A2 | 3/2002 |
| WO | WO 2003/049693 A2 | 6/2003 |
| WO | WO 2005/058956 A1 | 6/2005 |
| WO | WO 2005/070446 A1 | 8/2005 |
| WO | WO 2005/098041 A2 | 10/2005 |
| WO | WO 2008/003141 A1 | 1/2008 |
| WO | WO 2009/052588 A1 | 4/2009 |
| WO | WO 2014/121325 A1 | 8/2014 |
| WO | WO 2017/103108 A1 | 6/2017 |
| WO | WO 2018/109168 A1 | 6/2018 |
| WO | WO 2018/109170 A2 | 6/2018 |
| WO | WO 2018/109174 A2 | 6/2018 |
| WO | WO 2019/073057 A1 | 4/2019 |
| WO | WO 2019/117721 A2 | 6/2019 |
| WO | WO 2019/207122 A1 | 10/2019 |
| WO | WO 2019/238882 A1 | 12/2019 |
| WO | WO 2019/238884 A1 | 12/2019 |

OTHER PUBLICATIONS

Rudikoff et al. Proc. Natl. Acad. Sci. USA vol. 79, pp. 1979-1983 (Mar. 1982).*

Janeway et al. Immunology, 3rd ed., 1997, Garland Publications, Inc., pp. 3:1-3:11.*

International Preliminary Report on Patentability (Chapter II) for International Patent Application No. PCT/EP2017/083043, dated Dec. 6, 2018.

International Search Report and Written Opinion for Application No. PCT/EP2017/083051 dated Aug. 13, 2018.

International Preliminary Report on Patentability (Chapter II) for International Patent Application No. PCT/EP2017/083051, dated Jun. 27, 2019.

International Search Report and Written Opinion for Application No. PCT/EP2017/083043 dated Jul. 20, 2018.

[No Author Listed] Human IL-11 Antibody. Monoclonal Mouse IgG2A. Clone No. 22626. Cat. No. MAB218. R& D Systems: A Biotechne Brand. Rev. Feb. 7, 2018. 1 page.

[No Author Listed] Human IL-11 R? Antibody. Monoclonal Mouse IgG1. Clone No. 473143. Cat. No. MAB1977. R& D Systems: A Biotechne Brand. Rev. Feb. 7, 2018. 1 page.

[No Author Listed] Section 2, Definition, Pathophsiology and Pathogenesis of Asthma, and Natural History of Asthma. Aug. 28, 2007. 24 pages.

Blanc et al., Monoclonal antibodies against the human interleukin-11 receptor mononuclear cells. J Immunol alpha-chain (IL-11Ralpha) and their use in studies of human mononuclear cells. J Immunol Methods. Jul. 31, 2000;241(1-2):43-59.

Carr et al., Asthma heterogeneity and severity. World Allergy Organ J. 2016; 9(1): 41. EPub Nov. 29, 2016. doi: 10.1186/s40413-016-0131-2. 8 pages.

Chen et al., Enhancement and destruction of antibody function by somatic mutation: unequal occurrence is controlled by V gene combinatorial associations. The EMBO Journal. 1995;14(12):2784-94.

Cheng et al., Cross-reactivity of antibody against SARS-coronavirus nucleocapsid protein with IL-11. Biochem Biophys Res Commun. Dec. 23, 2005;338(3):1654-60. Epub Oct. 25, 2005.

Colman, Effects of Amino Acid Sequence Changes on Antibody-Antigen Interactions. Research in Immunology. 1994;145:33-6.

Cook et al., Hiding in Plain Sight: Interleukin-11 Emerges as a Master Regulator of Fibrosis, Tissue Integrity and Stromal Inflammation. Annu Rev Med. Jan. 27, 2020;71:263-276. doi: 10.1146/annurev-med-041818-011649.

Deguchi et al., Generation of and characterization of anti-IL-11 antibodies using newly established Il11-deficient mice. Biochem Biophys Res Commun. Oct. 28, 2018;505(2):453-459. doi: 10.1016/j.bbrc.2018.09.128. Epub Sep. 26, 2018.

Du et al., A bone marrow stromal-derived growth factor, interleukin-11, stimulates recovery of small intestinal mucosal cells after cytoablative therapy. Blood. Jan. 1, 1994;83(1):33-7.

Forth, et al., Allgemeine und spezielle Pharmakologie und Toxikologie. 11th Edition. Aktories et al., Editors. Urban & Fischer. Sep. 17, 2013;Chapter 16:362-4.

Friedlander, Fibrosis and diseases of the eye. J Clin Invest. Mar. 2007;117(3):576-86.

Hennersdorf, et al., Das Herz bei arterieller Hypertonie. Internist. 2007;48(3): 236-45. https://doi.org/10.1007/s00108-006-1762-0.

Hermann et al., Important immunoregulatory role of interleukin-11 in the inflammatory process in rheumatoid arthritis. Arthritis Rheum. Aug. 1998;41(8):1388-97.

Janeway, Jr et al., Immunobiology: The Immune System in Health and Disease. 3rd Ed. New York: Garland Science. 1997. Part II: The Recognition of Antigen. 3:1-3:11.

Keith et al., IL-11, a pleiotropic cytokine: exciting new effects of IL-11 on gastrointestinal mucosal biology. Stem Cells. 1994;12 Suppl 1:79-89; discussion 89-90.

King, A scar-y movie, starring IL-11. Science Translational Medicine. Nov. 29, 2017;9(418):eaar2443. doi: 10.1126/scitranslmed.aar2443.

Kussie et al., A single engineered amino acid substitution changes antibody fine specificity. J. Immunol. Jan. 1, 1994;152(1):146-52.

Lai et al., Interleukin-11 attenuates nephrotoxic nephritis in Wistar Kyoto rats. J Am Soc Nephrol. Nov. 2001;12(11):2310-20.

Lai et al., Interleukin-11 reduces renal injury and glomerular NF-kappa B activity in murine experimental glomerulonephritis. Nephron Exp Nephrol. 2005;101(4):e146-54. Epub Aug. 30, 2005.

Lee et al., Interleukin-11 protects against renal ischemia and reperfusion injury. Am J Physiol Renal Physiol. Oct. 15, 2012; 303(8): F1216-F1224. EPub Aug. 1, 2012. doi: 10.1152/ajprenal.00220.2012.

Lokau et al., Generation of soluble interleukin-11 and interleukin-6 receptors: a crucial function for proteases during inflammation. Mediators of Inflammation. 2016. Article ID:1785021.10 pages.

McCoy et al., IL-11 produced by breast cancer cells augments osteoclastogenesis by sustaining the pool of osteoclast progenitor cells. BMC Cancer. Jan. 11, 2013;13:16. doi: 10.1186/14712407-13-16. 11 pages.

Muhl, STAT3, a Key Parameter of Cytokine-Driven Tissue Protection during Sterile Inflammation—the Case of Experimental Acet-

(56) References Cited

OTHER PUBLICATIONS aminophen (Paracetamol)-Induced Liver Damage. Front Immunol. May 2, 2016;7:163. doi: 10.3389/fimmu.2016.00163. eCollection 2016.
Nishina et al., Critical Contribution of Nuclear Factor Erythroid 2-related Factor 2 (NRF2) to Electrophile-induced Interleukin-11 Production. J Biol Chem. Jan. 6, 2017;292(1):205-216. doi: 10.1074/jbc.M116.744755. Epub Nov. 21, 2016.
Nishina et al., Interleukin-11 Links Oxidative Stress and Compensatory Proliferation. Sci Signal. Jan. 17, 2012;5(207):ra5. doi: 10.1126/scisignal.2002056.
Panka et al., Variable region framework differences result in decreased or increased affinity of variant anti-digoxin antibodies. Proc. Natl. Acad. Sci. USA. 1988; 85(9): 3080-3084.
Park et al., Monoclonal antibody therapy. Advances in Protein Chemistry. 2001;56:369-421. https://doi.org/10.1016/S0065-3233(01)56010-6.
PGR2019-00053, Exhibit No. 1003. Declaration of Peter Bowers in Support of Petition for Post Grant Review for U.S. Pat. No. 10,106,603. Jul. 22, 2019. 106 pages.
PGR2019-00053, Exhibit No. 1004. Barton et al., Interleukin-11 signals through the formation of a hexameric receptor complex. J Biol Chem. Nov. 17, 2000;275(46):36197-203.
PGR2019-00053, Exhibit No. 1004. Declaration of Dr. Stephen Ledbetter, Ph.D. in Support of Petition for Post Grant Review for U.S. Pat. No. 10,106,603. Jul. 22, 2019. 79 pages.
PGR2019-00053, Reviewed Petition for Post Grant Review of U.S. Pat. No. 10,106,603. Issued Feb. 6, 2020. 41 pages.
Putoczki et al., IL-11 signaling as a therapeutic target for cancer. Immunotherapy. 2015;7(4):441-53. doi: 10.2217/imt.15.17.
Redlich et al., IL-11 enhances survival and decreases TNF production after radiation-induced thoracic injury. J Immunol. Aug. 15, 1996;157(4):1705-10.
Relevance of third-party observation dated Aug. 5, 2018. 3 pages.
Rudikoff et al., Single amino acid substitution altering antigen-binding specificity. Proc Natl Acad Sci U S A. Mar. 1982; 79(6): 1979-1983. doi: 10.1073/pnas.79.6.1979.
Tao et al., Cancer-associated fibroblasts treated with cisplatin facilitates chemoresistance of lung adenocarcinoma through IL-11/IL-11R/STAT3 signaling pathway. Sci Rep. Dec. 6, 2016;6:38408. doi: 10.1038/srep38408. 24 pages.
Third Party Observations for application No. EP20160822941, dated Aug. 5, 2018. 3 pages.
Trepicchio et al., Protective effect of rhIL-11 in a murine model of acetaminophen-induced hepatotoxicity. Toxicol Pathol. Mar.-Apr. 2001;29(2):242-9.
Winship et al., Targeting Interleukin-11 Receptor-? Impairs Human Endometrial Cancer Cell Proliferation and Invasion In Vitro and Reduces Tumor Growth and Metastasis In Vivo. Mol Cancer Ther. Apr. 2016;15(4):720-30. doi: 10.1158/1535-7163.MCT-15/0677. Epub Feb. 4, 2016.
Wong et al., Endogenous IL-11 is pro-inflammatory in acute methylated bovine serum albumin/interleukin-l-induced (mBSA/IL-1)arthritis. Cytokine. Jan. 21, 2005;29(2):72-6.
Wynn, Fibrotic Disease and the Th1/Th2 Paradigm. Nat Rev Immunol. Aug. 2004; 4(8): 583-594. doi: 10.1038/nri1412.
Zheng et al., IL-11: insights in asthma from overexpression transgenic modeling. J Allergy Clin Immunol. Oct. 2001;108(4):489-96.
Zong-Jiang et al., Anti-gp ciliary neurotrophic factor, interleukin-6, M. J. Immunol. Methods. 1996; 130 transducer monoclonal antibodies specifically inhibiting interleukin-11, leukemia inhibitory factor or oncostatin 190(1): 21-27.
[No Author Listed] Recombinant Human Anti-human Il1 1 Antibody. Creative Biolabs. May 8, 2018.
Ancey et al., A fusion protein of the gp130 and interleukin-6Ralpha ligand-binding domains acts as a potent interleukin-6 inhibitor. J Biol Chem. May 9, 2003;278(19):16968-72.
Bravo et al., Crystal structure of a cytokine-binding region of gp130. EMBO J. Mar. 16, 1998;17(6):1665-74.
Chapter II Demand filed Aug. 14, 2017 for International Patent Application No. PCT/EP2016/081430.
Chen et al., IL-11 receptor alpha in the pathogenesis of IL-13-induced inflammation and remodeling. J Immunol. Feb. 15, 2005;174(4):2305-13.
Chow et al., Structure of an extracellular gp130 cytokine receptor signaling complex. Science. Mar. 16, 2001;291(5511):2150-5.
Du et al., Interleukin-11: review of molecular, cell biology, and clinical use. Blood. Jun. 1, 1997;89(11):3897-908.
Garbers et al., Interleukin-6 and interleukin-11: same same but different. Biol Chem. Sep. 2013;394(9):1145-61. doi: 10.1515/hsz-2013-0166.
Gu et al., Anti-gp130 transducer monoclonal antibodies specifically inhibiting ciliary neurotrophic factor, interleukin-6, interleukin-11, leukemia inhibitory factor or oncostatin M. J Immunol Methods. Mar. 28, 1996;190(1):21-7.
Halwani et al., Airway remodeling in asthma. Curr Opin Pharmacol. Jun. 2010;10(3):236-45. doi: 10.1016/j.coph.2010.06.004.
Ham et al., Critical role of interleukin-11 in isoflurane-mediated protection against ischemic acute kidney injury in mice. Anesthesiology. Dec. 2013;1 19(6): 1389-401. doi: 10.1097 I ALN.ObO 1 3e3 1 82a950da.
International Preliminary Report on Patentability (Chapter II) for International Patent Application No. PCT/EP2016/081430, dated Nov. 6, 2017.
International Search Report and Written Opinion for International Patent Application No. PCT/EP2016/081430, dated Apr. 18, 2017.
Johnstone et al., Emerging roles for IL-11 signaling in cancer development and progression: Focus on breast cancer. Cytokine Growth Factor Rev. Oct. 2015;26(5):489-98. doi: 10.1016/j.cytogfr.2015.07.015. Epub Jul. 14, 2015.
Kapina et al., Interleukin-11 drives early lung inflammation during *Mycobacterium tuberculosis* infection in genetically susceptible mice. PLoS One. 2011;6(7):e21878. doi: 10.1371/journal.pone.0021878.
Khan et al., Fibrosis in heart disease: understanding the role of transforming growth factor-beta in cardiomyopathy, valvular disease and arrhythmia. Immunology. May 2006;118(1):10-24.
Kimura et al., Identification of cardiac myocytes as the target of interleukin 11, a cardioprotective cytokine. Cytokine. May 2007;38(2):107-15.
Lee et al., Cysteinyl leukotriene upregulates IL-11 expression in allergic airway disease of mice. J Allergy Clin Immunol. Jan. 2007;119(1):141-9.
Lee et al., Endogenous IL-11 signaling is essential in Th2- and IL-13-induced inflammation and mucus production. Am J Respir Cell Mol Biol. Dec. 2008;39(6):739-46. doi: 10.1165/rcmb.2008-0053OC. Epub Jul. 10, 2008.
Lemoli et al., Interleukin-11 (IL-11) acts as a synergistic factor for the proliferation of human myeloid leukaemic cells. Br J Haematol. Oct. 1995;91(2):319-26.
Lindahl et al., Microarray profiling reveals suppressed interferon stimulated gene program in fibroblasts from scleroderma-associated interstitial lung disease. Respir Res. Aug. 2, 2013;14:80. doi: 10.1186/1465-9921-14-80.
Lokau et al., Proteolytic Cleavage Governs Interleukin-11Trans-signaling. Cell Rep. Feb. 23, 2016;14(7):1761-1773. doi:10.1016/j.celrep.2016.01.053. Epub Feb. 11, 2016.
Lokau et al., Signal transduction of Interleukin-11 and Interleukin-6 α-Receptors. Recep Clin Investigation. 2016;3. 5 pages.
Metz et al., Characterization of the Interleukin (IL)-6 Inhibitor IL-6-RFP: fused receptor domains act as high affinity cytokine-binding proteins. J Biol Chem. Jan. 12, 2007;282(2):1238-48. Epub Nov. 3, 2006.
Minshall et al., IL-11 expression is increased in severe asthma: association with epithelial cells and eosinophils. J Allergy Clin Immunol. Feb. 2000;105(2 Pt 1):232-8.
Molet et al., IL-11 and IL-17 expression in nasal polyps: relationship to collagen deposition and suppression by intranasal fluticasone propionate. Laryngoscope. Oct. 2003;113(10):1803-12.
Murray et al., Targeting interleukin-13 with tralokinumab attenuates lung fibrosis and epithelial damage in a humanized SCID idiopathic

(56) References Cited

OTHER PUBLICATIONS pulmonary fibrosis model. Am J Respir Cell Mol Biol. May 2014;50(5):985-94. doi: 10.1165/rcmb.2013-0342OC.
Obana et al., Therapeutic activation of signal transducer and activator of transcription 3 by interleukin-11 ameliorates cardiac fibrosis after myocardial infarction. Circulation. Feb. 9, 2010;121(5):684-91. doi:10.1161/CIRCULATIONAHA.109.893677.
Obana et al., Therapeutic administration of IL-11 exhibits the postconditioning effects against ischemia-reperfusion injury via STAT3 in the heart. Am J Physiol Heart Circ Physiol. Sep. 1, 2012;303(5):H569-77. doi: 10.1152/ajpheart.00060.2012.
Putoczki et al., Interleukin-11 is the dominant IL-6 family cytokine during gastrointestinal tumorigenesis and can be targeted therapeutically. Cancer Cell. Aug. 12, 2013;24(2):257-71. doi: 10.1016/j.ccr.2013.06.017.
Ray et al., Regulated overexpression of interleukin 11 in the lung. Use to dissociate development-dependent and -independent phenotypes. J Clin Invest. Nov. 15, 1997;100(10):2501-11.
Schafer et al., IL-11 is a crucial determinant of cardiovascular fibrosis. Nature. Dec. 7, 2017;552(7683):110-115. doi: 10.1038/nature24676. Epub Nov. 13, 2017.
Shepelkova et al., Therapeutic Effect of Recombinant Mutated Interleukin 11 in the Mouse Model of Tuberculosis. J Infect Dis. Aug. 1, 2016;214(3):496-501. doi: 10.1093/infdis/jiw176.
Sommer et al., Constitutively active mutant gp130 receptor protein from inflammatory hepatocellular adenoma is inhibited by an anti-gp130 antibody that specifically neutralizes interleukin 11 signaling. J Biol Chem. Apr. 20, 2012;287(17):13743-51. doi: 10.1074/jbc.M111.349167.
Stangou et al., Effect of IL-11 on glomerular expression of TGF-beta and extracellular matrix in nephrotoxic nephritis in Wistar Kyoto rats. J Nephrol. Jan.-Feb. 2011;24(1): 106-11.
Tang et al., Targeted expression of IL-11 in the murine airway causes lymphocytic inflammation, bronchial remodeling, and airways obstruction. J Clin Invest. Dec. 15, 1996;98(12):2845-53.
Tang et al., Transforming growth factor-beta stimulates interleukin-11 transcription via complex activating protein-1-dependent pathways. J Biol Chem. Mar. 6, 1998;273(10):5506-13.
Third Party Submission Under 37 C.F.R. § 1.290 for U.S. Appl. No. 15/381,622, filed Apr. 30, 2018.
Toda et al., Polarized in vivo expression of IL-11 and IL-17 between acute and chronic skin lesions. J Allergy Clin Immunol. Apr. 2003;111(4):875-81.
Trepicchio et al., The therapeutic utility of Interleukin-11 in the treatment of inflammatory disease. Expert Opin Investig Drugs. Sep. 1998;7(9):1501-4.
Wynn, Cellular and molecular mechanisms of fibrosis. J Pathol. Jan. 2008;214(2):199-210.
Yashiro et al., Transforming growth factor-beta stimulates interleukin-11 production by human periodontal ligament and gingival fibroblasts. J Clin Periodontol. Mar. 2006;33(3):165-71.
Zhu et al., IL-11 Attenuates Liver Ischemia/Reperfusion Injury (IRI) through STAT3 Signaling Pathway in Mice. PLoS One. May 6, 2015;10(5):e0126296. doi: 10.1371/journal.pone.0126296.
International Search Report and Written Opinion for International Patent Application No. PCT/EP2020/051332, dated Apr. 28, 2020.
International Search Report and Written Opinion for International Patent Application No. PCT/EP2020/054580, dated Jun. 12, 2020.
International Search Report and Written Opinion for International Patent Application No. PCT/EP2020/062193, dated Jun. 23, 2020.
[No Author Listed] Mouse IL-11 R(alpha) Antibody Datasheet. Catalog No. AF490. R&D Systems: a Biotechne Brand. Retrieved Oct. 13, 20150. 2 pages.
[No Author Listed] Netralizing Interleukin-11 Antibodies Reduce Pressure Overload Induced Cardiac Fibrosis in Mice. Submitted in Opposition to EP 3298040B1. 4 pages.
[No Author Listed] Neumega® Drug Label. Last accessed Jul. 1, 2020. 28 pages.
[No Author Listed] Pharmacologist's Review. PLA 96-1433. Sponsored by Genetics Institute, Inc.. May 27, 1997. 56 pages.

[No Author Listed] What is Pulmonary Fibrosis? Retrieved from pulmonaryfibrosisnow.org. Feb. 16, 2018. 5 pages.
Abbas-Terki et al., Lentiviral-mediated RNA interference. Hum Gene Ther. 2002;13(18):2197-2201.
Aceves et al., Airway fibrosis and angiogenesis due to eosinophil trafficking in chronic asthma. Curr Mol Med. 2008;8(5):350-358. doi:10.2174/156652408785161023.
Ackermann et al., Effects of nintedanib on the microvascular architecture in a lung fibrosis model. Angiogenesis. 2017;20(3):359-372. doi:10.1007/s10456-017-9543-z.
Agthe et al., Interleukin-11 classic but not trans-signaling is essential for fertility in mice. Placenta. Sep. 2017;57:13-16. doi: 10.1016/j.placenta.2017.05.015. Epub May 28, 2017.
Ahmad et al., Epidemiology and Genetic Risk Factors of Drug Hepatotoxicity. Clin Liver Dis. Feb. 2017;21(1):55-72. doi: 10.1016/j.cld.2016.08.004.
Almagro et al., Humanization of antibodies. Front Biosci. 2008;13:1619-1633. Published Jan. 1, 2008.
Altenhofer et al., Evolution of NADPH Oxidase Inhibitors: Selectivity and Mechanisms for Target Engagement. Antioxid Redox Signal. Aug. 10, 2015;23(5):406-27. doi: 10.1089/ars.2013.5814.
Anguita et al., Selective anti-inflammatory action of interleukin-11 in murine Lyme disease: arthritis decreases while carditis persists. J Infect Dis. Mar. 1999;179(3):734-7.
Baeuerle et al., Bispecific T-cell engaging antibodies for cancer therapy. Cancer Res. 2009;69(12):4941-4944.
Balic et al., Interleukin-11-driven gastric tumourigenesis is independent of trans-signalling. Cytokine. Apr. 2017;92:118-123. doi: 10.1016/j.cyto.2017.01.015. Epub Feb. 1, 2017.
Barbas et al., In vitro evolution of a neutralizing human antibody to human immunodeficiency virus type 1 to enhance affinity and broaden strain cross-reactivity. Proc Natl Acad Sci U S A. 1994;91(9):3809-3813.
Barrett et al., Evaluating coverage of genome-wide association studies. Nat Genet. 2006;38(6):659-662.
Barton et al., Retroviral delivery of small interfering RNA into primary cells. Proc Natl Acad Sci U S A. 2002;99(23):14943-14945.
Bedinger et al., Development and characterization of human monoclonal antibodies that neutralize multiple TGFβ isoforms. MAbs. 2016;8(2):389-404. doi:10.1080/19420862.2015.1115166.
Bernal et al., Acute liver failure. N Engl J Med. Mar. 20, 2014;370(12):1170-1. doi: 10.1056/NEJMc1400974.
Bernstein aet al., Role for a bidentate ribonuclease in the initiation step of RNA interference. Nature. 2001;409(6818):363-366.
Bettaieb et al., Hepatocyte Nicotinamide Adenine Dinucleotide Phosphate Reduced Oxidase 4 Regulates Stress Signaling, Fibrosis, and Insulin Sensitivity During Development of Steatohepatitis in Mice. Gastroenterology. Aug. 2015;149(2):468-80.e10. doi: 10.1053/j.gastro.2015.04.009. Epub Apr. 14, 2015.
Better et al., *Escherichia coli* secretion of an active chimeric antibody fragment. Science. 1988;240(4855):1041-1043.
Bhushan et al., Liver Regeneration after Acetaminophen Hepatotoxicity: Mechanisms and Therapeutic Opportunities. Am J Pathol. Apr. 2019;189(4):719-729. doi: 10.1016/j.ajpath.2018.12.006. Epub Jan. 14, 2019.
Bird et al., Single-chain antigen-binding proteins [published correction appears in Science Apr. 28, 1989;244(4903):409]. Science. 1988;242(4877):423-426.
Boardman et al., Chapter 106: Chronic Obstructive Pulmonary Disease from Buttaro et al., Primary Care: A collaborative Practice. 4th Ed. Elsevier. 2010.
Bockhorn et al., MicroRNA-30c Inhibits Human Breast Tumour Chemotherapy Resistance by Regulating TWF1 and IL-11. Nat Commun. 2013;4:1393. doi: 10.1038/ncomms2393.
Boerma et al., Local administration of interleukin-11 ameliorates intestinal radiation injury in rats. Cancer Res. Oct. 1, 2007;67(19):9501-6.
Bolger et al., Trimmomatic: a flexible trimmer for Illumina sequence data. Bioinformatics. Aug. 1, 2014;30(15):2114-20. doi: 10.1093/bioinformatics/btu170. Epub Apr. 1, 2014.
Borkhardt, Blocking oncogenes in malignant cells by RNA interference—new hope for a highly specific cancer treatment?. Cancer Cell. 2002;2(3):167-168.

(56) References Cited

OTHER PUBLICATIONS

Bourdi et al., Protection against acetaminophen-induced liver injury and lethality by interleukin 10: role of inducible nitric oxide synthase. Hepatology. Feb. 2002;35(2):289-98.

Bozza et al., Interleukin-11 modulates Th1/Th2 cytokine production from activated CD4+ T cells. J Interferon Cytokine Res. Jan. 2001;21(1):21-30.

Bozza et al., Interleukin-11 Reduces T-cell-dependent Experimental Liver Injury in Mice. Hepatology. Dec. 1999;30(6):1441-7. doi: 10.1002/hep.510300616.

Brenner et al., Origin of myofibroblasts in liver fibrosis. Fibrogenesis Tissue Repair. 2012;5(Suppl 1):S17. Published Jun. 6, 2012. doi:10.1186/1755-1536-5-S1-S17.

Brookes et al., The Essence of SNPs. Gene. Jul. 8, 1999;234(2):177-86. doi: 10.1016/s0378-1119(99)00219-x.

Castanotto et al., The promises and pitfalls of RNA-interference-based therapeutics. Nature. 2009;457(7228):426-433.

Chan et al., The role of phage display in therapeutic antibody discovery. Int Immunol. 2014;26(12):649-657. doi:10.1093/intimm/dxu082.

Chiang et al., Targeting bile acids and lipotoxicity for Nash treatment. Hepatol Commun. Dec. 2017; 1(10): 1002-1004. Epub Dec. 4, 2017. doi: 10.1002/hep4.1127.

Chiaramonte et al., An IL-13 inhibitor blocks the development of hepatic fibrosis during a T-helper type 2-dominated inflammatory response. J Clin Invest. 1999;104(6):777-785. doi:10.1172/JCI7325.

Chiew et al., Interventions for paracetamol (acetaminophen) overdose. Cochrane Database Syst Rev. Feb. 23, 2018;2:CD003328. doi: 10.1002/14651858.CD003328.pub3.

Chothani et al., Widespread Translational Control of Fibrosis in the Human Heart by RNA-Binding Proteins. Circulation. Sep. 10, 2019;140(11):937-951. doi: 10.1161/CIRCULATIONAHA.119.039596. Epub Jul. 9, 2019.

Ciliberto et al. Cytokine Inhibitors: Chapter 8. Marcel Dekker, Inc. 2001.

Clare et al., Genetic Factors Influencing Drug-Induced Liver Injury: Do They Have a Role in Prevention and Diagnosis? Curr Hepatol Rep. 2017;16(3):258-264. doi: 10.1007/s11901-0170363-9.

Curtis et al., Recombinant Soluble interleukin-11 (IL-11) Receptor Alpha-Chain Can Act as an IL-11 Antagonist. Blood. Dec. 1, 1997;90(11):4403-12.

Czauderna et al., Structural variations and stabilising modifications of synthetic siRNAs in mammalian cells. Nucleic Acids Res. 2003;31(11):2705-2716.

Daba et al., Drug-induced pulmonary fibrosis. Saudi Med J. 2004;25(6):700-706.

Dahlin et al., N-acetyl-p-benzoquinone Imine: A Cytochrome P-450-mediated Oxidation Product of Acetaminophen. Proc Natl Acad Sci U S A. Mar. 1984;81(5):1327-31. doi: 10.1073/pnas.81.5.1327.

De-Chao et al., Soluble Vascular Endothelial Growth Factor Decoy Receptor FP3 Exerts Potent Antiangiogenic Effects. Mol Ther. May 2012;20(5):938-47. doi: 10.1038/mt.2011.285.

Declaration of Dr. Sebastian Schaefer submitted in Opposition to EP 3298040B1. Aug. 23, 2019. 1 page.

Declaration of Dr. Stuart Cook submitted in Opposition to EP 3298040B1. May 1, 2020. 25 pages Declaration of Scott L. Friedman submitted in Opposition to EP 3298040B1. Apr. 30, 2020. 79 pages.

Denton et al., Therapeutic interleukin-6 blockade reverses transforming growth factor-beta pathway activation in dermal fibroblasts: insights from the faSScinate clinical trial in systemic sclerosis. Ann Rheum Dis. Sep. 2018;77(9):1362-1371. doi: 10.1136/annrheumdis-2018-213031. Epub May 31, 2018.

Devroe et al., Retrovirus-delivered siRNA. BMC Biotechnol. 2002;2:15. Published Aug. 28, 2002. doi:10.1186/1472-6750-2-15.

Dobin et al., STAR: ultrafast universal RNA-seq aligner. Bioinformatics. Jan. 1, 2013;29(1):1521. doi: 10.1093/bioinformatics/bts635. Epub Oct. 25, 2012.

Du et al., Protective effects of interleukin-11 in a murine model of ischemic bowel necrosis. Am J Physiol. Mar. 1997;272(3 Pt 1):G545-52.

Dzau et al., Gene therapy for cardiovascular disease. Trends Biotechnol. 1993;11(5):205-210.

Elbashir et al., Duplexes of 21-nucleotide RNAs mediate RNA interference in cultured mammalian cells. Nature. 2001;411(6836):494-498.

Elbashir et al., RNA interference is mediated by 21- and 22-nucleotide RNAs. Genes Dev. 2001;15(2):188-200.

Elshabrawy et al., IL-11 facilitates a novel connection between RA joint fibroblasts and endothelial cells. Angiogenesis. May 2018;21(2):215-228. doi: 10.1007/s10456-017-9589-y. Epub Jan. 11, 2018.

Fan et al., Highly Parallel SNP Genotyping. Cold Spring Harb Symp Quant Biol. 2003;68:69-78. doi: 10.1101/sqb.2003.68.69.

Fire et al., Potent and specific genetic interference by double-stranded RNA in Caenorhabditis elegans. Nature. 1998;391(6669):806-811.

Fire, RNA-triggered gene silencing. Trends Genet. 1999;15(9):358-363.

Fontan et al., Interleukin-11 for Treatment of Hepatitis C-associated ITP. Acta Haematol. 2008;119(2):126-32. doi: 10.1159/000125192. Epub Apr. 8, 2008.

French, How to make bispecific antibodies. Methods Mol Med. 2000;40:333-339.

Fujimoto et al., Combined Pulmonary Fibrosis and Emphysema (CPFE). Mahadeva ed. Emphysema. IntechOpen. 2012.

Gibson et al., Interleukin-11 reduces TLR4-induced colitis in TLR2-deficient mice and restores intestinal STAT3 signaling. Gastroenterology. Oct. 2010;139(4):1277-88. doi: 10.1053/j.gastro.2010.06.057. Epub Jun. 25, 2010.

Gicquel et al., Quantitative analysis of acetaminophen and its primary metabolites in small plasma volumes By liquid chromatography-tandem mass spectrometry. J Anal Toxicol. Mar. 2013;37(2):110-6. doi: 10.1093/jat/bks139. Epub Jan. 12, 2013.

Gilbert et al., A purpose-synthesised anti-fibrotic agent attenuates experimental kidney diseases in the rat. PLoS One. 2012;7(10):e47160. doi:10.1371/journal.pone.0047160.

Gold et al., Aptamer-based Multiplexed Proteomic Technology for Biomarker Discovery. PLoS One. Dec. 7, 2010;5(12):e15004. doi: 10.1371/journal.pone.0015004.

Gowda et al., A Review on Laboratory Liver Function Tests. Pan Afr Med J. Nov. 22, 2009;3:17.

Greenwood-Van Meerveld et al., Recombinant human interleukin-11 modulates ion transport and mucosal inflammation in the small intestine and colon. Lab Invest. Aug. 2000;80(8):1269-80.

Grivennikov et al., Autocrine IL-6 signaling: a key event in tumorigenesis?. Cancer Cell. 2008;13(1):7-9.

GTEx Consortium, Human genomics. The Genotype-Tissue Expression (GTEx) pilot analysis: multitissue gene regulation in humans. Science. 2015;348(6235):648-660.

Gunawan et al., c-Jun N-terminal kinase plays a major role in murine acetaminophen hepatotoxicity. Gastroenterology. Jul. 2006;131(1):165-78.

Guo et al., Signaling cross-talk between TGF-beta/BMP and other pathways. Cell Res. 2009;19(1):71-88.

Hahne et al., Visualizing Genomic Data Using Gviz and Bioconductor. Methods Mol Biol. 2016;1418:335-51. doi: 10.1007/978-1-4939-3578-9_16.

Hamilton et al., A species of small antisense RNA in posttranscriptional gene silencing in plants. Science. 1999;286(5441):950-952.

Hammond et al., An RNA-directed nuclease mediates post-transcriptional gene silencing in Drosophila cells. Nature. 2000;404(6775):293-296.

Hammond et al., Post-transcriptional gene silencing by double-stranded RNA. Nat Rev Genet. 2001;2(2):110-119.

Hannon et al., RNA interference. Nature. 2002;418(6894):244-251.

Hawkins et al., Selection of phage antibodies by binding affinity. Mimicking affinity maturation. J Mol Biol. 1992;226(3):889-896.

(56) References Cited

OTHER PUBLICATIONS

Hecker et al., NADPH oxidase-4 mediates myofibroblast activation and fibrogenic responses to lung injury. Nat Med. Sep. 2009;15(9):1077-81. doi: 10.1038/nm.2005. Epub Aug. 23, 2009.
Herrlinger et al., Randomized, double blind controlled trial of subcutaneous recombinant human interleukin-11 versus prednisolone in active Crohn's disease. Am J Gastroenterol. Apr. 2006;101(4):793-7.
Hill et al., Interleukin-11 promotes T cell polarization and prevents acute graft-versus-host disease after allogeneic bone marrow transplantation. J Clin Invest. Jul. 1, 1998;102(1):115-23.
Hilton et al., Cloning of a Murine IL-11 Receptor Alpha-Chain; Requirement for gp130 for High Affinity Binding and Signal Transduction. EMBO J. Oct. 17, 1994;13(20):4765-75.
Holgate et al., The mechanisms, diagnosis, and management of severe asthma in adults. Lancet. 2006;368(9537):780-793. doi:10.1016/S0140-6736(06)69288-X.
Holgate, The airway epithelium is central to the pathogenesis of asthma. Allergol Int. 2008;57(1):1-10. doi:10.2332/allergolint.R-07-154.
Hoogenboom, Selecting and screening recombinant antibody libraries. Nat Biotechnol. 2005;23(9):1105-1116. doi:10.1038/nbt1126.
Hornbeck, Enzyme-Linked Immunosorbent Assays. Curr Protoc Immunol. 2015;110:2.1.1-2.1.23.
Hornig et al., Production of bispecific antibodies: diabodies and tandem scFv. Methods Mol Biol. 2012;907:713-727. doi:10.1007/978-1-61779-974-7_40.
Hsu et al., Whole genome expression differences in human left and right atria ascertained by RNA sequencing. Circ Cardiovasc Genet. 2012;5(3):327-335.
Hurrell, Monoclonal Hybridoma Antibodies: Techniques and Applications. CRC Press. 1982.
Huston et al., Protein engineering of antibody binding sites: recovery of specific activity in an anti-digoxin single-chain Fv analogue produced in *Escherichia coli*. Proc Natl Acad Sci U S A. 1988;85(16):5879-5883.
Jackson et al., In vitro antibody maturation. Improvement of a high affinity, neutralizing antibody against IL-1 beta. J Immunol. 1995;154(7):3310-3319.
Jaeschke et al., Acetaminophen: Dose-Dependent Drug Hepatotoxicity and Acute Liver Failure in Patients. Dig Dis. 2015;33(4):464-71. doi: 10.1159/000374090. Epub Jul. 6, 2015.
John et al., Human MicroRNA targets [published correction appears in PLoS Biol. Jul. 2005;3(7):e264]. PLoS Biol. 2004;2(11):e363. doi:10.1371/journal.pbio.0020363.
Jollow et al., Acetaminophen-induced Hepatic Necrosis. II. Role of Covalent Binding In Vivo. J Pharmacol Exp Ther. Oct. 1973;187(1):195-202.
Karpovich et al., Expression and Function of interleukin-11 and Its Receptor Alpha in the Human Endometrium. Mol Hum Reprod. Feb. 2003;9(2):75-80. doi: 10.1093/molehr/gag012.
Khoury et al., Drug Induced Liver Injury: Review With a Focus on Genetic Factors, Tissue Diagnosis, and Treatment Options. J Clin Transl Hepatol. Jun. 28, 2015;3(2):99-108. doi: 10.14218/JCTH.2015.00007.
Klein et al., The IL-6-gp130-STAT3 pathway in hepatocytes triggers liver protection in T cell-mediated liver injury. J Clin Invest. Apr. 2005;115(4):860-9. Epub Mar. 3, 2005.
Knight et al., STAT3 in tissue fibrosis: is there a role in the lung?. Pulm Pharmacol Ther. 2011;24(2):193-198. doi:10.1016/j.pupt.2010.10.005.
Knight et al., The role of gp130/IL-6 cytokines in the development of pulmonary fibrosis: critical determinants of disease susceptibility and progression?. Pharmacol Ther. 2003;99(3):327-338. doi:10.1016/s0163-7258(03)00095-0.
Konner et al., Use of soluble recombinant decoy receptor vascular endothelial growth factor trap (VEGF Trap) to inhibit vascular endothelial growth factor activity. Clin Colorectal Cancer. 2004;4 Suppl 2:S81-S85.
Kontermann, Dual targeting strategies with bispecific antibodies. MAbs. 2012;4(2):182-197.
Kroy et al., Lack of interleukin-6/glycoprotein 130/signal transducers and activators of transcription-3 signaling in hepatocytes predisposes to liver steatosis and injury in mice. Hepatology. Feb. 2010;51(2):463-73. doi: 10.1002/hep.23322.
Kyle et al., Metabolism of Acetaminophen by Cultured Rat Hepatocytes. Depletion of Protein Thiol Groups Without Any Loss of Viability. Biochem Pharmacol. Sep. 15, 1990;40(6):1211-8. doi: 10.1016/0006-2952(90)90385-x.
Langmead et al., Ultrafast and memory-efficient alignment of short DNA sequences to the human genome. Genome Biol. 2009;10(3):R25. doi: 10.1186/gb-2009-10-3-r25. Epub Mar. 4, 2009.
Lapidoth et al., AbDesign: An algorithm for combinatorial backbone design guided by natural conformations and sequences. Proteins. 2015;83(8):1385-1406. doi:10.1002/prot.24779.
Lawitz et al., A pilot study of interleukin-11 in subjects with chronic hepatitis C and advanced liver disease nonresponsive to antiviral therapy. Am J Gastroenterol. Dec. 2004;99(12):2359-64.
Lay et al., Interleukin 11 Regulates Endometrial Cancer Cell Adhesion and Migration via STAT3. Int J Oncol. Aug. 2012;41(2):759-64. doi: 10.3892/ijo.2012.1486.
Lee et al., Intravenous N-acetylcysteine improves transplant-free survival in early stage non-acetaminophen acute liver failure. Gastroenterology. Sep. 2009;137(3):856-64, 864.e1. doi: 10.1053/j.gastro.2009.06.006. Epub Jun. 12, 2009.
Lee et al., Transgenic modeling of transforming growth factor-beta(1): role of apoptosis in fibrosis and alveolar remodeling. Proc Am Thorac Soc. 2006;3(5):418-423. doi:10.1513/pats.200602-017AW.
Leng et al., Interleukin-11. Int J Biochem Cell Biol. 1997;29(8-9):1059-1062. doi:10.1016/s1357-2725(97)00017-4.
Lentsch et al., Regulatory effects of interleukin-11 during acute lung inflammatory injury. J Leukoc Biol. 1999;66(1):151-157.
Lewis et al., Efficient delivery of siRNA for inhibition of gene expression in postnatal mice. Nat Genet. 2002;32(1):107-108.
Li et al., OptMAVEn—a new framework for the de novo design of antibody variable region models targeting specific antigen epitopes. PLoS One. 2014;9(8):e105954. Published Aug. 25, 2014. doi:10.1371/journal.pone.0105954.
Liang et al., In vitro scratch assay: a convenient and inexpensive method for analysis of cell migration in vitro. Nat Protoc. 2007;2(2):329-333.
Liao et al., featureCounts: an efficient general purpose program for assigning sequence reads to genomic features. Bioinformatics. Apr. 1, 2014;30(7):923-30. doi: 10.1093/bioinformatics/btt656. Epub Nov. 13, 2013.
Lim et al., Transgenic interleukin 11 expression causes cross-tissue fibro-inflammation and an inflammatory bowel phenotype in mice. PLoS One. 2020;15(1):e0227505. Published Jan. 9, 2020. .doi:10.37371/journal.pone.0227505.
Lo et al., Antibody Engineering. Microbiol Spectr. 2014;2(1):.. doi:10.1128/microbiolspec.AID-0007-12.
Lori et al., Gene therapy approaches to HIV infection. Am J Pharmacogenomics. 2002;2(4):245-252.
Maeshima et al., A Protective Role of Interleukin 11 on Hepatic Injury in Acute Endotoxemia. Shock. Feb. 2004;21(2):134-8. doi: 10.1097/01.shk.0000103386.98235.f6.
Marcos et al., Liver regeneration and function in donor and recipient after right lobe adult to adult living donor liver transplantation. Transplantation. Apr. 15, 2000;69(7):1375-9.
Marks et al., By-passing immunization: building high affinity human antibodies by chain shuffling. Biotechnology (N Y). 1992;10(7):779-783.
Marra et al., Mononuclear cells in liver fibrosis. Semin Immunopathol. 2009;31(3):345-358. doi:10.1007/s00281-009-0169-0.
Matsuzaki et al., Parallel Genotyping of Over 10,000 SNPs Using a One-Primer Assay on a High-Density Oligonucleotide Array. Genome Res. Mar. 2004;14(3):414-25. doi: 10.1101/gr.2014904.
Matta et al., Use of lentiviral vectors for delivery of small interfering RNA. Cancer Biol Ther. 2003;2(2):206-210.

(56) References Cited

OTHER PUBLICATIONS

Matthews et al., Interleukin-6-deficient mice develop hepatic inflammation and systemic insulin resistance. Diabetologia. Nov. 2010;53(11):2431-41. doi: 10.1007/s00125-010-1865-y. Epub Aug. 11, 2010.
McClain et al., Acetaminophen Hepatotoxicity: An Update. Curr Gastroenterol Rep. Feb.-Mar. 1999;1(1):42-9. doi: 10.1007/s11894-999-0086-3.
McManus et al., Gene silencing in mammals by small interfering RNAs. Nat Rev Genet. 2002;3(10):737-747.
Menkhorst et al., IL11 Antagonist Inhibits Uterine Stromal Differentiation, Causing Pregnancy Failure in Mice. Biol Reprod. May 2009;80(5):920-7. doi: 10.1095/biolreprod.108.073601.
Michalopoulos et al., Hepatostat: Liver regeneration and normal liver tissue maintenance. Hepatology. Apr. 2017;65(4):1384-1392. doi: 10.1002/hep.28988. Epub Mar. 6, 2017.
Mims, Asthma: definitions and pathophysiology. Int Forum Allergy Rhinol. 2015;5 Suppl 1:S2-S6. doi:10.1002/alr.21609.
Moore et al., The Toxicity of Acetaminophen and N-acetyl-p-benzoquinone Imine in Isolated Hepatocytes Is Associated With Thiol Depletion and Increased Cytosolic Ca2+. J Biol Chem. Oct. 25, 1985;260(24):13035-40.
Moreland et al., Results of a phase-I/II randomized, masked, placebo-controlled trial of recombinant human interleukin-11 (rhIL-11) in the treatment of subjects with active rheumatoid arthritis. Arthritis Res. 2001;3(4):247-52. Epub Apr. 10, 2001.
Morris et al., Translocating peptides and proteins and their use for gene delivery. Curr Opin Biotechnol. 2000;11(5):461-466.
Morrison et al., Chimeric human antibody molecules: mouse antigen-binding domains with human constant region domains. Proc Natl Acad Sci U S A. 1984;81(21):6851-6855.
Muller et al., Bispecific antibodies for cancer immunotherapy: Current perspectives. BioDrugs. 2010;24(2):89-98.
Murray et al., NADPH oxidase 4 regulates homocysteine metabolism and protects against acetaminophen-induced liver damage in mice. Free Radic Biol Med. Dec. 2015;89:918-30. doi: 10.1016/j.freeradbiomed.2015.09.015. Epub Oct. 22, 2015.
Myers et al., Recombinant Dicer efficiently converts large dsRNAs into siRNAs suitable for gene silencing. Nat Biotechnol. 2003;21(3):324-328.
Nandurkar et al., The Human IL-11 Receptor Requires gp130 for Signalling: Demonstration by Molecular Cloning of the Receptor. Oncogene. Feb. 1, 1996;12(3):585-93.
Negahdaripour et al., A panoramic review and in silico analysis of IL-11 structure and function. Cytokine Growth Factor Rev. 2016;32:41-61. doi:10.1016/j.cytogfr.2016.06.002.
Neuberger et al. Antibody Engineering. 8th International Biotechnology Symposium Part 2. 1988:792-799.
Ng et al., Interleukin-11 Is a Therapeutic Target in Idiopathic Pulmonary Fibrosis. Sci Transl Med. Sep. 25, 2009;11(511):eaaw1237. doi: 10.1126/scitranslmed.aaw1237.
Nimrod et al., Computational Design of Epitope-Specific Functional Antibodies. Cell Rep. 2018;25(8):2121-2131.e5. doi:10.1016/j.celrep.2018.10.081.
Njoku et al., Drug-induced Hepatotoxicity: Metabolic, Genetic and Immunological Basis. Int J Mol Sci. Apr. 22, 2014;15(4):6990-7003. doi: 10.3390/ijms15046990.
Nordan et al., Purification and NH2-terminal sequence of a plasmacytoma growth factor derived from the murine macrophage cell line P388D1. J Immunol. 1987;139(3):813-817.
Obana et al., Therapeutic activation of signal transducer and activator of transcription 3 by interleukin-11 ameliorates cardiac fibrosis after myocardial infarction. Circulation. Feb. 9, 2010;121(Supplemental Info). 14 pages. doi: 10.1161/CIRCULATIONAHA.109.893677. Epub Jan. 25, 2010.
Olman, Epithelial cell modulation of airway fibrosis in asthma. Am J Respir Cell Mol Biol. 2003;28(2):125-128. doi:10.1165/rcmb.F257.
Opal et al., Orally administered recombinant human interleukin-11 is protective in experimental neutropenic sepsis. J Infect Dis. Jan. 1, 2003;187(1):70-6. Epub Dec. 13, 2002.
Opal et al., Recombinant human interleukin-11 has anti-inflammatory actions yet does not exacerbate systemic Listeria infection. J Infect Dis. Feb. 2000;181(2):754-6.
Opposition Document 01—Communication of notices of opposition (r. 79(1) EPC) for Application No. EP 16822941.7, mailed May 15, 2019. 1 page.
Opposition Document 02—Communication of a notice of opposition for Application No. EP 16822941.7, mailed May 7, 2019.
Opposition Document 03—Mewburn Ellis repsonse to Communication dated May 15, 2019 in Opposition to EP 16822941, dated Sep. 24, 2019. 39 pages.
Opposition Document 04—Summons to attend oral proceedings pursuant to Rule 115(1) EPC for Application No. EP 16822941.7, mailed Dec. 2, 2019. 11 pages.
Opposition Document 05—Mewburn Ellis Response to Summons to oral proceeding in Application No. EP 16822941.7, mailed Mar. 4, 2020. 1 page.
Opposition Document 06—Brief Communication regarding Oral Proceedings on May 27, 2020 and Letter from Opponent date Mar. 11, 2020, for Application No. EP 16822941.7, mailed Mar. 24, 2020. 30 pages.
Opposition Document 07—Proprietors' Submissions Under Rule 116 EPC in Application No. EP 16822941.7, mailed Mar. 27, 2020. 51 pages.
Opposition Document 08—Request for postponement of the oral proceedings in Application No. EP 16822941.7, mailed Mar. 27, 2020. 3 pages.
Opposition Document 09—Brief Communication regarding Letters from the opponent dated Mar. 27 and Mar. 30, 2020, in Application No. EP 16822941.7, mailed Apr. 2, 2020. 6 pages.
Opposition Document 10—Bayer Submission No. 4: Reply to the observations made by the patent proprietor(s) in Application No. EP 16822941.7, filed Apr. 17 2020. 17 pages.
Opposition Document 11—Bayer Submission No. 5: Response to the Proprietor's reply in Application No. EP 16822941.7, mailed Apr. 27, 2020. 22 pages.
Opposition Document 12—Proprietors' Observations on Opponent's Submissions Under Rule 116 EPC, in Application No. EP 16822941.7, mailed May 4, 2020. 27 pages.
Opposition Document 13—Brief Communication regarding Summons to Attend Oral Proceedings/Taking of Evidence and New Date to be set later, in Application No. EP 16822941.7, mailed May 14, 2020. 1 page.
Opposition Document 14—Proprietors' Observations on Opponent's Further Submissions in Application No. EP 16822941.7, mailed Jun. 4, 2020. 21 pages.
Opposition Document 15—Bayer Submission—Response to Oral Proceedings in Application No. EP 16822941.7, mailed Jun. 18, 2020. 38 pages.
Opposition Document 16—Annex 1 of the response to the response of the patentee from Sep. 24, 2019, in Application No. EP 1822941.7. 2 pages.
Opposition Document 17—Neutralizing Interleukin-11 Antibodies Reduce Pressure Overload Induced Cardiac Fibrosis in Mice, submitted in Opposition to Application No. EP 16822941.7, by Proprietors: Singapore Health Services PTE Ltd & National University of Singapore. 4 pages.
Orazi et al., Interleukin-11 prevents apoptosis and accelerates recovery of small intestinal mucosa in mice treated with combined chemotherapy and radiation. Lab Invest. Jul. 1996;75(1):33-42.
Park et al., Paracetamol (Acetaminophen) Poisoning. BMJ Clin Evid. Oct. 19, 2015;2015:2101.
Pasqualini et al., Targeting the interleukin-11 Receptor ? in Metastatic Prostate Cancer: A First-In-Man Study. Cancer. Jul. 15, 2015;121(14):2411-21. doi: 10.1002/cncr.29344.
Paul et al., Effective expression of small interfering RNA in human cells. Nat Biotechnol. 2002;20(5):505-508.

(56) References Cited

OTHER PUBLICATIONS

Peterson et al., Pharmacogenomic analysis of rhIL-11 treatment in the HLA-B27 rat model of inflammatory bowel disease. Pharmacogenomics J. 2002;2(6):383-399. doi:10.1038/sj.tpj.6500137.

Petrov et al., RNAcentral: a comprehensive database of non-coding RNA sequences. Nucleic Acids Res. Jan. 4, 2017;45(D1):D128-D134. doi: 10.1093/nar/gkw1008. Epub Oct. 28, 2016.

Pflanz et al., A Fusion Protein of interleukin-11 and Soluble interleukin-11 Receptor Acts as a Superagonist on Cells Expressing gp130. FEBS Lett. Apr. 30, 1999;450(1-2):117-22. doi: 10.1016/s0014-5793(99)00477-9.

Post Grant Review 2019-00053 for U.S. Pat. No. 10,106,603—Ex. 1002: Reduced File History for U.S. Pat. No. 10,106,603. 43 pages.

Post Grant Review 2019-00053 for U.S. Pat. No. 10,106,603—Ex. 1012: Yang et a., Developability studies before initiation of process development. mAbs. 2013;5(5):787-794. doi: 10.4161/mabs.25269.

Post Grant Review 2019-00053 for U.S. Pat. No. 10,106,603—Ex. 1013: Opalinski et al., High Affinity Promotes Internalization of Engineered Antibodies Targeting FGFR1. Int. J. Mol. Sci. 2018;19:1435. 14 pages.

Post Grant Review 2019-00053 for U.S. Pat. No. 10,106,603—Ex. 1014: Zhou et al., Ocular immune provilege. Biology Reports. 2010;2:3. 3 pages.

Post Grant Review 2019-00053 for U.S. Pat. No. 10,106,603—Ex. 1016: Briney et al. Commonality despite exceptional diversity in the baseline human antibody repertoire. Nat. Rev. 2019. 19 pages.

Post Grant Review 2019-00053 for U.S. Pat. No. 10,106,603—Ex. 1017: Curtis et al., Recombinant Soluble Interleukin-11 (IL-11) Receptor (alpha)-Chain Can Act as an IL-11 Antagonist. Blood. 1997;90(110:4403-4412.

Post Grant Review 2019-00053 for U.S. Pat. No. 10,106,603—Ex. 1019: Garvers et al., Plasticity and cross-talk of Interleukin 6-type cytokines. Cytokin & Growth Factor Reviews. 2012;23:85-97.

Post Grant Review 2019-00053 for U.S. Pat. No. 10,106,603—Ex. 1020: Jones et al., Recent insights into targeting the IL-6 cytokine family in inflammatory diseases and cancer. Nat. Rev. Immunol. 2018;18:773-89.

Post Grant Review 2019-00053 for U.S. Pat. No. 10,106,603—Ex. 1021: Kang et al., Therapeutic uses of anti-interleukin-6 receptor antibody. Int. Immunol. Aug. 20, 2014;27(1):21-29.

Post Grant Review 2019-00053 for U.S. Pat. No. 10,106,603—Ex. 1022: Matadeen et al., The Dynamics of Signal Triggering in a gp130-Receptor Complex. Structure. 2007;15:441-8.

Post Grant Review 2019-00053 for U.S. Pat. No. 10,106,603—Ex. 1023: Nishimoto et a., Toxicity, pharmocokinetics, and dose-finding study of repetitive treatment with the humanized anti-interleukin 6 receptor antibody MRA in rheumatoid arthritis. Phase I/II clinical study. J Rheumatol. 2003;30:1426-35.

Post Grant Review 2019-00053 for U.S. Pat. No. 10,106,603—Ex. 1024: Rossi et al., Interleukin-6 as a Therapeutic Target. Clin Canc Res. 2015;21(6). 11 pages.

Post Grant Review 2019-00053 for U.S. Pat. No. 10,106,603—Ex. 1025: Salazar et al., BMP signalling in skeletal development, disease and repair. Nat. Rev. Endocrinol. 2016;12:203. 19 pages.

Post Grant Review 2019-00053 for U.S. Pat. No. 10,106,603—Ex. 1026: Schiff et al., Efficacy and safety of tabalumab, an anti-BAF monoclonal antibody, in patients with moderate-to-severe rheumatoid arthritis and inadequate response to TNF inhibitors: results of a randomised, double-blind, placebo-controlled, phase 3 study. Rheum. Musculoskel. Dis. Open. 2015;1:e000037. doi:10.1136/rmdopen-2014- 000037. 9 pages.

Post Grant Review 2019-00053 for U.S. Pat. No. 10,106,603—Ex. 1027: Sidhu, Phage display in pharmaceutical biotechnology. Curr Opin Biotechnol. 2000;11:610-616.

Post Grant Review 2019-00053 for U.S. Pat. No. 10,106,603—Ex. 1028: Unver et al., IL-6 Family Cytokins: Key inflammatory mediators as biomarkers and potential therapeutic targets. Cytokine Growth Factor Rev. Jun. 2018;41:10-17.

Post Grant Review 2019-00053 for U.S. Pat. No. 10,106,603—Ex. 1029: Wallace et al., Efficacy and safety of an interleukin 6 monoclonal antibody for the treatment of systemic lupus erythematosus: a phase II dose-ranging randomised controlled trial. Annu. Rheum. Dis. 2017;76:534-542.

Post Grant Review 2019-00053 for U.S. Pat. No. 10,106,603—Ex. 1030: West, Coordination of Immune-Stroma Crosstalk by IL-6 Family Cytokines. Front. Immunol. May 15, 2019;10(1093). 16 pages.

Post Grant Review 2019-00053 for U.S. Pat. No. 10,106,603—Ex. 1031: Ciliberto, Cytokine Inhibitors. Chapter 8. Marcel Dekker, Inc. NY. 2001. 369 pages.

Post Grant Review 2019-00053 for U.S. Pat. No. 10,106,603—Ex. 1032: Carmen et al., Concepts in antibody phage display. Brief. Funct. Genom. Proteom. Jul. 2002;1(2):189-203.

Post Grant Review 2019-00053 for U.S. Pat. No. 10,106,603—Ex. 1033: Foote et al., Antibody Framework Residues Affecting the Conformation of the Hypervariable Loops. J. Mol. Biol. 1992;224:487-499.

Post Grant Review 2019-00053 for U.S. Pat. No. 10,106,603—Ex. 1034: McKean et al., Generation of antibody diversity in the immune response of BALB/c mice to influenza virus hemagglutinin. PNAS USA. May 1984;81:3180-4.

Post Grant Review 2019-00053 for U.S. Pat. No. 10,106,603—Ex. 1035: Pedotti et al., Computational Docking of Antibody-Antigen Complexes, Opportunities and Pitfalls Illustrated by Influenza Hemagglutinin. Int. J. Mol. Sci. 2011;12:226-251. doi:10.3390/ijms12010226.

Post Grant Review 2019-00053 for U.S. Pat. No. 10,106,603—Ex. 1036. Ponomarenko et al., Antibody-protein interactions: benchmark datasets and prediction tools evaluation. BMC Struct. Biol. 2007;7:64. doi: 10.1186/1472-6807-64. 19 pages.

Post Grant Review 2019-00053 for U.S. Pat. No. 10,106,603—Ex. 1037. U.S. Pat. No. 6,043,344. Jacobs et al. Mar. 28, 2000. 25 pages.

Post Grant Review 2019-00053 for U.S. Pat. No. 10,106,603—Ex. 1038: Janeway Immunobiology. Chapter 3. 2001. Garland Publishing. 35 pages.

Post Grant Review 2019-00053 for U.S. Pat. No. 10,106,603—Ex. 1039: Janeway Immunobiology. Chapter 4. 2001. Garland Publishing. 37 pages.

Post Grant Review 2019-00053 for U.S. Pat. No. 10,106,603—Ex. 1040: Janeway Immunobiology. Chapter 9. 2001. Garland Publishing. 44 pages.

Post Grant Review 2019-00053 for U.S. Pat. No. 10,106,603—Ex. 1041: Janeway Immunobiology. Appendix 1. 2001. Garland Publishing. 51 pages.

Post Grant Review 2019-00053 for U.S. Pat. No. 10,106,603—Ex. 1042. Alberts, Molecular Biology of the Cell. 4th ed. Chapter 24. 2002. 1363-1419.

Post Grant Review 2019-00053 for U.S. Pat. No. 10,106,603—Ex. 1043: Roitt, Essential Immunology. Chapter 3. 9th ed. 1997. 43-62.

Post Grant Review 2019-00053 for U.S. Pat. No. 10,106,603—Ex. 1044: Roitt, Essential Immunology. Chapter 5. 9th ed. 1997. 80-103.

Post Grant Review 2019-00053 for U.S. Pat. No. 10,106,603—Ex. 1045: Roitt, Essential Immunology. Chapter 6. 9th ed. 1997. 107-129.

Post Grant Review 2019-00053 for U.S. Pat. No. 10,106,603—Ex. 1046: Hudson et al., Engineered antibodies. Nat Med. 2003;9(1): 129-134.

Post Grant Review 2019-00053 for U.S. Pat. No. 10,106,603—Ex. 1047: Cater, Improving the efficacy of antibody-based cancer therapies. Nat. Rev. 2001;1:118. 12 pages.

Post Grant Review 2019-00053 for U.S. Pat. No. 10,106,603—Ex. 1048: Kettleborough et al., Humanization of a mouse monoclonal antibody by CDR-grafting: the importance of framework residues on loop conformation. Prot. Eng. 1991;4(7):773-783.

Post Grant Review 2019-00053 for U.S. Pat. No. 10,106,603—Ex. 1049: Gerhardt et al., Structure of IL-17A in Complex with a Potent, Fully Human Neutralizing Antibody. JMB. 2009;394:905-921.

Post Grant Review 2019-00053 for U.S. Pat. No. 10,106,603—Ex. 1050: Vajdos et al., Comprehensive Functional Maps of the Antigen-binding Site of an Anti-ErbB2 Antibody Obtained with Shotgun Scanning Mutagenesis. J. Mol. Biol. 2002;320:415-428.

(56) References Cited

OTHER PUBLICATIONS

Post Grant Review 2019-00053 for U.S. Pat. No. 10,106,603—Ex. 1051: Antigen Recognition by an Antibody Light Chain. J. Biol. Chem. 1994;269(1):734-738.
Post Grant Review 2019-00053 for U.S. Pat. No. 10,106,603—Ex. 1052: Mariuzza et al., The Structural Basis of Antigen-Antibody Recognition. Ann. Rev. Biophys. Biophys. Chem. 1987;16:139-59.
Post Grant Review 2019-00053 for U.S. Pat. No. 10,106,603—Ex. 1053: Tiller et al., Advances in Antibody Design. Annu Rev Biomed Eng. 2015;17:191-216.
Post Grant Review 2019-00053 for U.S. Pat. No. 10,106,603—Ex. 1054: Reilly, Cardiac Fibrosis: New Treatments in Cardiovascular Medicine. US Pharm. 2015;40(2):32-35.
Post Grant Review 2019-00053 for U.S. Pat. No. 10,106,603—Ex. 1055: Frank, Immunology and Evolution of Infectious Disease. University Press. 2002. 359 pages.
Post Grant Review 2019-00053 for U.S. Pat. No. 10,106,603—Ex. 1056: Regenmortel, Specificity, polyspecificity, and heterospecificity of antibody-antigen recognition. Mol. Rec. 2014;27:627-639.
Post Grant Review 2019-00053 for U.S. Pat. No. 10,106,603—Ex. 1057: Brekke et al., Therapeutics Antibodies for Human Diseases at the Dawn of the Twenty-First Century. Nature. Jan. 2003;2:52. 11 pages.
Post Grant Review 2019-00053 for U.S. Pat. No. 10,106,603—Ex. 1058: Maynard et a., Antibody Engineering. Annu. Rev. Biomed. Eng. 2000;02:339-6.
Post Grant Review 2019-00053 for U.S. Pat. No. 10,106,603—Ex. 1059: Djavadi-Ohaniance et al., Measuring antibody affinity in solution from Antibody Engineering: A Practical Solution. McCafferty et al., eds.. Oxford University Press. 1996. 19 pages.
Post Grant Review 2019-00053 for U.S. Pat. No. 10,106,603—Ex. 1060: Queen et al., A humanized antibody that binds to the interleukin 2 receptor. PNAS USA. Dec. 1989;86:10029-10033.
Post Grant Review 2019-00053 for U.S. Pat. No. 10,106,603—Ex. 1061: Tucker et al., Immunoassays for the quantification of ALK and phosphorylated ALK support the evaluation of on-target ALK inhibitors in neuroblastoma. Mol. Oncol. 2017;11:996-1006.
Post Grant Review 2019-00053 for U.S. Pat. No. 10,106,603—Ex. 1062: Vasquez et al., Connecting the sequence dots: shedding light on the genesis of antibodies reported to be designed in silico. mAbs. 2019;11(5):803-8.
Post Grant Review 2019-00053 for U.S. Pat. No. 10,106,603—Ex. 1063: Ablynx Drug Fails Again in Mid-Stage Trial. BioSpace. Mar. 26, 2018. 3 pages.
Post Grant Review 2019-00053 for U.S. Pat. No. 10,106,603—Ex. 1064: U.S. FDA rejects J&J's arthritis drug. Reuters. Sep. 22, 2017. 2 pages.
Post Grant Review 2019-00053 for U.S. Pat. No. 10,106,603—Ex. 1065: US 2008-0300147 A1. Chegini et al. Dec. 4, 2008. 112 pages.
Post Grant Review 2019-00053 for U.S. Pat. No. 10,106,603—Ex. 1067: Lebeau et al., Reconstitution of two isoforms of the human interleukin-11 receptor and comparison of their functional properties. FEBS Lett. 1997;407:141-7.
Post Grant Review 2019-00053 for U.S. Pat. No. 10,106,603—Ex. 2001: Full File History for U.S. Appl. No. 15/988,463. 1871 pages.
Post Grant Review 2019-00053 for U.S. Pat. No. 10,106,603—Ex. 2008: Fersht, The most influential journals: Impact Factor and Eigenfactor. PNAS. 2009;106(17):6883-4.
Post Grant Review 2019-00053 for U.S. Pat. No. 10,106,603—Ex. 2009. Pflanz et al., A fusion protein of interleukin-11 and soluble interleukin-11 receptor acts as a superagonnist on cells expressing gp130. FEBS Lett. 1999;450:117-122.
Post Grant Review 2019-00053 for U.S. Pat. No. 10,106,603—Ex. 2010: Schleinkofer et al., Identification of the Domain in the Human Interleukin-11 Receptor that Mediates Ligand Binding. J. Mol. Biol. 2011;206(263-274).
Post Grant Review 2019-00053 for U.S. Pat. No. 10,106,603—Ex. 2011: WO2015/184009. Academia Sinica. Dec. 3, 2015. 98 pages.
Post Grant Review 2019-00053 for U.S. Pat. No. 10,106,603—Ex. 2012: WO 2017/070170. Dyax corp. Apr. 27, 2017. 99 pages.
Post Grant Review 2019-00053 for U.S. Pat. No. 10,106,603—Ex. 2013: What Is Pulmonary Fibrosis? Retrieved from https://PulmonaryFibrosisNow.org on Nov. 14, 2019.6 pages.
Post Grant Review 2019-00053 for U.S. Pat. No. 10,106,603—Paper No. 8: Patent Owner's Preliminary Response. Nov. 14, 2019. 102 pages.
Post Grant Review 2019-00053 for U.S. Pat. No. 10,106,603—Paper No. 10: Decision Denying Post-Grant Review. Feb. 6, 2020. 41 pages.
Post Grant Review 2019-00053 for U.S. Pat. No. 10,106,603—Paper No. 3: Patent Owner's Mandatory Notices. Aug. 13, 2019. 6 pages.
Post Grant Review 2019-00053 for U.S. Pat. No. 10,106,603—Paper No. 6: Notice of Accord. Aug. 14, 2019. 6 pages.
Post Grant Review 2019-00053 for U.S. Pat. No. 10,106,603—Paper No. 7: Patent Owner's First Updated Mandatory Notices. Nov. 14, 2019. 6 pages.
Post Grant Review 2019-00053 for U.S. Pat. No. 10,106,603—Paper No. 9: Patent Owner's Second Updated Mandatory Notices. Dec. 30. 2019. 6 pages.
Potten et al., Protection of the small intestinal clonogenic stem cells from radiation-induced damage by pretreatment with interleukin 11 also increases murine survival time. Stem Cells. Jul. 1996;14(4):452-9.
Prêle et al., STAT3: a central mediator of pulmonary fibrosis? [published correction appears in Proc Am Thorac Soc. Oct. 2012;9(4):210]. Proc Am Thorac Soc. 2012;9(3):177-182. doi:10. 1513/pats.201201-007AW.
Putoczki et al., More Than a Sidekick: The IL-6 Family Cytokine IL-11 Links Inflammation to Cancer. J Leukoc Biol. Dec. 2010;88(6):1109-17. doi: 10.1189/jlb.0410226.
Qin et al., Inhibiting HIV-1 infection in human T cells by lentiviral-mediated delivery of small interfering RNA against CCR5. Proc Natl Acad Sci U S A. 2003;100(1):183-188.
Qiu et al., Protection by recombinant human interleukin-11 against experimental TNB-induced colitis in rats. Dig Dis Sci. Aug. 1996;41(8):1625-30.
Rainger et al., Cellular pathology of atherosclerosis: smooth muscle cells prime cocultured endothelial cells for enhanced leukocyte adhesion. Circ Res. Mar. 30, 2001;88(6):615-22.
Richter et al., Subcutaneous absorption of biotherapeutics: knowns and unknowns. Drug Metab Dispos. 2014;42(11):1881-1889. doi:10. 1124/dmd.114.059238.
Robbins et al., Pathologic Basis of Disease. 8th Ed. Saunders Elsevier. Philadelphia, PA. 2010. pp. 677-737.
Robbins et al., Pathologic Basis of Disease. Elsevier. 2010:688-692.
Ropeleski et al., Interleukin-11-induced heat shock protein 25 confers intestinal epithelial-specific cytoprotection from oxidant stress. Gastroenterology. May 2003;124(5):1358-68.
Rowe et al., Hepatocyte-derived Snaill propagates liver fibrosis progression. Mol Cell Biol. Jun. 2011;31(12):2392-403. doi: 10.1128/MCB.01218-10.
Safdari et al., Antibody humanization methods—a review and update. Biotechnol Genet Eng Rev. 2013;29:175-186. doi:10.1080/02648725.2013.801235.
Sands et al., Randomized, controlled trial of recombinant human interleukin-11 in patients with active Crohn's disease. Aliment Pharmacol Ther. Mar. 2002;16(3):399-406.
Scherr et al., Gene silencing mediated by small interfering RNAs in mammalian cells. Curr Med Chem. 2003;10(3):245-256.
Scherr et al., Modulation of gene expression by lentiviral-mediated delivery of small interfering RNA. Cell Cycle. 2003;2(3):251-257.
Schier et al.., Identification of functional and structural amino-acid residues by parsimonious mutagenesis. Gene. 1996;169(2):147-155.
Schleinkofer et al., Identification of the domain in the human interleukin-11 receptor that mediates ligand binding. J Mol Biol. Feb. 16, 2001;306(2):263-74.
Schmidt-Arras et al., IL-6 pathway in the liver: From physiopathology to therapy. J Hepatol. Jun. 2006;64(6):1403-15. doi: 10.1016/j.jhep.2016.02.004. Epub Feb. 8, 2016.

(56) References Cited

OTHER PUBLICATIONS

Schwabe et al., Apoptosis and necroptosis in the liver: a matter of life and death. Nat Rev Gastroenterol Hepatol. Dec. 2018;15(12):738-752. doi: 10.1038/s41575-018-0065-y.
Schwertschlag et al., Hematopoietic, immunomodulatory and epithelial effects of interleukin-11. Leukemia. 1999;13(9):1307-1315. doi:10.1038/sj.leu.2401514.
Segal et al., Production of bispecific antibodies. Curr Protoc Immunol. 2001;Chapter 2: doi:10.1002/0471142735.im0213s14.
Sekiya et al., Glycogen synthase kinase 3β-dependent Snail degradation directs hepatocyte proliferation in normal liver regeneration. Proc Natl Acad Sci U S A. Jul. 5, 2011;108(27):11175-80. doi: 10.1073/pnas.1016122108. Epub Jun. 20, 2011.
Shabalin, Matrix eQTL: ultra fast eQTL analysis via large matrix operations. Bioinformatics. 2012;28(10):1353-1358.
Sharp, RNA interference—2001. Genes Dev. 2001;15(5):485-490.
Shea-Donohue et al., Mechanisms of smooth muscle responses to inflammation. Neurogastroenterol Motil. Sep. 2012;24(9):802-11. doi:10.1111/j.1365-2982.2012.01986.x.
Shen et al., Gene silencing by adenovirus-delivered siRNA. FEBS Lett. 2003;539(1-3):111-114.
Sheridan et al., Interleukin-11 attenuates pulmonary inflammation and vasomotor dysfunction in endotoxin-induced lung injury. Am J Physiol. Nov. 1999;277(5):L861-7. doi: 10.1152/ajplung.1999.277.5.L861.
Shin et al., Optimization of linear double-stranded RNA for the production of multiple siRNAs targeting hepatitis C virus. RNA. 2009;15(5):898-910.
Shinagawa et al., Generation of Ski-knockdown mice by expressing a long double-strand RNA from an RNA polymerase II promoter. Genes Dev. 2003;17(11):1340-1345.
Shuey et al., RNAi: gene-silencing in therapeutic intervention. Drug Discov Today. 2002;7(20):1040-1046.
Simeoni et al., Insight into the mechanism of the peptide-based gene delivery system MPG: implications for delivery of siRNA into mammalian cells. Nucleic Acids Res. 2003;31(11):2717-2724.
Simon-Tillaux et al., Snail and kidney fibrosis. Nephrol Dial Transplant. 2017;32(2):224-233. doi:10.1093/ndt/gfw333.
Simpson et al., Inhibition of tumour necrosis factor alpha does not prevent experimental paracetamol-induced hepatic necrosis. J Pathol. Mar. 2000;190(4):489-94.
Skerra et al., Assembly of a functional immunoglobulin Fv fragment in *Escherichia coli*. Science. 1988;240(4855):1038-1041.
Sohal et al., Clinical significance of epithelial mesenchymal transition (EMT) in chronic obstructive pulmonary disease (COPD): potential target for prevention of airway fibrosis and lung cancer. Clin Transl Med. 2014;3(1):33. doi:10.1186/s40169-014-0033-2.
Song et al., RNA interference targeting Fas protects mice from fulminant hepatitis. Nat Med. 2003;9(3):347-351.
Sonis et al., Mitigating effects of interleukin 11 on consecutive courses of 5-fluorouracil-induced ulcerative mucositis in hamsters. Cytokine. Aug. 1997;9(8):605-12.
Sopel et al., Myocardial fibrosis in response to Angiotensin II is preceded by the recruitment of mesenchymal progenitor cells. Lab Invest. 2011;91(4):565-578. doi:10.1038/labinvest.2010.190.
Sorensen et al., Gene silencing by systemic delivery of synthetic siRNAs in adult mice. J Mol Biol. 2003;327(4):761-766.
Sormanni et al., Rational design of antibodies targeting specific epitopes within intrinsically disordered proteins. Proc Natl Acad Sci U S A. 2015;112(32):9902-9907. doi:10.1073/pnas.1422401112.
Souders et al., Cardiac fibroblast: the renaissance cell. Circ Res. 2009;105(12):1164-1176. doi:10.1161/CIRCRESAHA.109.209809.
Starkel et al., Genetic Factors Predicting Response to Interferon Treatment for Viral Hepatitis C. Gut. Apr. 2008;57(4):440-2. doi: 10.1136/gut.2007.137646.
Strutz et al., Renal fibroblasts and myofibroblasts in chronic kidney disease. J Am Soc Nephrol. 2006;17(11):2992-2998.

Szendroi et al., Polarization colours of collagen fibres: a sign of collagen production activity in fibrotic processes. Acta Morphol Hung. 1984;32(1):47-55.
Taki et al., Differential Inhibitory Effects of Indomethacin, Dexamethasone, and Interferon-Gamma (IFN-gamma) on IL-11 Production by Rheumatoid Synovial Cells. Clin Exp Immunol. Apr. 1998;112(1):133-8. doi: 10.1046/j.1365-2249.1998.00552.x.
Tamura et al., The cardioprotective effect of interleukin-11 against ischemia-reperfusion injury in a heart donor model. Ann Cardiothorac Surg. Jan. 2018;7(1):99-105. doi: 10.21037/acs.2017.09.11.
Tang et al., Airway remodelling in asthma: current understanding and implications for future therapies. Pharmacol Ther. 2006;112(2):474-488. doi:10.1016/j.pharmthera.2006.05.001.
The RNA Consortium et al., RNAcentral: a comprehensive database of non-coding RNA sequences. Nucleic Acids Res. 2017;45(D1):D128-D134. doi:10.1093/nar/gkw1008.
Trepicchio et al., IL-11 regulates macrophage effector function through the inhibition of nuclear factor-kappaB. J Immunol. Dec. 1, 1997;159(11):5661-70.
Trepicchio et al., Interleukin-11 therapy selectively downregulates type I cytokine proinflammatory pathways in psoriasis lesions. J Clin Invest. Dec. 1999;104(11):1527-37.
Trepicchio et al., Recombinant human IL-11 attenuates the inflammatory response through down-regulation of proinflammatory cytokine release and nitric oxide production. Oct. 15, 1996;157(8):3627-34.
Tuerk et al., Systematic Evolution of Ligands by Exponential Enrichment: RNA Ligands to Bacteriophage T4 DNA Polymerase. Science. Aug. 3, 1990;249(4968):505-10. doi: 10.1126/science.2200121.
Tuschl, RNA interference and small interfering RNAs. Chembiochem. 2001;2(4):239-245.
Underhill-Day et al., Functional Characterization of W147A: A High-Affinity interleukin-11 Antagonist. Endocrinology. Aug. 2003;144(8):3406-14. doi: 10.1210/en.2002-0144.
Unverdorben et al., Pharmacokinetic properties of IgG and various Fc fusion proteins in mice. MAbs. 2016;8(1):120-128.
Urban et al., Genetic Basis of Susceptibility to Drug-Induced Liver Injury: What Have We Learned and Where Do We Go From Here? Pharmacogenomics. May 2012;13(7):735-8. doi: 10.2217/pgs.12.45.
US National Institute of Health, Expert Panel Report 3: Guidelines for the Diagnosis and Management of Asthma. Aug. 2007.
Vanwagner et al., Evaluating Elevated Bilirubin Levels in Asymptomatic Adults. JAMA. Feb. 3, 2015;313(5):516-7. doi: 10.1001/jama.2014.12835.
Viola et al., Subcutaneous delivery of monoclonal antibodies: How do we get there?. J Control Release. 2018;286:301-314. doi:10.1016/j.jconrel.2018.08.001.
Walia et al., TGF-beta down-regulates IL-6 signaling in intestinal epithelial cells: critical role of SMAD-2. FASEB J. 2003;17(14):2130-2132.
Walmsley et al., An anti-inflammatory role for interleukin-11 in established murine collagen-induced arthritis. Immunology. Sep. 1998;95(1):31-7.
Wang et al., Delivery of siRNA therapeutics: barriers and carriers. AAPS J. 2010;12(4):492-503.
Wang et al., Genome-wide association studies: theoretical and practical concerns. Nat Rev Genet. 2005;6(2):109-118.
Wang et al., IL-11 selectively inhibits aeroallergen-induced pulmonary eosinophilia and Th2 cytokine production. J Immunol. 2000;165(4):2222-2231. doi:10.4049/jimmunol.165.4.2222.
Ward et al., Binding activities of a repertoire of single immunoglobulin variable domains secreted from *Escherichia coli*. Nature. 1989;341(6242):544-546.
Waxman et al., Targeted lung expression of interleukin-11 enhances murine tolerance of 100% oxygen and diminishes hyperoxia-induced DNA fragmentation. J Clin Invest. May 1, 1998;101(9):1970-82.
Wei, Immunological aspect of cardiac remodeling: T lymphocyte subsets in inflammation-mediated cardiac fibrosis. Exp. Mol Pathol. 2011;90(1):74-78. doi:10.1016/j.yexmp.2010.10.004.

(56) References Cited

OTHER PUBLICATIONS

Wermuth et al., Abrogation of transforming growth factor-?-induced tissue fibrosis in mice with a global genetic deletion of Nox4. Lab Invest. Apr. 2019;99(4):470-482. doi: 10.1038/s41374-018-0161-1. Epub Nov. 23, 2018.

Widjaja et al., Abstract 00417: Neutralizing Anti-IL-11 Antibodies Protect Against Hepatic Fibrosis in Non-alcoholic Steatohepatitis. 69th Annual Meeting of the American Association for the Stuyd of Liver Diseases, AASLD Nov. 9-13, 2018. Hepatology. Nov. 9, 2018;68(Supplement 1):1348A.

Widjaja et al., Inhibiting Interleukin 11 Signaling Reduces Hepatocyte Death and Liver Fibrosis, Inflammation, and Steatosis in Mouse Models of Nonalcoholic Steatohepatitis. Gastroenterology. Sep. 2019;157(3):777-792.e14. doi: 10.1053/j.gastro.2019.05.002.

Widjaja et al., Redefining Interleukin 11 as a regeneration-limiting hepatotoxin. BioRxiv. Nov. 4, 2019. Retrieved from https://www.biorxiv.org/content/10.1101/830018v.1.full.pdf. 40 pages.

Win et al., New insights into the role and mechanism of c-Jun-N-terminal kinase signaling in the pathobiology of liver diseases. Hepatology. May 2018;67(5):2013-2024. doi: 10.1002/hep.29689. Epub Apr. 6, 2018.

Winter et al., Man-made antibodies. Nature. 1991;349(6307):293-299.

Wollin et al., Antifibrotic and anti-inflammatory activity of the tyrosine kinase inhibitor nintedanib in experimental models of lung fibrosis. J Pharmacol Exp Ther. 2014;349(2):209-220. doi:10.1124/jpet.113.208223.

Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297.

Wright et al., Upregulation of c-MYC in cis through a large chromatin loop linked to a cancer risk-associated single-nucleotide polymorphism in colorectal cancer cells. Mol Cell Biol. 2010;30(6):1411-1420.

Wuesterfeld et al., Interleukin-6/glycoprotein 130-dependent pathways are protective during liver regeneration. J Biol Chem. Mar. 28, 2003;278(13):11281-8. Epub Dec. 30, 2002.

Wynn et al., Mechanisms of fibrosis: therapeutic translation for fibrotic disease. Nat Med. 2012;18(7):1028-1040.

Xie et al., Inhibitor of apoptosis signal-regulating kinase 1 protects against acetaminophen-induced liver injury. Toxicol Appl Pharmacol. Jul. 1, 2015;286(1):1-9. doi: 10.1016/j.taap.2015.03.019. Epub Mar. 25, 2015.

Yelton et al., Affinity maturation of the BR96 anti-carcinoma antibody by codon-based mutagenesis. J Immunol. 1995;155(4):1994-2004.

Yu et al., Interleukin-11 Protects Mouse Liver From Warm Ischemia/Reperfusion (WI/Rp) Injury. Clin Res Hepatol Gastroenterol. Nov. 2016;40(5):562-570. doi: 10.1016/j.clinre.2015.11.009. Epub Mar. 23, 2016.

Yu et al., Soluble vascular endothelial growth factor decoy receptor FP3 exerts potent antiangiogenic effects. Mol Ther. 2012;20(5):938-947.

Zamore et al., RNAi: double-stranded RNA directs the ATP-dependent cleavage of mRNA at 21 to 23 nucleotide intervals. Cell. 2000;101(1):25-33.

Zeisberg et al., Fibroblasts derive from hepatocytes in liver fibrosis via epithelial to mesenchymal transition. J Biol Chem. 2007;282(32):23337-23347.

Zhang et al., Reduction of liver Fas expression by an antisense oligonucleotide protects mice from fulminant hepatitis. Nat Biotechnol. Aug. 2000;18(8):862-7.

Zheng et al., Inducible targeting of IL-13 to the adult lung causes matrix metalloproteinase-and cathepsin-dependent emphysema. J Clin Invest. 2000;106(9):1081-1093. doi:10.1172/JCI10458.

Zhou et al., MTA2 enhances colony formation and tumor growth of gastric cancer cells through IL-11. BMC Cancer. 2015;15:343. Published May 2, 2015. doi:10.1186/s12885-015-1366-y.

Zhu et al., Pulmonary expression of interleukin-13 causes inflammation, mucus hypersecretion, subepithelial fibrosis, physiologic abnormalities, and eotaxin production. J Clin Invest. Mar. 15, 1999; 103(6): 779-788. doi: 10.1172/JCI5909.

Zola, Monoclonal Antibodies: A Manual of Techniques. CRC Press. 1988.

U.S. Appl. No. 16/748,698, filed Jan. 21, 2020, Cook et al.
U.S. Appl. No. 16/798,101, filed Feb. 21, 2020, Cook et al.
U.S. Appl. No. 16/865,259, filed May 1, 2020, Cook et al.
PCT/EP2020/051332, Apr. 28, 2020, International Search Report and Written Opinion.
PCT/EP2020/054580, Jun. 12, 2020, International Search Report and Written Opinion.
PCT/EP2020/062193, Jun. 23, 2020, International Search Report and Written Opinion.

\* cited by examiner

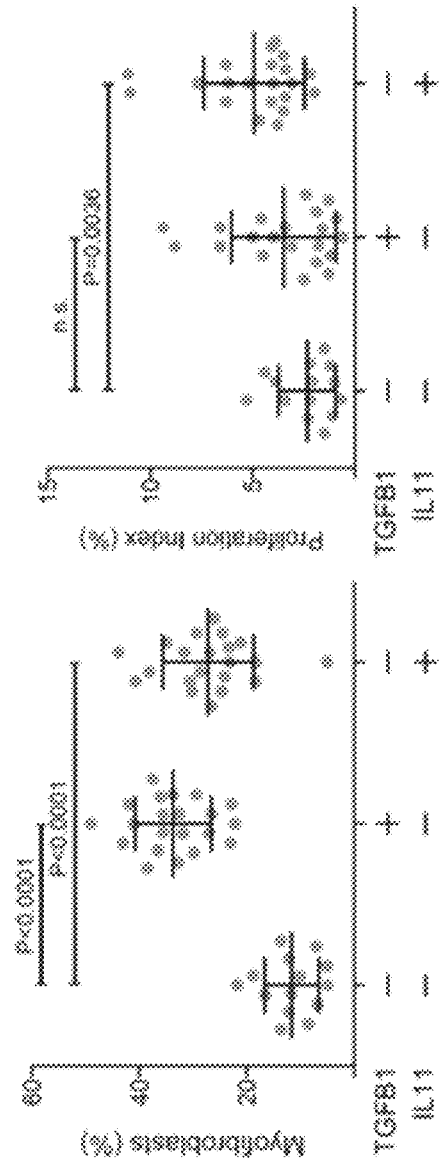
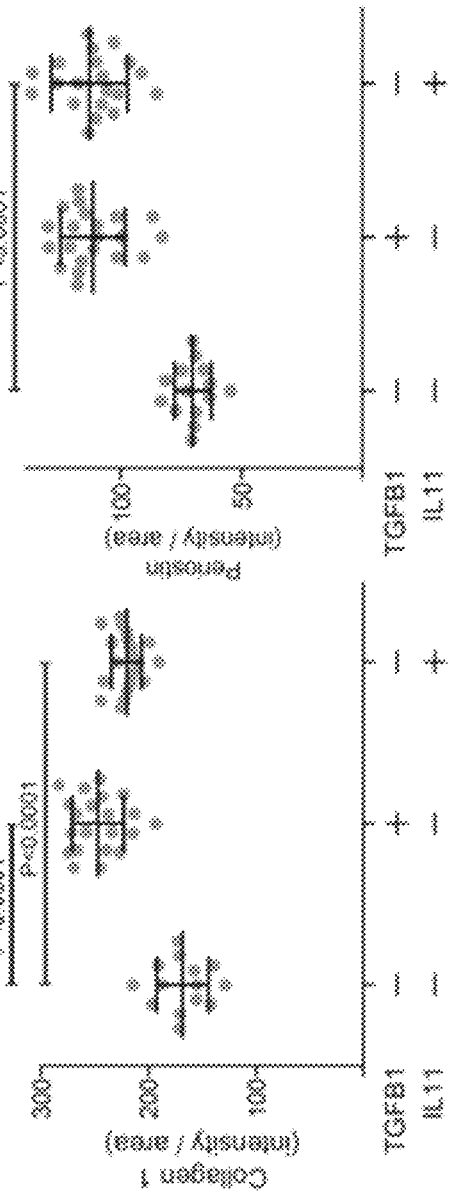
Figure 2A
Figure 2B
Figure 2C
Figure 2D

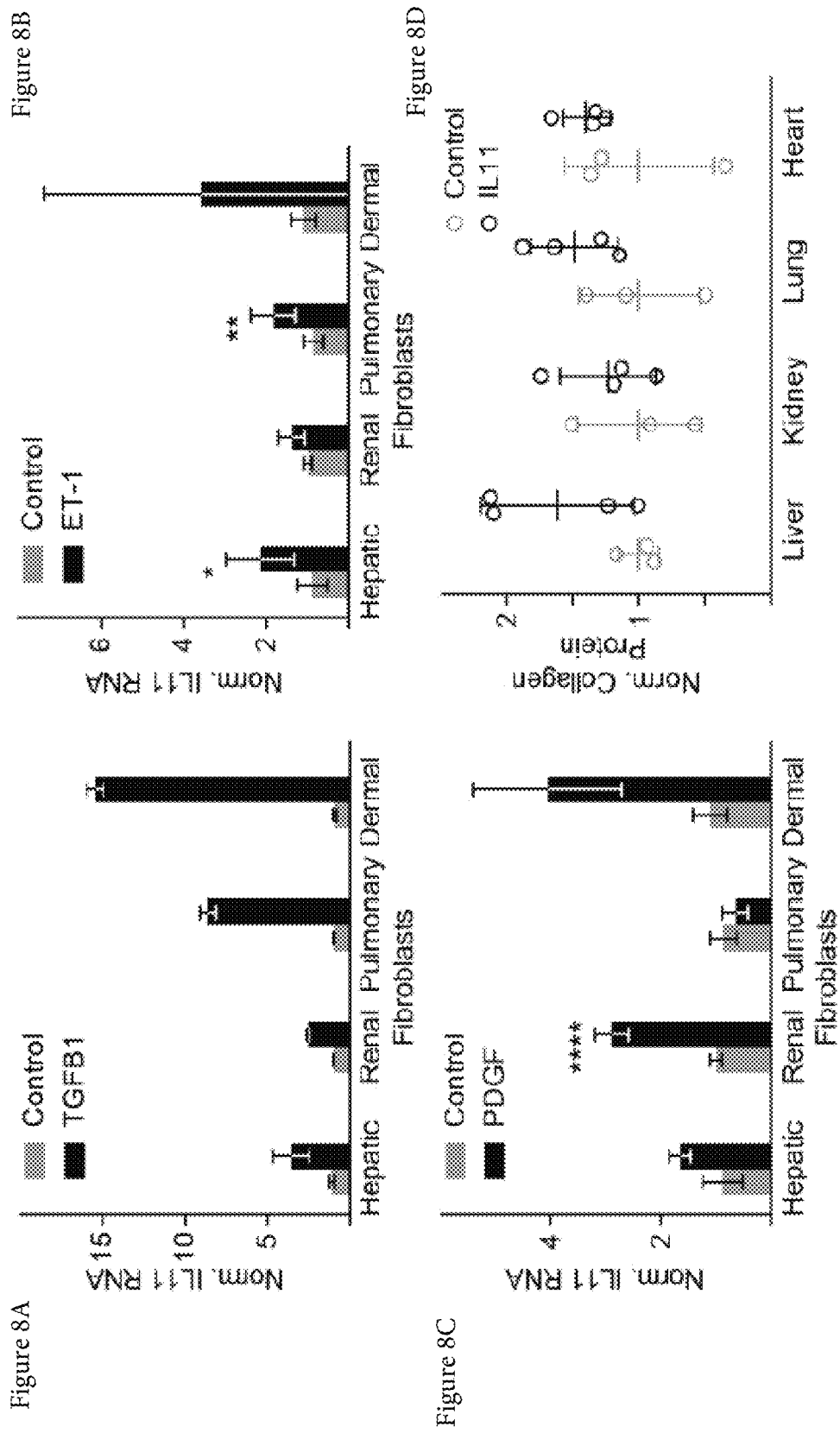

ACTGCCGCGGCCCTGCTGCTCAGGGCACATGCCTCCCCTCCCCAGGCCGCGGCCCAGCTGACCCTCGGGG
CTCCCCCGGCAGCGGACAGGGAAGGGTTAAAGGCCCCCGGCTCCCTGCCCCCTGCCCTGGGGAACCCCTG
GCCCTGTGGGGACATGAACTGTGTTTGCCGCCTGGTCCTGGTCGTGCTGAGCCTGTGGCCAGATACAGCT
GTCGCCCCTGGGCCACCACCTGGCCCCCCTCGAGTTTCCCCAGACCCTCGGGCCGAGCTGGACAGCACCG
TGCTCCTGACCCGCTCTCTCCTGGCGGACACGCGGCAGCTGGCTGCACAGCTGAGGGACAAATTCCCAGC
TGACGGGGACCACAACCTGGATTCCCTGCCCACCCTGGCCATGAGTGCGGGGGCACTGGGAGCTCTACAG
CTCCCAGGTGTGCTGACAAGGCTGCGAGCGGACCTACTGTCCTACCTGCGGCACGTGCAGTGGCTGCGCC
GGGCAGGTGGCTCTTCCCTGAAGACCCTGGAGCCCGAGCTGGGCACCCTGCAGGCCCGACTGGACCGGCT
GCTGCGCCGGCTGCAGCTCCTGATGTCCGCCTGGCCCTGCCCCAGCCACCCCGGACCCGCCGGCGCCC
CCGCTGGCGCCCCCCTCCTCAGCCTGGGGGGGCATCAGGGCCGCCCACGCCATCCTGGGGGGCTGCACC
TGACACTTGACTGGGCCGTGAGGGGACTGCTGCTGCTGAAGACTCGGCTGTGACCCGGGGCCCAAAGCCA
CCACCGTCCTTCCAAAGCCAGATCTTATTTATTTATTTATTTCAGTACTGGGGGCGAAACAGCCAGGTGA
TCCCCCCGCCATTATCTCCCCTAGTTAGAGACAGTCCTTCCGTGAGGCCTGGGGGGCATCTGTGCCTTA
TTTATACTTATTTATTTCAGGAGCAGGGGTGGGAGGCAGGTGGACTCCTGGGTCCCCGAGGAGGAGGGGA
CTGGGGTCCCGGATTCTTGGGTCTCCAAGAAGTCTGTCCACAGACTTCTGCCCTGGCTCTTCCCCATCTA
GCCTGGGCAGGAACATATATTATTTATTTAAGCAATTACTTTTCATGTTGGGGTGGGACGGAGGGGAA
AGGGAAGCCTGGGTTTTTGTACAAAAATGTGAGAAACCTTTGTGAGACAGAGAACAGGGAATTAAATGTG
TCATACATATCCACTTGAGGGCGATTTGTCTGAGAGCTGGGGCTGGATGCTTGGGTAACTGGGGCAGGGC
AGGTGGAGGGGAGACCTCCATTCAGGTGGAGGTCCCGAGTGGGCGGGGCAGCGACTGGGAGATGGGTCGG
TCACCCAGACAGCTCTGTGGAGGCAGGGTCTGAGCCTTGCCTGGGCCCCGCACTGCATAGGGCCTTTTG
TTTGTTTTTTGAGATGGAGTCTCGCTCTGTTGCCTAGGCTGGAGTGCAGTGAGGCAATCTGAGGTCACTG
CAACCTCCACCTCCCGGGTTCAAGCAATTCTCCTGCCTCAGCCTCCCGATTAGCTGGGATCACAGGTGTG
CACCACCATGCCCAGCTAATTATTTATTTCTTTTGTATTTTTAGTAGAGACAGGGTTTCACCATGTTGGC
CAGGCTGGTTTCGAACTCCTGACCTCAGGTGATCCTCCTGCCTCGGCCTCCCAAAGTGCTGGGATTACAG
GTGTGAGCCACCACACCTGACCCATAGGTCTTCAATAAATATTTAATGGAAGGTTCCACAAGTCACCCTG
TGATCAACAGTACCCGTATGGGACAAAGCTGCAAGGTCAAGATGGTTCATTATGGCTGTGTTCACCATAG
CAAACTGGAAACAATCTAGATATCCAACAGTGAGGGTTAAGCAACATGGTGCATCTGTGGATAGAACGCC
ACCCAGCCGCCCGGAGCAGGGACTGTCATTCAGGGAGGCTAAGGAGAGAGGCTTGCTTGGGATATAGAAA
GATATCCTGACATTGGCCAGGCATGGTGGCTCACGCCTGTAATCCTGGCACTTTGGGAGGACGAAGCGAG
TGGATCACTGAAGTCCAAGAGTTCGAGACCGGCCTGCGAGACATGGCAAAACCCTGTCTCAAAAAAGAAA
GAATGATGTCCTGACATGAAACAGCAGGCTACAAAACCACTGCATGCTGTGATCCCAATTTTGTGTTTTT
CTTTCTATATATGGATTAAAACAAAAATCCTAAAGGGAAATACGCCAAAATGTTGACAATGACTGTCTCC
AGGTCAAAGGAGAGAGGTGGGATTGTGGGTGACTTTTAATGTGTATGATTGTCTGTATTTTACAGAATTT
CTGCCATGACTGTGTATTTTGCATGACACATTTTAAAAATAATAAACACTATTTTAGAATAACAGAAAA
A         [SEQ ID NO:1]

CCTTCCAAAGCCAGATCTT [SEQ ID NO:2]

GCCTGGGCAGGAACATATA [SEQ ID NO:3]

CCTGGGCAGGAACATATAT [SEQ ID NO:4]

GGTTCATTATGGCTGTGTT [SEQ ID NO:5]

Figure 11

```
GCTGTAGCTGGTGAGAGGAAGTCCTAGAGGCTATGGACACTCTGCTGCTGGGATCACCGAGATGAGCAGC
AGCTGCTCAGGGCTGAGCAGGGTCCTGGTGGCCGTGGCTACAGCCCTGGTGTCTGCCTCCTCCCCCTGCC
CCCAGGCCTGGGGCCCCCAGGGGTCCAGTATGGGCAGCCAGGGAGGTCCGTGAAGCTGTGTTGTCCTGG
AGTGACTGCCGGGGACCCAGTGTCCTGGTTTCGGGATGGGGAGCCAAAGCTGCTCCAGGGACCTGACTCT
GGGCTAGGGCATGAACTGGTCCTGGCCCAGGCAGACAGCACTGATGAGGGCACCTACATCTGCCAGACCC
TGGATGGTGCACTTGGGGGCACAGTGACCCTGCAGCTGGGCTACCCTCCAGCCCGCCCTGTTGTCTCCTG
CCAAGCAGCCGACTATGAGAACTTCTCTTGCACTTGGAGTCCCAGCCAGATCAGCGGTTTACCCACCCGC
TACCTCACCTCCTACAGGAAGAAGACAGTCCTAGGAGCTGATAGCCAGAGGAGGAGTCCATCCACAGGGC
CCTGGCCATGCCCACAGGATCCCCTAGGGGCTGCCCGCTGTTGTCCACGGGGCTGAGTTCTGGAGCCA
GTACCGGATTAATGTGACTGAGGTGAACCCACTGGGTGCCAGCACACGCCTGCTGGATGTGAGCTTGCAG
AGCATCTTGCGCCCTGACCCACCCCAGGGCCTGCGGGTAGAGTCAGTACCAGGTTACCCCGACGCCTGC
GAGCCAGCTGGACATACCCTGCCTCCTGGCCGTGCCAGCCCCACTTCCTGCTCAAGTTCCGTTTGCAGTA
CCGTCCGGCGCAGCATCCAGCCTGGTCCACGGTGGAGCCAGCTGGACTGGAGGAGGTGATCACAGATGCT
GTGGCTGGGCTGCCCCATGCTGTACGAGTCAGTGCCCGGGACTTTCTAGATGCTGGCACCTGGAGCACCT
GGAGCCCGGAGGCCTGGGGAACTCCGAGCACTGGGACCATACCAAAGGAGATACCAGCATGGGGCCAGCT
ACACACGCAGCCAGAGGTGGAGCCTCAGGTGGACAGCCCTGCTCCTCCAAGGCCCTCCCTCCAACCACAC
CCTCGGCTACTTGATCACAGGGACTCTGTGGAGCAGGTAGCTGTGCTGCGTCTTTGGGAATCCTTTCTT
TCCTGGGACTGGTGGCTGGGGCCCTGGCACTGGGCTCTGGCTGAGGCTGAGACGGGGTGGGAAGGATGG
ATCCCCAAAGCCTGGGTTCTTGGCCTCAGTGATTCCAGTGGACAGGCGTCCAGGAGCTCCAAACCTGTAG
AGGACCCAGGAGGGCTTCGGCAGATTCCACCTATAATTCTGTCTTGCTGGTGTGGATAGAAACCAGGCAG
GACAGTAGATCCCTATGGTTGGATCTCAGCTGGAAGTTCTGTTTGGAGCCCATTTCTGTGAGACCCTGTA
TTTCAAATTTGCAGCTGAAAGGTGCTTGTACCTCTGATTTCACCCCAGAGTTGGAGTTCTGCTCAAGGAA
CGTGTGTAATGTGTACATCTGTGTCCATGTGTGACCATGTGTCTGTGAAGGCCAGGGAACATGTATTCCT
CTGCATGCATGTATGTAGGTGCCTGGGAGTGTGTGTGGTCCTTGCTCTGGCCCTTTCCCTTGCAGGGTTG
TGCAGGTGTGAATAAA        [SEQ ID NO:6]

GGACCATACCAAAGGAGAT     [SEQ ID NO:7]

GCGTCTTTGGGAATCCTTT     [SEQ ID NO:8]

GCAGGACAGTAGATCCCT      [SEQ ID NO:9]

GCTCAAGGAACGTGTGTAA     [SEQ ID NO:10]
```

Figure 12

| Gene Name | Gene ID/ Accession no. | siRNA name | siRNA sequence(5'-3') | SEQ ID NO. |
|---|---|---|---|---|
| IL-11 | NM_000641.3 | siRNA 1 | CCUUCCAAAGCCAGAUCUUdTdT AAGAUCUGGCUUUGGAAGGdTdT | 11 |
| IL-11 | NM_000641.3 | siRNA 2 | GCCUGGCAGGAACAUAUAdTdT UAUAUGUUCCUGCCCAGGCdTdT | 12 |
| IL-11 | NM_000641.3 | siRNA 3 | CCUGGGCAGGAACAUAUAUdTdT AUAUAUGUUCCUGCCCAGGdTdT | 13 |
| IL-11 | NM_000641.3 | siRNA 4 | GGUUCAUUAUGGCUGUGUUdTdT AACACAGCCAUAAUGAACCdTdT | 14 |

Figure 13

| Gene Name | Gene ID/ Accession no. | siRNA name | siRNA sequence(5'-3') | SEQ ID NO: |
|---|---|---|---|---|
| IL-11R | U32324.1 | siRNA 5 | GGACCAUACCAAAGGAGAUdTdT AUCUCCUUUGGUAUGGUCCdTdT | 15 |
| IL-11R | U32324.1 | siRNA 6 | GCGUCUUUGGGAAUCCUUUdTdT AAAGGAUUCCCAAAGACGCdTdT | 16 |
| IL-11R | U32324.1 | siRNA 7 | GCAGGACAGUAGAUCCCUAdTdT UAGGGAUCUACUGUCCUGCdTdT | 17 |
| IL-11R | U32324.1 | siRNA 8 | GCUCAAGGAACGUGUGUAAdTdT UUACACGUUCCUUGAGCdTdT | 18 |

Figure 14

| SNP ID | Position (hg19) | P value | FDR | Genotype | Minor Allele | Sequence | SEQ ID NO |
|---|---|---|---|---|---|---|---|
| rs10831850 | 11-12566917 | 1.76E-07 | 0.0248 | G/A | A | GTAAGGGATGTGAATCGGGTACTGA[A/G]GAAAGAGCCTGGATGCAGAGCCAGC | 19 |
| rs47756936 | 11-12599138 | 1.76E-07 | 0.0248 | C/T | T | TTGATAAGTTCAGCATCTGGATCAC[C/T]GTGGGATTAGCATCTGTTTGTATT | 20 |
| rs6485827 | 11-12578182 | 1.76E-07 | 0.0248 | C/T | C | GTGTGATTGCTTAAAAAAACTACT[C/T]ACATTGTTTTGAATCACACCTCACA | 21 |
| rs7120273 | 11-12581045 | 1.44E-07 | 0.0248 | T/C | T | GCTCAGCTAATCAATGACCAGTCTC[C/T]TTAATTCTTCTAATGCCTATATGGT | 22 |
| rs895468 | 2-223621273 | 2.70E-07 | 0.0306 | G/A | G | GCAGTGCTCAGAAGAGCAGCAGCCA[A/G]TGACATTTTGGGGCTATAAGAGGTA | 23 |

Figure 33

| SNP ID | Position (hg19) | P value | FDR | Genotype | Minor Allele | Sequence | SEQ ID NO |
|---|---|---|---|---|---|---|---|
| rs1000574 | 19-55114775 | 0.0432 | 0.6581 | C/T | T | TGTCCAGTAAATACTTAACATTTTA[C/T]GTGCAATGTATGTCATAAATATGGG | 24 |
| rs10403345 | 19-56741808 | 0.0355 | 0.6372 | G/A | G | GGgtgaagtttgaaacagtatac[A/G]ttgtgatgcaatcgtcagaaccaag | 25 |
| rs10419994 | 19-55726220 | 0.0334 | 0.6372 | C/T | T | aaaccataGTATCATCCTTCCCAAA[C/T]AGTCAACCCAGggaatcacagagat | 26 |
| rs10426177 | 19-56269096 | 0.0103 | 0.6372 | C/T | T | TAAGACGCTATTCTCTAATTCTGAA[C/T]GGAAGAACTCCTCCCAAGACATG | 27 |
| rs11084337 | 19-54916104 | 0.0370 | 0.6372 | C/T | C | aggtggaacaacaaagggtgggg[C/T]gaggcgtgcaattaaacattttct | 28 |
| rs11671244 | 19-56502995 | 0.0242 | 0.6372 | C/A | A | TATTAGATTTTGTGTGGGATTTCAT[A/C]GTTACATTTGTTACCAGCCCAATTT | 29 |
| rs11882068 | 19-56227165 | 0.0005 | 0.2204 | A/G | G | GATTCCAGTTCCAAGTCACATCATC[A/G]CCAGCTGGAAGACCTAGGGCAAAAG | 30 |
| rs12104147 | 19-54935505 | 0.0150 | 0.6372 | G/A | A | ACCATGACGGTGTCCTCATTGCTT[A/G]ACCATTAGTAAtcattcattcattc | 31 |
| rs12608558 | 19-55715090 | 0.0275 | 0.6372 | A/G | G | ACCTGTCACATTTGTCAGCTCCCA[A/G]CCACCCCTACCACTGTCCTTATAA | 32 |

Figure 33 cont.

| | | | | | |
|---|---|---|---|---|---|
| rs12610132 | 19-55032293 | 0.0408 | 0.6372 | A/G | G | GACACGATGTCTTCAGTCTCCAGCT[A/G]AGCTTGGACTGTGAGGATGGGTCAG | 33 |
| rs12610617 | 19-56443519 | 0.0030 | 0.3650 | C/T | T | CTCTCAAGTTGCCCAGGGGATACG[C/T]GGGAAGTGCCCCTGGGGGGCCGACC | 34 |
| rs160104 | 19-56433203 | 0.0012 | 0.2352 | G/T | T | ctggtctcttccagctctgggtggc[G/T]ccagtatttcttggtgtggctc | 35 |
| rs16986899 | 19-56549510 | 0.0265 | 0.6372 | T/C | C | AACAAGGTGACAGACCAGGAGTAA[C/T]GCCTCTCAGTGATGCCTTGAGAGTC | 36 |
| rs178153373 | 19-56608900 | 0.0483 | 0.7007 | G/A | A | CGGCAGGCAGTAGGATGGACTGCGT[A/G]GACGGCGGCCAGCATGTAAATGAAA | 37 |
| rs1895375 | 19-55035001 | 0.0329 | 0.6372 | T/C | C | AAGTAAGGTGTCAAGGAGGCCATGC[C/T]CACTCTGTAGGTTCTAGGAAAGAAT | 38 |
| rs20043690 | 19-56383651 | 0.0305 | 0.6372 | T/C | T | ATGCCTGAAAGAAACAAGAGCAAAT[C/T]GTCTCAGGAGGTAGGTAATAGGATG | 39 |
| rs2194 | 19-56257259 | 0.0064 | 0.5195 | G/A | A | AGCATATTCATTGATTTCCTTACAT[A/G]CAAATGCTCCTTTTTAAGTGCTCAA | 40 |
| rs2288419 | 19-55693244 | 0.0140 | 0.6372 | A/G | G | TCAGTACGTATTCCTGCATCAGTGC[A/G]TCCTGCGGTTCCTCCAACAGTCAGC | 41 |
| rs2288521 | 19-55708557 | 0.0262 | 0.6372 | T/C | T | AGTGGAGGCCCTGGAACCCGGACG[C/T]TGTACAATTTCACCGTGTGGGCAGA | 42 |
| rs2288527 | 19-55699077 | 0.0454 | 0.6738 | A/G | G | TGCCATATAATCTCAGGGTGCAACG[A/G]ATAAACAAGGGGTGATGCCGAAGAA | 43 |

Figure 33 cont.

| SNP | Position | Value1 | Value2 | Allele | Sequence | SEQ ID |
|---|---|---|---|---|---|---|
| rs2637107 | 19-56566741 | 0.0317 | A | G/A | CTCTGTCCCCTCAACTTCTTTCTAC[A/G]TGGTCATGTCCCTTCTTAGTTCCT | 44 |
| rs299164 | 19-56319796 | 0.0273 | 0.6372 | A/C | C | GCAACAAAATCTTATACATCACCA[A/C]ATGTCTGCTTAGCGGCAGAATTGCC | 45 |
| rs299169 | 19-56316796 | 0.0324 | 0.6372 | G/A | G | GCTAGGTAAAGGACTCTGAAAATAC[A/G]GCAACATGGAAAACATCCAGTCTCC | 46 |
| rs303997 | 19-56424443 | 0.0007 | 0.2204 | T/C | T | TCCATTTGCCCAGTGCAGCATAGCC[C/T]GCATTGCCAAGGTGGTCTTCCCAAC | 47 |
| rs304001 | 19-56423668 | 0.0015 | 0.2352 | C/T | C | CGTTTAACAAAGAAGAACACTGAGAT[C/T]GAGGGCCTGGAAGTGCCTTCATTG | 48 |
| rs304002 | 19-56423254 | 0.0141 | 0.6372 | C/T | C | TTCTACGACTTTTCACTGCCTACA[C/T]GAGTCCCAGGAGGAAGACTTCACAA | 49 |
| rs306463 | 19-56497077 | 0.0068 | 0.5195 | T/G | T | gccaaatgtgtttgaaaattccatt[G/T]gaagaaattatggtgaatgcatttt | 50 |
| rs310445 | 19-56173551 | 0.0396 | 0.6372 | G/A | G | GAAGATTGTTCAAGAAAAGGCAGAG[A/G]GCATGATGACAACACAAAATGAAGA | 51 |
| rs3745429 | 19-54937593 | 0.0233 | 0.6372 | A/G | G | CCTGGGACTATCCCCTGCCGGGCC[A/G]CACACATGTGCCCTGTGACCAGGGA | 52 |
| rs3786867 | 19-55684200 | 0.0394 | 0.6372 | C/T | T | GCTGGCTGTGAGGAGTCCGGCGAGAA[C/T]TCCCTTGCTTGTCCATGAATTTATC | 53 |
| rs4629084 | 19-56420157 | 0.0243 | 0.6372 | G/T | G | AAGGTGAAGAGTGGGAAAAGGCAGA[G/T]GATCAGGAAAAATAACTAATGGGTA | 54 |

Figure 33 cont.

| | | | | | |
|---|---|---|---|---|---|
| rs464765 | 19-56430224 | 0.0208 | 0.6372 | A/C | A | ggcttaataaaggaattagagagc[A/C]ctccctcctctccaacatcttttc | 55 |
| rs4801278 | 19-56246520 | 0.0268 | 0.6372 | G/A | A | TGGTCTGTGTCTCCTTGCACACTG[A/G]TCTGTGGACATCACAGGAGGAACA | 56 |
| rs4801635 | 19-56372705 | 0.0352 | 0.6372 | C/T | C | GTGCGTATATGTGTTACAAGTGGCT[C/T]GTGTTGACCGCCTGCCTGTGGAAAG | 57 |
| rs516022 | 19-56609371 | 0.0408 | 0.6372 | C/A | C | GCCTCGGTGCTGACCGGGGGTGCC[A/C]TTGCTGGGCTTAGCAGGCCGGGCTT | 58 |
| rs6509882 | 19-55030183 | 0.0400 | 0.6372 | A/G | G | TGATGTGCCACATCCTGTATAGGAA[A/G]CAGGTGATGTGGAAATGAGTCAGAC | 59 |
| rs6509883 | 19-55030376 | 0.0378 | 0.6372 | A/G | G | CATGAAAACCCCTCAGATGGTACCA[A/G]AAATATAGACAATTGATCCAGAGAG | 60 |
| rs6509933 | 19-55683104 | 0.0188 | 0.6372 | T/C | T | gtcccagtcactcacacaggaggat[C/T]gcaggagtttgaaaccagcctgtgc | 61 |
| rs6509939 | 19-55851708 | 0.0337 | 0.6372 | T/C | C | CACCCTCAGGGCCCTCTCCCTGACC[C/T]TCTCTCACCCCGGGACCTCCCTGC | 62 |
| rs8110255 | 19-56568978 | 0.0045 | 0.4527 | T/C | C | GCAGGTCTGTGTTCCTTGTTATGTT[C/T]CCTTGCTACAGGCACTCTCAGCCTT | 63 |
| rs8112791 | 19-56723492 | 0.0236 | 0.6372 | C/A | C | gtcagtttgaacaggtaaaatca[A/C]aatgctcatgttctctacagggaaa | 64 |
| rs873732 | 19-56745520 | 0.0194 | 0.6372 | G/A | A | AGCCAATTCGTCAGTGAATGAGGCA[A/G]AGAAATTGGTAAAAGAAGGAAAGT | 65 |

Figure 34

| SNP ID | Position (hg19) | P value | FDR | Genotype | Minor Allele | Sequence | SEQ ID NO |
|---|---|---|---|---|---|---|---|
| rs2823699 | 21-17628689 | 1.62E-08 | 0.0033 | T/C | T | TACATAGTAGGCTTAAGAGCAAATG[C/T]CTACCTTTCCTCTGTTTCAACTC | 66 |
| rs4973978 | 3-41667545 | 1.69E-08 | 0.0033 | T/G | G | GTTGGTTGGTTTGTTCCCCTTTAA[G/T]GGTGCCATTTAATGACAGATTTCAT | 67 |
| rs11744285 | 5-124622296 | 1.75E-08 | 0.0033 | A/G | G | GCCCCGGTGACAAGAATGGCAAAAC[A/G]TTTATTCGGCATTAACAATGTGTAA | 68 |
| rs71202733 | 11-12581045 | 3.32E-08 | 0.0041 | T/C | T | GCTCAGCTAATCAATGACCAGTCTC[C/T]TTAATTCTTCTAATGCCTATATGGT | 69 |
| rs10831850 | 11-12566917 | 5.12E-08 | 0.0041 | G/A | A | GTAAGGGATGTGAATCGGGTACTGA[A/G]GAAAGAGCCTGGATGCAGAGCCAGC | 70 |
| rs4756936 | 11-12599138 | 5.12E-08 | 0.0041 | C/T | T | TTGATAACTTCAGCATCTGGATCAC[C/T]GTGGGATTAGCATCTGTTTGTATTT | 71 |
| rs6485827 | 11-12578182 | 5.12E-08 | 0.0041 | C/T | C | GTGTGATTGCTTAAAAAAACTAC[C/T]ACATTGTTTGAATCACACCTCACA | 72 |

Figure 34 cont.

| | | | | | |
|---|---|---|---|---|---|
| rs7079768 | 10-131271870 | 9.92E-08 | 0.0070 | G/A | A | ACTTGTGCCAGGCTGGCTTTGCAAC[A/G]ATGAGCCTGAGAAGCTGTTAGAAGT | 73 |
| rs1293764 | 12-113425679 | 1.27E-07 | 0.0080 | A/G | A | GAGACACAAGAGGTGGGCAGGTCTT[A/G]GGGATTTAGGAGTTGGGTTCAAGGC | 74 |
| rs1862945 | 7-50936184 | 6.84E-07 | 0.0387 | G/A | A | TGAGTCTGTGAGGAGAAATGAACAA[A/G]TCTACCACAGTCATCCAGAATGAGA | 75 |
| rs10496038 | 2-55340963 | 9.41E-07 | 0.0484 | C/T | T | ATCAGAAGGCTAAGGAACCACCTGT[C/T]TAATAGTCTGGTGCCAAACACAGGC | 76 |
| rs12669489 | 7-50961697 | 1.05E-06 | 0.0493 | G/A | A | catcaataagaaaaacaaaataat[A/G]taatagaaaaatgcataagagactt | 77 |

Figure 35

SEQUENCE LISTING

<160> NUMBER OF SEQ ID NOS: 77

<210> SEQ ID NO 1
<211> LENGTH: 2381
<212> TYPE: DNA
<213> ORGANISM: Homo sapiens

<400> SEQUENCE: 1

```
actgccgcgg ccctgctgct cagggcacat gcctccctc cccaggccgc ggcccagctg      60
accctcgggg ctcccccggc agcggacagg gaagggttaa aggcccccgg ctccctgccc     120
cctgccctgg ggaacccctg gccctgtggg gacatgaact gtgtttgccg cctggtcctg     180
gtcgtgctga gcctgtggcc agatacagct gtcgcccctg ggccaccacc tggcccccct     240
cgagtttccc cagaccctcg ggccgagctg gacagcaccg tgctcctgac ccgctctctc     300
ctggcggaca cgcggcagct ggctgcacag ctgagggaca aattcccagc tgacggggac     360
cacaacctgg attccctgcc caccctggcc atgagtgcgg gggcactggg agctctacag     420
ctcccaggtg tgctgacaag gctgcgagcg gacctactgt cctacctgcg gcacgtgcag     480
tggctgcgcc gggcaggtgg ctcttccctg aagaccctgg agcccgagct gggcaccctg     540
caggcccgac tggaccggct gctgcgccgg ctgcagctcc tgatgtcccg cctggccctg     600
ccccagccac ccccggaccc gccggcgccc ccgctggcgc ccccctcctc agcctggggg     660
ggcatcaggg ccgcccacgc catcctgggg gggctgcacc tgacacttga ctgggccgtg     720
aggggactgc tgctgctgaa gactcggctg tgacccgggg cccaaagcca ccaccgtcct     780
tccaaagcca gatcttattt atttatttat ttcagtactg ggggcgaaac agccaggtga     840
tccccccgcc attatctccc cctagttaga gacagtcctt ccgtgaggcc tgggggcat      900 ctgtgcctta tttatactta tttatttcag gagcaggggt gggaggcagg tggactcctg     960
ggtccccgag gaggagggga ctgggtccc ggattcttgg gtctccaaga agtctgtcca    1020
cagacttctg ccctggctct tccccatcta ggcctgggca ggaacatata ttatttattt    1080
aagcaattac ttttcatgtt ggggtgggga cggagggaa agggaagcct gggtttttgt    1140
acaaaaatgt gagaaacctt tgtgagacag agaacaggga attaaatgtg tcatacatat    1200
ccacttgagg gcgatttgtc tgagagctgg ggctggatgc ttgggtaact ggggcagggc    1260
aggtggaggg gagacctcca ttcaggtgga ggtcccgagt gggcgggggca gcgactggga    1320 gatgggtcgg tcacccagac agctctgtgg aggcagggtc tgagccttgc ctggggcccc    1380
```

-continued

| | | |
|---|---|---|
| gcactgcata gggcctttg tttgttttt gagatggagt ctcgctctgt tgcctaggct | 1440 | |
| ggagtgcagt gaggcaatct gaggtcactg caacctccac ctcccgggtt caagcaattc | 1500 | |
| tcctgcctca gcctcccgat tagctgggat cacaggtgtg caccaccatg cccagctaat | 1560 | |
| tatttatttc ttttgtattt ttagtagaga cagggtttca ccatgttggc caggctggtt | 1620 | |
| tcgaactcct gacctcaggt gatcctcctg cctcggcctc ccaaagtgct gggattacag | 1680 | |
| gtgtgagcca ccacacctga cccataggtc ttcaataaat atttaatgga aggttccaca | 1740 | |
| agtcaccctg tgatcaacag tacccgtatg ggacaaagct gcaaggtcaa gatggttcat | 1800 | |
| tatggctgtg ttcaccatag caaactggaa acaatctaga tatccaacag tgagggttaa | 1860 | |
| gcaacatggt gcatctgtgg atagaacgcc acccagccgc ccggagcagg gactgtcatt | 1920 | |
| cagggaggct aaggagagag gcttgcttgg gatatagaaa gatatcctga cattggccag | 1980 | |
| gcatggtggc tcacgcctgt aatcctggca ctttgggagg acgaagcgag tggatcactg | 2040 | |
| aagtccaaga gttcgagacc ggcctgcgag acatggcaaa accctgtctc aaaaaagaaa | 2100 | |
| gaatgatgtc ctgacatgaa acagcaggct acaaaaccac tgcatgctgt gatcccaatt | 2160 | |
| ttgtgttttt ctttctatat atggattaaa acaaaaatcc taaagggaaa tacgccaaaa | 2220 | |
| tgttgacaat gactgtctcc aggtcaaagg agagaggtgg gattgtgggt gacttttaat | 2280 | |
| gtgtatgatt gtctgtattt tacagaattt ctgccatgac tgtgtatttt gcatgacaca | 2340 | |
| ttttaaaaat aataaacact atttttagaa taacagaaaa a | 2381 | |

<210> SEQ ID NO 2
<211> LENGTH: 19
<212> TYPE: DNA
<213> ORGANISM: Homo sapiens

<400> SEQUENCE: 2
ccttccaaag ccagatctt                                              19

<210> SEQ ID NO 3
<211> LENGTH: 19
<212> TYPE: DNA
<213> ORGANISM: Homo sapiens

<400> SEQUENCE: 3
gcctgggcag gaacatata                                              19

<210> SEQ ID NO 4
<211> LENGTH: 19
<212> TYPE: DNA
<213> ORGANISM: Homo sapiens

<400> SEQUENCE: 4
cctgggcagg aacatatat                                              19

<210> SEQ ID NO 5
<211> LENGTH: 19
<212> TYPE: DNA
<213> ORGANISM: Homo sapiens

<400> SEQUENCE: 5
ggttcattat ggctgtgtt                                              19

<210> SEQ ID NO 6
<211> LENGTH: 1696
<212> TYPE: DNA
<213> ORGANISM: Homo sapiens

<400> SEQUENCE: 6

```
gctgtagctg gtgagaggaa gtcctagagg ctatggacac tctgctgctg ggatcaccga        60
gatgagcagc agctgctcag ggctgagcag ggtcctggtg gccgtggcta cagccctggt       120
gtctgcctcc tccccctgcc cccaggcctg gggcccccca ggggtccagt atgggcagcc       180
agggaggtcc gtgaagctgt gttgtcctgg agtgactgcc ggggacccag tgtcctggtt       240
tcggatggg gagccaaagc tgctccaggg acctgactct gggctagggc atgaactggt        300
cctggcccag gcagacagca ctgatgaggg cacctacatc tgccagaccc tggatggtgc       360
acttgggggc acagtgaccc tgcagctggg ctaccctcca gcccgccctg ttgtctcctg       420
ccaagcagcc gactatgaga acttctcttg cacttggagt cccagccaga tcagcggttt       480
acccacccgc tacctcacct cctacaggaa gaagacagtc ctaggagctg atagccagag       540
gaggagtcca tccacagggc cctggccatg cccacaggat cccctagggg ctgcccgctg       600
tgttgtccac ggggctgagt tctggagcca gtaccggatt aatgtgactg aggtgaaccc       660
actgggtgcc agcacacgcc tgctggatgt gagcttgcag agcatcttgc gccctgaccc       720
accccagggc ctgcgggtag agtcagtacc aggttacccc cgacgcctgc gagccagctg       780
gacataccct gcctcctggc cgtgccagcc ccacttcctg ctcaagttcc gtttgcagta       840
ccgtccggcg cagcatccag cctggtccac ggtggagcca gctggactgg aggaggtgat       900
cacagatgct gtggctgggc tgccccatgc tgtacgagtc agtgcccggg actttctaga       960
tgctggcacc tggagcacct ggagcccgga ggcctgggga actccgagca ctggaccat      1020
accaaaggag ataccagcat ggggccagct acacacgcag ccagaggtgg agcctcaggt      1080
ggacagccct gctcctccaa ggccctccct ccaaccacac cctcggctac ttgatcacag      1140
ggactctgtg gagcaggtag ctgtgctggc gtctttggga atcctttctt tcctgggact      1200
ggtggctggg gccctggcac tggggctctg gctgaggctg agacggggtg gaaggatgg      1260
atccccaaag cctgggttct tggcctcagt gattccagtg acaggcgtc caggagctcc      1320
aaacctgtag aggacccagg agggcttcgg cagattccac ctataattct gtcttgctgg      1380
tgtggataga aaccaggcag gacagtagat ccctatggtt ggatctcagc tggaagttct      1440
gtttggagcc catttctgtg agaccctgta tttcaaattt gcagctgaaa ggtgcttgta      1500
cctctgattt caccccagag ttggagttct gctcaaggaa cgtgtgtaat gtgtacatct      1560
gtgtccatgt gtgaccatgt gtctgtgaag gccagggaac atgtattcct ctgcatgcat      1620
gtatgtaggt gcctgggagt gtgtgtggtc cttgctctgg ccctttccct tgcagggttg      1680
tgcaggtgtg aataaa                                                      1696
```

<210> SEQ ID NO 7
<211> LENGTH: 19
<212> TYPE: DNA
<213> ORGANISM: Homo sapiens

<400> SEQUENCE: 7

```
ggaccatacc aaaggagat                                                     19
```

<210> SEQ ID NO 8
<211> LENGTH: 19
<212> TYPE: DNA
<213> ORGANISM: Homo sapiens

<400> SEQUENCE: 8

```
gcgtctttgg gaatcctttt                                              19

<210> SEQ ID NO 9
<211> LENGTH: 18
<212> TYPE: DNA
<213> ORGANISM: Homo sapiens

<400> SEQUENCE: 9
gcaggacagt agatccct                                                18

<210> SEQ ID NO 10
<211> LENGTH: 19
<212> TYPE: DNA
<213> ORGANISM: Homo sapiens

<400> SEQUENCE: 10
gctcaaggaa cgtgtgtaa                                               19

<210> SEQ ID NO 11
<211> LENGTH: 21
<212> TYPE: RNA
<213> ORGANISM: Homo sapiens
<220> FEATURE:
<221> NAME/KEY: misc_feature
<222> LOCATION: (20)..(21)
<223> OTHER INFORMATION: n = deoxythymidine

<400> SEQUENCE: 11
ccuuccaaag ccagaucuun n                                            21

<210> SEQ ID NO 12
<211> LENGTH: 21
<212> TYPE: RNA
<213> ORGANISM: Homo sapiens
<220> FEATURE:
<221> NAME/KEY: misc_feature
<222> LOCATION: (20)..(21)
<223> OTHER INFORMATION: n = deoxythymidine

<400> SEQUENCE: 12
gccugggcag gaacauauan n                                            21

<210> SEQ ID NO 13
<211> LENGTH: 21
<212> TYPE: RNA
<213> ORGANISM: Homo sapiens
<220> FEATURE:
<221> NAME/KEY: misc_feature
<222> LOCATION: (20)..(21)
<223> OTHER INFORMATION: n = deoxythymidine

<400> SEQUENCE: 13
ccugggcagg aacauauaun n                                            21

<210> SEQ ID NO 14
<211> LENGTH: 21
<212> TYPE: RNA
<213> ORGANISM: Homo sapiens
<220> FEATURE:
<221> NAME/KEY: misc_feature
<222> LOCATION: (20)..(21)
<223> OTHER INFORMATION: n = deoxythymidine

<400> SEQUENCE: 14
gguucauuau ggcuguguun n                                            21
```

```
<210> SEQ ID NO 15
<211> LENGTH: 21
<212> TYPE: RNA
<213> ORGANISM: Homo sapiens
<220> FEATURE:
<221> NAME/KEY: misc_feature
<222> LOCATION: (20)..(21)
<223> OTHER INFORMATION: n = deoxythymidine

<400> SEQUENCE: 15
ggaccauacc aaaggagaun n                                              21

<210> SEQ ID NO 16
<211> LENGTH: 21
<212> TYPE: RNA
<213> ORGANISM: Homo sapiens
<220> FEATURE:
<221> NAME/KEY: misc_feature
<222> LOCATION: (20)..(21)
<223> OTHER INFORMATION: n = deoxythymidine

<400> SEQUENCE: 16
gcgucuuugg gaauccuuun n                                              21

<210> SEQ ID NO 17
<211> LENGTH: 21
<212> TYPE: RNA
<213> ORGANISM: Homo sapiens
<220> FEATURE:
<221> NAME/KEY: misc_feature
<222> LOCATION: (20)..(21)
<223> OTHER INFORMATION: n = deoxythymidine

<400> SEQUENCE: 17
gcaggacagu agaucccuan n                                              21

<210> SEQ ID NO 18
<211> LENGTH: 21
<212> TYPE: RNA
<213> ORGANISM: Homo sapiens
<220> FEATURE:
<221> NAME/KEY: misc_feature
<222> LOCATION: (20)..(21)
<223> OTHER INFORMATION: n = deoxythymidine

<400> SEQUENCE: 18
gcucaaggaa cguguguaan n                                              21

<210> SEQ ID NO 19
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 19
gtaagggatg tgaatcgggt actgangaaa gagcctggat gcagagccag c             51

<210> SEQ ID NO 20
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T
```

<400> SEQUENCE: 20
ttgataactt cagcatctgg atcacngtgg gattagcatc tgtttgtatt t         51

<210> SEQ ID NO 21
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 21
gtgtgattgc ttaaaaaaaa ctactnacat tgttttgaat cacacctcac a         51

<210> SEQ ID NO 22
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 22
gctcagctaa tcaatgacca gtctcnttaa ttcttctaat gcctatatgg t         51

<210> SEQ ID NO 23
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 23
gcagtgctca gaagagcagc agccantgac attttggggc tataagaggt a         51

<210> SEQ ID NO 24
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 24
tgtccagtaa atacttaaca ttttangtgc aatgtatgtc ataaatatgg g         51

<210> SEQ ID NO 25
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 25
gggtgaagtt tggaaacagg tatacnttgt gatgcaatcg tcagaaccaa g         51

<210> SEQ ID NO 26
<211> LENGTH: 51
<212> TYPE: DNA
<213> ORGANISM: Homo sapiens

```
<220> FEATURE:
<221> NAME/KEY: misc_feature
<222> LOCATION: (26)..(26)
<223> OTHER INFORMATION: n = C or T

<400> SEQUENCE: 26
aaaccatagt atcatccttc ccaaanagtc aacccaggga atcacagaga t           51

<210> SEQ ID NO 27
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 27
taagacgcta ttctctaatt ctgaanggaa gaactcctct cccaagacat g           51

<210> SEQ ID NO 28
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 28
aggtggaaca acacaaaggg tggggngagg cgtgcaattt aaacattttc t           51

<210> SEQ ID NO 29
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or A

<400> SEQUENCE: 29
tattagattt tgtgtgggat ttcatngtta catttgttac cagcccaatt t           51

<210> SEQ ID NO 30
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 30
gattccagtt ccaagtcaca tcatcnccag ctggaagacc tagggcaaaa g           51

<210> SEQ ID NO 31
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 31
accatgacgg tgtcctcatt gctttnacca ttagtaatca ttcattcatt c           51
```

```
<210> SEQ ID NO 32
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 32
acctgtcaca ttttgtcagc tcccanccac ccctaccac tgtccttata a         51

<210> SEQ ID NO 33
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 33
gacacgatgt cttcagtctc cagctnagct tggactgtga ggatgggtca g         51

<210> SEQ ID NO 34
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 34
ctctcaagtt tgcccagggg atacgnggga agtgcccctg ggggccgac c           51

<210> SEQ ID NO 35
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or T

<400> SEQUENCE: 35
ctggtctctt ccagctctgg tggctnccag tatttcttgg gttgtggcct c          51

<210> SEQ ID NO 36
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 36
aacaaggtga cagaccaggg agtaangcct ctcagtgatg ccttgagagt c          51

<210> SEQ ID NO 37
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A
```

```
<400> SEQUENCE: 37
cggcaggcag taggatggac tgcgtngacg gcggccagca tgtaaatgaa a          51

<210> SEQ ID NO 38
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 38
aagtaaggtg tcaaggaggc catgcncact ctgtaggttc taggaaagaa t          51

<210> SEQ ID NO 39
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 39
atgcctgaaa gaaacaagag caaatngtct caggaggtag gtaataggat g          51

<210> SEQ ID NO 40
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 40
agcatattca ttgatttcct tacatncaaa tgctcctttt taagtgctca a          51

<210> SEQ ID NO 41
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 41
tcagtacgta ttcctgcatc agtgcntcct gcggttcctc caacagtcag c          51

<210> SEQ ID NO 42
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 42
agtggaggcc ctggaacccg ggacgntgta caatttcacc gtgtgggcag a          51

<210> SEQ ID NO 43
<211> LENGTH: 51
<212> TYPE: DNA
```

```
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 43
tgccatataa tctcagggtg caacgnataa acaaggggtg atgccgaaga a            51

<210> SEQ ID NO 44
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 44
ctctgtcccc tcaacttctt tctacntggt catgtccctt ctttagttcc t            51

<210> SEQ ID NO 45
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or C

<400> SEQUENCE: 45
gcaacaaaaa tcttatacat caccanatgt ctgcttagcg cagaattgc c             51

<210> SEQ ID NO 46
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 46
gctaggtaaa ggactctgaa aatacngcaa catggaaaac atccagtctc c            51

<210> SEQ ID NO 47
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 47
tccatttgcc cagtgcagca tagccngcat tgccaaggtg gtcttcccaa c            51

<210> SEQ ID NO 48
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 48
cgtttaacaa agaagacact gagatngagg gcctggaagt gcctttcatt g            51
```

<210> SEQ ID NO 49
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 49
ttctacgact ttttcactgc ctacangagt cccaggagga agacttcaca a         51

<210> SEQ ID NO 50
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or T

<400> SEQUENCE: 50
gccaaatgtg tttgaaaatt ccattngaag aatttatggt gaatgcattt t         51

<210> SEQ ID NO 51
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 51
gaagattgtt caagaaaagg cagagngcat gatgacaaca caaaatgaag a         51

<210> SEQ ID NO 52
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 52
cctgggacta tcccctggcc gggccncaca catgtgccct gtgaccaggg a         51

<210> SEQ ID NO 53
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 53
gctggctgtg aggagtccgc gagaantccc ttgcttgtcc atgaatttat c         51

<210> SEQ ID NO 54
<211> LENGTH: 51
<212> TYPE: DNA
<213> ORGANISM: Homo sapiens
<220> FEATURE:
<221> NAME/KEY: misc_feature
<222> LOCATION: (26)..(26)

<223> OTHER INFORMATION: n = G or T

<400> SEQUENCE: 54
aaggtgaaga gtgggaaaag gcagangatc aggaaaaata actaatgggt a            51

<210> SEQ ID NO 55
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or C

<400> SEQUENCE: 55
ggcttaataa aaggaattag agagcnctcc ctcctctcca acatctttttt c           51

<210> SEQ ID NO 56
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 56
tggtctgtgc tctccttgca cactcntctg tggacatcac aggagggaac a           51

<210> SEQ ID NO 57
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 57
gtgcgtatat gtgttacaag tggctngtgt tgaccgcctg cctgtggaaa g           51

<210> SEQ ID NO 58
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or C

<400> SEQUENCE: 58
gcctcgggtg ctgaccgggg gtgccnttgc tgggcttagc aggccgggct t           51

<210> SEQ ID NO 59
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 59
tgatgtgcca catcctgtat aggaancagg tgatgtggaa atgagtcaga c           51

<210> SEQ ID NO 60
<211> LENGTH: 51

```
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 60
catgaaaacc cctcagatgg taccanaaat atagacaatt gatccagaga g          51

<210> SEQ ID NO 61
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 61
gtcccagcta ctcacacagg aggatngcag gagtttgaaa ccagcctgtg c          51

<210> SEQ ID NO 62
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 62
caccctcagg gcctctccct gaccntctc tcaccccgg acctccctg c             51

<210> SEQ ID NO 63
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 63
gcaggtctgt gttccttgtt atgttncctt gctacaggca ctctcagcct t          51

<210> SEQ ID NO 64
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or A

<400> SEQUENCE: 64
gtcagtttgt gaacaggtaa aatcanaatg ctcatgttct ctacagggaa a          51

<210> SEQ ID NO 65
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 65
```
agccaattcg tcagtgaatg aggcanagaa attggtaaaa agaaggaaag t         51

<210> SEQ ID NO 66
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 66
tacatagtag gcttaagagc aaatgnctac cttttcctct gttttcaact c         51

<210> SEQ ID NO 67
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or G

<400> SEQUENCE: 67
gttggttggt ttgtttcccc tttaanggtg ccatttaatg acagatttca t         51

<210> SEQ ID NO 68
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 68
gccccggtga caagaatggc aaaacnttta ttcggcatta acaatgtgta a         51

<210> SEQ ID NO 69
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = T or C

<400> SEQUENCE: 69
gctcagctaa tcaatgacca gtctcnttaa ttcttctaat gcctatatgg t         51

<210> SEQ ID NO 70
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 70
gtaagggatg tgaatcgggt actgangaaa gagcctggat gcagagccag c         51

<210> SEQ ID NO 71
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 71
ttgataactt cagcatctgg atcacngtgg gattagcatc tgtttgtatt t          51

<210> SEQ ID NO 72
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 72
gtgtgattgc ttaaaaaaaa ctactnacat tgttttgaat cacacctcac a          51

<210> SEQ ID NO 73
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 73
acttgtgcca ggctggcttt gcaacnatga gcctgagaag ctgttagaag t          51

<210> SEQ ID NO 74
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = A or G

<400> SEQUENCE: 74
gagacacaag aggtgggcag gtcttnggga tttaggagtt gggttcaagg c          51

<210> SEQ ID NO 75
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 75
tgagtctgtg aggagaaatg aacaantcta ccacagtcat ccagaatgag a          51

<210> SEQ ID NO 76
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = C or T

<400> SEQUENCE: 76
atcagaaggc taaggaacca cctgtntaat agtctggtgc caaacacagg c          51

<210> SEQ ID NO 77

-continued

```
<211> LENGTH: 51
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n = G or A

<400> SEQUENCE: 77
catcaataag aaaaacaaaa ataatntaat agaaaaatgc ataagagact t            51
```

TREATMENT OF FIBROSIS WITH INTERLEUKIN-11 ANTIBODY

RELATED APPLICATIONS

The present application is a continuation application of U.S. application Ser. No. 15/988,463, filed May 24, 2018, which is a divisional application of U.S. application Ser. No. 15/381,622, filed Dec. 16, 2016, now U.S. Pat. No. 10,035, 852, which claims priority under 35 USC § 119(a)-(d) to United Kingdom Application No. 1522186.4, filed Dec. 16, 2015. The entire contents of the aforementioned applications are hereby incorporated by reference herein.

FIELD OF THE INVENTION

The present invention relates to the diagnosis and treatment of conditions such as fibrosis.

BACKGROUND TO THE INVENTION

Fibrosis is an essential process that is a critical part of wound healing. Excessive fibrosis is common in many rare and common disease conditions and is important in disease pathogenesis. Diseases characterized by excessive fibrosis include but are not restricted to: systemic sclerosis, scleroderma, hypertrophic cardiomyopathy, dilated cardiomyopathy (DCM), atrial fibrillation, ventricular fibrillation, myocarditis, liver cirrhosis, kidney diseases, diseases of the eye, asthma, cystic fibrosis, arthritis and idiopathic pulmonary fibrosis. Despite the large impact on human health, therapeutic and diagnostic approaches to fibrosis are still an unmet medical need.

The real physiological role of Interleukin 11 (IL-11) remains unclear. IL-11 has been most strongly linked with activation of haematopoetic cells and with platelet production but also found to be pro- as well as anti-inflammatory, pro-angiogenic and important for neoplasia. It is known that TGFβ1 or tissue injury can induce IL-11 expression (Zhu, M. et al. IL-11 Attenuates Liver Ischemia/Reperfusion Injury (IRI) through STAT3 Signaling Pathway in Mice. PLOS ONE 10, (2015); Yashiro, R. et al. Transforming growth factor-beta stimulates interleukin-11 production by human periodontal ligament and gingival fibroblasts. J. Clin. Periodontol. 33, 165-71 (2006); Obana, M. et al. Therapeutic activation of signal transducer and activator of transcription 3 by interleukin-11 ameliorates cardiac fibrosis after myocardial infarction. Circulation 121, 684-91 (2010); Tang, W., Yang, L., Yang, Y. C., Leng, S. X. & Elias, J. A. Transforming growth factor-beta stimulates interleukin-11 transcription via complex activating protein-1-dependent pathways. J. Biol. Chem. 273, 5506-13 (1998)).

The role for IL-11 in fibrosis is not clear from the published literature. IL-11 is thought to be important for fibrosis and inflammation in the lung (Tang, W. et al. Targeted expression of IL-11 in the murine airway causes lymphocytic inflammation, bronchial remodeling, and airways obstruction. J. Clin. Invest. 98, 2845-53 (1996)) and its expression level is correlated with collagen levels in the skin (Toda, M. et al. Polarized in vivo expression of IL-11 and IL-17 between acute and chronic skin lesions. Journal of Allergy and Clinical Immunology 111, 875-881 (2003)) and the respiratory system (Molet, S., Hamid, Q. & Hamilos, D. IL-11 and IL-17 expression in nasal polyps: Relationship to collagen deposition and suppression by intranasal fluticasone propionate. The Laryngoscope 113, (2003); Minshall et al. IL-11 expression is increased in severe asthma: association with epithelial cells and eosinophils. The Journal of allergy and clinical immunology 105, (2000)).

However, the majority of studies suggest that IL-11 is anti-fibrotic: in the heart (Obana, M. et al. Therapeutic activation of signal transducer and activator of transcription 3 by interleukin-11 ameliorates cardiac fibrosis after myocardial infarction. Circulation 121, 684-91 (2010); Obana, M. et al. Therapeutic administration of IL-11 exhibits the postconditioning effects against ischemia-reperfusion injury via STAT3 in the heart. American Journal of Physiology. Heart and circulatory physiology 303, H569-77 (2012)) and kidney (Stangou, M. et al. Effect of IL-11 on glomerular expression of TGF-beta and extracellular matrix in nephrotoxic nephritis in Wistar Kyoto rats. Journal of nephrology 24, 106-11 (2011); Ham, A. et al. Critical role of interleukin-11 in isoflurane-mediated protection against ischemic acute kidney injury in mice. Anesthesiology 119, 1389-401 (2013)) and anti-inflammatory in several tissues and chronic inflammatory diseases (Trepicchio & Dorner. The therapeutic utility of Interleukin-11 in the treatment of inflammatory disease. (1998). doi:10.1517/13543784.7.9.1501). The molecular mode of action of IL-11 in general, is thought to be regulation of RNA expression of mRNA levels via STAT3-mediated transcription (Zhu, M. et al. IL-11 Attenuates Liver Ischemia/Reperfusion Injury (IRI) through STAT3 Signaling Pathway in Mice. PLOS ONE 10, (2015)).

SUMMARY OF THE INVENTION

One aspect of the present invention concerns the treatment, prevention or alleviation of fibrosis in a subject in need of treatment through the administration of an agent capable of inhibiting the action of Interleukin 11 (IL-11). The inventors have identified IL-11 to have a pro-fibrotic action. The present invention is particularly concerned with inhibiting the pro-fibrotic action of IL-11. Embodiments of the invention concern inhibition or prevention of the IL-11 mediated pro-fibrotic signal, e.g. as mediated by binding of IL-11 to an IL-11 receptor.

In some embodiments an agent capable of inhibiting the action of IL-11 may prevent or reduce the binding of IL-11 to an IL-11 receptor.

In some embodiments an agent capable of inhibiting the action of IL-11 may bind IL-11 to form a complex comprising the agent and IL-11. The complex may be a non-covalent or covalent complex. In some embodiments, the formation of the agent:IL-11 complex may prevent or reduce the ability of IL-11 to bind to an IL-11 receptor. In some embodiments such prevention or reduction may be the result of a reduction of the productive binding of IL-11 to an IL-11 receptor, i.e. reduction in the ability of IL-11 to initiate IL-11 receptor mediated signalling. In some embodiments formation of the agent:IL-11 complex may sequester IL-11 away from the IL-11 receptor, thereby preventing or reducing the contact of IL-11 with an IL-11 receptor and/or preventing or reducing the amount of IL-11 available for binding to an IL-11 receptor. In some embodiments the agent may be a decoy receptor.

In some embodiments an agent capable of inhibiting the action of IL-11 may bind to an IL-11 receptor. An agent that binds an IL-11 receptor may prevent or reduce the ability of IL-11 to bind to an IL-11 receptor (IL-11R).

Another aspect of the present invention concerns the treatment, prevention or alleviation of fibrosis in a subject in need of treatment through the administration of an agent capable of preventing or reducing the expression of IL-11 or an IL-11 receptor (IL-11R).

In one aspect of the present invention an agent capable of inhibiting the action of Interleukin 11 (IL-11) for use in a method of treating or preventing fibrosis is provided.

In another aspect of the present invention the use of an agent capable of inhibiting the action of IL-11 in the manufacture of a medicament for use in a method of treating or preventing fibrosis is provided.

In another aspect of the present invention a method of treating or preventing fibrosis is provided, the method comprising administering to a subject in need of treatment a therapeutically effective amount of an agent capable of inhibiting the action of IL-11.

In some embodiments the agent capable of inhibiting the action of IL-11 is an agent capable of preventing or reducing the binding of IL-11 to an IL-11 receptor.

In some embodiments the agent capable of inhibiting the action of IL-11 is an IL-11 binding agent. IL-11 binding agents may be selected from the group consisting of: an antibody, polypeptide, peptide, oligonucleotide, aptamer or small molecule. In some embodiments the IL-11 binding agent is an antibody. In some embodiments the IL-11 binding agent is a decoy receptor.

In some embodiments the agent capable of inhibiting the action of IL-11 is an IL-11 receptor (IL-11R) binding agent. IL-11R binding agents may be selected from the group consisting of: an antibody, polypeptide, peptide, oligonucleotide, aptamer or small molecule. In some embodiments the IL-11R binding agent is an antibody.

In another aspect of the present invention an agent capable of preventing or reducing the expression of IL-11 or IL-11R for use in a method of treating or preventing fibrosis is provided.

In another aspect of the present invention the use of an agent capable of preventing or reducing the expression of IL-11 or IL-11R in the manufacture of a medicament for use in a method of treating or preventing fibrosis is provided.

In another aspect of the present invention a method of treating or preventing fibrosis is provided, the method comprising administering to a subject in need of treatment a therapeutically effective amount of an agent capable of preventing or reducing the expression of IL-11 or IL-11R.

In some embodiments the agent capable of preventing or reducing the expression of IL-11 or IL-11R is a small molecule or oligonucleotide.

In some embodiments the fibrosis to be treated or prevented is fibrosis of the heart, liver or kidney. In some embodiments the fibrosis to be treated or prevented is fibrosis of the eye. In some embodiments the fibrosis is in the heart and is associated with dysfunction of the musculature or electrical properties of the heart, or thickening of the walls or valves of the heart. In some embodiments the fibrosis is in the liver and is associated with chronic liver disease or liver cirrhosis. In some embodiments the fibrosis is in the kidney and is associated with chronic kidney disease.

In some embodiments the method of treating or preventing comprises administering a said agent to a subject in which IL-11 or IL-11R expression is upregulated. In some embodiments the method of treating or preventing comprises administering a said agent to a subject in which IL-11 or IL-11R expression has been determined to be upregulated. In some embodiments the method of treating or preventing comprises determining whether IL-11 or IL-11R expression is upregulated in the subject and administering a said agent to a subject in which IL-11 or IL-11R expression is upregulated.

In another aspect of the present invention a method of determining the suitability of a subject for the treatment or prevention of fibrosis with an agent capable of inhibiting the action of IL-11 is provided, the method comprising determining, optionally in vitro, whether IL-11 or IL-11R expression is upregulated in the subject.

In another aspect of the present invention a method of selecting a subject for the treatment or prevention of fibrosis with an agent capable of inhibiting the action of IL-11 is provided, the method comprising determining, optionally in vitro, whether IL-11 or IL-11R expression is upregulated in the subject.

In another aspect of the present invention a method of diagnosing fibrosis or a risk of developing fibrosis in a subject is provided, the method comprising determining, optionally in vitro, the upregulation of IL-11 or IL-11R in a sample obtained from the subject.

In some embodiments the method is a method of confirming a diagnosis of fibrosis in a subject suspected of having fibrosis.

In some embodiments the method further comprises selecting the subject for treatment with an agent capable of inhibiting the action of IL-11 or with an agent capable of preventing or reducing the expression of IL-11 or IL-11R.

In another aspect of the present invention a method of providing a prognosis for a subject having, or suspected of having fibrosis, is provided, the method comprising determining, optionally in vitro, whether IL-11 or IL-11R is upregulated in a sample obtained from the subject and, based on the determination, providing a prognosis for treatment of the subject with an agent capable of inhibiting the action of IL-11 or with an agent capable of preventing or reducing the expression of IL-11 or IL-11R.

The method may further comprise selecting a subject determined to have upregulated IL-11 or IL-11R for treatment with an agent capable of inhibiting the action of IL-11 or with an agent capable of preventing or reducing the expression of IL-11 or IL-11R.

In another aspect of the present invention a method of diagnosing fibrosis or a risk of developing fibrosis in a subject is provided, the method comprising determining, optionally in vitro, one or more genetic factors in the subject that are predictive of upregulation of IL-11 or IL-11R expression, or of upregulation of IL-11 or IL-11R activity.

In some embodiments the method is a method of confirming a diagnosis of fibrosis in a subject suspected of having fibrosis.

In some embodiments the method further comprises selecting the subject for treatment with an agent capable of inhibiting the action of IL-11 or with an agent capable of preventing or reducing the expression of IL-11 or IL-11R.

In another aspect of the present invention a method of providing a prognosis for a subject having, or suspected of having, fibrosis, is provided, the method comprising determining, optionally in vitro, one or more genetic factors in the subject that are predictive of upregulation of IL-11 or IL-11R expression, or of upregulation of IL-11 or IL-11R activity.

The following numbered paragraphs (paras) describe further aspects and embodiments of the present invention:

1. An agent capable of inhibiting the action of Interleukin 11 (IL-11) for use in a method of treating or preventing fibrosis.
2. Use of an agent capable of inhibiting the action of Interleukin 11 (IL-11) in the manufacture of a medicament for use in a method of treating or preventing fibrosis.
3. A method of treating or preventing fibrosis, the method comprising administering to a subject in need of treatment a therapeutically effective amount of an agent capable of inhibiting the action of Interleukin 11 (IL-11).

4. The agent for use in a method of treating or preventing fibrosis according to para 1, use according to para 2 or method according to para 3, wherein the agent is an agent capable of preventing or reducing the binding of IL-11 to an IL-11 receptor.

5. The agent for use in a method of treating or preventing fibrosis according to para 1 or 4, use according to para 2 or 4, or method according to para 3 or 4, wherein the agent is an IL-11 binding agent.

6. The agent for use in a method of treating or preventing fibrosis, use or method according to para 5, wherein the IL-11 binding agent is selected from the group consisting of: an antibody, polypeptide, peptide, oligonucleotide, aptamer or small molecule.

7. The agent for use in a method of treating or preventing fibrosis, use or method according to para 5, wherein the IL-11 binding agent is an antibody.

8. The agent for use in a method of treating or preventing fibrosis, use or method according to para 5, wherein the IL-11 binding agent is a decoy receptor.

9. The agent for use in a method of treating or preventing fibrosis according to para 1 or 4, use according to para 2 or 4, or method according to para 3 or 4, wherein the agent is an IL-11 receptor (IL-11R) binding agent.

10. The agent for use in a method of treating or preventing fibrosis, use or method according to para 9, wherein the IL-11R binding agent is selected from the group consisting of: an antibody, polypeptide, peptide, oligonucleotide, aptamer or small molecule.

11. The agent for use in a method of treating or preventing fibrosis, use or method according to para 9, wherein the IL-11R binding agent is an antibody.

12. An agent capable of preventing or reducing the expression of Interleukin 11 (IL-11) or an Interleukin 11 receptor (IL-11R) for use in a method of treating or preventing fibrosis.

13. Use of an agent capable of preventing or reducing the expression of Interleukin 11 (IL-11) or an Interleukin 11 receptor (IL-11R) in the manufacture of a medicament for use in a method of treating or preventing fibrosis.

14. A method of treating or preventing fibrosis, the method comprising administering to a subject in need of treatment a therapeutically effective amount of an agent capable of preventing or reducing the expression of Interleukin 11 (IL-11) or an Interleukin 11 receptor (IL-11R).

15. The agent for use in a method of treating or preventing fibrosis according to para 12, use according to para 13 or method according to para 14, wherein the agent is a small molecule or oligonucleotide.

16. The agent for use in a method of treating or preventing fibrosis, use or method according to any one of the preceding paras, wherein the fibrosis is fibrosis of the heart, liver, kidney or eye.

17. The agent for use in a method of treating or preventing fibrosis, use or method according to any one of the preceding paras, wherein the fibrosis is in the heart and is associated with dysfunction of the musculature or electrical properties of the heart, or thickening of the walls or valves of the heart.

18. The agent for use in a method of treating or preventing fibrosis, use or method according to any one of the preceding paras, wherein the fibrosis is in the liver and is associated with chronic liver disease or liver cirrhosis.

19. The agent for use in a method of treating or preventing fibrosis, use or method according to any one of the preceding paras, wherein the fibrosis is in the kidney and is associated with chronic kidney disease.

20. The agent for use in a method of treating or preventing fibrosis, use or method according to any one of the preceding paras, wherein the fibrosis is in the eye and is retinal fibrosis, epiretinal fibrosis, or subretinal fibrosis.

21. The agent for use in a method of treating or preventing fibrosis, use or method according to any one of the preceding paras, wherein the method of treating or preventing comprises administering said agent to a subject in which IL-11 or IL-11R expression is upregulated.

22. The agent for use in a method of treating or preventing fibrosis, use or method according to any one of the preceding paras, wherein the method of treating or preventing comprises administering said agent to a subject in which IL-11 or IL-11R expression has been determined to be upregulated.

23. The agent for use in a method of treating or preventing fibrosis, use or method according to any one of the preceding paras, wherein the method of treating or preventing comprises determining whether IL-11 or IL-11R expression is upregulated in the subject and administering said agent to a subject in which IL-11 or IL-11R expression is upregulated.

24. A method of determining the suitability of a subject for the treatment or prevention of fibrosis with an agent capable of inhibiting the action of Interleukin 11 (IL-11), the method comprising determining, optionally in vitro, whether IL-11 or an Interleukin 11 receptor (IL-11R) expression is upregulated in the subject.

25. A method of selecting a subject for the treatment or prevention of fibrosis with an agent capable of inhibiting the action of Interleukin 11 (IL-11), the method comprising determining, optionally in vitro, whether IL-11 or an Interleukin 11 receptor (IL-11R) expression is upregulated in the subject.

26. A method of diagnosing fibrosis or a risk of developing fibrosis in a subject, the method comprising determining, optionally in vitro, the upregulation of Interleukin 11 (IL-11) or an Interleukin 11 receptor (IL-11R) in a sample obtained from the subject.

27. The method of para 26, wherein the method is a method of confirming a diagnosis of fibrosis in a subject suspected of having fibrosis.

28. The method of para 26 or 27, wherein the method further comprises selecting the subject for treatment with an agent capable of inhibiting the action of IL-11 or with an agent capable of preventing or reducing the expression of IL-11 or IL-11R.

29. A method of providing a prognosis for a subject having, or suspected of having fibrosis, the method comprising determining, optionally in vitro, whether Interleukin 11 (IL-11) or an Interleukin 11 receptor (IL-11R) is upregulated in a sample obtained from the subject and, based on the determination, providing a prognosis for treatment of the subject with an agent capable of inhibiting the action of IL-11 or with an agent capable of preventing or reducing the expression of IL-11 or IL-11R.

30. The method of para 29, wherein the method further comprises selecting a subject determined to have upregulated IL-11 or IL-11R for treatment with an agent capable of inhibiting the action of IL-11 or with an agent capable of preventing or reducing the expression of IL-11 or IL-11R.

31. A method of diagnosing fibrosis or a risk of developing fibrosis in a subject, the method comprising determining, optionally in vitro, one or more genetic factors in the subject that are predictive of upregulation of Interleukin 11 (IL-11) or an Interleukin 11 receptor (IL-11R) expression, or of upregulation of IL-11 or IL-11R activity.

32. The method of para 31, wherein the method is a method of confirming a diagnosis of fibrosis in a subject suspected of having fibrosis.

33. The method of para 32 or 32, wherein the method further comprises selecting the subject for treatment with an agent capable of inhibiting the action of IL-11 or with an agent capable of preventing or reducing the expression of IL-11 or IL-11R.

34. A method of providing a prognosis for a subject having, or suspected of having, fibrosis, the method comprising determining, optionally in vitro, one or more genetic factors in the subject that are predictive of upregulation of Interleukin 11 (IL-11) or an Interleukin 11 receptor (IL-11R) expression, or of upregulation of IL-11 or IL-11R activity.

BRIEF DESCRIPTION OF THE FIGURES

Embodiments and experiments illustrating the principles of the invention will now be discussed with reference to the accompanying figures in which:

FIGS. 2A, 2B, 2C and 2D. Human atrial fibroblasts were incubated either with 5 ng/ml TGFβ1 or 5 ng/ml IL-11 for 24 hours. Charts show cell staining for (2A) α-SMA (myofibroblasts), (2B) EdU (proliferation), (2C) collagen and (2D) periostin to identify myofibroblasts and highly proliferative cells and to quantify the production of extracellular matrix proteins. IL-11 was found to increase the myofibroblast ratio and induce the production of collagen and periostin at a similar rate as TGFβ1 signaling. This experiment was repeated a number of times with similar results.

FIGS. 8A, 8B, 8C, 8D and 8E. IL-11 is a fibrosis marker and activator across multiple tissues. Expression of IL-11 can be induced by a diverse set of upstream pro-fibrotic stimulants in addition to TGFβ1. (8A) Chart showing effect of TGFβ1 on IL-11 expression. (8B) Chart showing ET-1 (Endothelin) upregulates IL-11 in hepatic and pulmonary fibroblasts; (8C) Chart showing PDGF (platelet derived growth factor) induces IL-11 expression in renal fibroblasts. IL-11 RNA levels were measured by RT-qPCR; adjusted P-values are given as *P<0.05, P<0.01 or **P<0.0001 (Dunnett). To investigate the systemic effect of IL-11, saline only (grey) or recombinant IL-11 (black) was injected 6 times a week in C57BL/6 mice (200 μg/kg). Collagen content in tissue was assessed with a hydroxyproline assay (QuickZyme) on the protein level and the results are shown in chart (8D). Tissues of animals treated with rIL-11 have higher collagen protein content than controls (ANOVA; p=0.012). (8E) Photographs of western blot showing αSMA levels are increased in the kidney and heart of IL-11 treated mice, indicating the presence of myofibroblasts.

FIG. 11. Nucleotide sequence of human IL-11, taken from Genbank accession number gi|391353405|ref|NM_000641.3 (Homo sapiens interleukin 11 (IL11), transcript variant 1, Mrna) [SEQ ID NO:1]. Underlined sequence encodes IL-11 mRNA. Shaded sequences were used for design of IL-11 knockdown siRNA and are shown separately as SEQ ID NOs 2 to 5. SEQ ID NOs 3 and 4 overlap with each other within SEQ ID NO:1.

FIG. 12. Nucleotide sequence of human IL-11Rα, taken from Genbank accession number gi|975336|gb|U32324.1|HSU32324 (Human interleukin-11 receptor alpha chain mRNA, complete cds) [SEQ ID NO:6]. Underlined sequence encodes IL-11Rα mRNA. Shaded sequences were used for design of IL-11Rα knockdown siRNA and are shown separately as SEQ ID NOs 7 to 10.

FIG. 13. Table showing siRNA sequences [SEQ ID NOs 11 to 14] for knockdown of IL-11.

FIG. 14. Table showing siRNA sequences [SEQ ID NOs 15 to 18] for knockdown of IL-11Rα.

Fluorescence was normalized to the control group without stimulation. [Mean±SD, Dunnett] *P<0.05, P<0.01, *P<0.001 or ****P<0.0001.

Figure 23A:
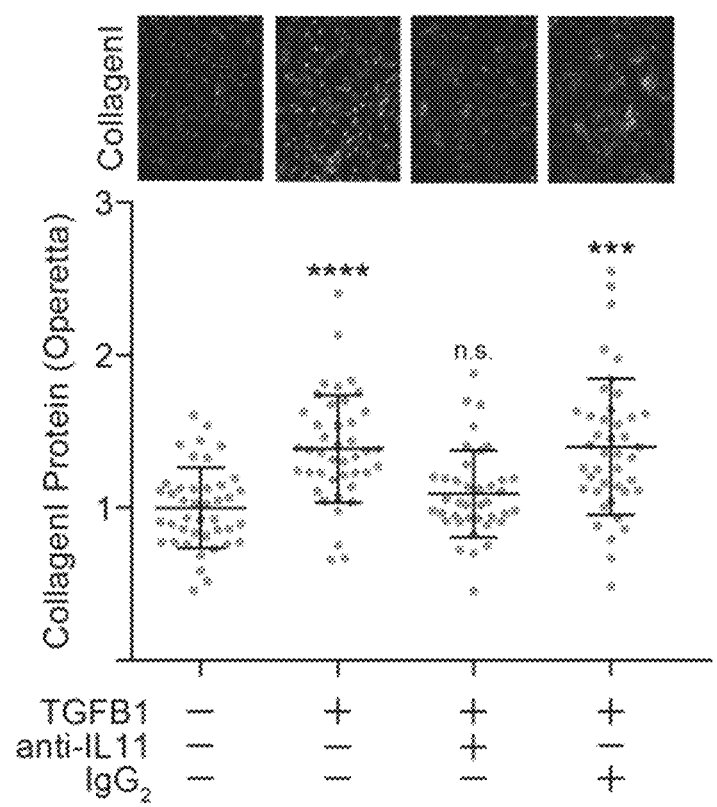
Figure 23B:
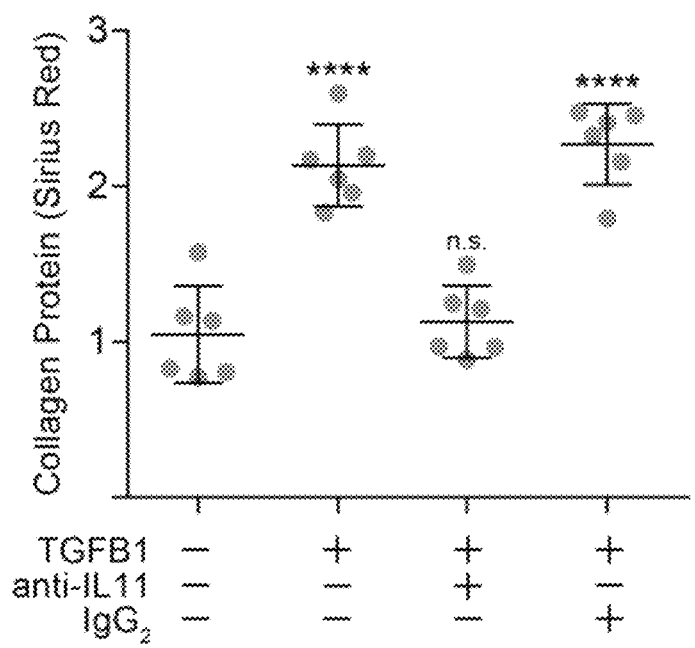

FIGS. 23A and 23B. Graphs and images showing the effect of neutralisation of IL-11 on collagen production triggered by TGFβ1. Collagen production by cardiac fibroblasts with or without stimulation with TGFβ1, and in the presence/absence of neutralising anti-IL-11 antibody or isotype control IgG, as determined by (23A) Operetta assay or (23B) Sirius Red staining. [Mean±SD, Dunnett] *P<0.05, P<0.01, *P<0.001 or ****P<0.0001.

Figure 24:
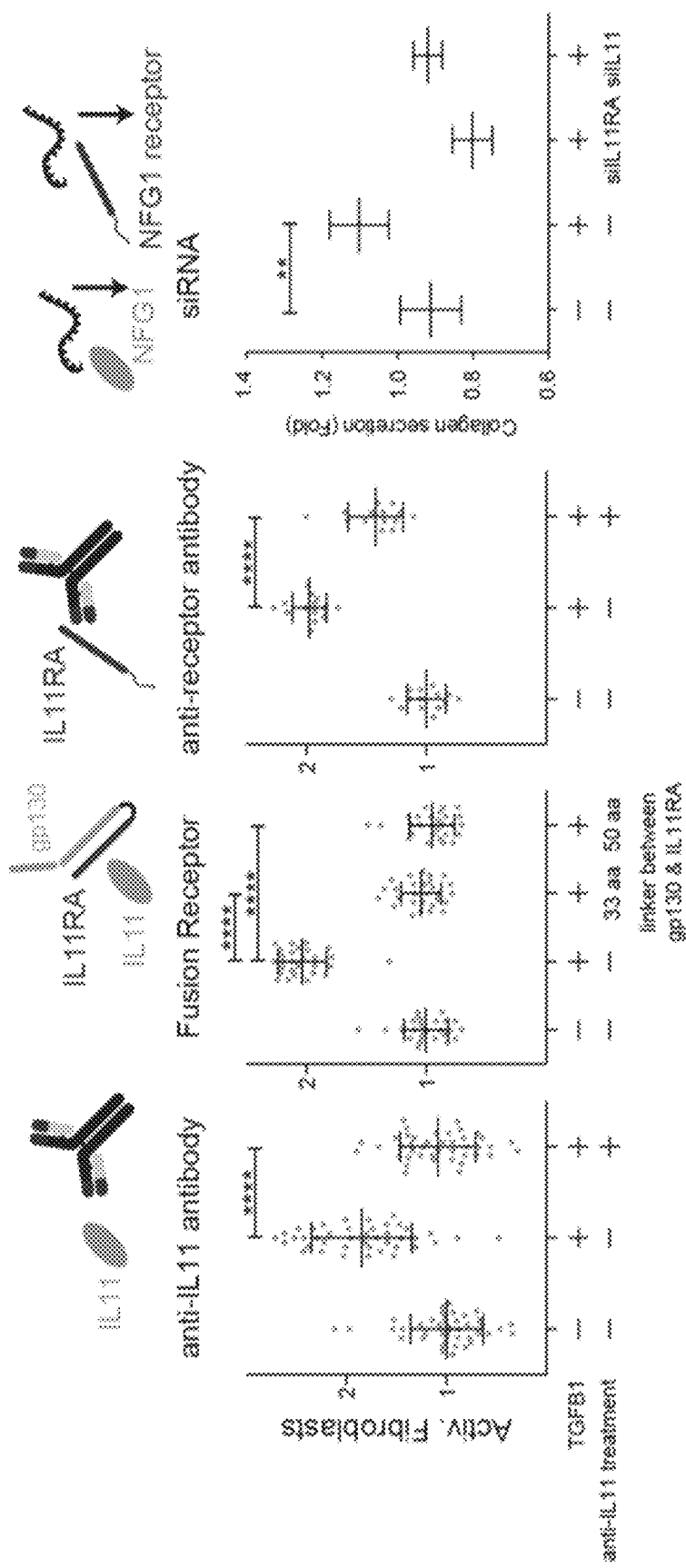
Figure 25A:
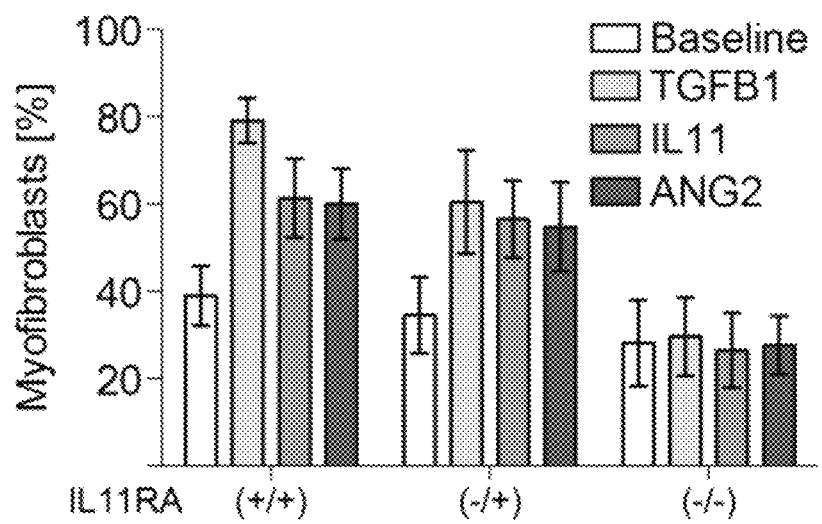
Figure 25B:
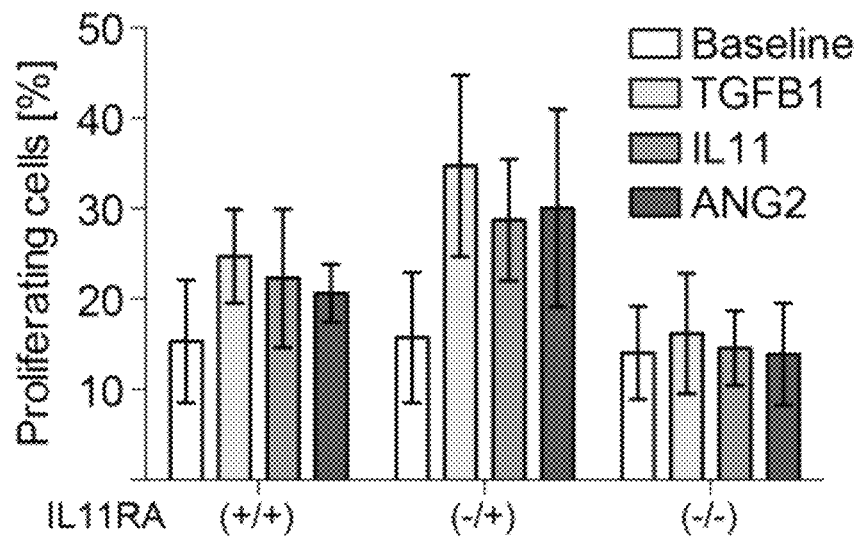
Figure 25C:
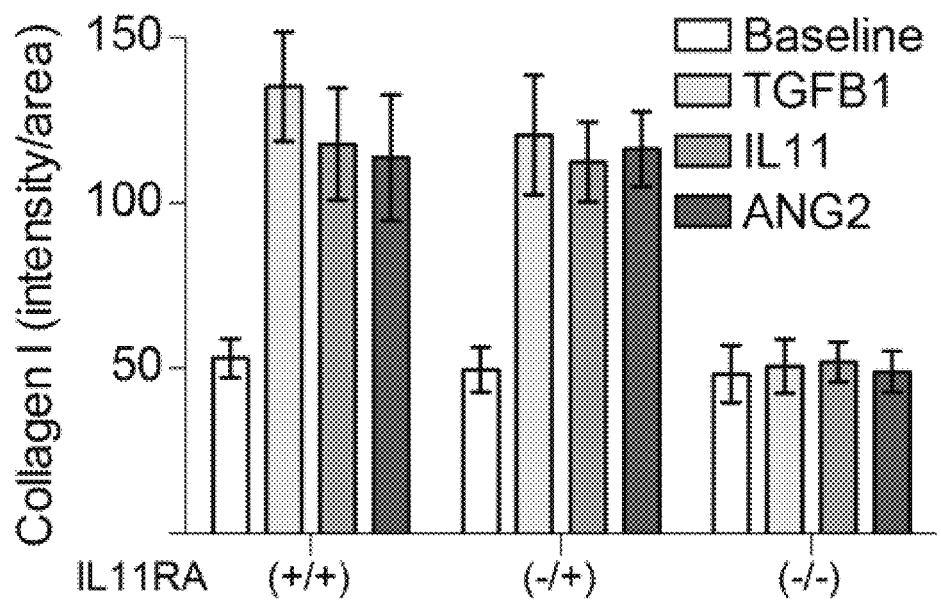
Figure 25D:
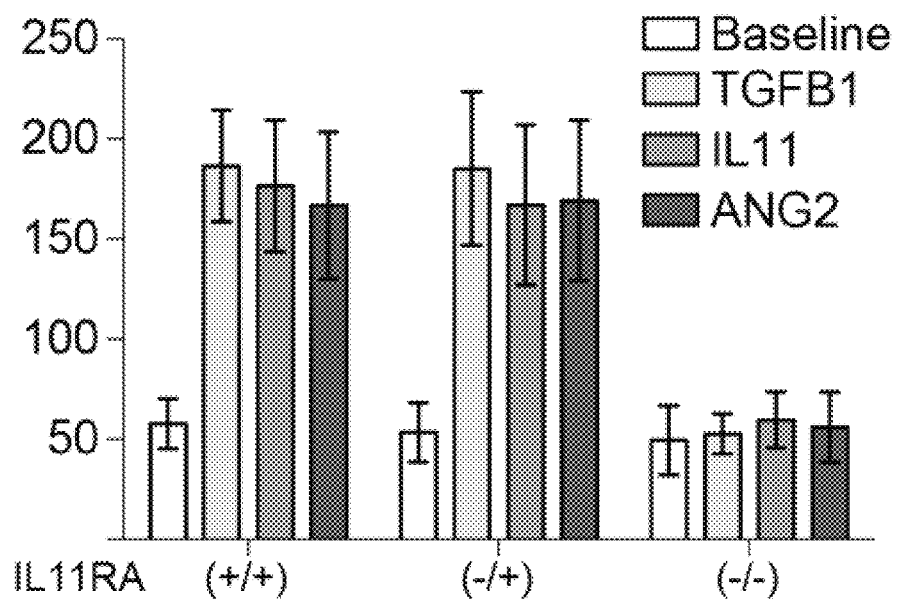

FIG. 24. Graphs showing the ability of various IL-11 and IL-11Rα antagonists to inhibit fibrosis. Human atrial fibroblasts were treated with neutralizing antibody against IL-11, neutralizing antibody against IL-11Rα, decoy IL-11 receptor molecule that binds to IL-11, siRNA that downregulates IL-11 expression or siRNA that downregulates IL-11RA expression and the effect on the TGFβ1-driven pro-fibrotic response in fibroblasts in vitro was analysed. [Mean±SD, Dunnett] *P<0.05, P<0.01, *P<0.001 or ****P<0.0001.

FIGS. 25A, 25B, 25C and 25D. Bar charts showing the response of fibroblasts from IL-11-RA knockout mice to pro-fibrotic treatment. Fibroblasts derived from IL-11RA WT (+/+), Heterozygous (+/−) and Homozygous null (−/−) mice were incubated for 24 h with TGFβ1, IL-11 or AngII (5 ng/ml). (25A) Percentage of myofibroblasts as determined by analysis αSMA content, (25B) Percentage proliferating cells as determined by staining for EdU, (25C) Collagen content and (25D) ECM production as measured by detection of periostin [Mean±SD].

Figure 26A:
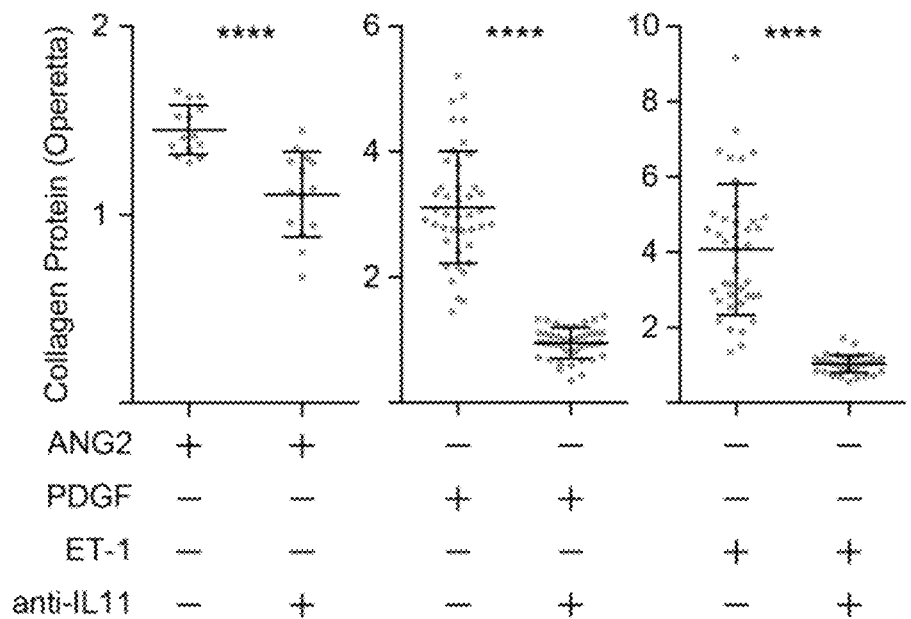
Figure 26B:
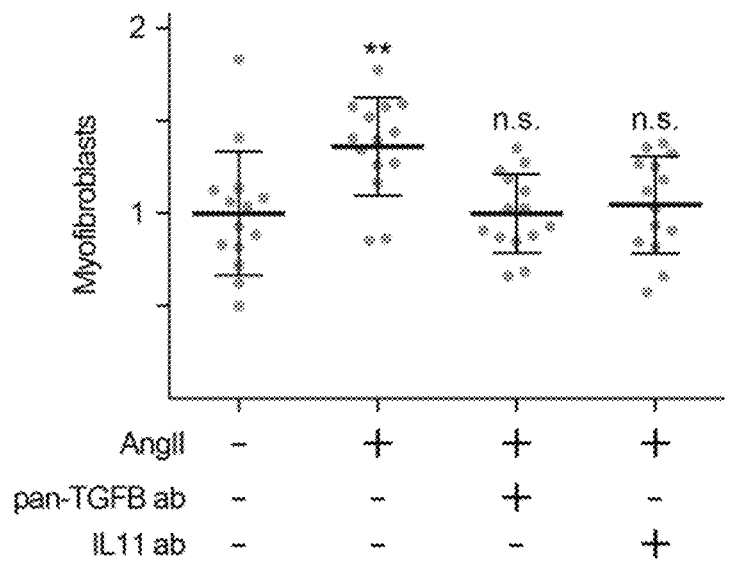
Figure 27A:
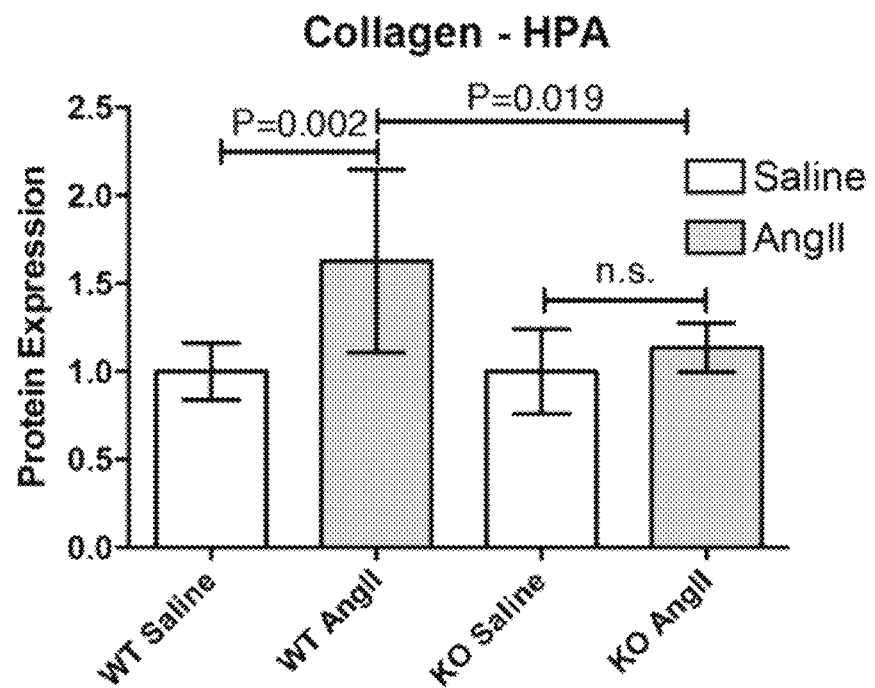
Figure 27B:
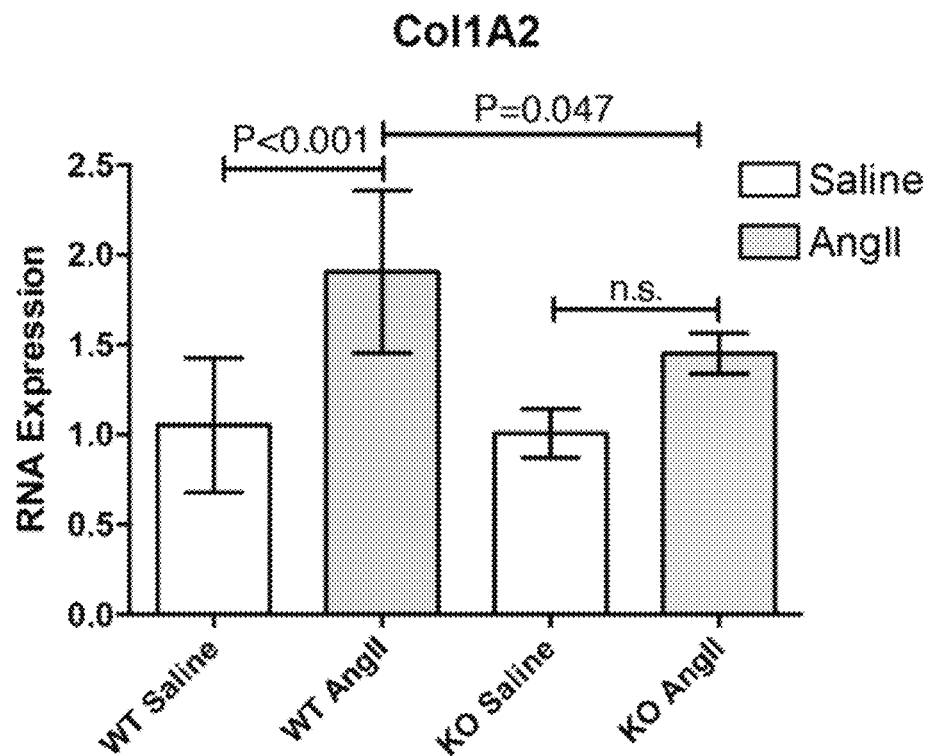
Figure 27C:
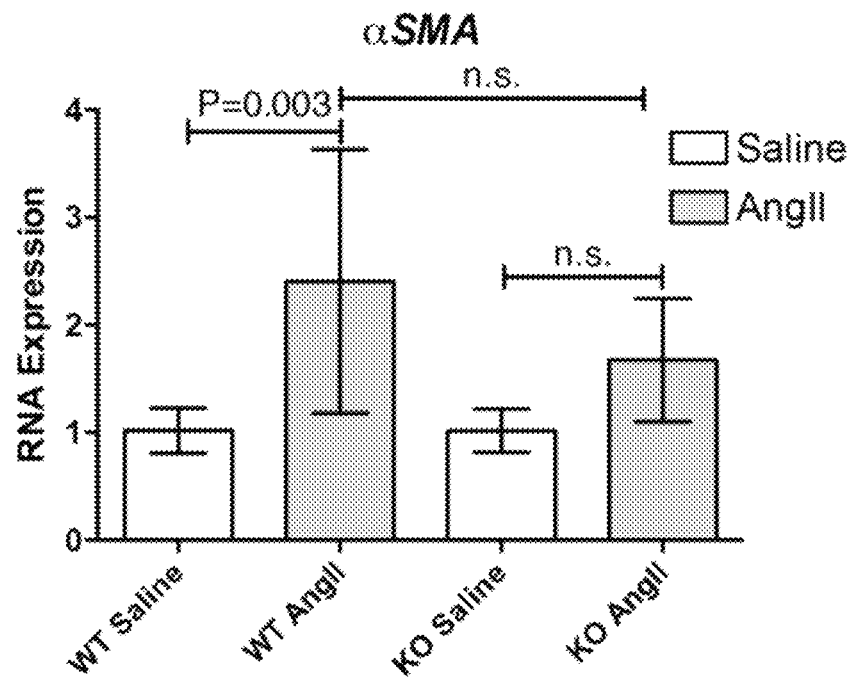
Figure 27D:
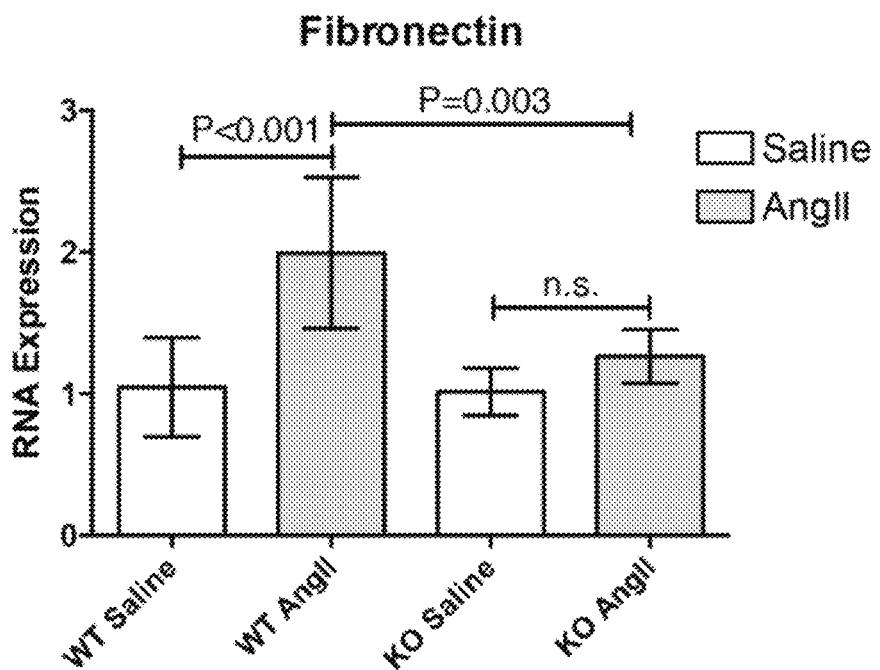

FIGS. 26A and 26B. Graphs showing the effect of IL-11 neutralisation on fibrosis in response to various pro-fibrotic stimuli. Fibroblasts were cultured in vitro in the presence/absence of various different pro-fibrotic factors, and in the presence/absence of neutralising anti-IL-11 antibody or pan anti-TGFβ antibody (26A) Collagen production and (26B) myofibroblast generation as determined by analysis of αSMA expression. [Mean±SD, Dunnett] *P<0.05, P<0.01, *P<0.001 or ****P<0.0001.

FIGS. 27A, 27B, 27C and 27D. Bar charts showing expression of markers of fibrosis in the atrium and heart of WT and IL-11RA (−/−) animals following treatment with AngII treatment. (27A) Collagen content, as measured by hydroxyproline assay. (27B) Collagen (Col1A2) expression. (27C) αSMA (ACTA2) expression. (27D) Fibronectin (Fn1) expression.

Figure 28:
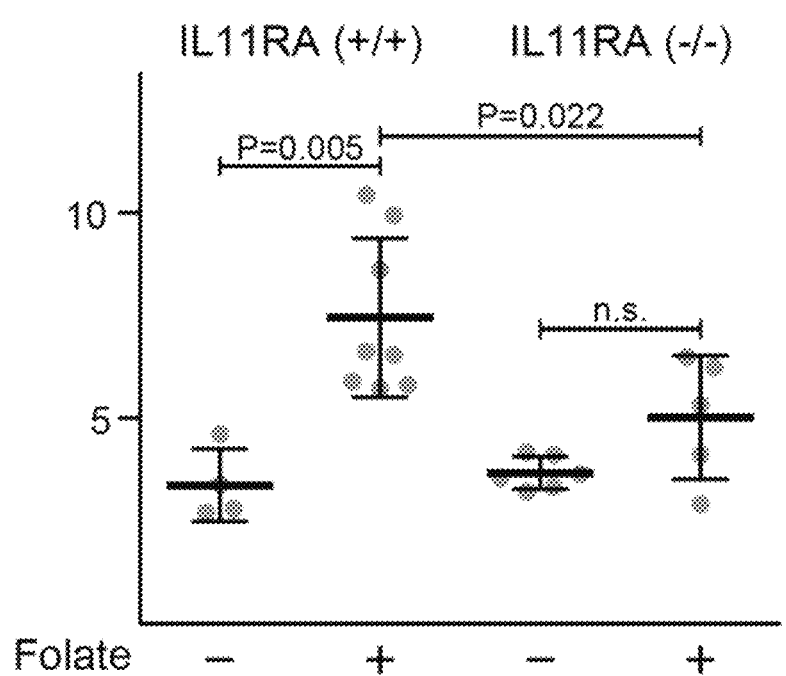

FIG. 28. Graphs showing the effect of IL-11RA knockout on folate-induced kidney fibrosis as measured by collagen content in kidney tissue.

Figure 29A:
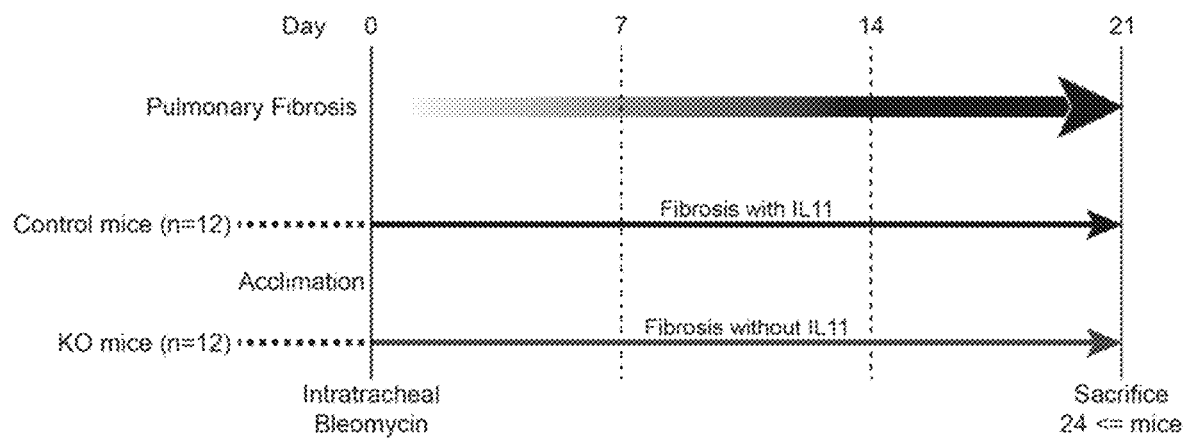
Figure 29B:
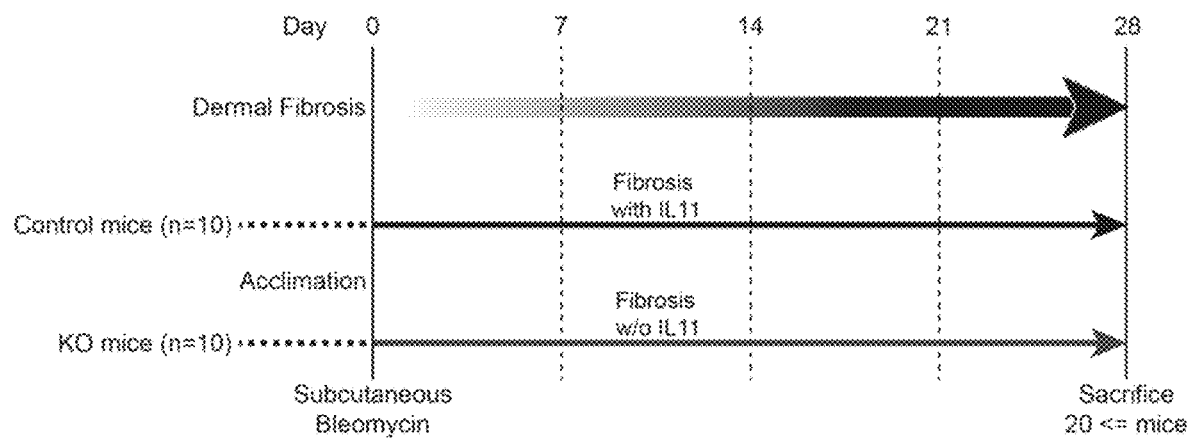
Figure 29C:
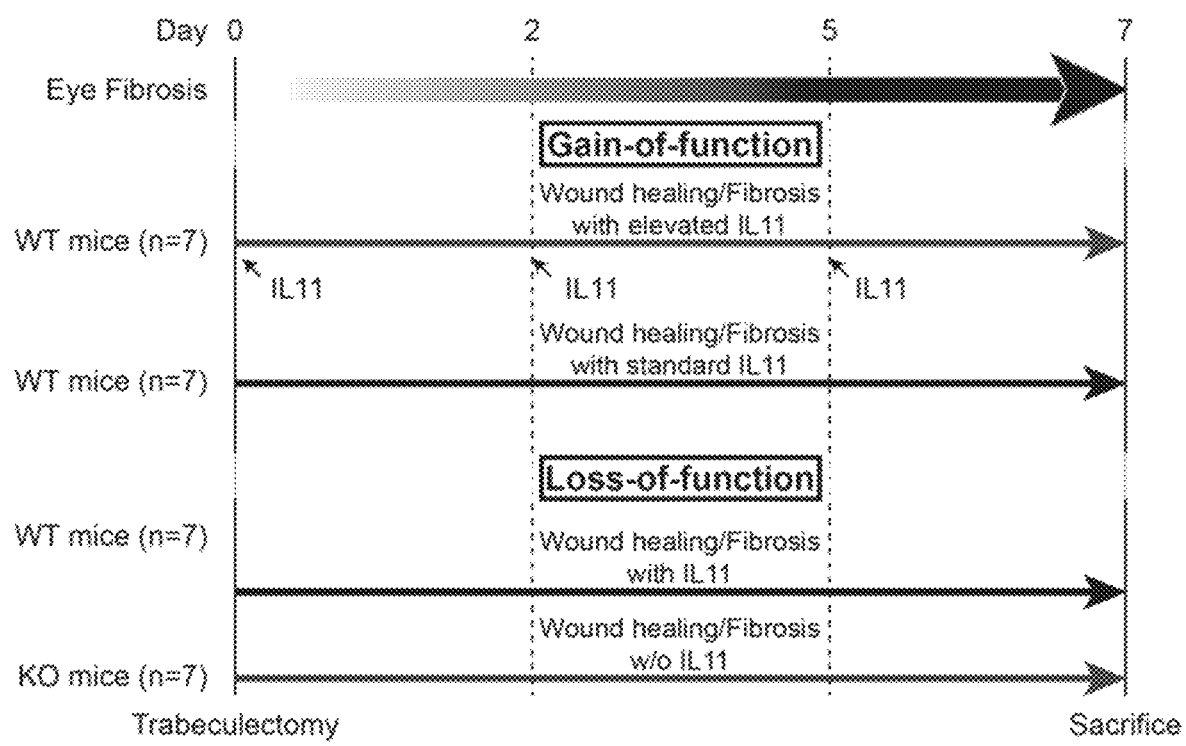

FIGS. 29A, 29B and 29C. Schematics of the experimental procedures for analysing fibrosis in (29A) lung, (29B) skin and (29C) eye for IL-11RA −/− mice as compared to IL-11RA +/+ mice.

Figure 30A:
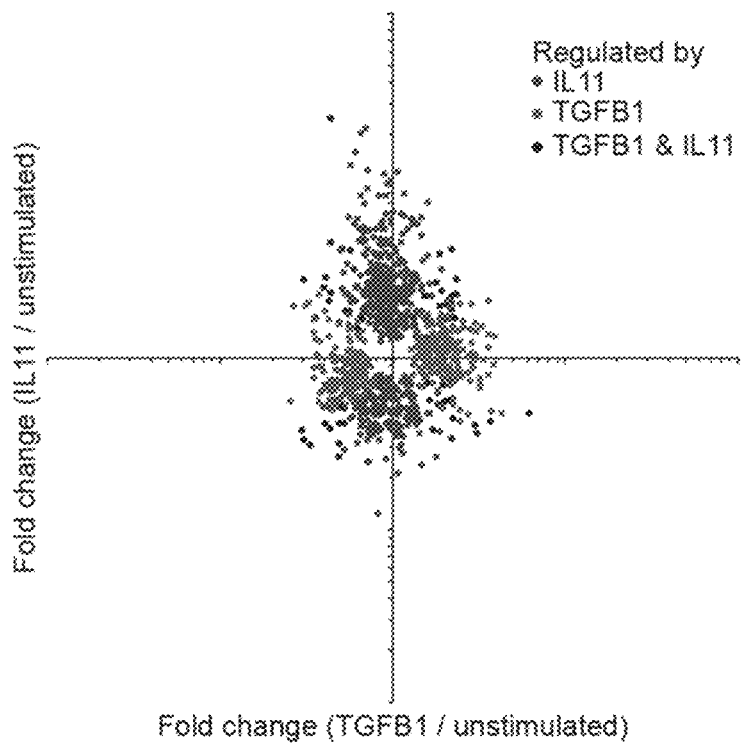
Figure 30B:
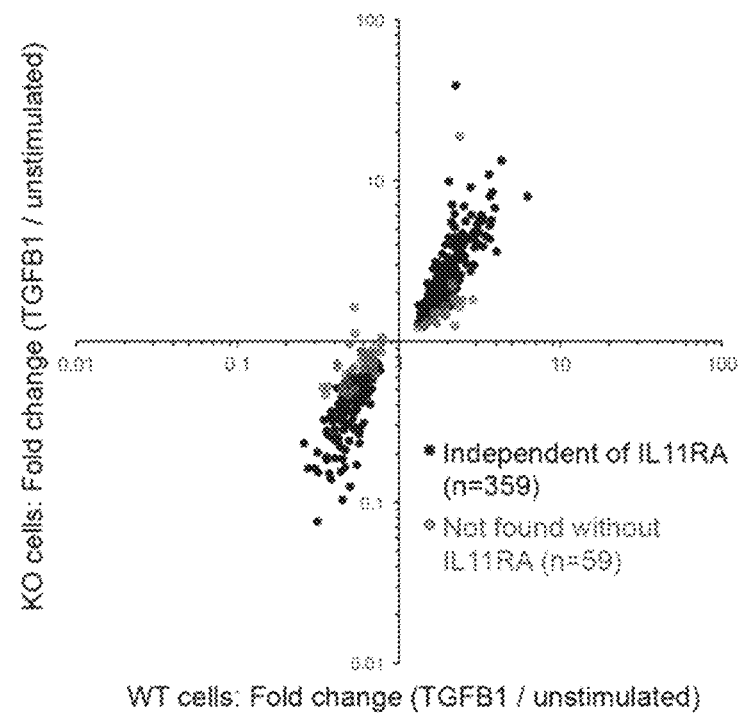

FIGS. 30A and 30B. Scatterplots showing fold change in gene expression. (30A) Fold changes in gene expression in fibroblasts following stimulation with TGFβ1, IL-11 or TGFβ1 and IL-11. (30B) Fold changes in gene expression in fibroblasts obtained from IL-11RA+/+ and IL-11RA−/− mice following stimulation with TGFβ1.

Figure 31A:
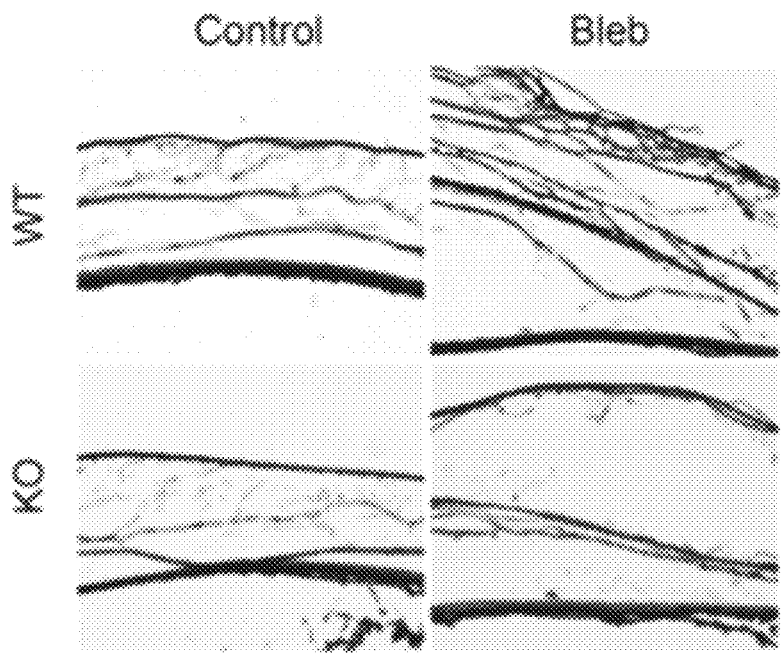
Figure 31B:
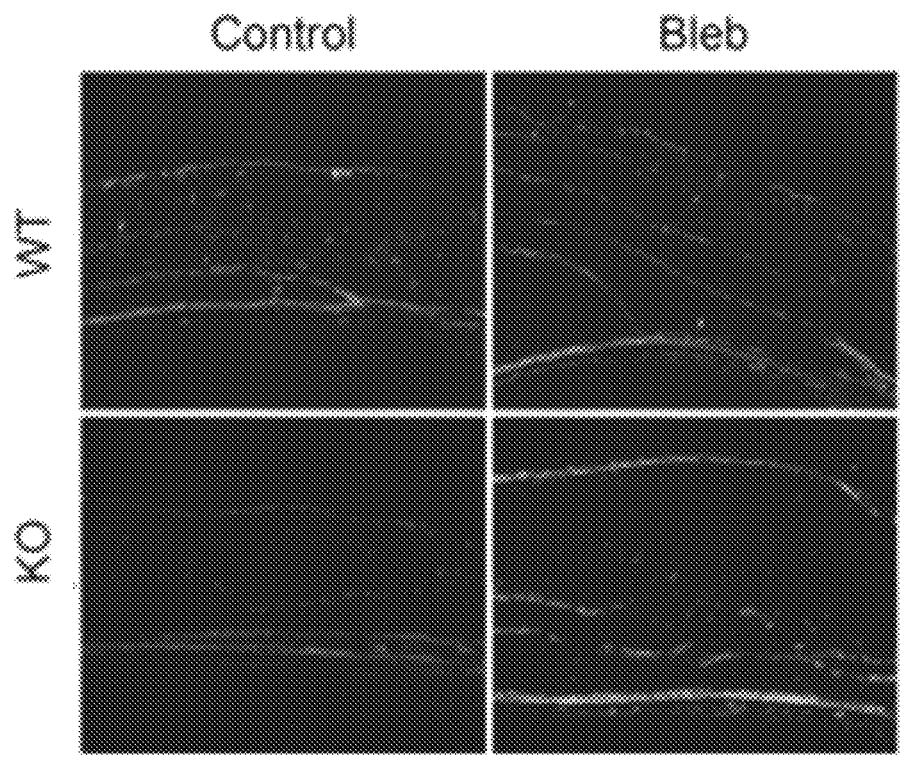

FIGS. 31A and 31B. Photographs showing the effect of IL-11RA knockout on wound healing and fibrosis in the eye following trabeculectomy (filtration surgery). (31A) Eye sections of IL-11RA+/+ (WT) and IL-11RA−/− (KO) animals 7 days after filtration surgery. (31B) Maturation of collagen fibres as evaluated by picro-sirius red/polarization light technique (Szendroi et al. 1984, Acta Morphol Hung 32, 47-55); more fibrosis is observed in WT mice than KO mice.

Figure 32A:
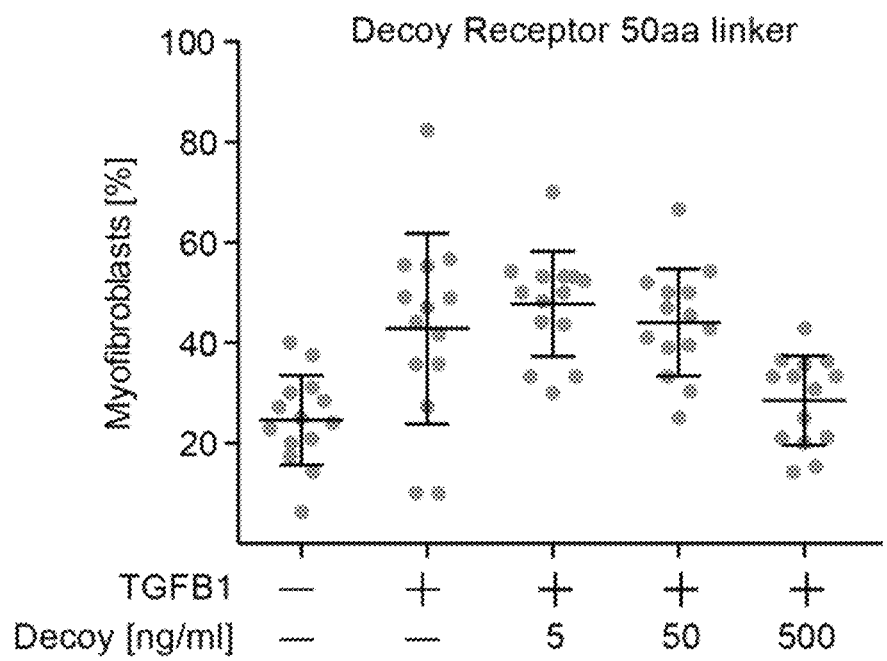
Figure 32B:
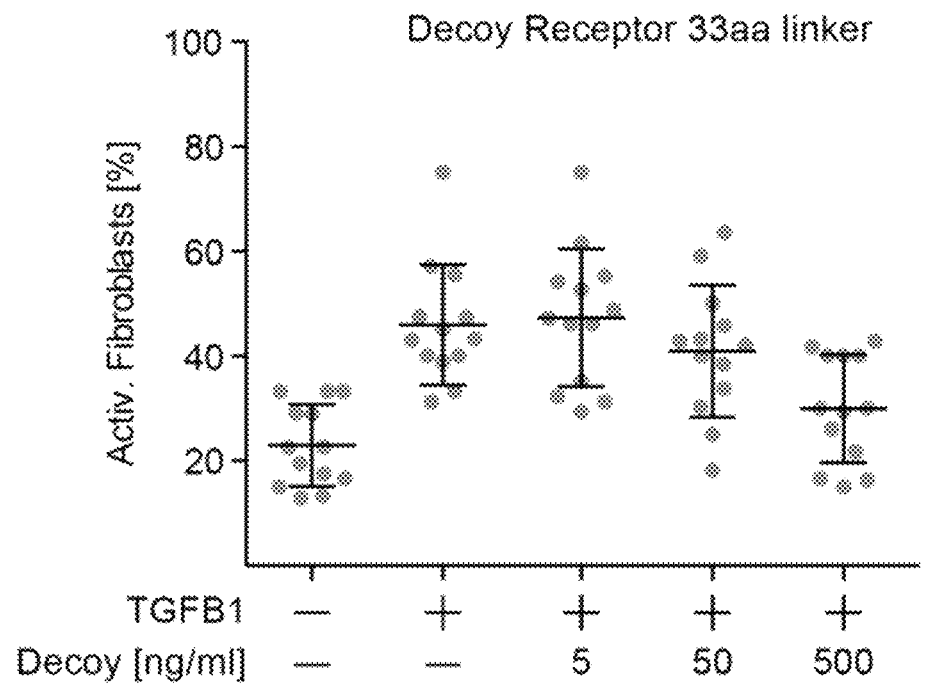
Figure 36A:
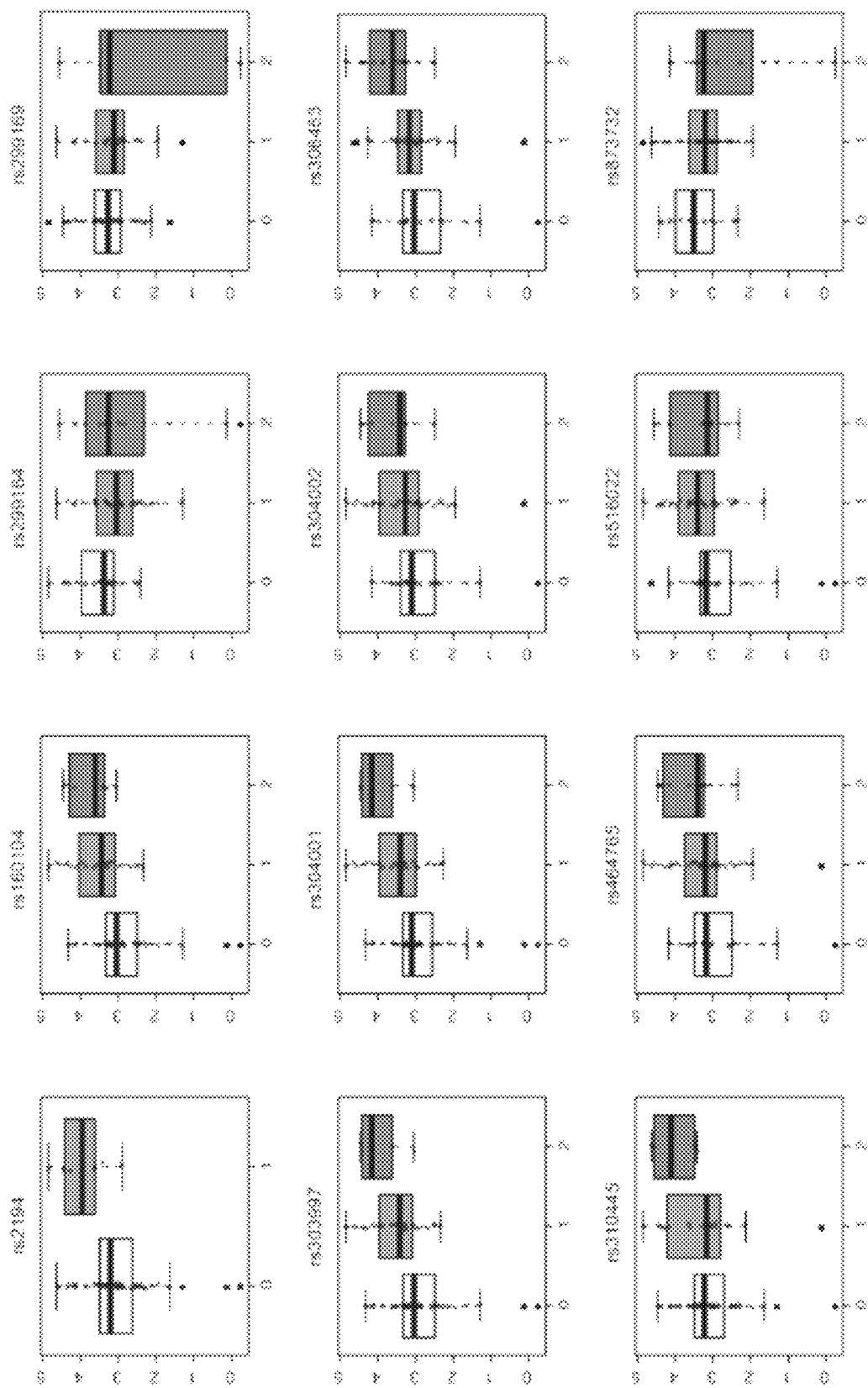
Figure 36B:
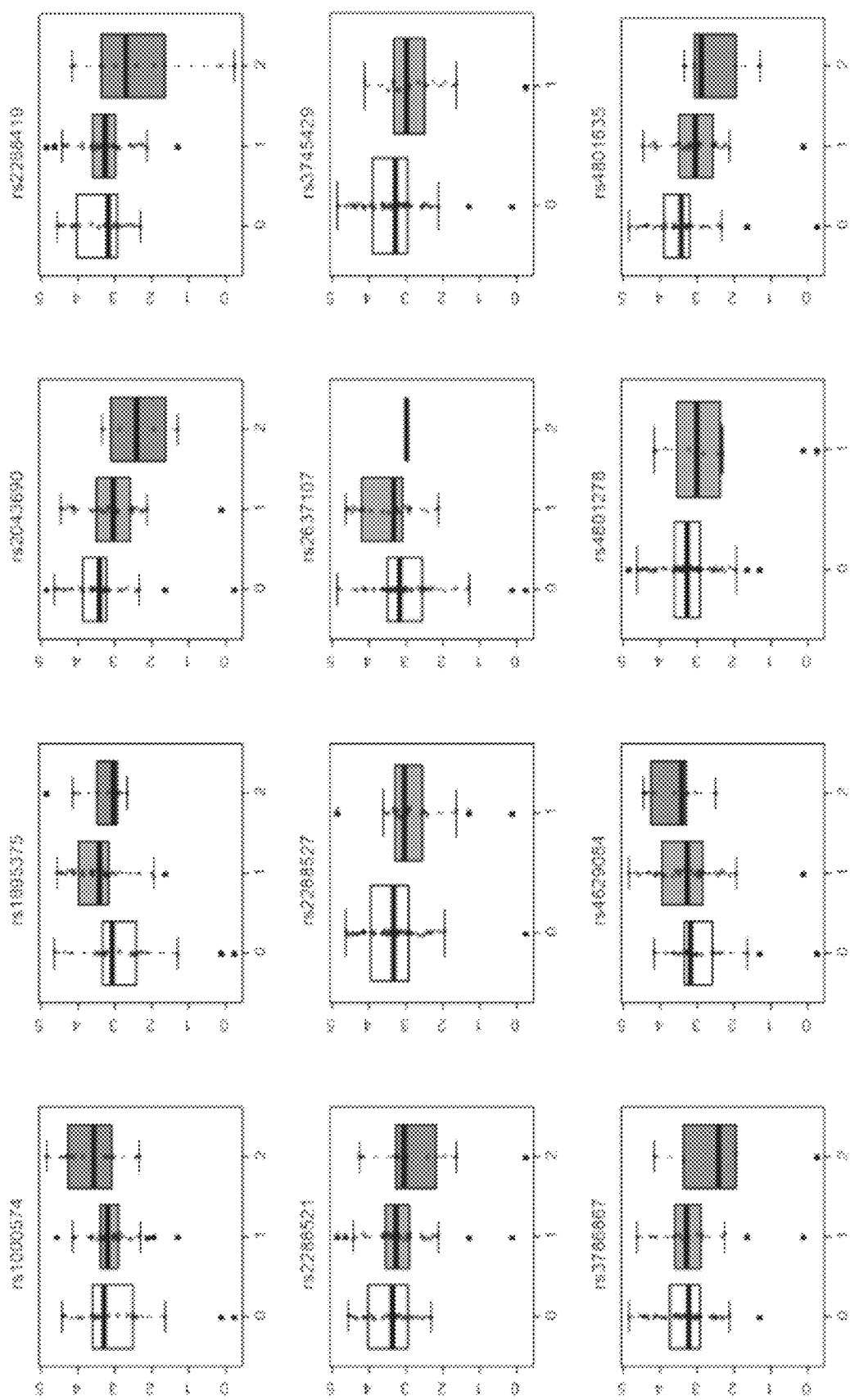
Figure 36C:
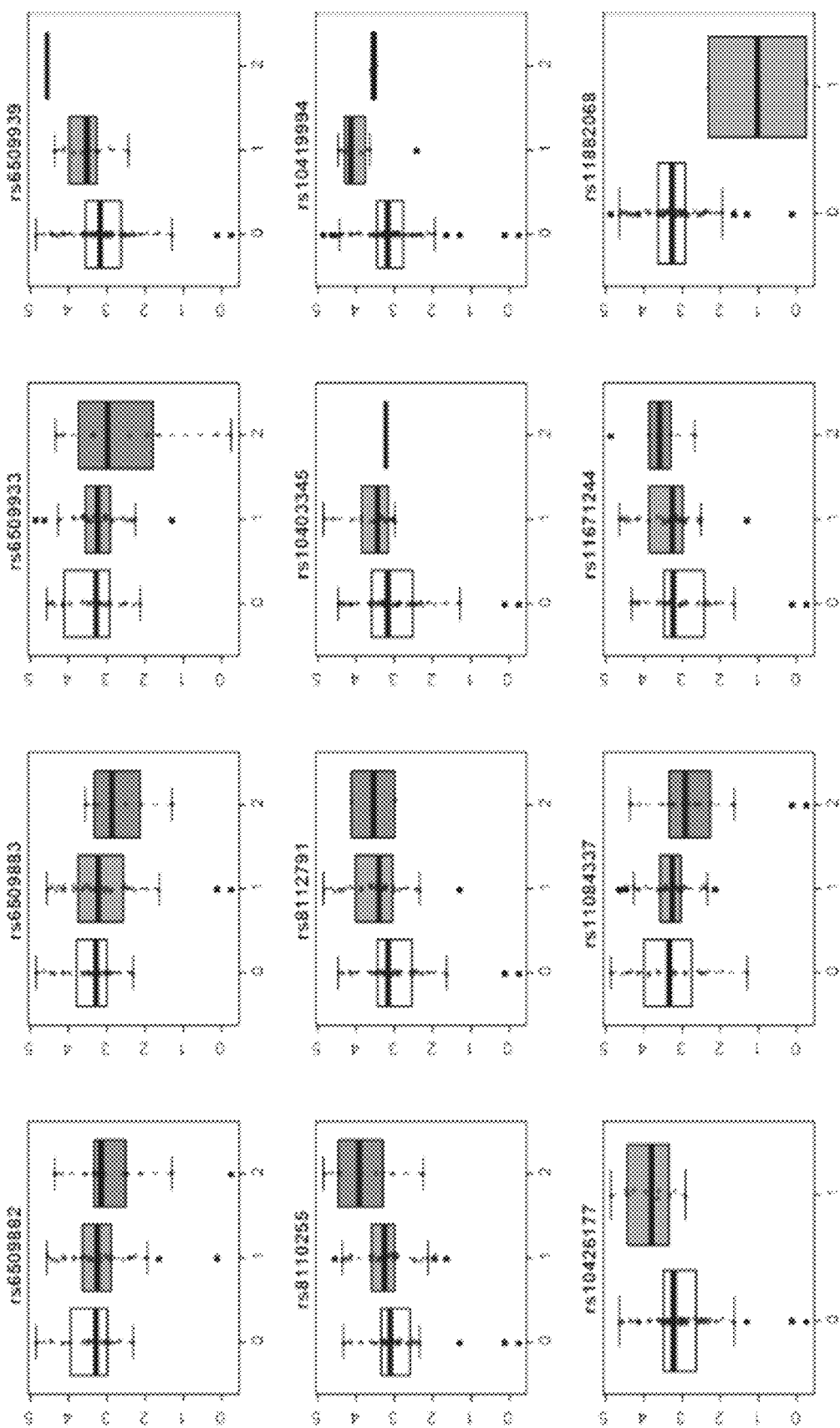
Figure 36D:
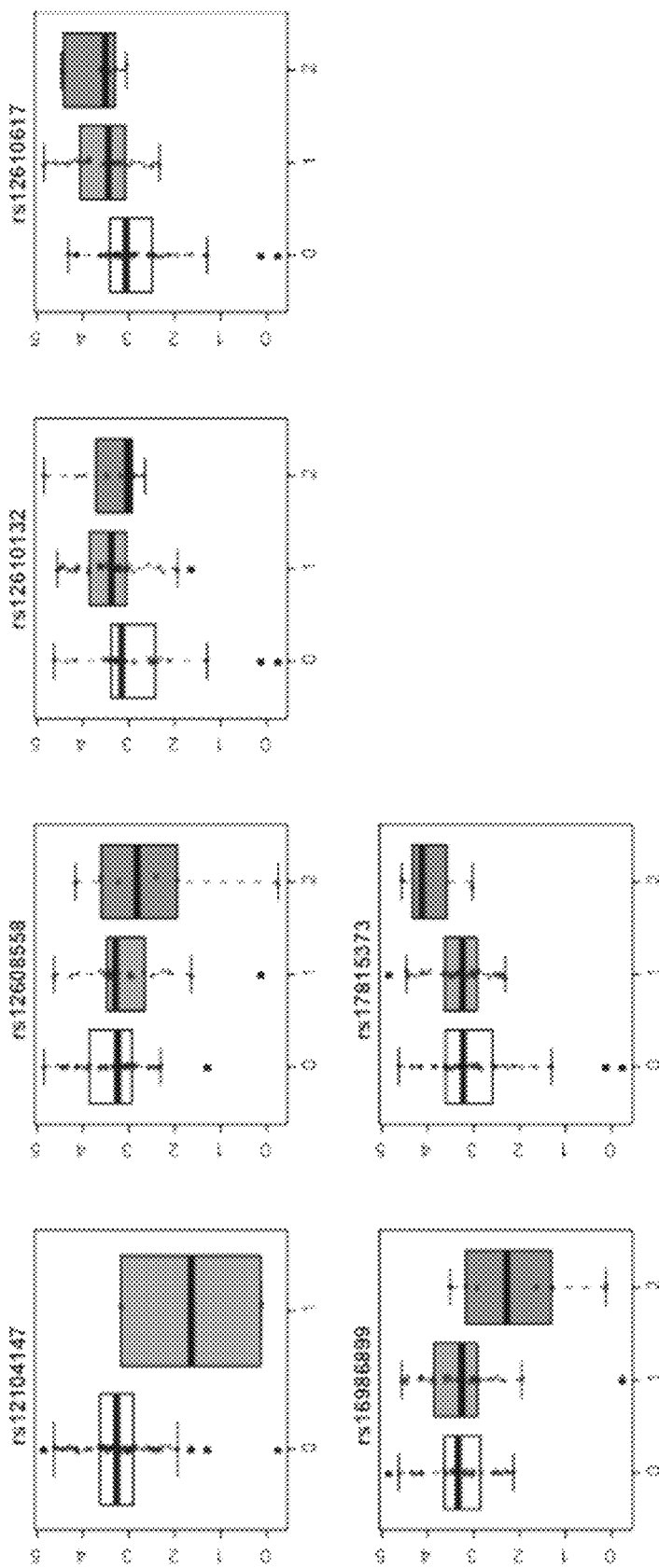

FIGS. 32A and 32B. Graphs showing the effect of decoy IL-11 receptors on fibrosis in response to stimulation with TGFβ1. Fibroblasts were cultured in vitro in the presence/absence of TGFβ1 (5 ng/ml), in the presence or absence of (32A) D11R1 (Decoy Receptor 50aa Linker) or (32B) D11R2 (Decoy Receptor 33aa Linker), at various different concentrations. Myofibroblast generation after 24 hours (i.e. the percentage of activated fibroblasts) was determined by analysis of αSMA expression.

FIG. 33. Table showing SNPs regulation of IL-11 $VST_{stim}$ in trans.

FIG. 34. Table showing SNPs regulation of IL-11 $VST_{stim}-VST_{unstim}$ in cis.

FIG. 35. Table showing SNPs regulation of IL-11 $VST_{stim}-VST_{unstim}$ in trans.

FIGS. 36A, 36B, 36C and 36D Charts showing regulation of IL-11 response by local SNPs. The RNA of unstimulated and stimulated (TGFB1, 5 ng/ml, 24 h) fibroblasts derived from 69 genotyped individuals was sequenced. Samples were grouped according to genotype and the increase in IL-11 expression ($VST_{stim}-VST_{unstim}$) was compared between groups with 0, 1 or 2 minor alleles.

Figure 37:
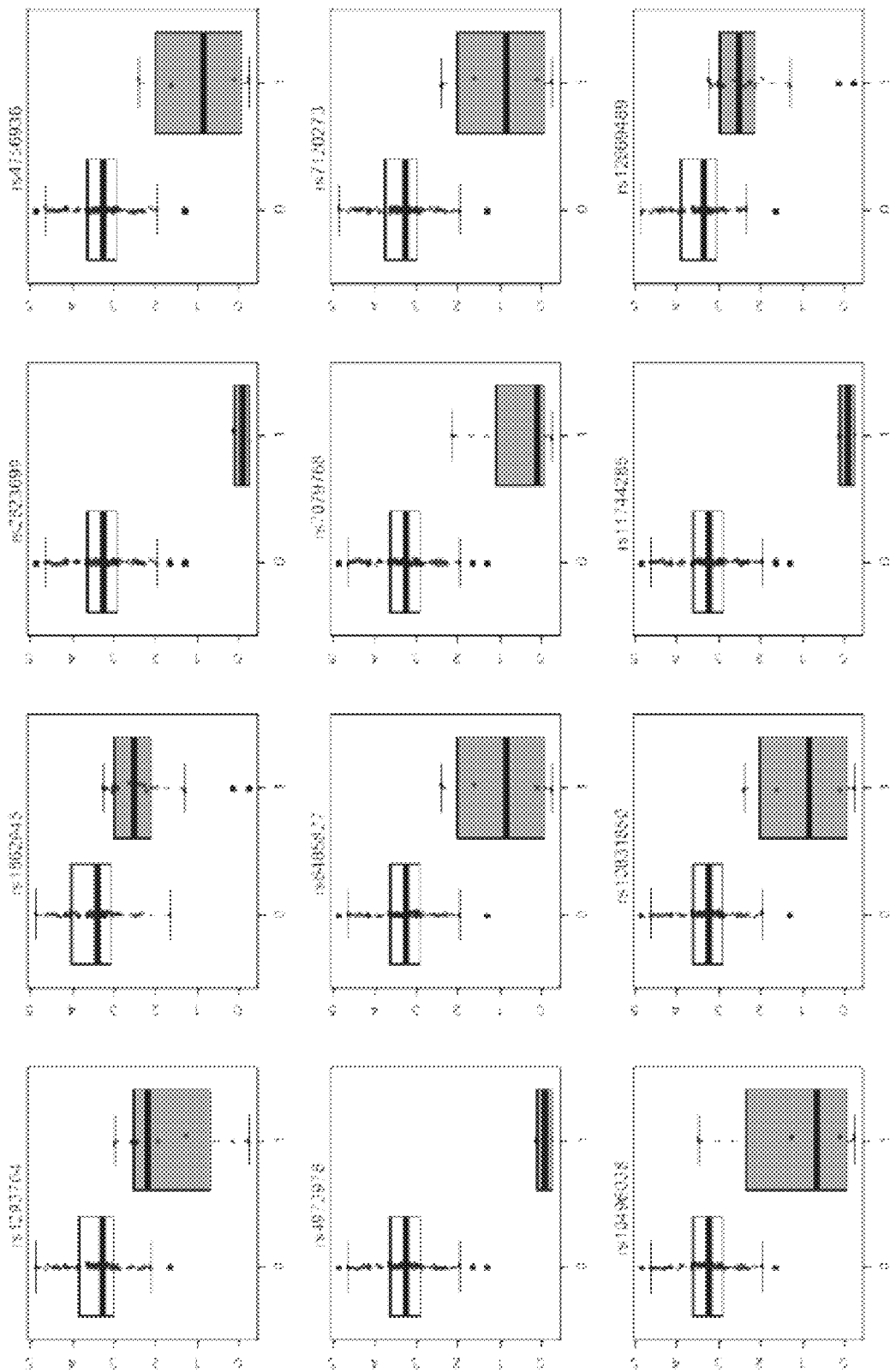
Figure 38A:
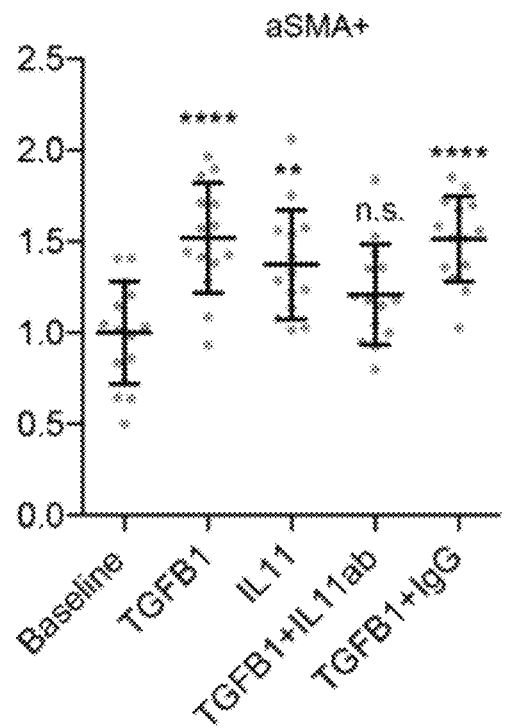
Figure 38B:
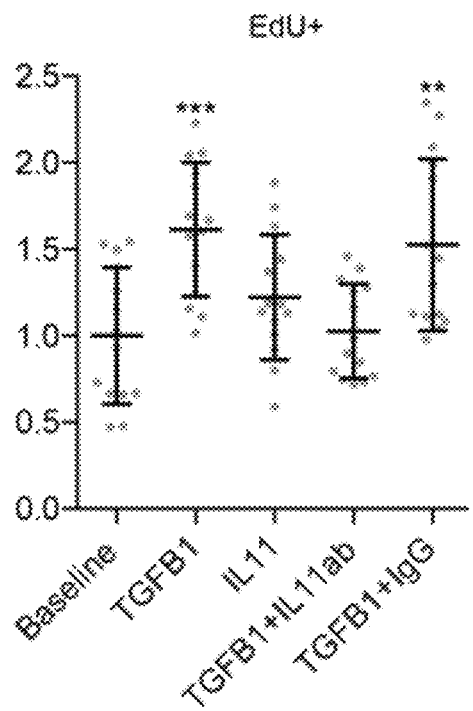
Figure 38C:
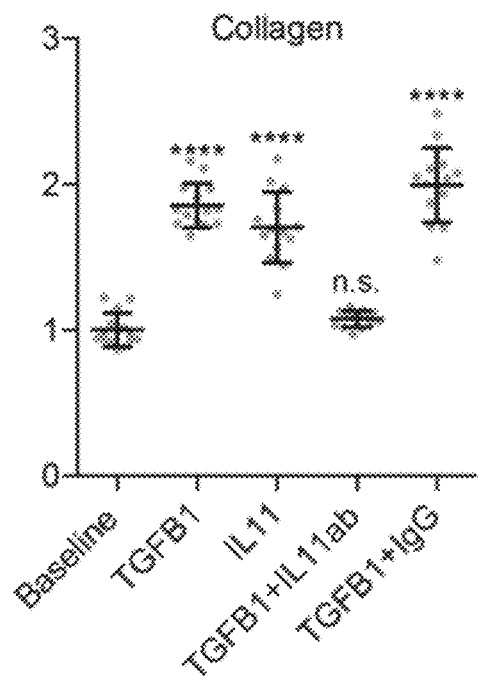
Figure 38D:
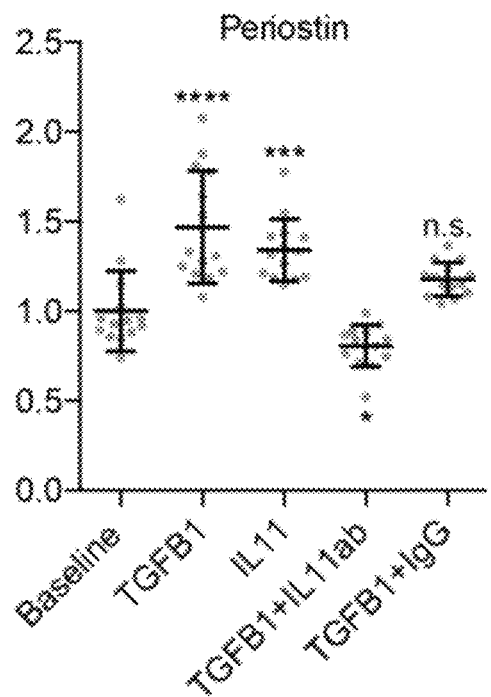

FIG. 37. Charts showing regulation of IL-11 response by distant SNPs. The RNA of unstimulated and stimulated (TGFB1, 5 ng/ml, 24 h) fibroblasts derived from 69 genotyped individuals was sequenced. Samples were grouped according to genotype and the increase in IL11 expression ($VST_{stim}-VST_{unstim}$) was compared between groups with 0, or 1 minor allele.

FIGS. 38A, 38B, 38C and 38D. Graphs showing that IL-11 is required the pro-fibrotic effects of TGFβ1 in liver fibroblasts. Activation and proliferation of primary human liver fibroblasts, with or without stimulation with TGFβ1, and in the presence/absence of neutralising anti-IL-11 antibody or isotype control IgG, as measured by analysis of the proportion of (38A) α-SMA positive cells, (38B) EdU positive cells, (38C) Collagen positive cells and (38D) Periostin positive cells as compared to the unstimulated cells (Baseline). [Mean±SD, Dunnett] *P<0.05, P<0.01, *P<0.001 or ****P<0.0001.

Figure 39:
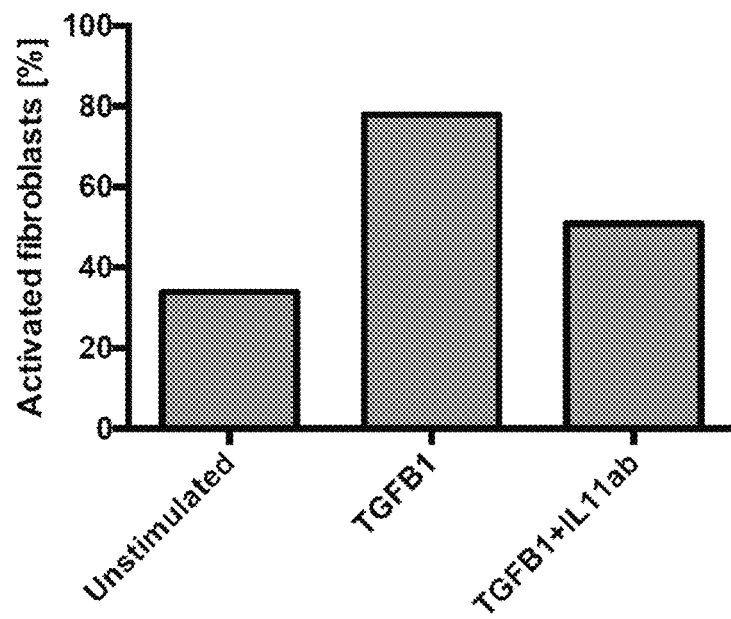

FIG. 39. Bar chart showing that IL-11 is required for the pro-fibrotic effects of TGFβ1 in skin fibroblasts. Activation of mouse skin fibroblasts, with or without stimulation with TGFβ1, and in the presence/absence of neutralising anti-IL-11 antibody, as measured by analysis of the percentage of α-SMA positive cells (activated fibroblasts).

Figure 40:
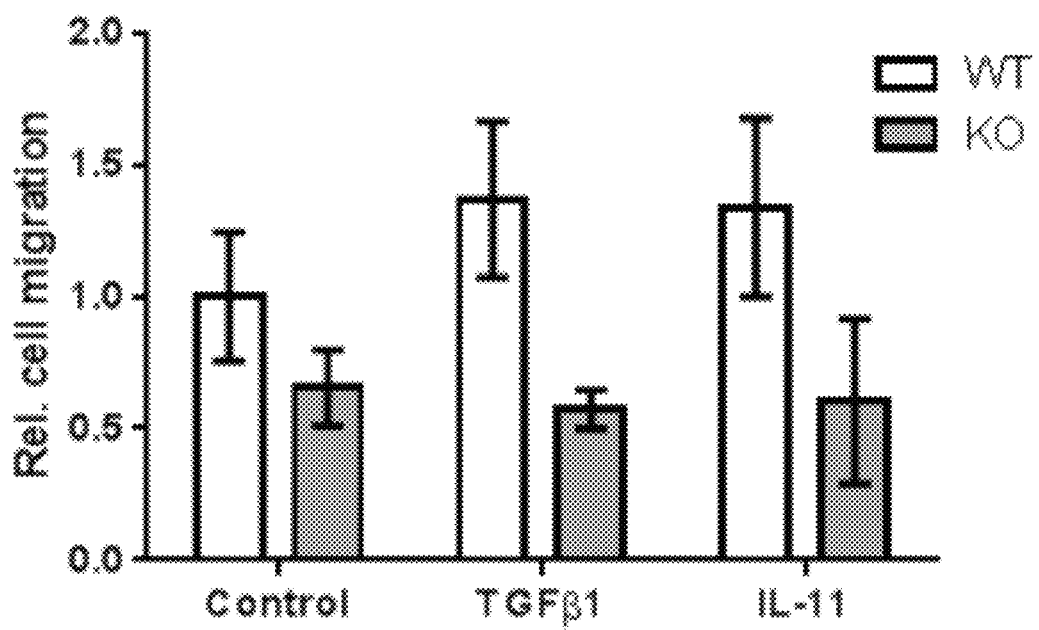

FIG. 40. Bar chart showing lung fibroblast cell migration with and without IL-11 signalling. Migration of lung fibroblasts from IL-11RA+/+(WT) and IL-11RA−/− (KO) animals was analysed in an in vitro scratch assay without stimulus, or in the presence of TGFβ1 or IL-11.

DETAILED DESCRIPTION OF CERTAIN EMBODIMENTS OF THE INVENTION

IL-11 and IL-11 Receptor

Interleukin 11 (IL-11), also known as adipogenesis inhibitory factor, is a pleiotropic cytokine and a member of the IL-6 family of cytokines that includes IL-6, IL-11, IL-27, IL-31, oncostatin, leukemia inhibitory factor (LIF), cardiotrophin-1 (CT-1), cardiotrophin-like cytokine (CLC), ciliary neurotrophic factor (CNTF) and neuropoetin (NP-1).

IL-11 is transcribed with a canonical signal peptide that ensures efficient secretion from cells. The immature form of human IL-11 is a 199 amino acid polypeptide whereas the mature form of IL-11 encodes a protein of 178 amino acid residues (Garbers and Scheller., Biol. Chem. 2013; 394(9): 1145-1161). The human IL-11 amino acid sequence is available under UniProt accession no. P20809 (P20809.1 GI:124294). Recombinant human IL-11 (oprelvekin) is also commercially available. IL-11 from other species, including mouse, rat, pig, cow, several species of bony fish and primates, have also been cloned and sequenced.

In this specification IL-11 refers to an IL-11 from any species and includes isoforms, fragments, variants or homologues of an IL-11 from any species. In preferred embodiments the species is human (*Homo sapiens*). Isoforms, fragments, variants or homologues of an IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature IL-11 from a given species, e.g. human. Isoforms, fragments, variants or homologues of an IL-11 may optionally be characterised by ability to bind IL-11Rα (preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80). A fragment of IL-11 may be of any length (by number of amino acids), although may optionally be at least 25% of the length of mature IL-11 and may have a maximum length of one of 50%, 75%, 80%, 85%, 90%, 91%, 92%, 93%, 94%, 95%, 96%, 97%, 98%, or 99% of the length of mature IL-11. A fragment of IL-11 may have a minimum length of 10 amino acids, and a maximum length of one of 15, 20, 25, 30, 40, 50, 100, 110, 120, 130, 140, 150, 160, 170, 180, 190 or 195 amino acids IL-11 signals through a homodimer of the ubiquitously expressed β-receptor glycoprotein 130 (gp130; also known as glycoprotein 130, IL6ST, IL6-beta or CD130). Gp130 is a transmembrane protein that forms one subunit of the type I cytokine receptor with the IL-6 receptor family. Specificity is gained through an individual IL-11 α-receptor (IL-11Rα), which does not directly participate in signal transduction, although the initial cytokine binding event to the α-receptor leads to the final complex formation with the β-receptors. IL-11 activates a downstream signaling pathway, which is predominantly the mitogen-activated protein kinase (MAPK)-cascade and the Janus kinase/signal transducer and activator of transcription (Jak/STAT) pathway (Garbers and Scheller, supra).

Human gp130 (including the 22 amino acid signal peptide) is a 918 amino acid protein, and the mature form is 866 amino acids, comprising a 597 amino acid extracellular domain, a 22 amino acid transmembrane domain, and a 277 amino acid intracellular domain. The extracellular domain of the protein comprises the cytokine-binding module (CBM) of gp130. The CBM of gp130 comprises the Ig-like domain D1, and the fibronectin-type III domains D2 and D3 of gp130. The amino acid sequence of human gp130 is available from Genbank accession no. NP_002175.2.

Human IL-11Rα is a 422 amino acid polypeptide (Genbank accession no. NP_001136256.1 GI:218505839) and shares ~85% nucleotide and amino acid sequence identity with the murine IL-11Rα (Du and Williams., Blood Vol, 89, No. 11, Jun. 1, 1997). Two isoforms of IL-11Rα have been reported, which differ in the cytoplasmic domain (Du and Williams, supra). The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain (34 amino acids) lacks the Box 1 and 2 regions that are required for activation of the JAK/STAT signaling pathway.

IL-11Rα binds its ligand with a low affinity (Kd~10 nmol/L) and alone is insufficient to transduce a biological signal. The generation of a high affinity receptor (Kd~400 to 800 pmol/L) capable of signal transduction requires co-expression of the IL-11Rα and gp130 (Curtis et al (Blood 1997 Dec. 1; 90 (11):4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and MAPK and/or Jak/STAT signalling as described above.

The receptor binding sites on murine IL-11 have been mapped and three sites—sites I, II and III—identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In principle, a soluble IL-11Rα can also form biologically active soluble complexes with IL-11 (Pflanz et al., 1999 FEBS Lett, 450, 117-122) raising the possibility that, similar to IL-6, IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11 receptor alpha chain (sIL-11R) and examined signaling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT3 and SHP2 similar to signalling through transmembrane IL-11R.

In this specification an IL-11 receptor (IL-11R) refers to a polypeptide capable of binding IL-11 and inducing signal transduction in cells expressing gp130. An IL-11 receptor may be from any species and includes isoforms, fragments, variants or homologues of an IL-11 receptor from any species. In preferred embodiments the species is human (*Homo sapiens*). In some embodiments the IL-11 receptor may be IL-11Rα. Isoforms, fragments, variants or homologues of an IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of IL-11Rα from a given species, e.g. human. Isoforms, fragments, variants or homologues of an IL-11Rα may optionally be characterised by ability to bind IL-11 (preferably from the same species) and stimulate signal transduction in cells expressing the IL-11Rα and gp130 (e.g. as described in Curtis et al. Blood, 1997, 90(11) or Karpovich et al. Mol. Hum. Reprod. 2003 9(2): 75-80). A fragment of an IL-11 receptor may be of any length (by number of amino acids), although may optionally be at least 25% of the length of the mature IL-11Rα and have a maximum length of one of 50%, 75%, 80%, 85%, 90%, 91%, 92%, 93%, 94%, 95%, 96%, 97%, 98%, or 99% of the length of the mature IL-11Rα. A fragment of an IL-11 receptor fragment may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

Agent Capable of Inhibiting the Action of IL-11

The IL-11 signaling pathway offers multiple routes for inhibition of IL-11 signaling. For example, inhibition may be achieved by preventing or reducing the binding of IL-11 to an IL-11 receptor. As a result, suitable agents may target either IL-11 or its receptor.

In some embodiments agents capable of inhibiting the action of IL-11 may bind to IL-11 and prevent or reduce IL-11 mediated signalling, e.g. through an IL-11 receptor. In some embodiments agents capable of inhibiting the action of IL-11 may bind to the IL-11 receptor and prevent or reduce IL-11 stimulated signalling.

Agents that bind to IL-11 may inhibit IL-11 mediated signalling by blocking the binding of IL-11 to an IL-11 receptor and/or by reducing the amount of IL-11 available to bind to its receptor. Suitable IL-11 binding agents may be IL-11 inhibitors or IL-11 antagonists.

IL-11 binding agents, e.g. anti-IL-11 antibodies, according to the present invention may exhibit at least one of the following properties:
  a) Bind to human IL-11 with a $K_D$ of 1 μM or less, preferably one of ≤1 μM, ≤100 nM, ≤10 nM, ≤1 nM or ≤100 pM;
  b) Inhibit IL-11 mediated signalling via the IL-11Rα receptor, e.g. in a cell based assay in which the cells co-express IL-11Rα and gp130. Suitable cell based assays are $^3$H-thymidine incorporation and Ba/F3 cell proliferation assays described in e.g. Curtis et al. Blood, 1997, 90(11) and Karpovich et al. Mol. Hum. Reprod. 2003 9(2): 75-80. For example, $IC_{50}$ for an IL-11 binding agent may be determined by culturing Ba/F3 cells expressing IL-11Rα and gp130 in the presence of human IL-11 and the IL-11 binding agent, and measuring $^3$H-thymidine incorporation into DNA. Suitable IL-11 binding agents may exhibit an $IC_{50}$ of 10 μg/ml or less, preferably one of ≤5 μg/ml, ≤4 μg/ml, ≤3.5 μg/ml, ≤3 μg/ml, ≤2 μg/ml, ≤1 μg/ml, ≤0.9 μg/ml, ≤0.8 μg/ml, ≤0.7 μg/ml, ≤0.6 μg/ml, or ≤0.5 μg/ml in such an assay.
  c) Inhibit fibroblast proliferation, e.g. proliferation of cardiac/atrial fibroblasts. This can, for example, be evaluated in an assay wherein fibroblasts are stimulated with IL-11 or TGFβ1 and cell proliferation is monitored as described herein.
  d) Inhibit myofibroblast generation, e.g. from cardiac/atrial fibroblasts. This can, for example, be evaluated in an assay wherein fibroblasts are stimulated with IL-11 or TGFβ31 and myofibroblast generation is monitored, e.g. by measuring αSMA levels.
  e) Inhibit extracellular matrix production by fibroblasts, e.g. cardiac/atrial fibroblasts. This can, for example, be evaluated in an assay wherein fibroblasts are stimulated with IL-11 or TGFβ1 and production of extracellular matrix components is measured.
  f) Inhibit collagen and/or periostin gene or protein expression in fibroblasts, e.g. cardiac/atrial fibroblasts. This can, for example, be evaluated in an assay wherein fibroblasts are stimulated with IL-11 or TGFβ1 and collagen and/or periostin gene or protein expression is measured.

IL-11 binding agents may be of any kind, but in some embodiments an IL-11 binding agent may be an antibody, polypeptide, peptide, oligonucleotide, aptamer or small molecule.

Suitable anti-IL-11 antibodies will preferably bind to IL-11 (the antigen), preferably human IL-11, and may have a dissociation constant ($K_D$) of one of ≤1 μM, ≤100 nM, ≤10 nM, ≤1 nM or ≤100 pM. Binding affinity of an antibody for its target is often described in terms of its dissociation constant ($K_D$). Binding affinity can be measured by methods known in the art, such as by Surface Plasmon Resonance (SPR), or by a radiolabeled antigen binding assay (RIA) performed with the Fab version of the antibody and antigen molecule.

Anti-IL-11 antibodies may be antagonist antibodies that inhibit or reduce a biological activity of IL-11.

Anti-IL-11 antibodies may be neutralising antibodies that neutralise the biological effect of IL-11, e.g. its ability to stimulate productive signalling via an IL-11 receptor.

Neutralising activity may be measured by ability to neutralise IL-11 induced proliferation in the T11 mouse plasmacytoma cell line (Nordan, R. P. et al. (1987) J. Immunol. 139:813).

Examples of known anti-IL-11 antibodies include monoclonal antibody clone 6D9A, clone KT8 (Abbiotec), clone M3103F11 (BioLegend), clone 1F1, clone 3C6 (Abnova Corporation), clone GF1 (LifeSpan Biosciences), clone 13455 (Source BioScience) and clone 22626 (R & D Systems, used in Bockhorn et al. Nat. Commun. (2013) 4(0): 1393; Monoclonal Mouse $IgG_{2,4}$; Catalog No. MAB218; R&D Systems, MN, USA).

Antibodies may optionally be selected to exhibit substantially no cross-reactivity with one or more of human, e.g. recombinant human, IL-6, CNTF, LIF, OSM, CLC or CT-1.

Peptide or polypeptide based IL-11 binding agents may be based on the IL-11 receptor, e.g. a IL-11 binding fragment of an IL-11 receptor. In one embodiment, suitable IL-11 binding agents may comprise an IL-11 binding fragment of the IL-11Rα chain, and may preferably be soluble and/or exclude one or more, or all, of the transmembrane domain(s). Such molecules may be described as decoy receptors.

Curtis et al (Blood 1997 Dec. 1; 90 (11):4403-12) report that a soluble murine IL-11 receptor alpha chain (sIL-11R) was capable of antagonizing the activity of IL-11 when tested on cells expressing the transmembrane IL-11R and gp130. They proposed that the observed IL-11 antagonism by the sIL-11R depends on limiting numbers of gp130 molecules on cells already expressing the transmembrane IL-11R.

The use of soluble decoy receptors as the basis for inhibition of signal transduction and therapeutic intervention has also been reported for other signalling molecule:receptor pairs, e.g. VEGF and the VEGF receptor (De-Chao Yu et al., Molecular Therapy (2012); 20 5, 938-947; Konner and Dupont Clin Colorectal Cancer 2004 October; 4 Suppl 2:S81-5).

As such, in some embodiments an IL-11 binding agent may be provided in the form of a decoy receptor, e.g. a soluble IL-11 receptor. Competition for IL-11 provided by a decoy receptor has been reported to lead to IL-11 antagonist action (Curtis et al., supra).

Decoy IL-11 receptors preferably bind IL-11 and/or IL-11 containing complexes, and thereby make these species unavailable for binding to gp130, IL-11Rα and/or gp130:IL-11Rα receptors. As such, they act as 'decoy' receptors for IL-11 and IL-11 containing complexes, much in the same way that etanercept acts as a decoy receptor for TNFα. IL-11 mediated signalling is reduced as compared to the level of signalling in the absence of the decoy receptor.

Decoy IL-11 receptors preferably bind to IL-11 through one or more cytokine binding modules (CBMs). The CBMs are, or are derived from or homologous to, the CBMs of naturally occurring receptor molecules for IL-11. For example, decoy IL-11 receptors may comprise, or consist of, one or more CBMs which are from, are derived from or homologous to the CBM of gp130 and/or IL-11Rα.

In some embodiments, a decoy IL-11 receptor may comprise, or consist of, an amino acid sequence corresponding to the cytokine binding module of gp130. In some embodiments, a decoy IL-11 receptor may comprise an amino acid sequence corresponding to the cytokine binding module of IL-11Rα. Herein, an amino acid sequence which 'corresponds' to a reference region or sequence of a given peptide/polypeptide has at least 60%, e.g. one of at least 65%, 70%, 75%, 80%, 85%, 90%, 91%, 92%, 93%, 94%, 95%, 96%, 97%, 98% or 99% sequence identity to the amino acid sequence of the reference region/sequence. The gp130, IL-11Rα and IL-11 may be from any species, and include isoforms, fragments, variants or homologues from any species.

In some embodiments a decoy receptor may be able to bind IL-11, e.g. with binding affinity of at least 100 µM or less, optionally one of 10 µM or less, 1 µM or less, 100 nM or less, or about 1 to 100 nM. In some embodiments a decoy receptor may comprise all or part of the IL-11 binding domain and may optionally lack all or part of the transmembrane domains. The decoy receptor may optionally be fused to an immunoglobulin constant region, e.g. IgG Fc region.

In some embodiments an IL-11 binding agent may be provided in the form of a small molecule inhibitor of IL-11, e.g. IL-11 inhibitor described in Lay et al., Int. J. Oncol. (2012); 41(2): 759-764.

Agents that bind to an IL-11 receptor (IL-11R) may inhibit IL-11 mediated signalling by blocking the binding of IL-11 to an IL-11R or by preventing signal transduction via the gp130 co-receptors. Suitable IL-11R binding agents may be IL-11R inhibitors or IL-11R antagonists. In preferred embodiments the IL-11R is IL-11Rα and suitable binding agents may bind the IL-11Rα polypeptide and may be inhibitors or antagonists of IL-11Rα.

IL-11R binding agents, e.g. anti-IL-11R antibodies, according to the present invention may exhibit at least one of the following properties:

(a) Bind to human IL-11R with a $K_D$ of 1 µM or less, preferably one of ≤1 µM, ≤100 nM, ≤10 nM, ≤1 nM or ≤100 pM;

(b) Inhibit IL-11R signalling, e.g. in a cell based assay in which the cells co-express IL-11Rα and gp130. Suitable cell based assays are $^3$H-thymidine incorporation and Ba/F3 cell proliferation assays described in e.g. Curtis et al. Blood, 1997, 90(11) and Karpovich et al. Mol. Hum. Reprod. 2003 9(2): 75-80. For example, $IC_{50}$ for an IL-11R binding agent may be determined by culturing Ba/F3 cells expressing IL-11Rα and gp130 in the presence of human IL-11 and the IL-11R binding agent, and measuring $^3$H-thymidine incorporation into DNA. Suitable IL-11R binding agents may exhibit an $IC_{50}$ of 10 µg/ml or less, preferably one of ≤5 µg/ml, ≤4 µg/ml, ≤3.5 µg/ml, ≤3 µg/ml, ≤2 µg/ml, ≤1 µg/ml, ≤0.9 µg/ml, ≤0.8 µg/ml, ≤0.7 µg/ml, ≤0.6 µg/ml, or ≤0.5 µg/ml in such an assay.

(c) Inhibit fibroblast proliferation, e.g. proliferation of cardiac/atrial fibroblasts. This can, for example, be evaluated in an assay wherein fibroblasts are stimulated with IL-11 or TGFβ1 and cell proliferation is monitored as described herein.

(d) Inhibit myofibroblast generation, e.g. from cardiac/atrial fibroblasts. This can, for example, be evaluated in an assay wherein fibroblasts are stimulated with IL-11 or TGFβ1 and myofibroblast generation is monitored, e.g. by measuring αSMA levels.

(e) Inhibit extracellular matrix production by fibroblasts, e.g. cardiac/atrial fibroblasts. This can, for example, be evaluated in an assay wherein fibroblasts are stimulated with IL-11 or TGFβ1 and production of extracellular matrix components is measured.

(f) Inhibit collagen and/or periostin gene or protein expression in fibroblasts, e.g. cardiac/atrial fibroblasts. This can, for example, be evaluated in an assay wherein fibroblasts are stimulated with IL-11 or TGFβ1 and collagen and/or periostin gene or protein expression is measured.

IL-11R binding agents may be of any kind, but in some embodiments an IL-11R binding agent may be an antibody, polypeptide, peptide, oligonucleotide, aptamer or small molecule.

Suitable anti-IL-11R antibodies will preferably bind to IL-11R (the antigen), preferably human IL-11R, and may have a dissociation constant ($K_D$) of one of ≤1 µM, ≤100 nM, ≤10 nM, ≤1 nM or ≤100 pM. Binding affinity of an antibody for its target is often described in terms of its dissociation constant (KO. Binding affinity can be measured by methods known in the art, such as by Surface Plasmon Resonance (SPR), or by a radiolabeled antigen binding assay (RIA) performed with the Fab version of the antibody and antigen molecule.

Anti-IL-11R antibodies may be antagonist antibodies that inhibit or reduce a biological activity of IL-11R. Anti-IL-11R antibodies may be antagonist antibodies that inhibit or reduce any function of IL-11R, in particular signalling. For example, antagonist IL-11R antibodies may inhibit or prevent binding of IL-11 to IL-11R, or may inhibit or prevent association of IL-11Rα with gp130 to form a functional receptor complex capable of productive signalling, e.g. in response to IL-11 binding.

Anti-IL-11R antibodies may be neutralising antibodies that neutralise the biological effect of IL-11R, e.g. its ability to initiate productive signalling mediated by binding of IL-11.

Neutralising activity may be measured by ability to neutralise IL-11 induced proliferation in the T11 mouse plasmacytoma cell line (Nordan, R. P. et al. (1987) J. Immunol. 139:813).

Examples of known anti-IL-11R antibodies include monoclonal antibody clone 025 (Sino Biological), clone EPR5446 (Abcam), clone 473143 (R & D Systems), clones 8E2 and 8E4 described in US 2014/0219919 A1 and the monoclonal antibodies described in Blanc et al (J. Immunol Methods. 2000 Jul. 31; 241(1-2); 43-59).

Peptide or polypeptide based IL-11R binding agents may be based on IL-11, e.g. mutant, variant or binding fragment of IL-11. Suitable peptide or polypeptide based agents may bind to IL-11R in a manner that does not lead to initiation of signal transduction or produces sub-optimal signaling. IL-11 mutants of this kind may act as competitive inhibitors of endogenous IL-11.

For example, W147A is an IL-11 antagonist in which the amino acid 147 is mutated from a tryptophan to an alanine, which destroys the so-called 'site III' of IL-11. This mutant can bind to the IL-11R, but engagement of the gp130 homodimer fails, resulting in efficient blockade of IL-11 signaling (Underhill-Day et al., 2003; Endocrinology 2003 August; 144(8):3406-14). Lee et al (Am J respire Cell Mol Biol. 2008 December; 39(6):739-746) also report the generation of an IL-11 antagonist mutant (a "mutein") capable of specifically inhibiting the binding of IL-11 to IL-11Rα.

Menkhorst et al (Biology of Reproduction May 1, 2009 vol. 80 no. 5 920-927) describe a PEGylated IL-11 antagonist, PEGIL11A (CSL Limited, Parkvill, Victoria, Australia) which is effective to inhibit IL-11 action in female mice.

Pasqualini et al. Cancer (2015) 121(14):2411-2421 describe a ligand-directed, peptidomimetic drug, bone metastasis-targeting peptidomimetic-11 (BMTP-11) capable of binding to IL-11Rα.

In some embodiments an IL-11R binding agent may be provided in the form of a small molecule inhibitor of IL-11R.

The inventors have identified that upregulation of IL-11 expression is consistent with the molecular mechanism of fibrosis and that inhibition of IL-11 activity leads to a reduction in the molecular basis for fibrosis. Accordingly, in some aspects of the present invention treatment, prevention or alleviation of fibrosis may be provided by administration of an agent capable of preventing or reducing the expression of IL-11 by cells of the subject, e.g. by fibroblasts or myofibroblasts.

Suitable agents may be of any kind, but in some embodiments an agent capable of preventing or reducing the expression of IL-11 may be a small molecule or an oligonucleotide.

Taki et al (Clin Exp Immunol. 1998 April; 112(1): 133-138) report a reduction in the expression of IL-11 in rheumatoid synovial cells upon treatment with indomethacin, dexamethasone or interferon-gamma (IFNγ).

In some embodiments an agent capable of preventing or reducing the expression of IL-11 may be an oligonucleotide capable of repressing or silencing expression of IL-11.

Accordingly, the present invention also includes the use of techniques known in the art for the therapeutic down regulation of IL-11 expression. These include the use of antisense oligonucleotides and RNA interference (RNAi). As in other aspects of the present invention, these techniques may be used in the treatment of fibrosis.

Accordingly, in one aspect of the present invention a method of treating or preventing fibrosis is provided, the method comprising administering to a subject in need of treatment a therapeutically effective amount of an agent capable of preventing or reducing the expression of IL-11, wherein the agent comprises a vector comprising a therapeutic oligonucleotide capable of repressing or silencing expression of IL-11.

In another aspect of the present invention a method of treating or preventing fibrosis is provided, the method comprising administering to a subject in need of treatment a therapeutically effective amount of an agent capable of preventing or reducing the expression of IL-11, wherein the agent comprises an oligonucleotide vector, optionally a viral vector, encoding a therapeutic oligonucleotide capable of being expressed in cells of the subject, the expressed therapeutic oligonucleotide being capable of repressing or silencing expression of IL-11.

The ability of an agent to prevent or reduce the expression of IL-11 may be assayed by determining the ability of the agent to inhibit IL-11 gene or protein expression by fibroblasts or myofibroblasts, e.g. cardiac/atrial fibroblasts or myofibroblasts. This can, for example, be evaluated in an assay wherein fibroblasts or myofibroblasts are stimulated with IL-11 or TGFβ1, and IL-11 gene or protein expression is measured.

Reducing the amount of IL-11R available for binding to IL-11 and initiation of productive signalling provides an alternative means of reducing the level of IL-11 stimulated signalling. Accordingly, in related aspects of the present invention, treatment, prevention or alleviation of fibrosis may be provided by administration of an agent capable of preventing or reducing the expression of IL-11R by cells of the subject, e.g. by fibroblasts or myofibroblasts.

In some embodiments an agent capable of preventing or reducing the expression of IL-11R may be an oligonucleotide capable of repressing or silencing expression of IL-11R.

Accordingly, the present invention also includes the use of techniques known in the art for the therapeutic down regulation of IL-11R expression. These include the use of antisense oligonucleotides and RNA interference (RNAi). As in other aspects of the present invention, these techniques may be used in the treatment of fibrosis.

Accordingly, in one aspect of the present invention a method of treating or preventing fibrosis is provided, the method comprising administering to a subject in need of treatment a therapeutically effective amount of an agent capable of preventing or reducing the expression of IL-11R, wherein the agent comprises a vector comprising a therapeutic oligonucleotide capable of repressing or silencing expression of IL-11R.

In another aspect of the present invention a method of treating or preventing fibrosis is provided, the method comprising administering to a subject in need of treatment a therapeutically effective amount of an agent capable of preventing or reducing the expression of IL-11R, wherein the agent comprises an oligonucleotide vector, optionally a viral vector, encoding a therapeutic oligonucleotide capable of being expressed in cells of the subject, the expressed therapeutic oligonucleotide being capable of repressing or silencing expression of IL-11R.

The ability of an agent to prevent or reduce the expression of IL-11R may be assayed by determining the ability of the agent to inhibit IL-11R gene or protein expression by fibroblasts or myofibroblasts, e.g. cardiac/atrial fibroblasts or myofibroblasts. This can, for example, be evaluated in an assay wherein fibroblasts or myofibroblasts are stimulated with IL-11 or TGFβ1, and IL-11R gene or protein expression is measured.

In preferred embodiments, the IL-11R may be IL-11Rα.

Antibodies

In this specification "antibody" includes a fragment or derivative of an antibody, or a synthetic antibody or synthetic antibody fragment.

Antibodies may be provided in isolated or purified form. Antibodies may be formulated as a pharmaceutical composition or medicament.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Polyclonal antibodies are useful in the methods of the invention. Monospecific polyclonal antibodies are preferred. Suitable polyclonal antibodies can be prepared using methods well known in the art.

Antigen binding fragments of antibodies, such as Fab and Fab$_2$ fragments may also be used/provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site. Synthetic antibodies which bind to IL-11 or IL-11R may also be made using phage display technology as is well known in the art.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Rio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

Antibodies according to the present invention preferably exhibit specific binding to IL-11 or IL-11R. An antibody that specifically binds to a target molecule preferably binds the target with greater affinity, and/or with greater duration than it binds to other targets. In one embodiment, the extent of binding of an antibody to an unrelated target is less than about 10% of the binding of the antibody to the target as measured, e.g., by ELISA, or by a radioimmunoassay (RIA). Alternatively, the binding specificity may be reflected in terms of binding affinity where the antibody binds to IL-11 or IL-11R with a $K_D$ that is at least 0.1 order of magnitude (i.e. 0.1×10n, where n is an integer representing the order of magnitude) greater than the $K_D$ of the antibody towards another target molecule, e.g. another member of the IL-11 family such as IL-6 or the IL-6 receptor. This may optionally be one of at least 0.2, 0.3, 0.4, 0.5, 0.6, 0.7, 0.8, 0.9, 1.0, 1.5, or 2.0.

Antibodies may be detectably labelled or, at least, capable of detection. Such antibodies being useful for both in vivo (e.g. imaging methods) and in vitro (e.g. assay methods) applications For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

Aspects of the present invention include bi-specific antibodies, e.g. composed of two different fragments of two different antibodies, such that the bi-specific antibody binds two types of antigen. One of the antigens is IL-11 or IL-11R, the bi-specific antibody comprising a fragment as described herein that binds to IL-11 or IL-11R. The antibody may contain a different fragment having affinity for a second antigen, which may be any desired antigen. Techniques for the preparation of bi-specific antibodies are well known in the art, e.g. see Mueller, D et al., (2010 *Biodrugs* 24 (2): 89-98), Wozniak-Knopp G et al., (2010 *Protein Eng Des* 23 (4): 289-297. Baeuerle, P A et al., (2009 *Cancer Res* 69 (12): 4941-4944).

In some embodiments, the bispecific antibody is provided as a fusion protein of two single-chain variable fragments (scFV) format, comprising a $V_H$ and $V_L$ of a IL-11 or IL-11R binding antibody or antibody fragment, and a $V_H$ and $V_L$ of an another antibody or antibody fragment.

Bispecific antibodies and bispecific antigen binding fragments may be provided in any suitable format, such as those formats described in Kontermann MAbs 2012, 4(2): 182-197, which is hereby incorporated by reference in its entirety. For example, a bispecific antibody or bispecific antigen binding fragment may be a bispecific antibody conjugate (e.g. an IgG2, F(ab')$_2$ or CovX-Body), a bispecific IgG or IgG-like molecule (e.g. an IgG, scFv$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tandAbs, tandem scFv (taFv), tandem dAb/VHH, triple body, triple head, Fab-scFv, or F(ab')$_2$-scFv$_2$), a bispecific Fc and $C_H3$ fusion protein (e.g. a taFv-Fc, Di-diabody, scDb-$C_H3$, scFv-Fc-scFv, HCAb-VHH, scFv-kih-Fc, or scFv-kih-$C_H3$), or a bispecific fusion protein (e.g. a scFv$_2$-albumin, scDb-albumin, taFv-toxin, DNL-Fab$_3$, DNL-Fab$_4$-IgG, DNL-Fab$_4$-IgG-cytokine$_2$). See in particular FIG. 2 of Kontermann MAbs 2012, 4(2): 182-19.

Methods for producing bispecific antibodies include chemically crosslinking antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH- groups, to create disulfide-linked bispecific F(ab)$_2$ heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen binding fragments can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Färber-Schwarz), or French, How to make bispecific antibodies, Methods Mol. Med. 2000; 40:333-339.

For example, a DNA construct encoding the light and heavy chain variable domains for the two antigen binding domains (i.e. the light and heavy chain variable domains for the antigen binding domain capable of binding IL-11 or IL-11R, and the light and heavy chain variable domains for the antigen binding domain capable of binding to another target protein), and including sequences encoding a suitable linker or dimerization domain between the antigen binding domains can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Aptamers

Aptamers, also called nucleic acid ligands, are nucleic acid molecules characterised by the ability to bind to a target molecule with high specificity and high affinity. Almost every aptamer identified to date is a non-naturally occurring molecule.

Aptamers to a given target (e.g. IL-11 or IL-11R) may be identified and/or produced by the method of Systematic Evolution of Ligands by EXponential enrichment (SELEX™). Aptamers and SELEX are described in Tuerk and Gold (Systematic evolution of ligands by exponential enrichment: RNA ligands to bacteriophage T4 DNA polymerase. Science. 1990 Aug. 3; 249(4968):505-10) and in WO091/19813.

Aptamers may be DNA or RNA molecules and may be single stranded or double stranded. The aptamer may comprise chemically modified nucleic acids, for example in which the sugar and/or phosphate and/or base is chemically modified. Such modifications may improve the stability of the aptamer or make the aptamer more resistant to degradation and may include modification at the 2' position of ribose.

Aptamers may be synthesised by methods which are well known to the skilled person. For example, aptamers may be chemically synthesised, e.g. on a solid support.

Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer.

Aptamers can be thought of as the nucleic acid equivalent of monoclonal antibodies and often have $K_d$'s in the nM or pM range, e.g. less than one of 500 nM, 100 nM, 50 nM, 10 nM, 1 nM, 500 pM, 100 pM. As with monoclonal antibodies, they may be useful in virtually any situation in which target binding is required, including use in therapeutic and diagnostic applications, in vitro or in vivo. In vitro diagnostic applications may include use in detecting the presence or absence of a target molecule.

Aptamers according to the present invention may be provided in purified or isolated form. Aptamers according to the present invention may be formulated as a pharmaceutical composition or medicament.

Suitable aptamers may optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides Suitable aptamers may optionally have a maximum length of one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides Suitable aptamers may optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Oligonucleotide Repression of IL-11 or IL-11R Expression

Oligonucleotide molecules, particularly RNA, may be employed to regulate gene expression. These include antisense oligonucleotides, targeted degradation of mRNAs by small interfering RNAs (siRNAs), post transcriptional gene silencing (PTGs), developmentally regulated sequence-specific translational repression of mRNA by micro-RNAs (miRNAs) and targeted transcriptional gene silencing.

An antisense oligonucleotide is an oligonucleotide, preferably single stranded, that targets and binds, by complementary sequence binding, to a target oligonucleotide, e.g. mRNA. Where the target oligonucleotide is an mRNA, binding of the antisense to the mRNA blocks translation of the mRNA and expression of the gene product. Antisense oligonucleotides may be designed to bind sense genomic nucleic acid and inhibit transcription of a target nucleotide sequence.

In view of the known nucleic acid sequences for IL-11 (e.g. the known mRNA sequences available from GenBank® under accession no.s: BC012506.1 GI:15341754 (human), BC134354.1 GI:126632002 (mouse), AF347935.1 GI:13549072 (rat)) and IL-11R (e.g. the known mRNA sequences available from GenBank® under accession no.s: NM_001142784.2 GI:391353394 (human), NM_001163401.1 GI:254281268 (mouse), NM_139116.1 GI:20806172 (rat)), oligonucleotides may be designed to repress or silence the expression of IL-11 or IL-11R. Such oligonucleotides may have any length, but may preferably be short, e.g. less than 100 nucleotides, e.g. 10-40 nucleotides, or 20-50 nucleotides, and may comprise a nucleotide sequence having complete- or near-complementarity (e.g. 80%, 85%, 90%, 91%, 92%, 93%, 94%, 95%, 96%, 97%, 98%, 99% or 100% complementarity) to a sequence of nucleotides of corresponding length in the target oligonucleotide, e.g. the IL-11 or IL-11R mRNA. The complementary region of the nucleotide sequence may have any length, but is preferably at least 5, and optionally no more than 50, nucleotides long, e.g. one of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

Repression of IL-11 or IL-11R expression will preferably result in a decrease in the quantity of IL-11 or IL-11R expressed by a cell, e.g. by a fibroblast or myofibroblast. For example, in a given cell the repression of IL-11 or IL-11R by administration of a suitable nucleic acid will result in a decrease in the quantity of IL-11 or IL-11R expressed by that cell relative to an untreated cell. Repression may be partial. Preferred degrees of repression are at least 50%, more preferably one of at least 60%, 70%, 80%, 85% or 90%. A level of repression between 90% and 100% is considered a 'silencing' of expression or function.

A role for the RNAi machinery and small RNAs in targeting of heterochromatin complexes and epigenetic gene silencing at specific chromosomal loci has been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA. RNAi based therapeutics have been progressed into Phase I, II and III clinical trials for a number of indications (Nature 2009 Jan. 22; 457(7228):426-433).

In the art, these RNA sequences are termed "short or small interfering RNAs" (siRNAs) or "microRNAs" (miRNAs) depending on their origin. Both types of sequence may be used to down-regulate gene expression by binding to complementary RNAs and either triggering mRNA elimination (RNAi) or arresting mRNA translation into protein. siRNA are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

Accordingly, the present invention provides the use of oligonucleotide sequences for down-regulating the expression of IL-11 or IL-11R.

siRNA ligands are typically double stranded and, in order to optimise the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed in John et al, PLoS Biology, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such the Ambion siRNA finder. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5' overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of IL-11 or IL-11R. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of IL-11 or IL-11R.

In one embodiment, the siRNA, longer dsRNA or miRNA is produced endogenously (within a cell) by transcription from a vector. The vector may be introduced into the cell in any of the ways known in the art. Optionally, expression of the RNA sequence can be regulated using a tissue specific (e.g. heart, liver, kidney or eye specific) promoter. In a further embodiment, the siRNA, longer dsRNA or miRNA is produced exogenously (in vitro) by transcription from a vector.

Suitable vectors may be oligonucleotide vectors configured to express the oligonucleotide agent capable of IL-11 or IL-11R repression. Such vectors may be viral vectors or plasmid vectors. The therapeutic oligonucleotide may be incorporated in the genome of a viral vector and be operably linked to a regulatory sequence, e.g. promoter, which drives its expression. The term "operably linked" may include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting transcription of a nucleotide sequence which forms part or all of the selected nucleotide sequence.

Viral vectors encoding promoter-expressed siRNA sequences are known in the art and have the benefit of long term expression of the therapeutic oligonucleotide. Examples include lentiviral (Nature 2009 Jan. 22; 457 (7228):426-433), adenovirus (Shen et al., FEBS Lett 2003 Mar. 27; 539(1-3)111-4) and retroviruses (Barton and Medzhitov PNAS Nov. 12, 2002 vol. 99, no. 23 14943-14945).

In other embodiments a vector may be configured to assist delivery of the therapeutic oligonucleotide to the site at which repression of IL-11 or IL-11R expression is required. Such vectors typically involve complexing the oligonucleotide with a positively charged vector (e.g., cationic cell penetrating peptides, cationic polymers and dendrimers, and cationic lipids); conjugating the oligonucleotide with small molecules (e.g., cholesterol, bile acids, and lipids), polymers, antibodies, and RNAs; or encapsulating the oligonucleotide in nanoparticulate formulations (Wang et al., AAPS J. 2010 December; 12(4): 492-503).

In one embodiment, a vector may comprise a nucleic acid sequence in both the sense and antisense orientation, such that when expressed as RNA the sense and antisense sections will associate to form a double stranded RNA.

Alternatively, siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through-O-or-S—.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3'position and other than a phosphate group at the 5'position. Thus modified nucleotides may also include 2'substituted sugars such as 2'-O-methyl-; 2'-O-alkyl; 2'-O-allyl; 2'-S-alkyl; 2'-S-allyl; 2'-fluoro-; 2'-halo or azido-ribose, carbocyclic sugar analogues, a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine, 5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methyl-thio-N6-isopentenyladenine, uracil-5-oxyacetic acid methyl ester, psueouracil, 2-thiocytosine, 5-methyl-2 thiouracil, 2-thiouracil, 4-thiouracil, 5methyluracil, N-uracil-5-oxyacetic acid methylester, uracil 5-oxyacetic acid, queosine, 2-thiocytosine, 5-propyluracil, 5-propylcytosine, 5-ethyluracil, 5ethylcytosine, 5-butyluracil, 5-pentyluracil, 5-pentylcytosine, and 2,6,diaminopurine, methylpsuedouracil, 1-methylguanine, 1-methylcytosine.

Methods relating to the use of RNAi to silence genes in C. elegans, Drosophila, plants, and mammals are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619, and Elbashir S M, et al., 2001 Nature 411:494-498).

Accordingly, the invention provides nucleic acid that is capable, when suitably introduced into or expressed within a mammalian, e.g. human, cell that otherwise expresses IL-11 or IL-11R, of suppressing IL-11 or IL-11R expression by RNAi.

The nucleic acid may have substantial sequence identity to a portion of IL-11 or IL-11R mRNA, as defined in GenBank accession no. NM_000641.3 GI:391353405 (IL-11) or U32324.1 GI:975336 (IL-11R), or the complementary sequence to said mRNA.

The nucleic acid may be a double-stranded siRNA. (As the skilled person will appreciate, and as explained further below, a siRNA molecule may include a short 3' DNA sequence also.)

Alternatively, the nucleic acid may be a DNA (usually double-stranded DNA) which, when transcribed in a mammalian cell, yields an RNA having two complementary portions joined via a spacer, such that the RNA takes the form of a hairpin when the complementary portions hybridise with each other. In a mammalian cell, the hairpin structure may be cleaved from the molecule by the enzyme DICER, to yield two distinct, but hybridised, RNA molecules.

In some preferred embodiments, the nucleic acid is generally targeted to the sequence of one of SEQ ID NOs 2 to 5 (IL-11; FIG. 11) or to one of SEQ ID NOs 7 to 10 (IL-11R; FIG. 12).

Only single-stranded (i.e. non self-hybridised) regions of an mRNA transcript are expected to be suitable targets for RNAi. It is therefore proposed that other sequences very close in the IL-11 or IL-11R mRNA transcript to the sequence represented by one of SEQ ID NOs 2 to 5 or 7 to 10 may also be suitable targets for RNAi. Such target sequences are preferably 17-23 nucleotides in length and preferably overlap one of SEQ ID NOs 2 to 5 or 7 to 10 by at least 1, 2, 3, 4, 5, 6, 7, 8, 9, 10, 11, 12, 13, 14, 15, 16, 17, 18 or all 19 nucleotides (at either end of one of SEQ ID NOs 2 to 5 or 7 to 10).

Accordingly, the invention provides nucleic acid that is capable, when suitably introduced into or expressed within a mammalian cell that otherwise expresses IL-11 or IL-11R, of suppressing IL-11 or IL-11R expression by RNAi, wherein the nucleic acid is generally targeted to the sequence of one of SEQ ID NOs 2 to 5 or 7 to 10.

By "generally targeted" the nucleic acid may target a sequence that overlaps with SEQ ID NOs 2 to 5 or 7 to 10. In particular, the nucleic acid may target a sequence in the mRNA of human IL-11 or IL-11R that is slightly longer or shorter than one of SEQ ID NOs 2 to 5 or 7 to 10 (preferably from 17-23 nucleotides in length), but is otherwise identical to one of SEQ ID NOs 2 to 5 or 7 to 10.

It is expected that perfect identity/complementarity between the nucleic acid of the invention and the target sequence, although preferred, is not essential. Accordingly, the nucleic acid of the invention may include a single mismatch compared to the mRNA of IL-11 or IL-11R. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

In one embodiment, the nucleic acid (herein referred to as double-stranded siRNA) includes the double-stranded RNA sequences shown in FIG. 13 (IL-11; SEQ ID NOs 11 to 14).

In another embodiment, the nucleic acid (herein referred to as double-stranded siRNA) includes the double-stranded RNA sequences shown in FIG. 14 (IL-11R; SEQ ID NOs 15 to 18).

However, it is also expected that slightly shorter or longer sequences directed to the same region of IL-11 or IL-11R mRNA will also be effective. In particular, it is expected that double-stranded sequences between 17 and 23 bp in length will also be effective.

The strands that form the double-stranded RNA may have short 3' dinucleotide overhangs, which may be DNA or RNA. The use of a 3' DNA overhang has no effect on siRNA activity compared to a 3' RNA overhang, but reduces the cost of chemical synthesis of the nucleic acid strands (Elbashir et al., 2001c). For this reason, DNA dinucleotides may be preferred.

When present, the dinucleotide overhangs may be symmetrical to each other, though this is not essential. Indeed, the 3' overhang of the sense (upper) strand is irrelevant for RNAi activity, as it does not participate in mRNA recognition and degradation (Elbashir et al., 2001a, 2001b, 2001c).

While RNAi experiments in *Drosophila* show that antisense 3' overhangs may participate in mRNA recognition and targeting (Elbashir et al. 2001c), 3' overhangs do not appear to be necessary for RNAi activity of siRNA in mammalian cells. Incorrect annealing of 3' overhangs is therefore thought to have little effect in mammalian cells (Elbashir et al. 2001c; Czauderna et al. 2003).

Any dinucleotide overhang may therefore be used in the antisense strand of the siRNA. Nevertheless, the dinucleotide is preferably -UU or -UG (or -TT or -TG if the overhang is DNA), more preferably -UU (or -TT). The -UU (or -TT) dinucleotide overhang is most effective and is consistent with (i.e. capable of forming part of) the RNA polymerase III end of transcription signal (the terminator signal is TTTTT). Accordingly, this dinucleotide is most preferred. The dinucleotides AA, CC and GG may also be used, but are less effective and consequently less preferred.

Moreover, the 3' overhangs may be omitted entirely from the siRNA.

The invention also provides single-stranded nucleic acids (herein referred to as single-stranded siRNAs) respectively consisting of a component strand of one of the aforementioned double-stranded nucleic acids, preferably with the 3'-overhangs, but optionally without. The invention also provides kits containing pairs of such single-stranded nucleic acids, which are capable of hybridising with each other in vitro to form the aforementioned double-stranded siRNAs, which may then be introduced into cells.

The invention also provides DNA that, when transcribed in a mammalian cell, yields an RNA (herein also referred to as an shRNA) having two complementary portions which are capable of self-hybridising to produce a double-stranded motif, e.g. including a sequence selected from the group consisting of SEQ ID No.s 11 to 14 or 15 to 18 or a sequence that differs from any one of the aforementioned sequences by a single base pair substitution.

The complementary portions will generally be joined by a spacer, which has suitable length and sequence to allow the two complementary portions to hybridise with each other. The two complementary (i.e. sense and antisense) portions may be joined 5'-3' in either order. The spacer will typically be a short sequence, of approximately 4-12 nucleotides, preferably 4-9 nucleotides, more preferably 6-9 nucleotides.

Preferably the 5' end of the spacer (immediately 3' of the upstream complementary portion) consists of the nucleotides -UU- or -UG-, again preferably -UU- (though, again, the use of these particular dinucleotides is not essential). A suitable spacer, recommended for use in the pSuper system of OligoEngine (Seattle, Wash., USA) is UUCAAGAGA. In this and other cases, the ends of the spacer may hybridise with each other, e.g. elongating the double-stranded motif beyond the exact sequences of SEQ ID NOs 11 to 14 or 15 to 18 by a small number (e.g. 1 or 2) of base pairs.

Similarly, the transcribed RNA preferably includes a 3' overhang from the downstream complementary portion. Again, this is preferably —UU or -UG, more preferably -UU.

Such shRNA molecules may then be cleaved in the mammalian cell by the enzyme DICER to yield a double-stranded siRNA as described above, in which one or each strand of the hybridised dsRNA includes a 3' overhang.

Techniques for the synthesis of the nucleic acids of the invention are of course well known in the art.

The skilled person is well able to construct suitable transcription vectors for the DNA of the invention using well-known techniques and commercially available materials. In particular, the DNA will be associated with control sequences, including a promoter and a transcription termination sequence.

Of particular suitability are the commercially available pSuper and pSuperior systems of OligoEngine (Seattle, Wash., USA). These use a polymerase-III promoter (H1) and a $T_5$ transcription terminator sequence that contributes two U residues at the 3' end of the transcript (which, after DICER processing, provide a 3' UU overhang of one strand of the siRNA).

Another suitable system is described in Shin et al. (RNA, 2009 May; 15(5): 898-910), which uses another polymerase-III promoter (U6).

The double-stranded siRNAs of the invention may be introduced into mammalian cells in vitro or in vivo using known techniques, as described below, to suppress expression of IL-11 or IL-11R.

Similarly, transcription vectors containing the DNAs of the invention may be introduced into tumour cells in vitro or in vivo using known techniques, as described below, for transient or stable expression of RNA, again to suppress expression of IL-11 or IL-11R.

Accordingly, the invention also provides a method of suppressing IL-11 or IL-11R expression in a mammalian, e.g. human, cell, the method comprising administering to the cell a double-stranded siRNA of the invention or a transcription vector of the invention.

Similarly, the invention further provides a method of treating fibrosis, the method comprising administering to a subject a double-stranded siRNA of the invention or a transcription vector of the invention.

The invention further provides the double-stranded siRNAs of the invention and the transcription vectors of the invention, for use in a method of treatment, preferably a method of treating fibrosis.

The invention further provides the use of the double-stranded siRNAs of the invention and the transcription vectors of the invention in the preparation of a medicament for the treatment of fibrosis.

The invention further provides a composition comprising a double-stranded siRNA of the invention or a transcription vector of the invention in admixture with one or more pharmaceutically acceptable carriers. Suitable carriers include lipophilic carriers or vesicles, which may assist in penetration of the cell membrane.

Materials and methods suitable for the administration of siRNA duplexes and DNA vectors of the invention are well known in the art and improved methods are under development, given the potential of RNAi technology.

Generally, many techniques are available for introducing nucleic acids into mammalian cells. The choice of technique will depend on whether the nucleic acid is transferred into cultured cells in vitro or in vivo in the cells of a patient. Techniques suitable for the transfer of nucleic acid into mammalian cells in vitro include the use of liposomes, electroporation, microinjection, cell fusion, DEAE dextran and calcium phosphate precipitation. In vivo gene transfer techniques include transfection with viral (typically retroviral) vectors and viral coat protein-liposome mediated transfection (Dzau et al. (2003) Trends in Biotechnology 11, 205-210).

In particular, suitable techniques for cellular administration of the nucleic acids of the invention both in vitro and in vivo are disclosed in the following articles:

General reviews: Borkhardt, A. 2002. Blocking oncogenes in malignant cells by RNA interference—new hope for a highly specific cancer treatment? Cancer Cell. 2:167-8. Hannon, G. J. 2002. RNA interference. Nature. 418:244-51. McManus, M. T., and P. A. Sharp. 2002. Gene silencing in mammals by small interfering RNAs. Nat Rev Genet. 3:737-47. Scherr, M., M. A. Morgan, and M. Eder. 2003b. Gene silencing mediated by small interfering RNAs in mammalian cells. Curr Med Chem. 10:245-56. Shuey, D. J., D. E. McCallus, and T. Giordano. 2002. RNAi: gene-silencing in therapeutic intervention. Drug Discov Today. 7:1040-6.

Systemic delivery using liposomes: Lewis, D. L., J. E. Hagstrom, A. G. Loomis, J. A. Wolff, and H. Herweijer. 2002. Efficient delivery of siRNA for inhibition of gene expression in postnatal mice. Nat Genet. 32:107-8. Paul, C. P., P. D. Good, I. Winer, and D. R. Engelke. 2002. Effective expression of small interfering RNA in human cells. Nat Biotechnol. 20:505-8. Song, E., S. K. Lee, J. Wang, N. Ince, N. Ouyang, J. Min, J. Chen, P. Shankar, and J. Lieberman. 2003. RNA interference targeting Fas protects mice from fulminant hepatitis. Nat Med. 9:347-51. Sorensen, D. R., M. Leirdal, and M. Sioud. 2003. Gene silencing by systemic delivery of synthetic siRNAs in adult mice. J Mol Biol. 327:761-6.

Virus mediated transfer: Abbas-Terki, T., W. Blanco-Bose, N. Deglon, W. Pralong, and P. Aebischer. 2002. Lentiviral-mediated RNA interference. Hum Gene Ther. 13:2197-201. Barton, G. M., and R. Medzhitov. 2002. Retroviral delivery of small interfering RNA into primary cells. Proc Natl Acad Sci USA. 99:14943-5. Devroe, E., and P. A. Silver. 2002. Retrovirus-delivered siRNA. BMC Biotechnol. 2:15. Lori, F., P. Guallini, L. Galluzzi, and J. Lisziewicz. 2002. Gene therapy approaches to HIV infection. Am J Pharmacogenomics. 2:245-52. Matta, H., B. Hozayev, R. Tomar, P. Chugh, and P. M. Chaudhary. 2003. Use of lentiviral vectors for delivery of small interfering RNA. Cancer Biol Ther. 2:206-10. Qin, X. F., D. S. An, I. S. Chen, and D. Baltimore. 2003. Inhibiting HIV-1 infection in human T cells by lentiviral-mediated delivery of small interfering RNA against CCR5. Proc Natl Acad Sci USA. 100:183-8. Scherr, M., K. Battmer, A. Ganser, and M. Eder. 2003a. Modulation of gene expression by lentiviral-mediated delivery of small interfering RNA. Cell Cycle. 2:251-7. Shen, C., A. K. Buck, X. Liu, M. Winkler, and S. N. Reske. 2003. Gene silencing by adenovirus-delivered siRNA. FEBS Lett. 539:111-4.

Peptide delivery: Morris, M. C., L. Chaloin, F. Heitz, and G. Divita. 2000. Translocating peptides and proteins and their use for gene delivery. Curr Opin Biotechnol. 11:461-6. Simeoni, F., M. C. Morris, F. Heitz, and G. Divita. 2003. Insight into, the mechanism of the peptide-based gene delivery system MPG: implications for delivery of siRNA into mammalian cells. Nucleic Acids Res. 31:2717-24. Other technologies that may be suitable for delivery of siRNA to the target cells are based on nanoparticles or nanocapsules such as those described in U.S. Pat. Nos. 6,649,192B and 5,843,509B.

Formulations

In therapeutic applications, agents capable of inhibiting the action of IL-11 or agents capable of preventing or reducing the expression of IL-11 or IL-11R are preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulations may be prepared for topical, parenteral, systemic, intravenous, intra-arterial, intramuscular, intrathecal, intraocular, intra-conjunctival, subcutaneous, oral or transdermal routes of administration which may include injection. Injectable formulations may comprise the selected agent in a sterile or isotonic medium.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Fibrosis

As used herein, "fibrosis" refers to the formation of excess fibrous connective tissue as a result of the excess deposition of extracellular matrix components, for example collagen. Fibrous connective tissue is characterised by having extracellular matrix (ECM) with a high collagen content. The collagen may be provided in strands or fibers, which may be arranged irregularly or aligned. The ECM of fibrous connective tissue may also include glycosaminoglycans.

As used herein, "excess fibrous connective tissue" refers to an amount of connective tissue at a given location (e.g. a given tissue or organ, or part of a given tissue or organ) which is greater than the amount of connective tissue present at that location in the absence of fibrosis, e.g. under normal, non-pathological conditions. As used herein, "excess deposition of extracellular matrix components" refers to a level of deposition of one or more extracellular matrix components which is greater than the level of deposition in the absence of fibrosis, e.g. under normal, non-pathological conditions.

The cellular and molecular mechanisms of fibrosis are described in Wynn, J. Pathol. (2008) 214(2): 199-210, and Wynn and Ramalingam, Nature Medicine (2012) 18:1028-1040, which are hereby incorporated by reference in their entirety.

The main cellular effectors of fibrosis are myofibroblasts, which produce a collagen-rich extracellular matrix.

In response to tissue injury, damaged cells and leukocytes produce pro-fibrotic factors such as TGFβ, IL-13 and PDGF, which activate fibroblasts to αSMA-expressing myofibroblasts, and recruit myofibroblasts to the site of injury. Myofibroblasts produce a large amount of extracellular matrix, and are important mediators in aiding contracture and closure of the wound. However, under conditions of persistent infection or during chronic inflammation there can be overactivation and recruitment of myofibroblasts, and thus over-production of extracellular matrix components, resulting in the formation of excess fibrous connective tissue.

In some embodiments fibrosis may be triggered by pathological conditions, e.g. conditions, infections or disease states that lead to production of pro-fibrotic factors such as TGFβ1. In some embodiments, fibrosis may be caused by physical injury/stimuli, chemical injury/stimuli or environmental injury/stimuli. Physical injury/stimuli may occur during surgery, e.g. iatrogenic causes. Chemical injury/stimuli may include drug induced fibrosis, e.g. following chronic administration of drugs such as bleomycin, cyclophosphamide, amiodarone, procainamide, penicillamine, gold and nitrofurantoin (Daba et al., Saudi Med J 2004 June; 25(6): 700-6). Environmental injury/stimuli may include exposure to asbestos fibres or silica.

Fibrosis can occur in many tissues of the body. For example, fibrosis can occur in the liver (e.g. cirrhosis), lungs, kidney, heart, blood vessels, eye, skin, pancreas, intestine, brain, and bone marrow. Fibrosis may also occur in multiple organs at once.

In embodiments herein, fibrosis may involve an organ of the gastrointestinal system, e.g. of the liver, small intestine, large intestine, or pancreas. In some embodiments, fibrosis may involve an organ of the respiratory system, e.g. the lungs. In embodiments, fibrosis may involve an organ of the cardiovascular system, e.g. of the heart or blood vessels. In some embodiments, fibrosis may involve the skin. In some embodiments, fibrosis may involve an organ of the nervous system, e.g. the brain. In some embodiments, fibrosis may involve an organ of the urinary system, e.g. the kidneys. In some embodiments, fibrosis may involve an organ of the musculoskeletal system, e.g. muscle tissue.

In some preferred embodiments, the fibrosis is cardiac or myocardial fibrosis, hepatic fibrosis, or renal fibrosis. In some embodiments cardiac or myocardial fibrosis is associated with dysfunction of the musculature or electrical properties of the heart, or thickening of the walls of valves of the heart. In some embodiments fibrosis is of the atrium and/or ventricles of the heart. Treatment or prevention of atrial or ventricular fibrosis may help reduce risk or onset of atrial fibrillation, ventricular fibrillation, or myocardial infarction.

In some preferred embodiments hepatic fibrosis is associated with chronic liver disease or liver cirrhosis. In some preferred embodiments renal fibrosis is associated with chronic kidney disease.

Diseases/conditions characterised by fibrosis in accordance with the present invention include but are not limited to: respiratory conditions such as pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma; chronic liver disease, primary biliary cirrhosis (PBC), schistosomal liver disease, liver cirrhosis; cardiovascular conditions such as hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, cerebral infarcts; neurological conditions such as gliosis and Alzheimer's disease; muscular dystrophy such as Duchenne muscular dystrophy (DMD) or Becker's muscular dystrophy (BMD); gastrointestinal conditions such as Chron's disease, microscopic colitis and primary sclerosing cholangitis (PSC); skin conditions such as scleroderma, nephrogenic systemic fibrosis and cutis keloid; arthrofibrosis; Dupuytren's contracture; mediastinal fibrosis; retroperitoneal fibrosis; myelofibrosis;

Peyronie's disease; adhesive capsulitis; kidney disease (e.g., renal fibrosis, nephritic syndrome, Alport's syndrome, HIV associated nephropathy, polycystic kidney disease, Fabry's disease, diabetic nephropathy, chronic glomerulonephritis, nephritis associated with systemic lupus); progressive systemic sclerosis (PSS); chronic graft versus host disease; diseases of the eye such as Grave's opthalmopathy, epiretinal fibrosis, retinal fibrosis, subretinal fibrosis (e.g. associated with macular degeneration (e.g. wet age-related macular degeneration (AMD)), diabetic retinopathy, glaucoma, corneal fibrosis, post-surgical fibrosis (e.g. of the posterior capsule following cataract surgery, or of the bleb following trabeculectomy for glaucoma), conjunctival fibrosis, subconjunctival fibrosis; arthritis; fibrotic pre-neoplastic and fibrotic neoplastic disease; and fibrosis induced by chemical or environmental insult (e.g., cancer chemotherapy, pesticides, radiation/cancer radiotherapy).

It will be appreciated that the many of the diseases/conditions listed above are interrelated. For example, fibrosis of the ventricle may occur post myocardial infarction, and is associated with DCM, HCM and myocarditis.

In particular embodiments, the disease/disorder may be one of pulmonary fibrosis, atrial fibrillation, ventricular fibrillation, hypertrophic cardiomyopathy (HCM), dilated cardiomyopathy (DCM), non-alcoholic steatohepatitis (NASH), cirrhosis, chronic kidney disease, scleroderma, systemic sclerosis, keloid, cystic fibrosis, Chron's disease, post-surgical fibrosis or retinal fibrosis.

Treatment, prevention or alleviation of fibrosis according to the present invention may be of fibrosis that is associated with an upregulation of IL-11, e.g. an upregulation of IL-11 in cells or tissue in which the fibrosis occurs or may occur, or upregulation of extracellular IL-11 or IL-11R.

Treatment or alleviation of fibrosis may be effective to prevent progression of the fibrosis, e.g. to prevent worsening of the condition or to slow the rate of development of the fibrosis. In some embodiments treatment or alleviation may lead to an improvement in the fibrosis, e.g. a reduction in the amount of deposited collagen fibres.

Prevention of fibrosis may refer to prevention of a worsening of the condition or prevention of the development of fibrosis, e.g. preventing an early stage fibrosis developing to a later, chronic, stage.

Subject

The subject to be treated may be any animal or human. The subject is preferably mammalian, more preferably human. The subject may be a non-human mammal, but is more preferably human. The subject may be male or female. The subject may be a patient.

Sample

A sample obtained from a subject may be of any kind. A biological sample may be taken from any tissue or bodily fluid, e.g. a blood sample, blood-derived sample, serum sample, lymph sample, semen sample, saliva sample, synovial fluid sample. A blood-derived sample may be a selected fraction of a patient's blood, e.g. a selected cell-containing fraction or a plasma or serum fraction. A sample may comprise a tissue sample or biopsy; or cells isolated from a subject. Samples may be collected by known techniques, such as biopsy or needle aspirate.

Samples may be stored and/or processed for subsequent determination of IL-11 expression levels.

Samples may be used to determine the upregulation of IL-11 or IL-11R in the subject from which the sample was taken.

In some preferred embodiments a sample may be a tissue sample, e.g. biopsy, taken from heart, liver or kidney tissue. In some embodiments a sample may be a tissue sample, e.g. biopsy, taken from the eye.

A sample may contain cells, and may preferably contain fibroblasts and/or myofibroblasts. In some embodiments, fibroblasts or myofibroblasts may be obtained from heart, liver or kidney tissue, e.g. they may be cardiac fibroblasts or cardiac myofibroblasts (e.g. see Colby et al., Circulation Research 2009; 105:1164-1176), hepatic fibroblasts or hepatic myofibroblasts (e.g. see Zeisberg et al., The Journal of Biological Chemistry, Aug. 10, 2007, 282, 23337-23347; Brenner., Fibrogenesis & Tissue Repair 2012, 5(Suppl 1):S17) or renal fibroblasts or renal myofibroblasts (e.g. see Strutz and Zeisberg. JASN November 2006 vol. 17 no. 11 2992-2998). In some embodiments, fibroblasts or myofibroblasts may be obtained from eye tissue, e.g. they may be corneal fibroblasts.

Upregulation of IL-11 or IL-11R Expression

Some aspects and embodiments of the present invention concern detection of expression of IL-11 or IL-11R, e.g. in a sample obtained from a subject.

In some aspects and embodiments the present invention concerns the upregulation of expression (over-expression) of IL-11 or IL-11R (as a protein or oligonucleotide encoding the respective IL-11 or IL-11R) and detection of such upregulation as an indicator of suitability for treatment with an agent capable of inhibiting the action of IL-11 or with an agent capable of preventing or reducing the expression of IL-11 or IL-11R.

Upregulation of IL-11 or IL-11R expression comprises expression of IL-11 or IL-11R at a level that is greater than would normally be expected for a cell or tissue of a given type. Upregulation may be determined by determining the level of expression of IL-11 or IL-11R in a cell or tissue. A comparison may be made between the level of IL-11 or IL-11R expression in a cell or tissue sample from a subject and a reference level of IL-11 or IL-11R, e.g. a value or range of values representing a normal level of expression of IL-11 or IL-11R for the same or corresponding cell or tissue type. In some embodiments reference levels may be determined by detecting IL-11 or IL-11R expression in a control sample, e.g. in corresponding cells or tissue from a healthy subject or from healthy tissue of the same subject. In some embodiments reference levels may be obtained from a standard curve or data set.

Levels of expression may be quantitated for absolute comparison, or relative comparisons may be made.

In some embodiments upregulation of IL-11 or IL-11R may be considered to be present when the level of expression in the test sample is at least 1.1 times that of a reference level. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that of the reference level.

IL-11 or IL-11R expression levels may be determined by one of a number of known in vitro assay techniques, such as PCR based assays, in situ hybridisation assays, flow cytometry assays, immunological or immunohistochemical assays.

By way of example suitable techniques involve a method of detecting the level of IL-11 or IL-11R in a sample by contacting the sample with an agent capable of binding IL-11 or IL-11R and detecting the formation of a complex of the agent and IL-11 or IL-11R. The agent may be any suitable binding molecule, e.g. an antibody, polypeptide, peptide, oligonucleotide, aptamer or small molecule, and may optionally be labelled to permit detection, e.g. visualisation, of the complexes formed. Suitable labels and means for their detection are well known to those in the art and include fluorescent labels (e.g. fluorescein, rhodamine, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5), isotope markers, radioisotopes (e.g. $^{32}$P, $^{33}$P, $^{35}$S), chemiluminescence labels (e.g. acridinium ester, luminol, isoluminol), enzymes (e.g. peroxidase, alkaline phosphatase, glucose oxidase, beta-galactosidase, luciferase), antibodies, ligands and receptors. Detection techniques are well known to those of skill in the art and can be selected to correspond with the labelling agent. Suitable techniques include PCR amplification of oligonucleotide tags, mass spectrometry, detection of fluorescence or colour, e.g. upon enzymatic conversion of a substrate by a reporter protein, or detection of radioactivity.

Assays may be configured to quantify the amount of IL-11 or IL-11R in a sample. Quantified amounts of IL-11 or IL-11R from a test sample may be compared with reference values, and the comparison used to determine whether the test sample contains an amount of IL-11 or IL-11R that is higher or lower than that of the reference value to a selected degree of statistical significance.

Quantification of detected IL-11 or IL-11R may be used to determine up- or down-regulation or amplification of genes encoding IL-11 or IL-11R. In cases where the test sample contains fibrotic cells, such up-regulation, down-regulation or amplification may be compared to a reference value to determine whether any statistically significant difference is present.

Subject Selection

A subject may be selected for treatment based on a determination that the subject has an upregulated level of IL-11 or IL-11R expression. IL-11 or IL-11R may therefore act as a marker of a fibrosis that is suitable for treatment with an agent capable of inhibiting the action of IL-11 or with an agent capable of preventing or reducing the expression of IL-11 or IL-11R.

Upregulation may be in a given tissue or in selected cells from a given tissue. A preferred tissue may be one of heart, liver or kidney. A preferred tissue may be eye. A preferred cell type may be fibroblasts or myofibroblasts. Upregulation may also be determined in a circulating fluid, e.g. blood, or in a blood derived sample. Upregulation of may be of extracellular IL-11 or IL-11R.

Determination of IL-11 or IL-11R levels may be performed by assay, preferably in vitro, on a sample obtained from a subject, as described herein.

Following selection, a subject may be provided with treatment for fibrosis by administration of an agent capable of inhibiting the action of IL-11 or an agent capable of preventing or reducing the expression of IL-11 or IL-11R.

In some embodiments a subject may have been diagnosed with fibrosis, be suspected of having fibrosis or be considered at risk of developing fibrosis and it is of interest whether the subject will benefit from treatment with an agent capable of inhibiting the action of IL-11 or with an agent capable of preventing or reducing the expression of IL-11 or IL-11R. In such embodiments, the suitability of the subject for such treatment may be determined by determining whether IL-11 or IL-11R expression is upregulated in the subject. In some embodiments, IL-11 or IL-11R expression is locally or systemically upregulated in the subject.

Diagnosis and Prognosis

The detection of upregulation of IL-11 or IL-11R expression may also be used in a method of diagnosing fibrosis or the risk of developing fibrosis in a subject, and in methods of prognosing or predicting a subject's response to treatment with an agent capable of inhibiting the action of IL-11 or an agent capable of preventing or reducing the expression of IL-11 or IL-11R.

In some embodiments a subject may be suspected of having fibrosis, e.g. based on the presence of other symptoms indicative of fibrosis in the subject's body or in selected cells/tissues of the subject's body, or be considered at risk of developing fibrosis, e.g. because of genetic predisposition or exposure to environmental conditions, such as asbestos fibres.

Determination of upregulation of IL-11 or IL-11R may confirm a diagnosis or suspected diagnosis of fibrosis or may confirm that the subject is at risk of developing fibrosis. The determination may also diagnose the condition or predisposition as one suitable for treatment with an agent capable of inhibiting the action of IL-11 or an agent capable of preventing or reducing the expression of IL-11 or IL-11R.

As such, a method of providing a prognosis for a subject having, or suspected of having fibrosis may be provided, the method comprising determining whether IL-11 or IL-11R is upregulated in a sample obtained from the subject and, based on the determination, providing a prognosis for treatment of the subject with an agent capable of inhibiting the action of IL-11 or an agent capable of preventing or reducing the expression of IL-11 or IL-11R.

In some aspects methods of diagnosis or methods of prognosing or predicting a subject's response to treatment with an agent capable of inhibiting the action of IL-11 or an agent capable of preventing or reducing the expression of IL-11 or IL-11R may not require determination of IL-11 or IL-11R levels, but may be based on determining genetic factors in the subject that are predictive of upregulation of IL-11 or IL-11R expression, or upregulation of IL-11 or IL-11R activity. Such genetic factors may include the determination of genetic mutations, single nucleotide polymorphisms (SNPs) or gene amplification in IL-11 and/or IL-11R that are correlated with and/or predictive of upregulation of IL-11 or IL-11R expression or activity or IL-11 mediated signaling activity. The use of genetic factors to predict predisposition to a disease state or response to treatment is known in the art, e.g. see Peter Stärkel Gut 2008; 57:440-442; Wright et al., Mol. Cell. Biol. March 2010 vol. 30 no. 6 1411-1420.

Genetic factors may be assayed by methods known to those of ordinary skill in the art, including PCR based assays, e.g. quantitative PCR, competitive PCR. By determining the presence of genetic factors, e.g. in a sample obtained from a subject, a diagnosis of fibrosis may be confirmed, and/or a subject may be classified as being at risk of developing fibrosis, and/or a subject may be identified as being suitable for treatment with an agent capable of inhibiting the action of IL-11 or an agent capable of preventing or reducing the expression of IL-11 or IL-11R.

Some methods may comprise determination of the presence of one or more SNPs linked to secretion of IL-11 or susceptibility to development of fibrosis. SNPs are usually bi-allelic and therefore can be readily determined using one of a number of conventional assays known to those of skill in the art (e.g. see Anthony J. Brookes. The essence of SNPs. Gene Volume 234, Issue 2, 8 Jul. 1999, 177-186; Fan et al., Highly Parallel SNP Genotyping. Cold Spring Harb Symp Quant Biol 2003. 68: 69-78; Matsuzaki et al., Parallel Genotyping of Over 10,000 SNPs using a one-primer assay on a high-density oligonucleotide array. Genome Res. 2004. 14: 414-425).

The methods may comprise determining which SNP allele is present in a sample obtained from a subject. In some embodiments determining the presence of the minor allele may be associated with increased IL-11 secretion or susceptibility to development of fibrosis.

Accordingly, in one aspect of the present invention a method for screening a subject is provided, the method comprising:
    obtaining a nucleic acid sample from the subject;
    determining which allele is present in the sample at the polymorphic nucleotide position of one or more of the SNPs listed in FIG. 33, and/or FIG. 34 and/or FIG. 35 or an SNP in linkage disequilibrium with one of the listed SNPs with an $r^2 \geq 0.8$.

The determining step may comprise determining whether the minor allele is present in the sample at the selected polymorphic nucleotide position. It may comprise determining whether 0, 1 or 2 minor alleles are present.

The screening method may be, or form part of, a method for determining susceptibility of the subject to development of fibrosis, or a method of diagnosis or prognosis as described herein.

The method may further comprise the step of identifying the subject as having susceptibility to, or an increased risk of, developing fibrosis, e.g. if the subject is determined to have a minor allele at the polymorphic nucleotide position. The method may further comprise the step of selecting the subject for treatment with an agent capable of inhibiting the action of Interleukin 11 (IL-11) and/or administering an agent capable of inhibiting the action of Interleukin 11 (IL-11) to the subject in order to provide a treatment for fibrosis in the subject or to prevent development or progression of fibrosis in the subject.

SNPs that may be determined include one or more of the SNPs listed in FIG. 33, FIG. 34, or FIG. 35. In some embodiments the method may comprise determining one or more of the SNPs listed in FIG. 33. In some embodiments the method may comprise determining one or more of the SNPs listed in FIG. 34. In some embodiments the method may comprise determining one or more of the SNPs listed in FIG. 35. SNPs may be selected for determination as having a low P value or FDR (false discovery rate).

In some embodiments SNPs are selected as being good predictors of response to anti-IL-11 treatment based on regulation of $VST_{stim}$ in trans (FIG. 33). In some embodiments a method may comprise determining which allele is present for one or more of the following SNPs: rs10831850, rs4756936, rs6485827, rs7120273, and rs895468. In some embodiments SNPs are selected as being good predictors of response to anti-IL-11 treatment based on regulation $VST_{stim}-VST_{unstim}$ in cis (FIG. 34).

In some embodiments SNPs are selected as being good predictors of response to anti-IL-11 treatment based on regulation $VST_{stim}-VST_{unstim}$ in trans (FIG. 35). In some embodiments a method may comprise determining which allele is present for one or more of the following SNPs: rs7120273, rs10831850, rs4756936, rs6485827 (FIG. 35).

SNPs: rs7120273, rs10831850, rs4756936, rs6485827 are in high linkage disequilibrium (LD) with one another on chromosome 11 (in a so-called LD block), and are therefore very commonly co-inherited.

The square of the correlation of gene frequencies ($r^2$) reflects the degree of linkage disequilibrium (LD) between two SNPs. As a result of LD between SNPs in local and therefore co-inherited regions of the genome, the genotype of a given SNP can be inferred by determining the genotype of a tagging/proxy SNP. The threshold of LD used in the art to identify pairwise tagging/proxy SNPs is an $r^2$ value of 0.8 (Wang et al. 2005, Nat. Rev. Genet. 6(2): 109-18; Barrett et al. 2006, Nat Genet., 38 (6): 659-662). The genotype of a given SNP can therefore be inferred by determining the genotype of a tagging/proxy SNP in linkage disequilibrium with an $r^2$ value $\geq 0.8$.

The nucleotide sequence of SNPs is indicated using the "rs" number. The full sequence is available from the National Center for biotechnology Information (NCBI) database of single nucleotide polymorphisms (dbSNP) accessible at: https://www.ncbi.nlm.nih.gov/snp.

Methods of diagnosis or prognosis may be performed in vitro on a sample obtained from a subject, or following processing of a sample obtained from a subject. Once the sample is collected, the patient is not required to be present for the in vitro method of diagnosis or prognosis to be performed and therefore the method may be one which is not practised on the human or animal body.

Other diagnostic or prognostic tests may be used in conjunction with those described here to enhance the accuracy of the diagnosis or prognosis or to confirm a result obtained by using the tests described here.

Methods according to the present invention may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. "Ex vivo" refers to something present or taking place outside an organism, e.g. outside the human or animal body, which may be on tissue (e.g. whole organs) or cells taken from the organism.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as

EXAMPLES

Example 1

The fibrotic response is characterized by widespread molecular changes in activated resident fibroblasts. To establish the role of IL-11 as a key marker of this transition we assessed and ranked global RNA expression differences in atrial fibroblasts derived from 80 individuals before and 24 hours after Transforming growth factor beta-1 (TGFβ1) activation. We cultured primary fibroblasts derived from the atrium of 80 individuals who were undergoing cardiac surgery for coronary artery disease. Fibroblasts were studied ex vivo at baseline and following stimulation with TGFβ1 (a powerful pro-fibrotic stimulus) using genome-wide expression profiling (RNA-Seq) combined with phenotypic assays and genotyping.

Figure 1A:
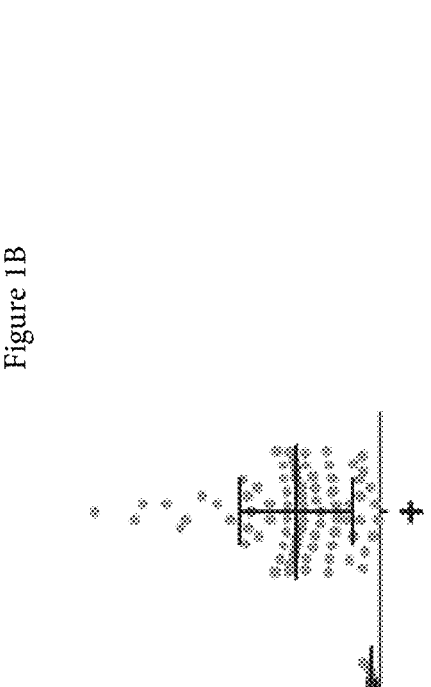
FIGS. 1A, 1B, 1C and 1D. TGFβ1 stimulation upregulates IL-11 in fibroblasts. Primary fibroblasts were derived from human atrial tissue of 80 individuals and incubated for 24 h with and without TGFβ1 (5 ng/ml). (1A) Chart showing IL-11 was the most upregulated gene in TGFβ1 stimulated fibroblasts compared to 11,433 expressed genes (FPKM≥0.5). (1B) Chart showing IL-11 expression significantly increased more than 8-fold on average after fibroblast activation with TGFβ1 (FDR=9.1×10$^{-125}$). (1C) Chart showing RT-qPCR confirmed IL-11 RNA expression-based fold changes (TGFB1+/TGFB1−; $R^2$=0.94) and (1D) Chart showing ELISA detected a significant increase in IL-11 protein secreted by stimulated fibroblasts.
Figure 1B:
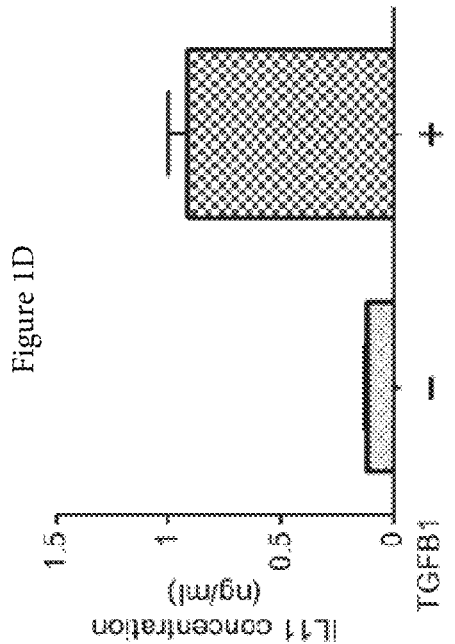
Figure 1C:
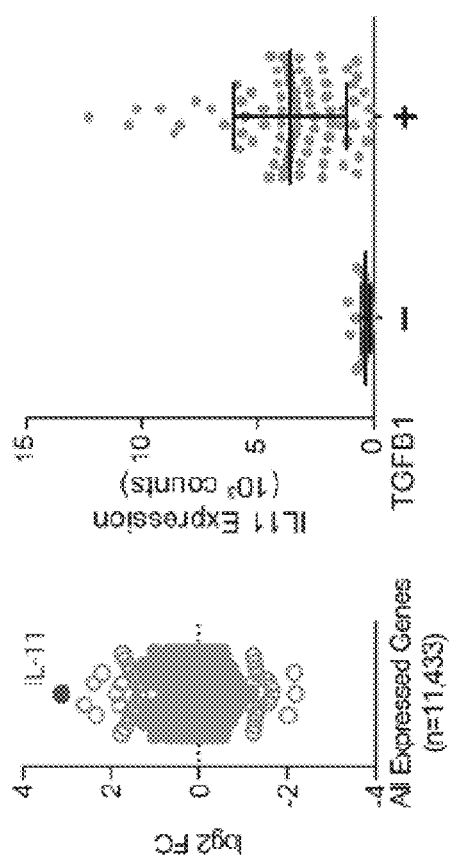
Figure 1D:
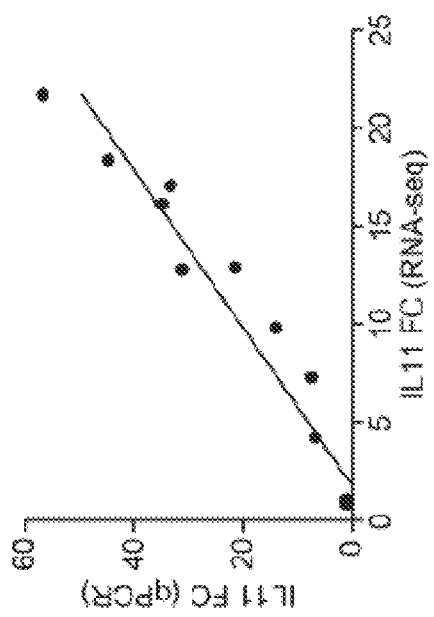

IL-11 expression was significantly induced in response to TGFβ1 treatment with RNA levels increasing as much 30× (>8× on average). IL-11 expression was higher than expression of all other individual genes (FIGS. 1a,b), meaning that of the ~11,500 genes expressed in fibroblasts IL-11 is the most markedly upregulated. This upregulation IL-11 was confirmed with RT-qPCR as well as ELISA experiments (FIGS. 1c,d), indicating increased production and release of IL-11 protein in activated fibroblasts is the main drivers of fibrosis.

To assess whether IL-11 acts as an autocrine signaling factor that drives fibrosis, we incubated non-stimulated atrial fibroblasts with recombinant IL-11 and monitored cell proliferation, myofibroblast generation as well as collagen and periostin expression at the protein level. We observed an increase in collagen production, cell proliferation and periostin expression at levels similar to those induced by the TGFβ1 signaling pathway. IL-11 activated fibroblasts also differentiated into α-SMA+ myofibroblasts (FIG. 2).

Figures 3A, 3B:
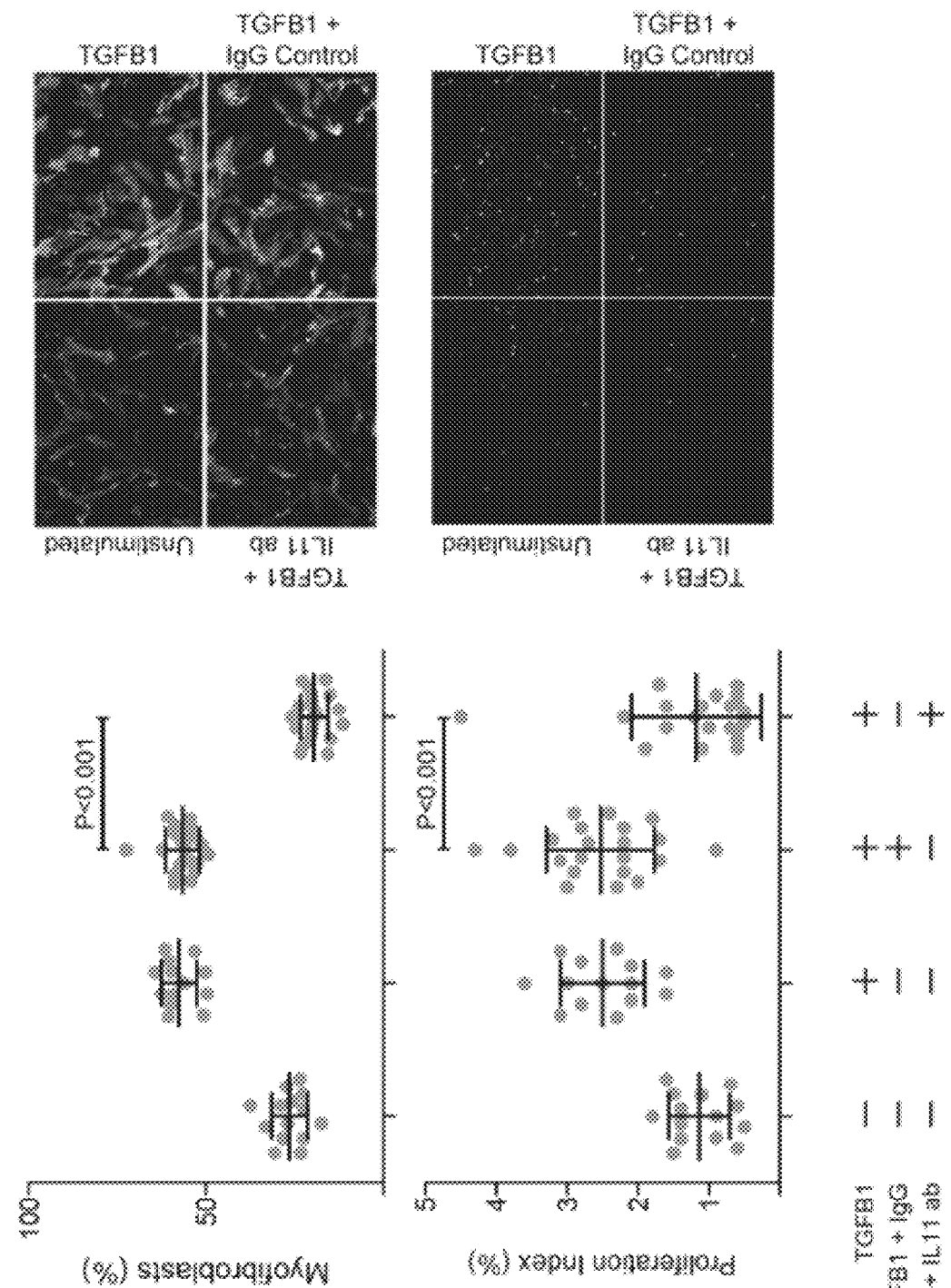
FIGS. 3A, 3B, 3C and 3D. Inhibition of IL-11 with a neutralizing antibody prevents TGFβ1-induced fibrosis. Human atrial fibroblasts were stimulated with TGFβ1 (5 ng/ml), TGFβ1 and an antibody against IL-11 or TGFβ1 and an isotype control. Charts and photographs show cell stained after 24 hours for (3A) α-SMA, (3A) EdU, (3C) collagen and (3D) periostin to identify myofibroblasts and highly proliferative cells and to quantify the production of extracellular matrix proteins. Fluorescence was quantified on the Operetta platform for up to 21 fields per condition. This experiment was repeated with fibroblasts derived from different individuals with similar results. In the presence of an antibody blocking IL-11, TGFβ1-stimulated fibroblasts have a decreased ratio of myofibroblasts, are less proliferative and express less collagen and periostin compared to control cells. This shows that IL-11 is an essential component of TGFβ1 signaling pathway acting in an autocrine and/or paracrine feed forward fashion and its inhibition reduces the pro-fibrotic effects of this key regulator of fibrosis in humans.

In addition to its pro-fibrotic function, IL-11 was also found to play a critical role in the TGFβ1 induced fibrotic response itself. Inhibition of IL-11 with a neutralising anti-human IL-11 monoclonal antibody (Monoclonal Mouse $IgG_{2A}$; Clone #22626; Catalog No. MAB218; R&D Systems, MN, USA) reduced the activation of fibroblasts through TGFβ1. Cells incubated with TGFβ1 did not generate more extracellular matrix proteins when the IL-11 antibody was present (FIG. 3).

We showed that IL-11 neutralizing antibodies prevent TGFβ1-induced fibroblast activation.

Example 2

Inflammation and tissue damage stimulates a dynamic process that involves the recruitment, proliferation and activation of fibroblasts to generate extracellular matrix and initiate wound healing and scarring. This fibrotic response is characterized by widespread molecular changes in activated resident fibroblasts that can be induced by TGFβ1, a multifunctional cytokine that is released by local and infiltrating cells.

Figure 4A:
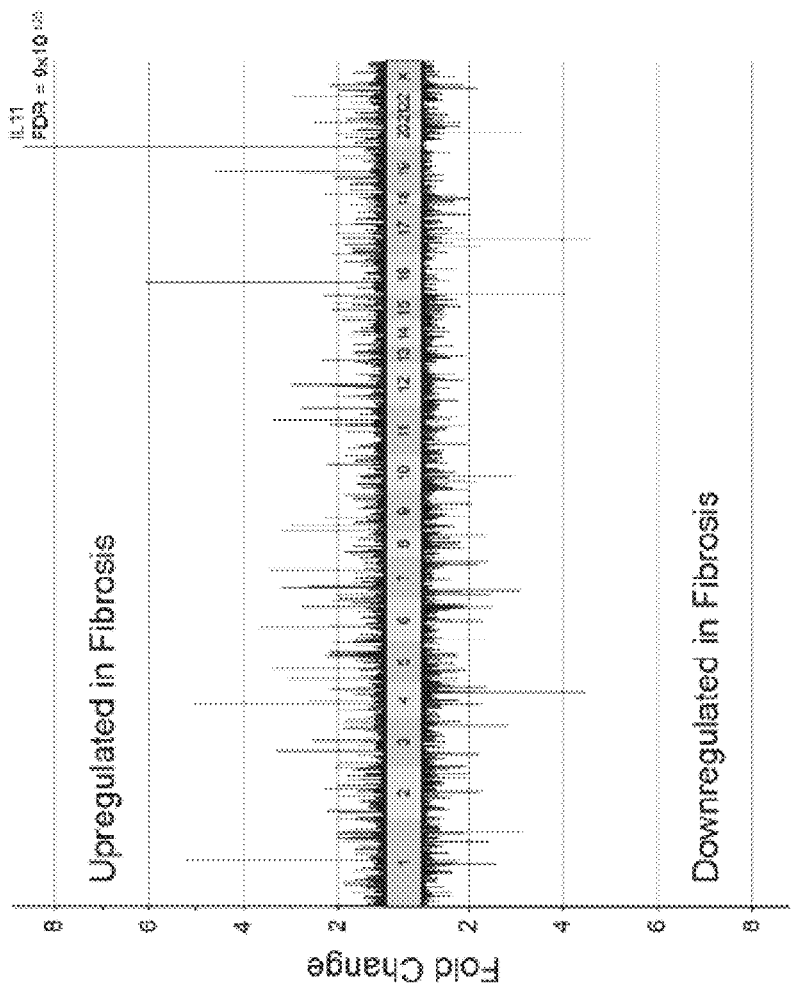
FIGS. 4A and 4B. TGFβ1 stimulation upregulates IL-11 in fibroblasts. Primary fibroblasts were derived from human atrial tissue of 80 individuals and incubated for 24 h with and without TGFβ1 (5 ng/ml). (4A) Chart showing IL-11 was the most upregulated RNA transcript in TGFβ1 stimulated fibroblasts compared to 11,433 expressed genes (FPKM≥0.5) across the genome as assessed by global transcriptome profiling. (4B) Chart showing IL-11 expression in non-stimulated (TGF-β−) and stimulated (TGF-8+) primary human fibroblasts compared to all human tissues as assessed by the GTEX project (Consortium, Gte. Human genomics. The Genotype-Tissue Expression (GTEx) pilot analysis: multitissue gene regulation in humans. *Science* (New York, N.Y.) 348, (2015)) reveals high specificity of elevated IL-11 levels to fibroblasts and specifically activated fibroblasts, the signature of which is not appreciated at the level of the whole organ that contains multiple cell types and few, IL11-expressing, fibroblasts.
Figure 4B:
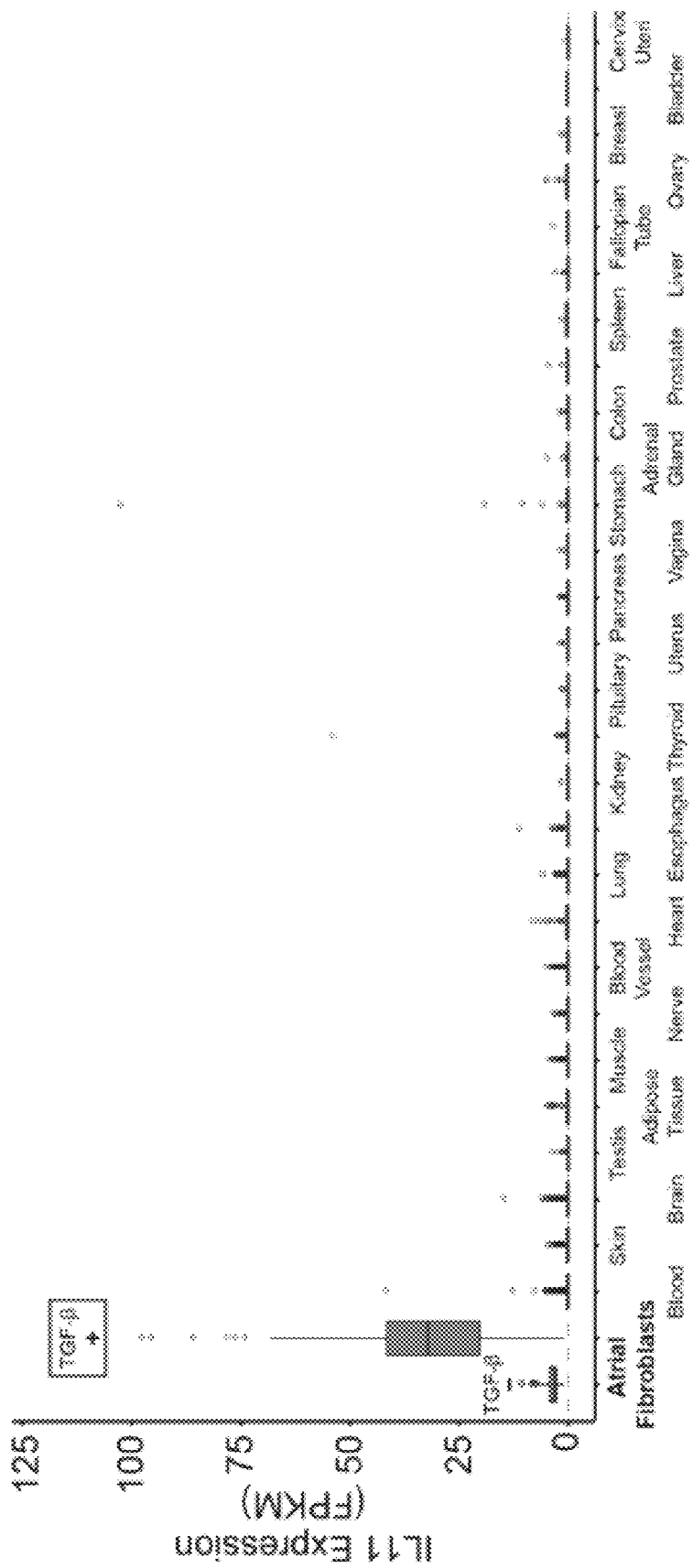

To identify key markers of this transition we assessed and ranked global RNA expression differences via transcriptome sequencing in atrial fibroblasts derived from 80 individuals before and 24 hours after TGFβ1 treatment. As discussed in Example 1, IL-11 expression was significantly upregulated in activated fibroblasts and we showed for the first time that the IL-11 transcriptional response is higher than the transcriptional response of all other individual genes regulated in fibrosis (FIG. 4a). Comparison of the IL-11 expression level in our model system to various human tissues indicated that high IL-11 levels were also very specific for the fibrotic response (FIG. 4b), making it an ideal marker to assess the extent of fibrosis in the human body.

Figures 5A, 5B, 5C, 5D:
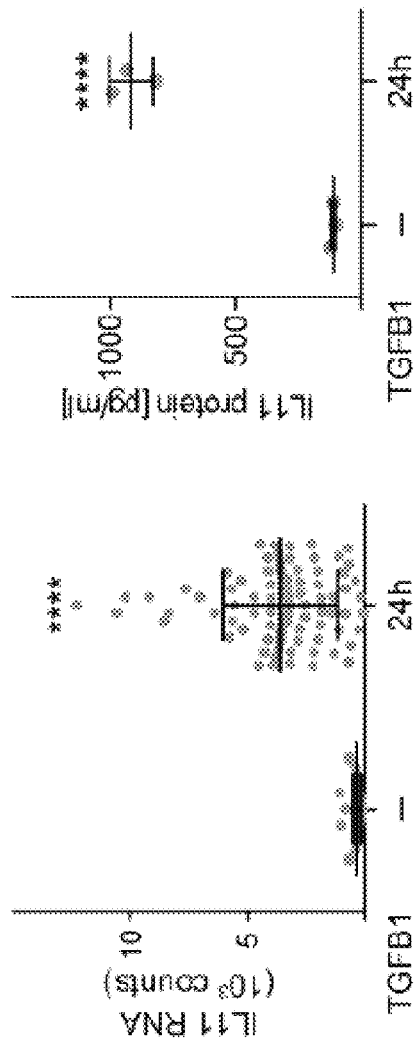
FIGS. 5A, 5B, 5C and 5D. IL-11 acts as an autocrine factor on fibroblasts and induces its own expression via translational regulation alone. Primary fibroblasts were stimulated with TGF-β for 24 hours. (5A) Chart showing IL-11 RNA expression increased significantly (FDR=9.1×10$^{-125}$) more than 8-fold on average across 80 individuals. (5B) Chart showing results of an ELISA assay confirming a significant increase in IL-11 protein secreted by stimulated fibroblasts (t-test). (5C) Chart showing incubation of primary fibroblasts with IL-11 does not increase IL-11 RNA levels (RT-qPCR). (5D) Chart showing incubation of primary fibroblasts with IL-11 induces IL-11 protein secretion significantly (Dunnett) as detected by ELISA. Adjusted P-values are given as ****P<0.0001.

To further assess whether IL-11 acts as an autocrine signaling factor that drives fibrosis, we confirmed that an upregulation of IL-11 RNA (FIG. 5a) lead to an increase in IL-11 secretion (FIG. 5b) from atrial fibroblasts. Incubation of fibroblasts with IL-11 did not increase IL-11 RNA expression (FIG. 5c), but lead to an increase in IL-11 secretion from the cells (FIG. 5d). This shows that IL-11 is having an autocrine effect on fibroblasts that regulates the production of IL-11 protein at the translational level.

Figures 6A, 6B:
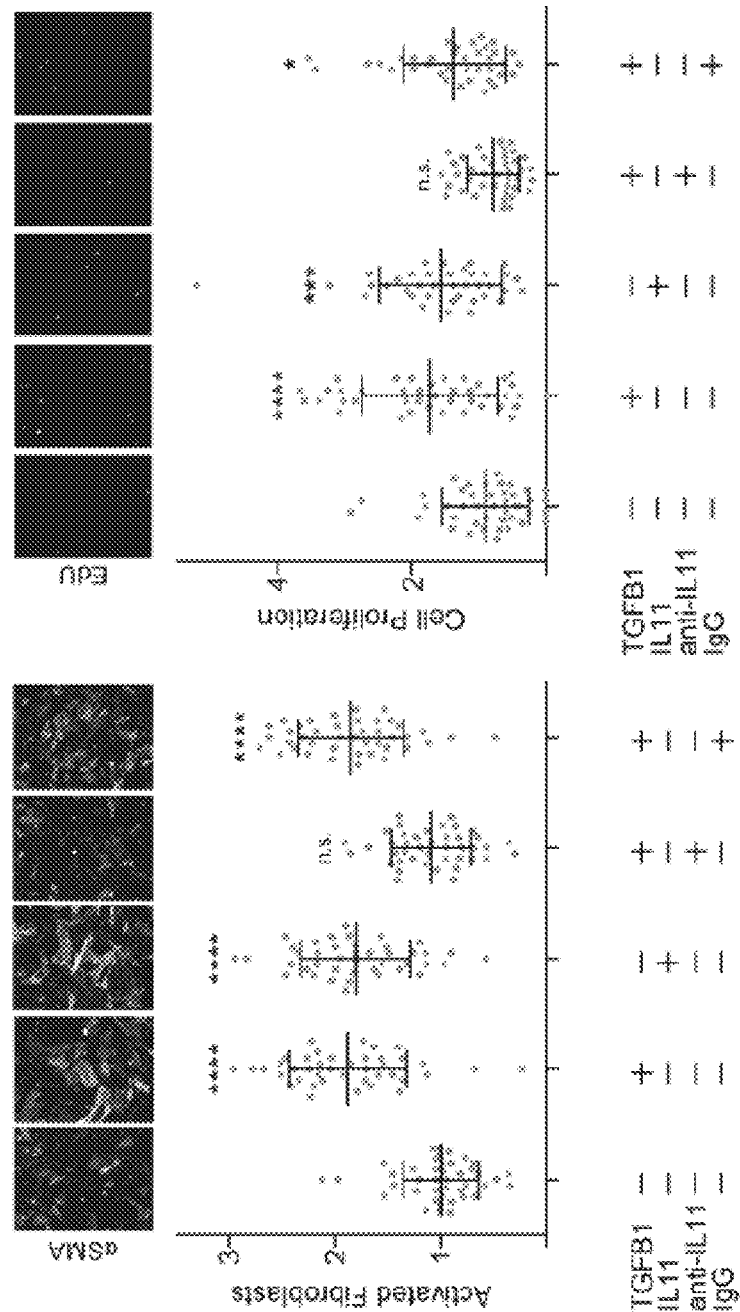
FIGS. 6A, 6B, 6C, 6D, 6E and 6F. IL-11 drives proliferation and activation of fibroblasts as well as extracellular matrix production and is required for the TGFβ1-mediated fibrotic response. Cardiac fibroblasts derived from 3 individuals were incubated for 24 h with TGFβ1 (5 ng/ml), IL-11 (5 ng/ml) or TGFβ1 and a neutralizing IL-11/control antibody. Charts and photographs show results of cell staining following incubation for (6A) α-SMA content to estimate the fraction of myofibroblasts, (6B) EdU to track actively proliferating cells (6C) Periostin to estimate ECM production. Fluorescence was measured with the Operetta platform for 14 fields across 2 wells for each patient. Charts also show the secretion of fibrosis markers IL-6 (6D), TIMP1 (6E) and MMP2 (6F) as assessed via ELISA. Fluorescence was normalized to the control group without stimulation and the mean with standard deviation is plotted. IL-11 induces a fibrotic response at similar levels as TGFβ1 and inhibition of IL-11 rescues the TGFβ1 phenotype on the protein level. Adjusted P-values are given as *P<0.05, P<0.01, *P<0.001 or ****P<0.0001 of experimental groups compared to unstimulated cells (Dunnett). Outliers were removed (ROUT, Q=2%).
Figure 6D:
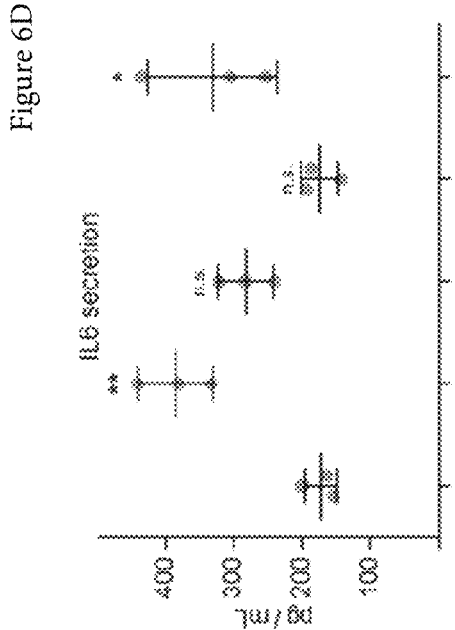
Figure 6F:
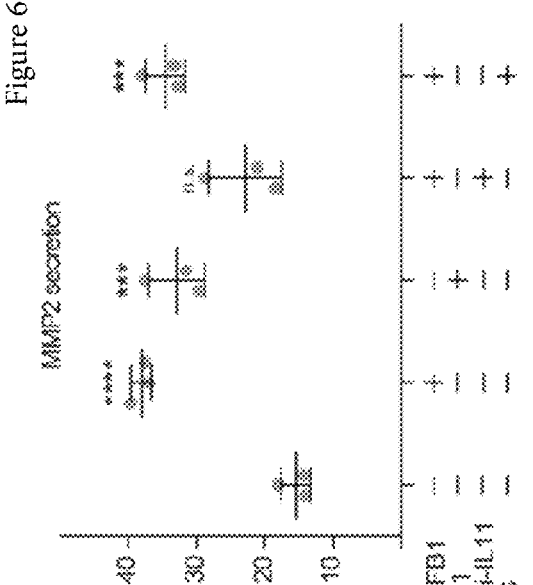
Figure 6C:
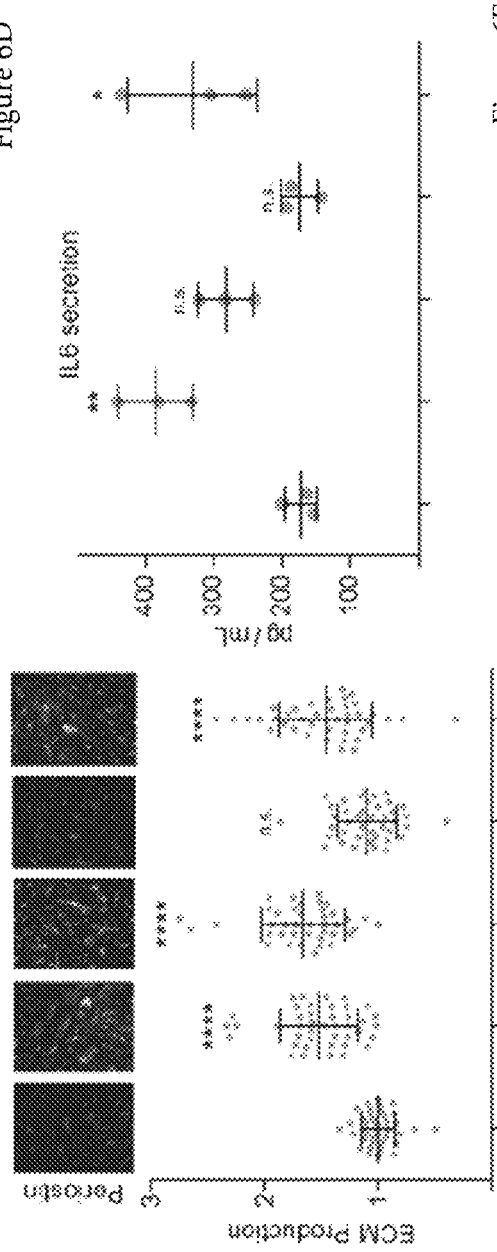
Figure 6E:
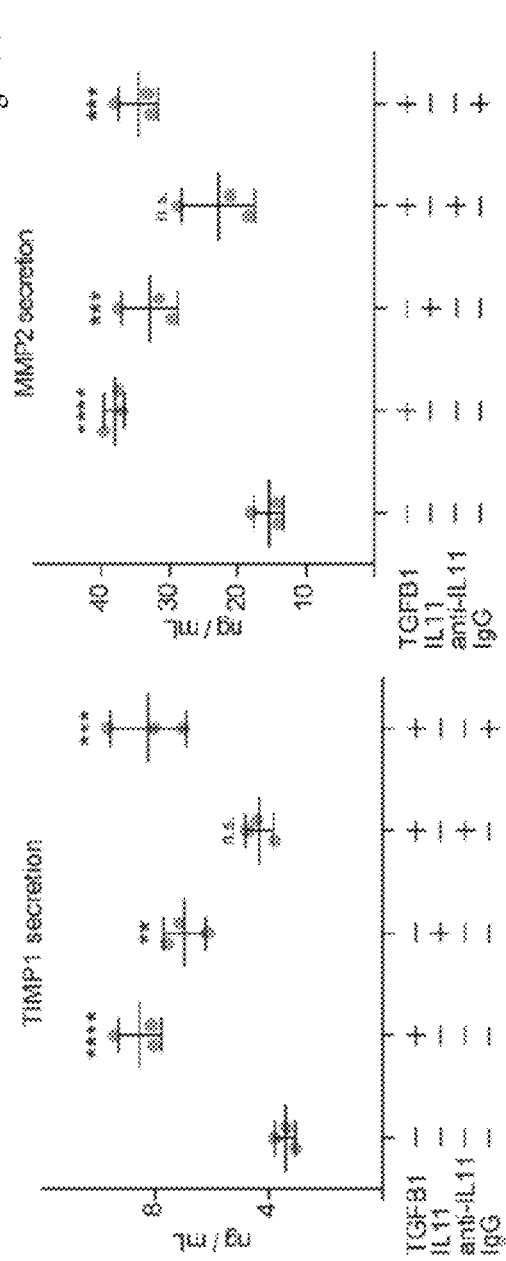

We then incubated atrial fibroblasts with TGFβ1, recombinant IL-11 or TGFβ1 and a neutralising anti-human IL-11 monoclonal antibody (Monoclonal Mouse $IgG_{2A}$; Clone #22626; Catalog No. MAB218; R&D Systems, MN, USA) and monitored cell proliferation, myofibroblast generation as well as periostin expression at the protein level. We observed an increase in activated fibroblasts (αSMA-positive cells), periostin production and cell proliferation at a similar level for both TGFβ1 and IL-11 stimulated fibroblasts. In addition to its pro-fibrotic function, IL-11 was also found to play a critical role in the TGFβ1 fibrosis itself. The pro-fibrotic effect of TGFβ1 was inhibited when we neutralized IL-11 with the antibody (FIGS. 6a-c). The same pattern was observed when we monitored the secretion of fibrosis markers such as IL6, MMP2 and TIMP1 (FIGS. 6d-f).

Figure 7A:
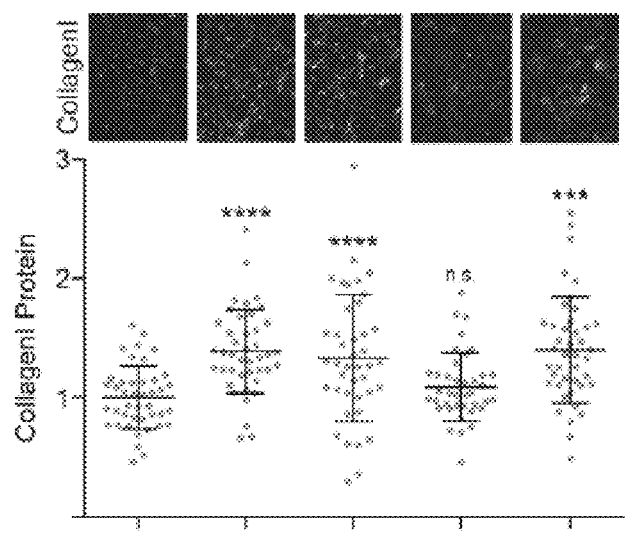
FIGS. 7A, 7B and 7C. IL-11 promotes collagen protein synthesis and stalls the pro-fibrotic effect of TGFβ1 at the RNA level. Cardiac fibroblasts derived from 3 individuals were incubated for 24 h with TGFβ1 (5 ng/ml), IL-11 (5 ng/ml) or TGFβ1 and a neutralizing IL-11 antibody. Following incubation (7A) Chart showing results following incubation of cell staining for collagen using the Operetta assay; florescence was quantified as described above for FIG. 6, (7B) Chart showing secreted collagen levels assessed with a Sirius Red staining and (7C) Chart showing collagen RNA levels measured by RT-qPCR. IL-11 induces a fibrotic response at similar levels as TGFβ1 only at the protein level. Higher expression of Collagen RNA transcripts by TGFβ1 did not lead to increased protein production if IL-11 was neutralized with an antibody. Adjusted P-values are given as *P<0.05, *P<0.001 or **P<0.0001 of experimental groups compared to unstimulated cell control group (Dunnett).
Figure 7B:
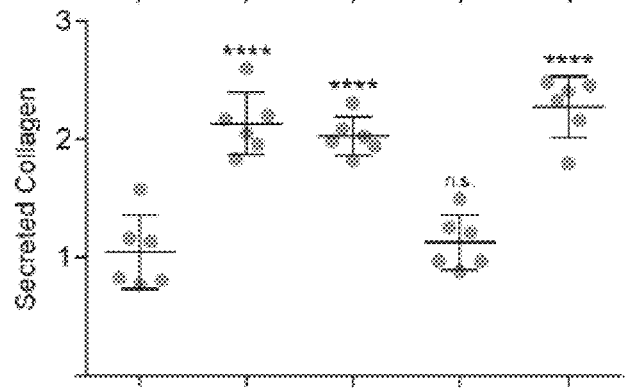
Figure 7C:
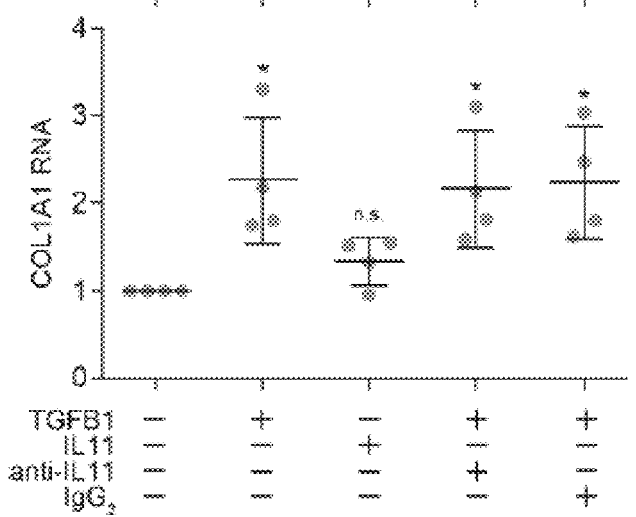

We then monitored the deposition of collagen, the pathognomonic hallmark of the fibrotic response, using a number of assays across several regulatory levels of gene expression. TGFβ1 was found to increase intracellular collagen (FIG. 7a), secreted collagen (FIG. 7b) as well as collagen RNA levels (FIG. 7c) as expected. The response to IL-11 was only observed at the protein level (FIG. 7a,b) and not on the RNA level (FIG. 7c). Stimulation with TGFβ1 in parallel to inhibiting IL-11 led to an increase in collagen RNA but this TGFβ1-driven effect was not forwarded to the protein level.

Figure 8E:
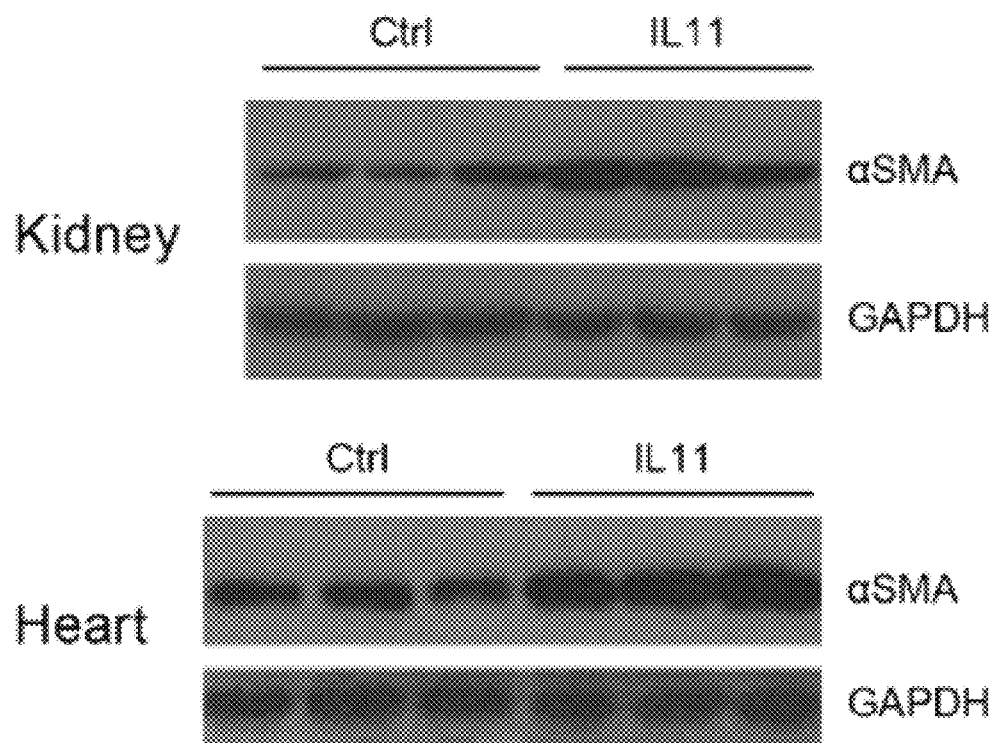

To establish further the central role of IL-11 in fibrosis downstream of multiple pro-fibrotic stimuli, we assessed IL-11 expression across fibroblast populations derived from four different tissues in response to TGFβ1 (FIG. 8a), ET-1, (FIG. 8b) and PDGF (FIG. 8c). We also administered recombinant IL-11 systemically to C57BL/6 mice and monitored collagen and αSMA expression. Collagen production was increased across kidney, heart and liver (FIG. 8d) and we also detected more activated fibroblasts in the heart and kidney, indicated by higher αSMA protein levels (FIG. 8e).

Figure 9:
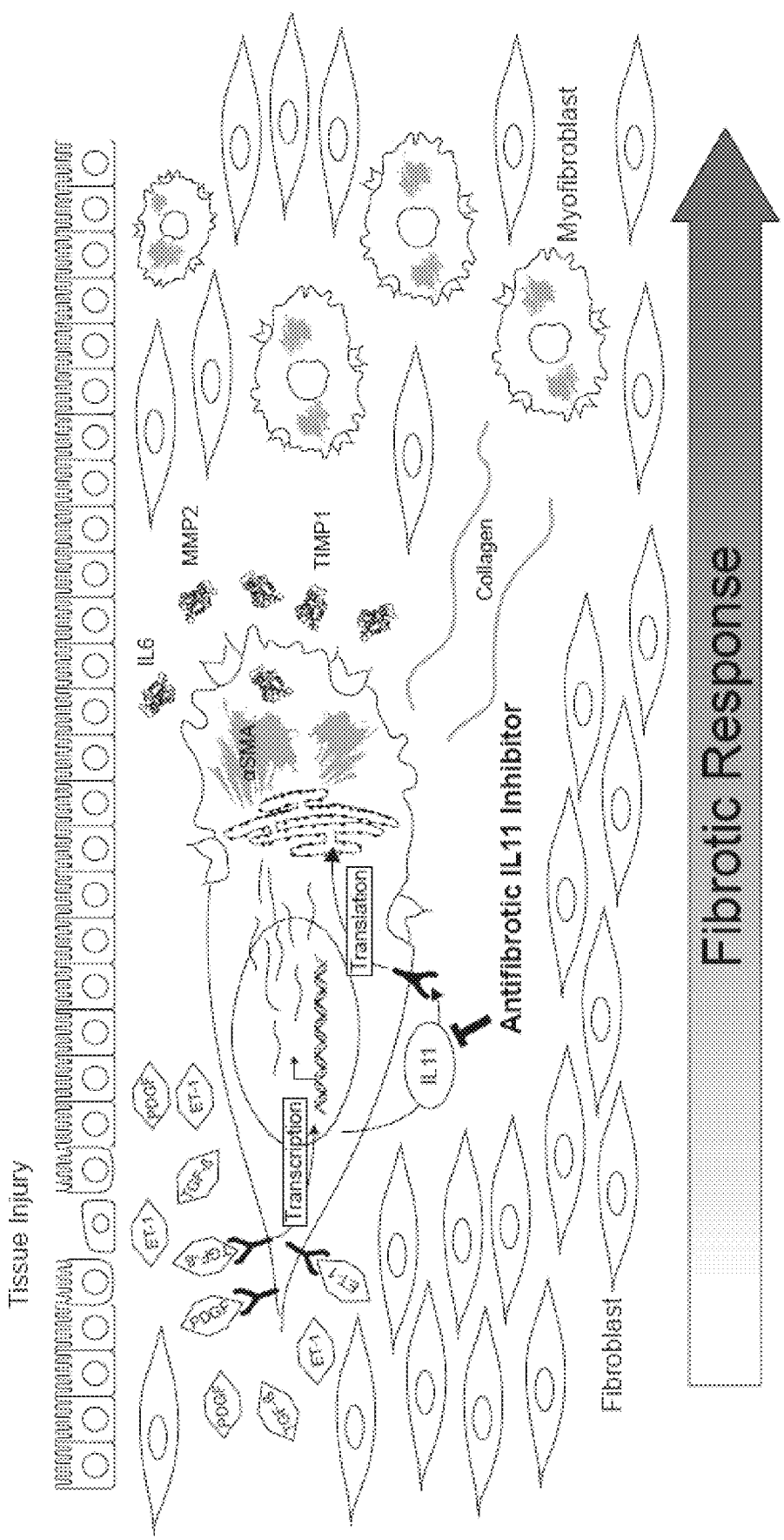
FIG. 9. Diagram illustrating role of IL-11 as an essential regulator of the fibrotic response. IL-11 is an essential regulator required for the fibrotic response. In response to tissue damage or chronic inflammation, cytokines such as TGFβ1, ET-1 or PDGF are released to upregulate the transcription of fibrosis marker genes. The autocrine agent IL-11 is then produced in response to these upstream stimuli to ensure efficient translation of upregulated transcripts into functionally relevant proteins in a cell-specific manner. Inhibition of IL-11 blocks the synthesis of key extracellular matrix and myofibroblast proteins and prevents the pro-fibrotic action of a diverse set of upstream stimuli.

Our findings demonstrate a novel and central role for IL-11 in fibrosis and, most importantly, show that IL-11 is downstream of the key pro-fibrotic stimuli across several tissues. These results show that IL-11 is required for TGFβ1 to proceed from transcriptional regulation to protein translation. Inhibition of IL-11 stalls the pro-fibrotic effect of TGFβ1 on the transcriptome (FIG. 9).

Example 3: Anti-IL-11 Antibodies Inhibit Pro-Fibrotic Stimuli

Figures 3C, 3D:
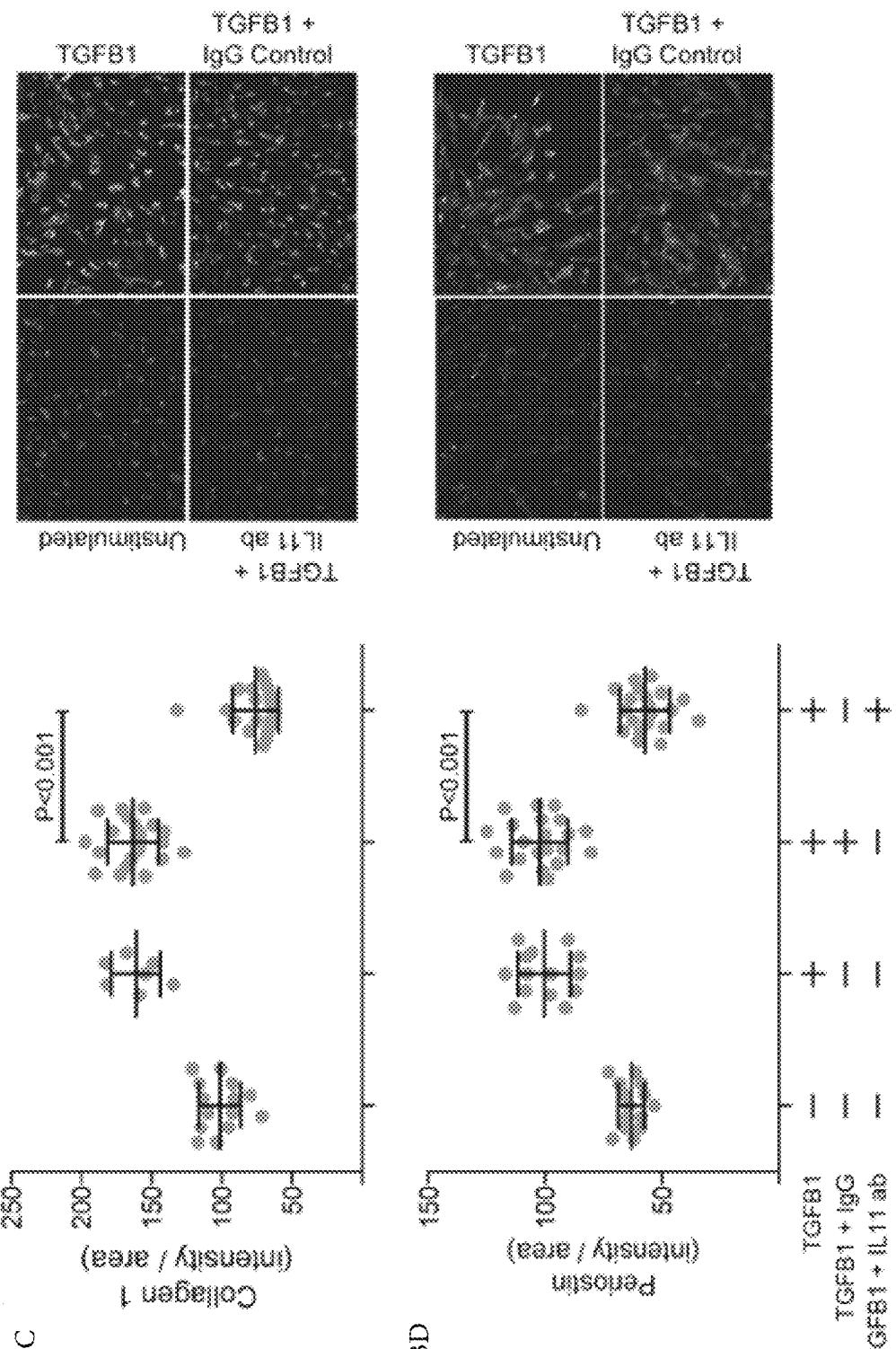

In experiments similar to those described in respect of FIG. 3c, atrial fibroblasts were exposed to other pro-fibrotic stimuli in the form of angiotensin II (ANG 2), platelet-derived growth factor (PDGF) and endothelin 1 (ET-1), and collagen production was measured.

Figure 10:
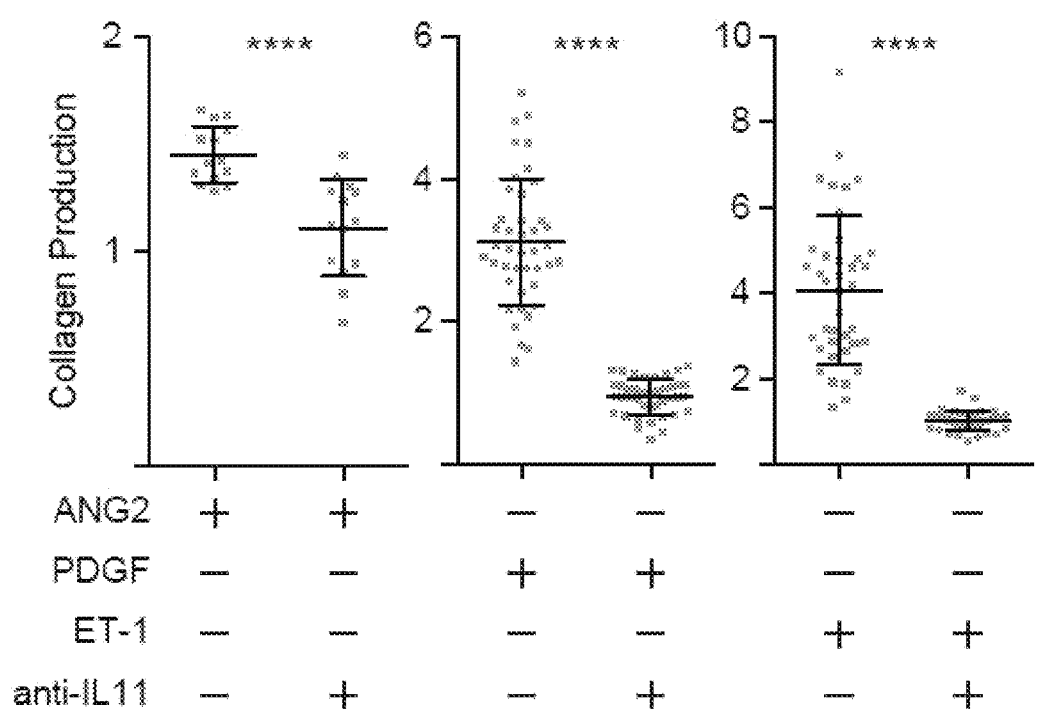
FIG. 10. Inhibition of IL-11 stops collagen protein synthesis in response to pro-fibrotic cytokines ANG2 (Angiotensin II), PDGF and ET-1. Cardiac fibroblasts were incubated for 24 h with ANG2, PDGF or ET-1 and a neutralizing IL-11 antibody. Following incubation cells were stained for collagen and florescence was quantified. These stimuli induce a fibrotic response at similar levels to TGFβ1. However, collagen expression is not increased if IL-11 is neutralized with an antibody. P-values are given as: ****P<0.0001 (t-test).

In addition to induction of IL-11 mRNA expression, each of ANG2, PDGF and ET-1 induced IL-11 protein expression. Inhibition of IL-11 with a neutralising anti-human IL-11 monoclonal antibody (Monoclonal Mouse IgG$_{2A}$; Clone #22626; Catalog No. MAB218; R&D Systems, MN, USA) blocked the pro-fibrotic effect of each of these pro-fibrotic stimuli (FIG. 10) indicating IL-11 to be the central effector of the major pro-fibrotic stimuli (TGFβ1, ANG2, PDGF and ET-1).

Example 4: IL-11R Knockdown

Figure 15:
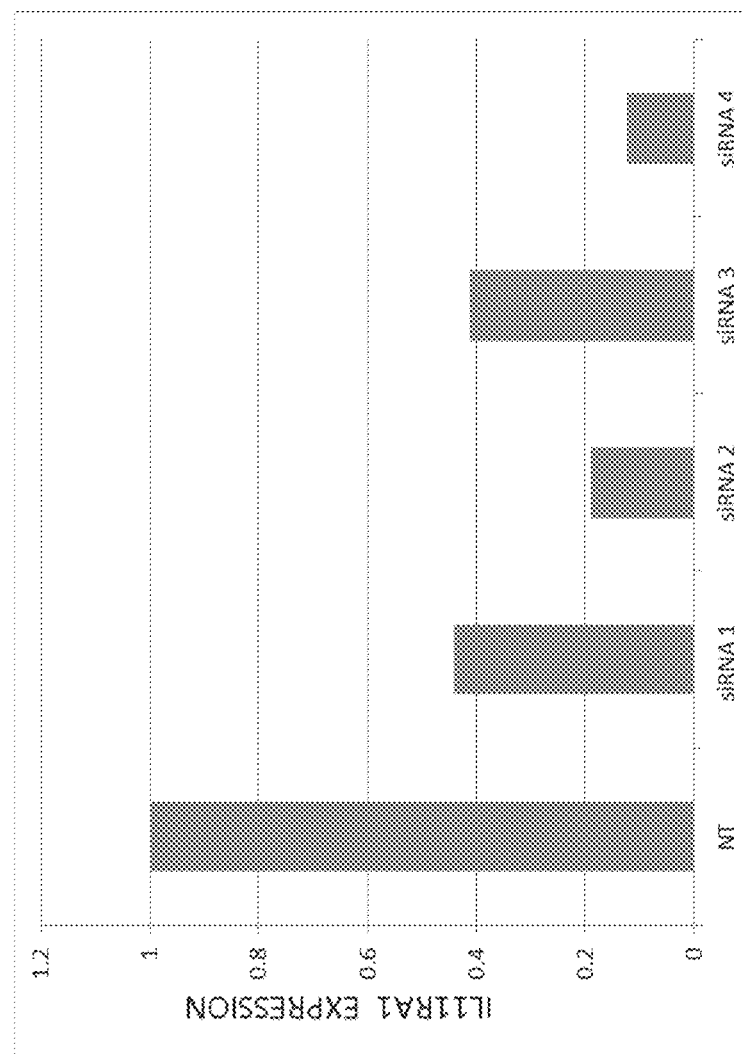
FIG. 15. Chart showing siRNA knockdown of IL-11Rα in HEK cells.

HEK cells were transfected (24 h) with non-targeting (NT) siRNA or one of four different siRNAs against the IL11RA1 receptor (siRNAs 5-8; FIG. 14; SEQ ID NOs 15 to 18). RNA was extracted and assayed for IL11RA1 mRNA expression by qPCR. Data are shown in FIG. 15 as mRNA expression levels relative to the control (NT).

Example 5: A Role for IL-11 in Fibrosis 5.1 IL-11 is Upregulated in Fibrosis

Figure 16:
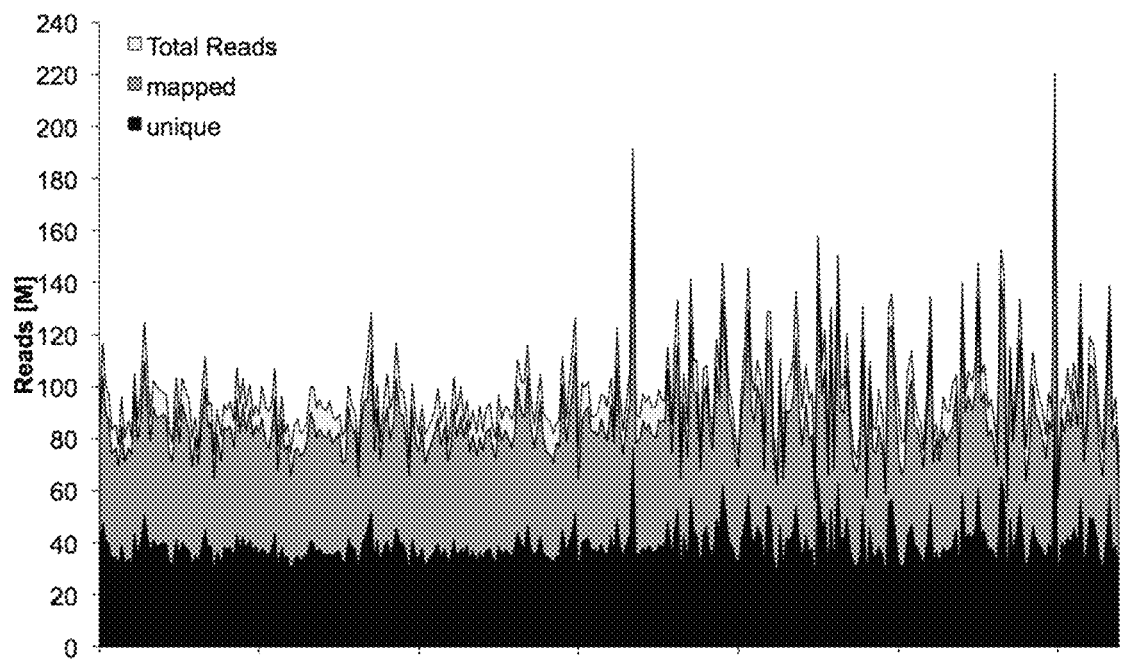
FIG. 16. Graph showing read depth for whole transcriptome sequencing of human atrial fibroblasts from 160 individuals with and without stimulation with TGFβ1.
Figure 17A:
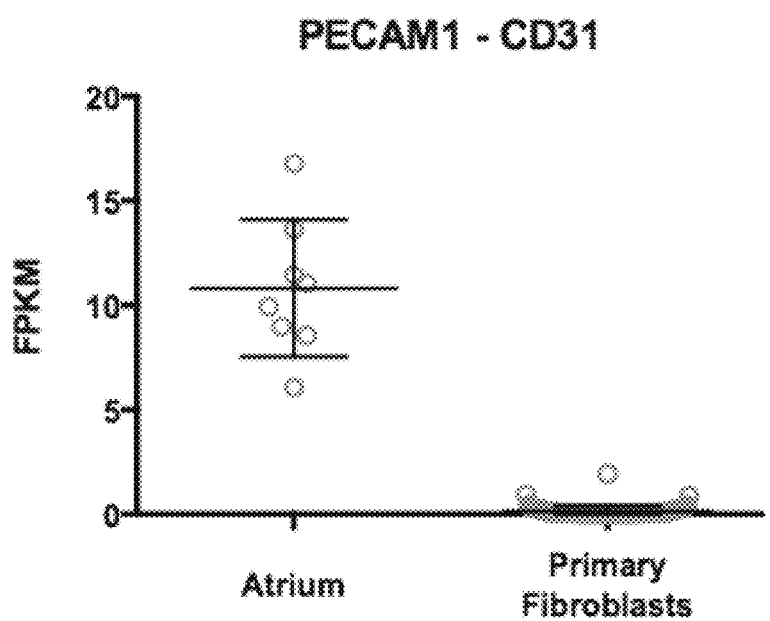
FIGS. 17A, 17B, 17C, 17D and 17E. Graphs showing expression of endothelial, cardiomyocyte and fibroblast marker genes as determined by RNA-seq of the tissue of origin (human atrial tissues samples, n=8) and primary, unstimulated fibroblast cultures. (17A) PECAM1, (17B) MYH6 (17C) TNNT2, (17D) COL1A2, and (17E) ACTA2.
Figure 17B:
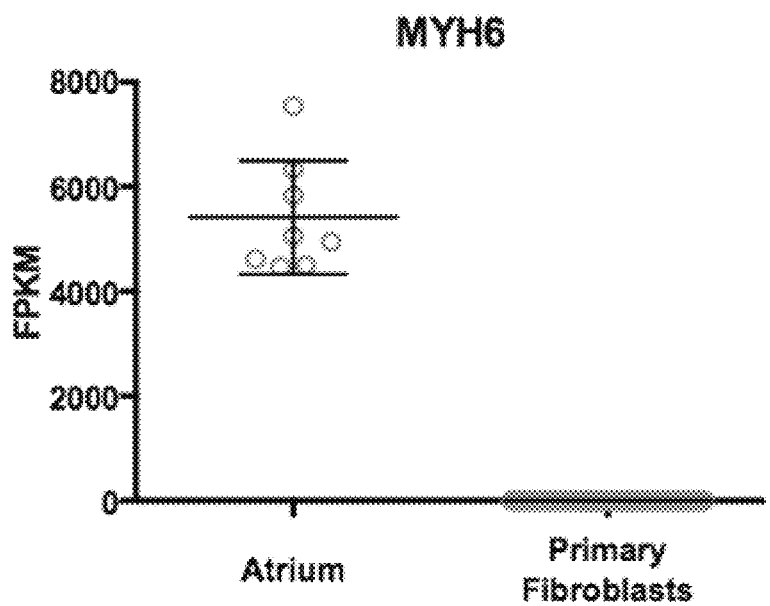
Figure 17C:
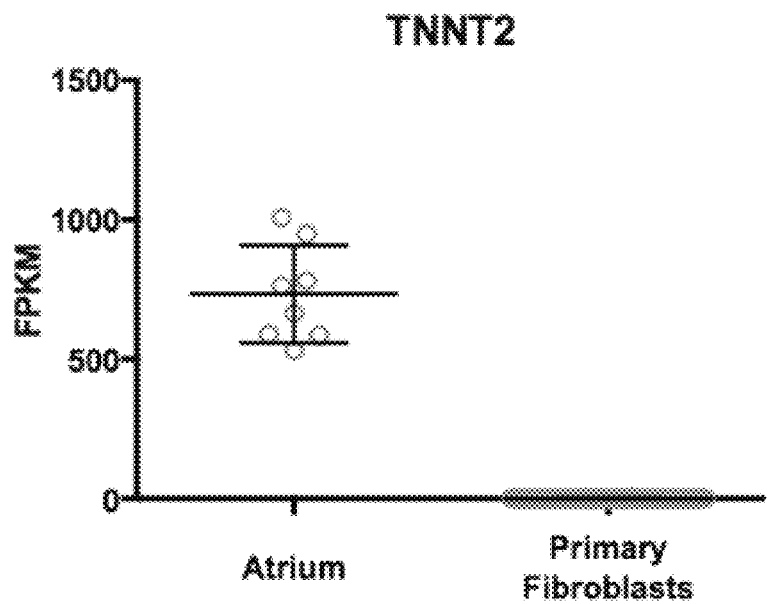
Figure 17D:
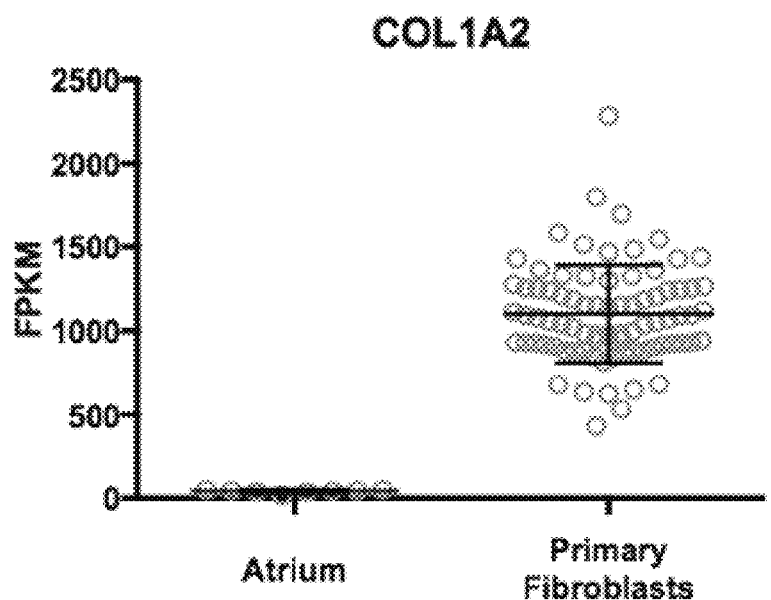
Figure 17E:
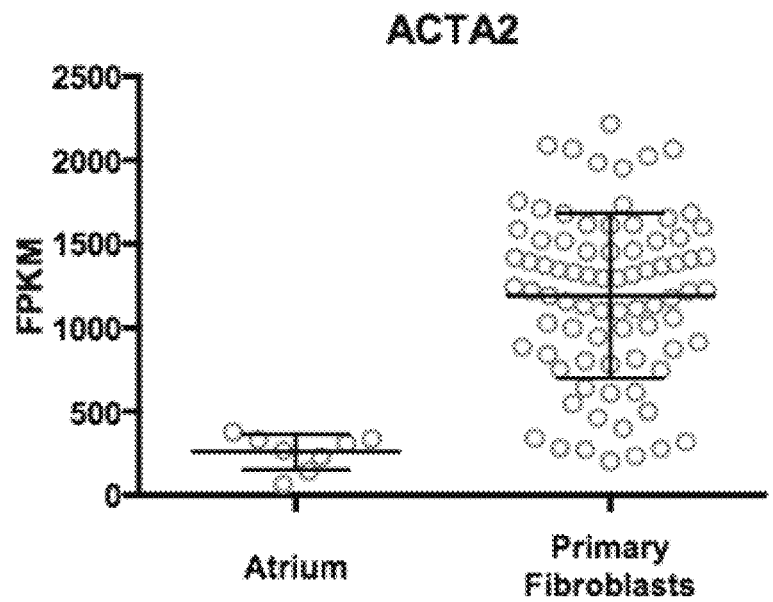

To understand the molecular processes underlying the transition of fibroblasts to activated myofibroblasts, atrial tissue was obtained from more than 200 patients that underwent cardiac bypass surgery at the National Heart Centre Singapore. Cells were cultured in vitro at low passage (passage<4), and either not stimulated or stimulated with TGFβ1 for 24 h. We subsequently performed high-throughput RNA sequencing (RNA-seq) analysis of unstimulated fibroblasts and cells stimulated with the prototypic pro-fibrotic stimulus TGFβ1 across 160 individuals; average read depth was ~70M reads per sample (paired-end 100 bp; FIG. 16).

To ensure the purity of the atrial fibroblast cell cultures, we analysed expression of endothelial cell, cardiomyocyte and fibroblast cell type marker genes from the atrium (Hsu et al., 2012 Circulation Cardiovasc Genetics 5, 327-335) in the RNA-seq dataset.

The results are shown in FIGS. 17A to 17E, and confirm the purity of the atrial fibroblast cultures.

Gene expression was assessed by RNA-seq of the tissue of origin (human atrial tissues samples, n=8) and primary, unstimulated fibroblast cultures. No/very low expression of the endothelial cell marker PECAM1 (FIG. 17A), and the cardiomyocyte markers MYH6 (FIG. 17B) and TNNT2 (FIG. 17C) was detected in the fibroblast cell culture samples. Markers for fibroblasts COL1A2 (FIG. 17D) and ACTA2 (FIG. 17E) were highly expressed compared to the tissue of origin.

Next, the RNA-seq data was analysed to identify genes whose expression was increased or decreased upon stimulation with TGFβ1, and this information was integrated with the large RNA-seq dataset across 35+ human tissues provided by the GTEx project (The GTEx Consortium, 2015 Science 348, 648-660). This enabled the identification of gene expression signatures that were specific to the fibroblast-myofibroblast transition.

Figure 18A:
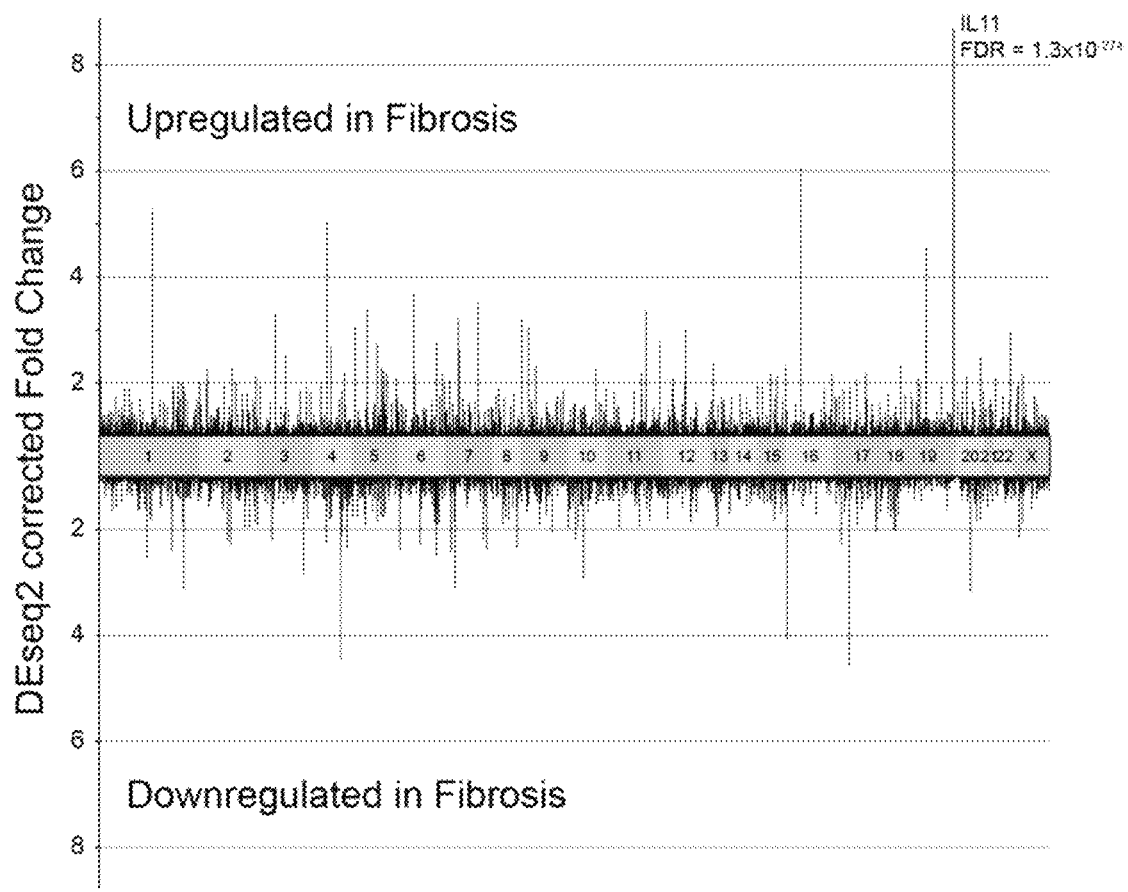
FIGS. 18A, 18B, 18C, 18D and 18E. Graphs showing upregulation of IL-11 expression in fibroblasts in response to stimulation with TGFβ1. (18A and 18B) Graphs showing fold change in gene expression in fibrosis; IL-11 is the most upregulated gene in response to TGFβ1 treatment. (18C) IL-11 secretion by fibroblasts in response to stimulation with TGFβ1. (18D) Comparison of IL-11 gene expression in tissues of healthy individuals and in atrial fibroblasts, with or without TGFβ1 stimulation. (18E) Correspondence of fold change in IL-11 expression as determined by RNA-seq vs. qPCR.
Figure 18B:
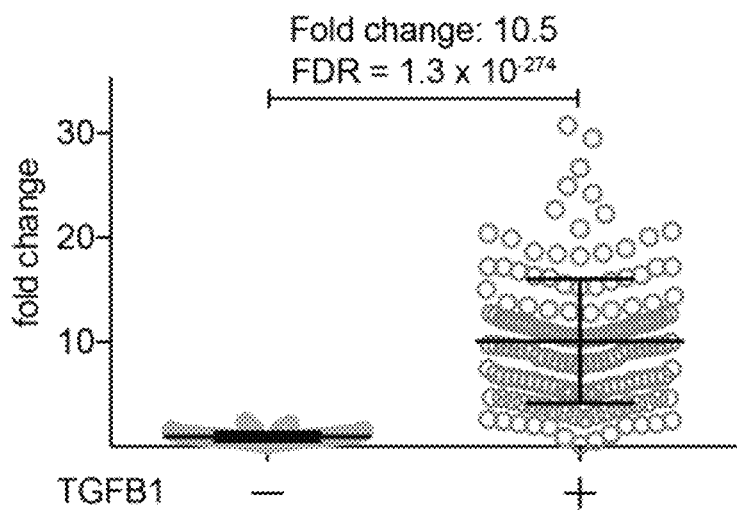

The results are shown in FIGS. 18A to 18E. Across the 10000+ genes expressed in the fibroblasts, IL-11 was the most strongly upregulated gene in response to stimulation with TGFβ1, and on average across the 160 individuals was upregulated more than 10-fold (FIG. 18A).

Figure 18C:
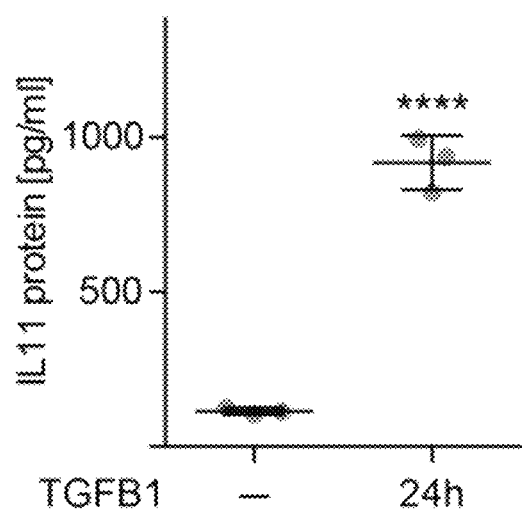
Figure 18D:
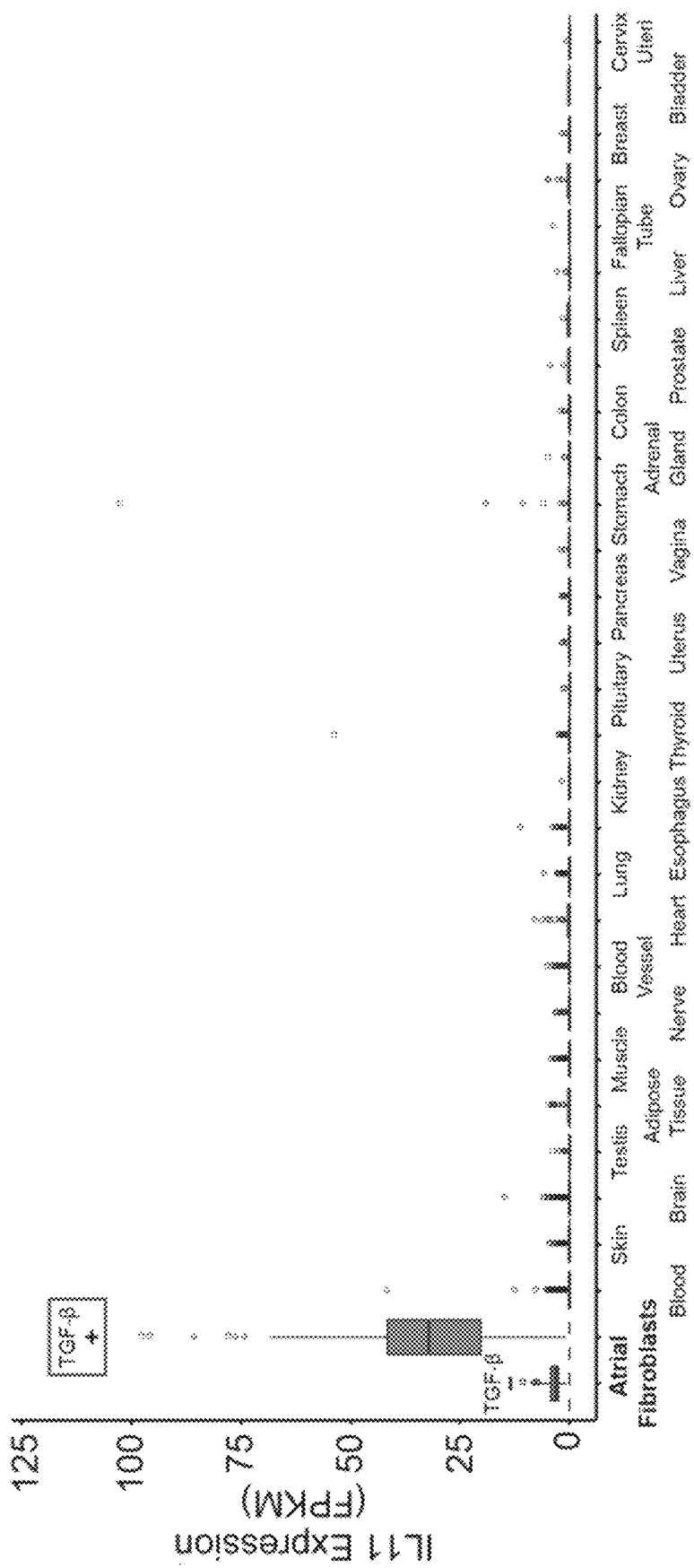
Figure 18E:
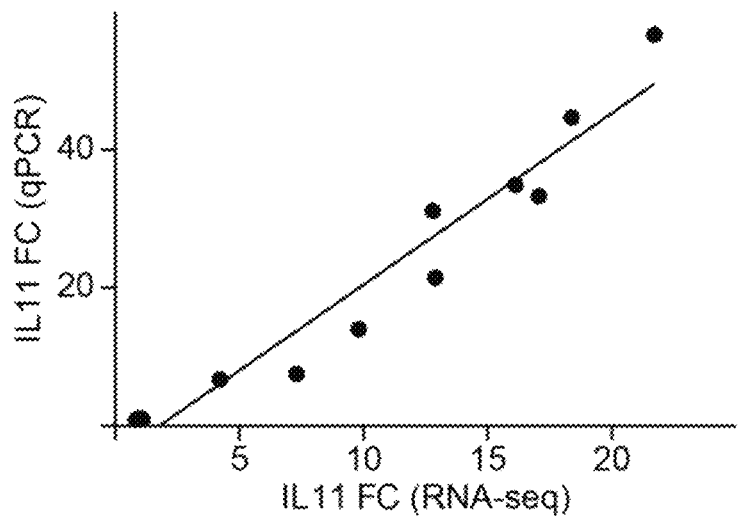

Upregulation of IL-11 expression was confirmed by ELISA analysis of the cell culture supernatant of TGFβ1 stimulated fibroblasts (FIG. 18C). As compared to the level of expression level of IL-11 in other tissues of healthy individuals, this response was observed to be highly specific to activated fibroblasts (FIG. 18D). Various fold changes of IL-11 RNA expression were also confirmed by qPCR analysis (FIG. 18E).

Next, fibroblasts were cultured in vitro and stimulated with several other known pro-fibrotic factors: ET-1, ANGII, PDGF, OSM and IL-13, and also with human recombinant IL-11. For analysing upregulation of IL-11 produced in response to stimulation with IL-11, it was confirmed that the ELISA was only able to detect native IL-11 secreted from cells and does not detect recombinant IL-11 used for the stimulations (FIG. 19B).

Figure 19A:
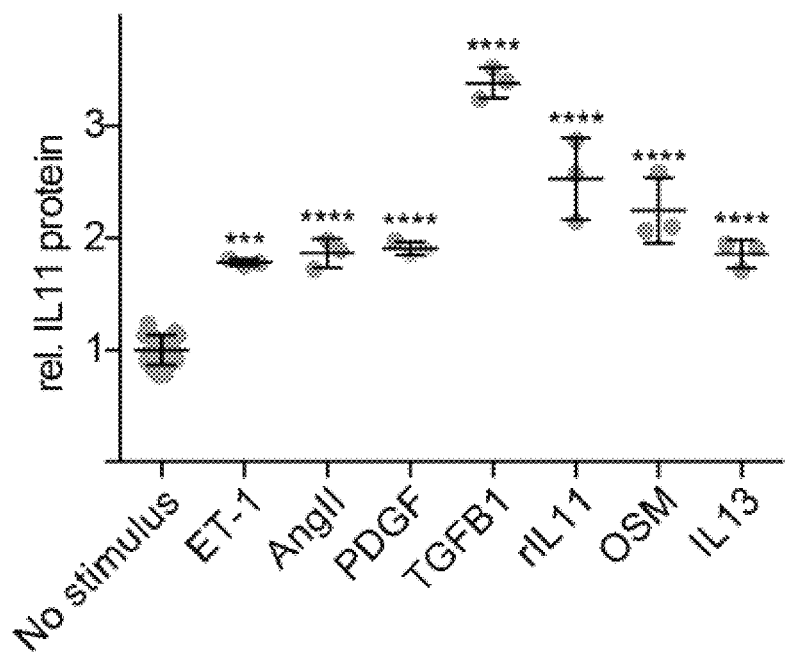
FIGS. 19A, 19B, 19C and 19D. Graphs showing induction of IL-11 secretion in primary fibroblasts by various profibrotic cytokines, as determined by ELISA. (19A) TGFβ1, ET-1, AngII, PDGF, OSM and IL-13 induce IL-11 secretion, and IL-11 also induces IL-11 expression in a positive feedback loop. (19B) Graph showing that the ELISA only detects native IL-11 secreted from cells, and does not detect recombinant IL-11 used for the IL-11 stimulation condition. (19C) and (19D) Cells were stimulated with recombinant IL-11, IL-11 RNA was measured and the native IL-11 protein level was measured in the cell culture supernatant by ELISA at the indicated time points.
Figure 19B:
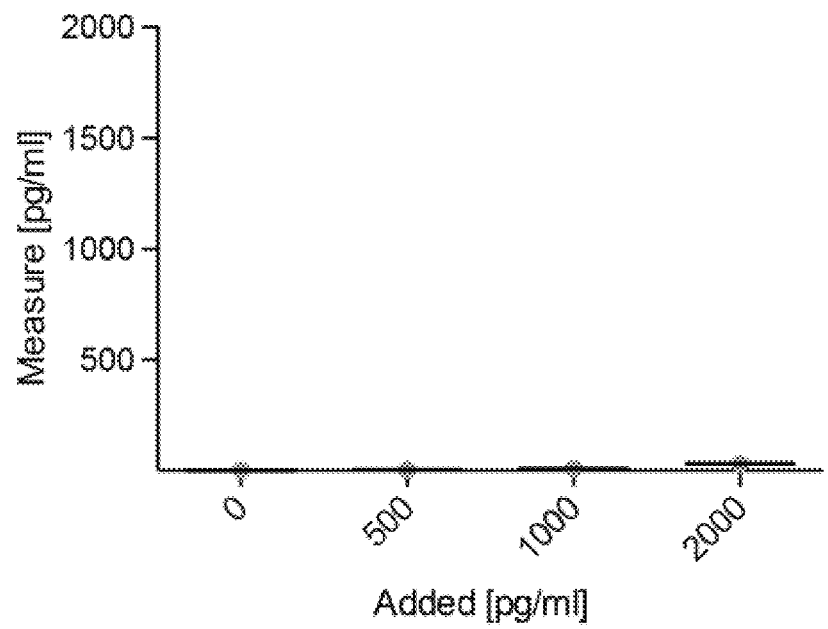
Figure 19C:
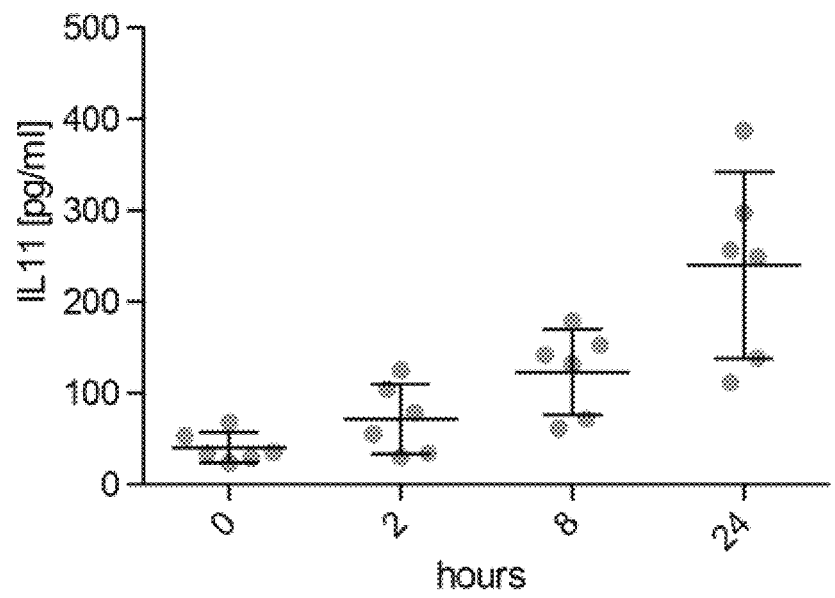

The results are shown in FIG. 19A. Each factor was found to significantly induce IL-11 secretion from fibroblasts. IL-11 is shown to act in an autocrine loop in fibroblasts, which can result in an upregulation of IL-11 protein as much as 100-fold after 72 hours (FIG. 19D).

Interestingly, this autocrine loop for IL-11 is similar to the autocrine production of IL-6. IL-6 is from the same cytokine family and also signals via the gp130 receptor (Garbers and Scheller, 2013 Biol Chem 394, 1145-1161), which is proposed to ensure the continued survival and growth of lung and breast cancer cells (Grivennikov and Karin, 2008 Cancer Cell 13, 7-9).

Figure 19D:
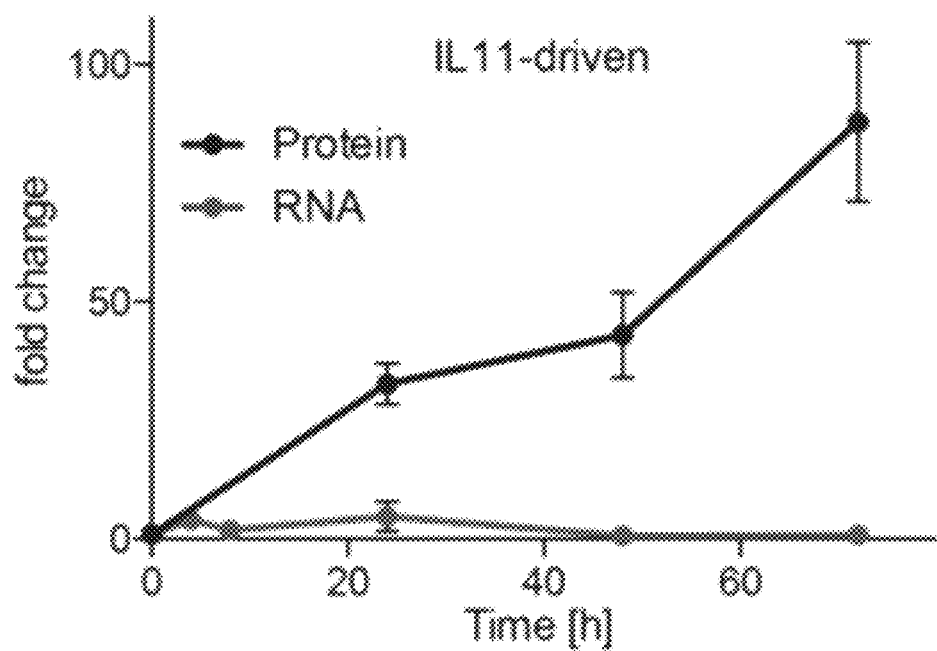

No increase in IL-11 RNA level was detected in response to stimulation with IL-11 (FIG. 19D). Unlike TGFβ1, which increases IL-11 expression at both the RNA and protein level, therefore IL-11 seems to upregulate IL-11 expression only at the post-transcriptional level.

5.2 IL-11 has a Profibrotic Role in Fibrosis of Heart Tissue

To explore whether the autocrine production of IL-11 is pro- or anti-fibrotic, fibroblasts were cultured in vitro with recombinant IL-11, and the fraction of myofibroblasts (αSMA-positive cells) and extracellular matrix production was analysed.

The expression of αSMA, collagen and periostin was monitored with the Operetta High-Content Imaging System in an automated, high-throughput fashion. In parallel, secretion of fibrosis marker proteins such as MMP2, TIMP1 and IL-6 was analysed by ELISA assays, and the levels of collagen were confirmed by calorimetric Sirius Red analysis of the cell culture supernatant.

Briefly, atrial fibroblasts derived from 3 individuals were incubated in 2 wells each for 24 h without stimulation, with TGFβ1 (5 ng/ml), or with IL-11 (5 ng/ml). Following incubation, cells were stained to analyse α-SMA content to estimate the fraction of myofibroblasts, and for collagen and periostin to estimate ECM production. Fluorescence was measured in 7 fields per well. The supernatant of 2 wells per individual was also assessed for collagen content by Sirius Red staining. The signal was normalized to the control group without stimulation. Secretion of the fibrosis markers IL-6, TIMP1 and MMP2 was analysed via ELISA.

Figure 20A:
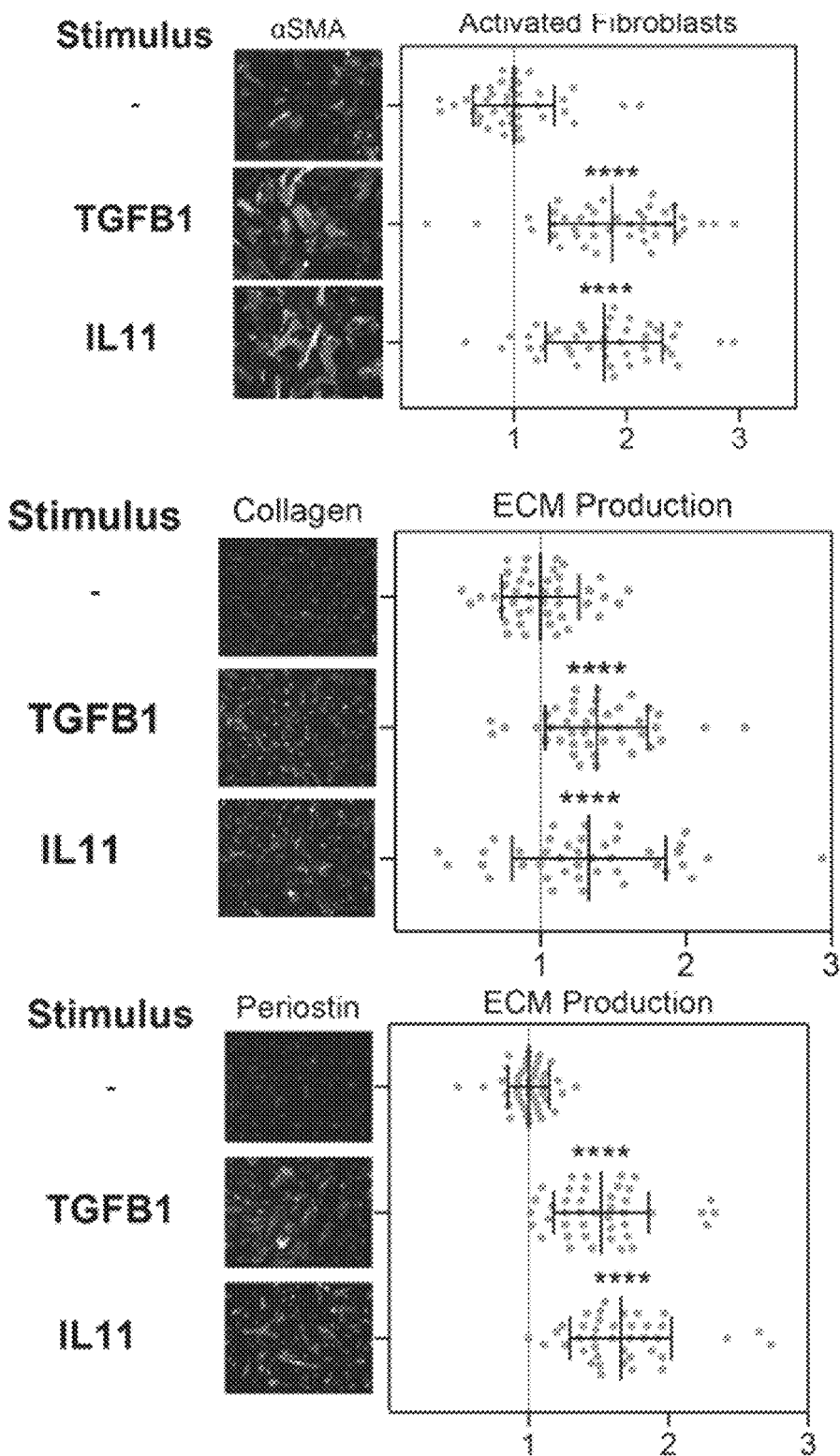
FIGS. 20A, 20B, 20C, 20D, 20E and 20F. Graphs and images showing myofibroblast generation from, and production of ECM and cytokine expression by, atrial fibroblasts in response to stimulation with TGFβ1 or IL-11. (20A) myofibroblast generation and ECM production by primary atrial fibroblasts following stimulation with TGFβ1 or IL-11, as measured by fluorescence microscopy following staining for a α-SMA, collagen or periostin. (20B) Collagen content of cell culture supernatant as determined by Sirius Red staining. Secretion of the fibrosis markers (20C) IL-6, (20D) TIMP1 and (20E) MMP2 as measured by ELISA. (20F) Activation of murine fibroblasts by stimulation with human or mouse recombinant IL-11. *P<0.05, P<0.01, *P<0.001, ****P<0.0001 [Mean±SD, Dunnett].
Figure 20B:
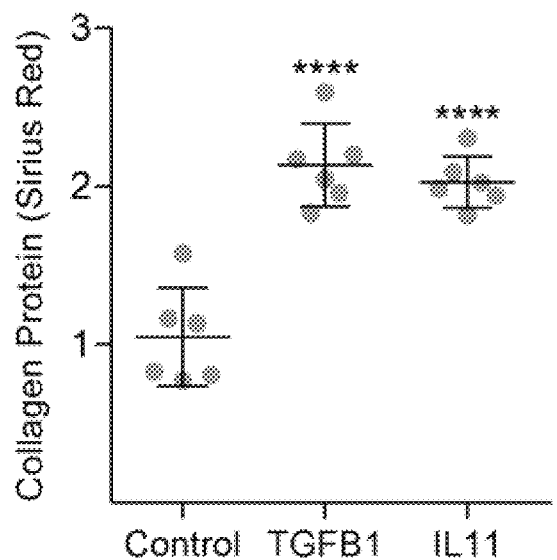
Figure 20C:
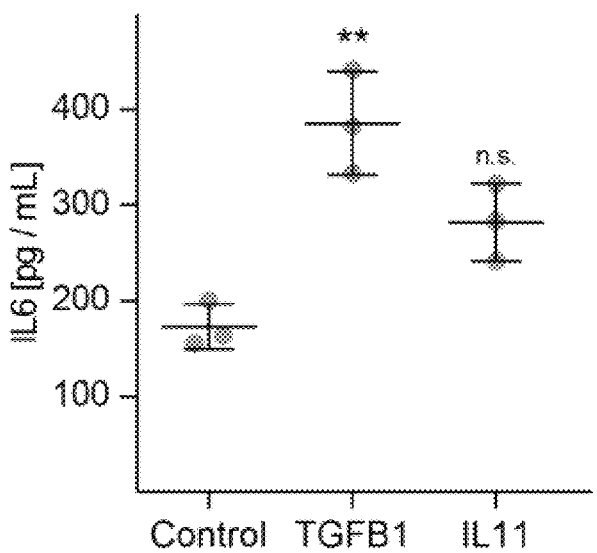
Figure 20D:
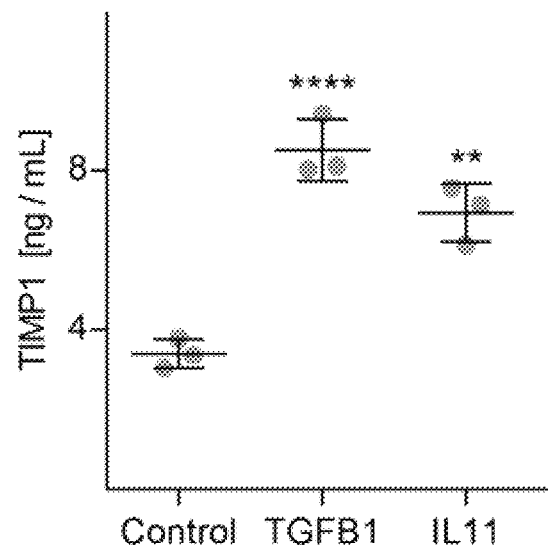
Figure 20E:
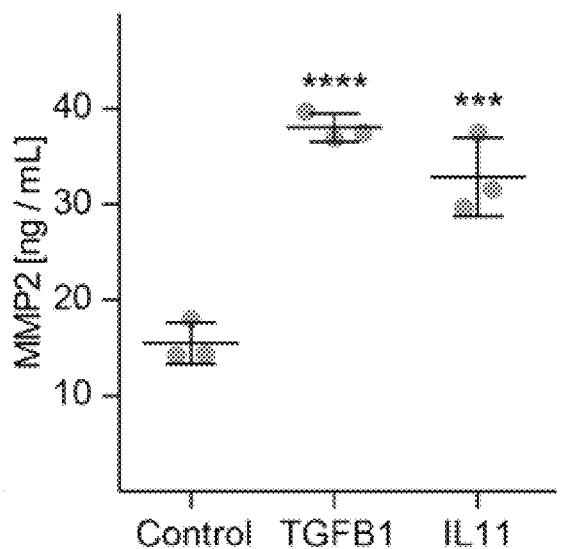

The results are shown in FIGS. 20A to 20F. TGFβ1 activated fibroblasts and increased ECM production (FIG. 20A). Unexpectedly, and in contrast with the anti-fibrotic role described for IL-11 in heart tissue in the scientific literature, recombinant IL-11 caused an increase in the fraction of myofibroblasts in fibroblast cultures, and also promoted the production of extracellular matrix proteins collagen and periostin to the same extent as TGFβ1 (FIG. 20A). Both of IL-11 and TGFβ1 cytokines also significantly increased the secretion of pro-fibrotic markers IL-6, TIMP1 and MMP2 (FIGS. 20B to 20E), and to a similar level.

The inventors hypothesized that the contradiction between the present finding that IL-11 is profibrotic in heart tissue and the antifibrotic role described in the literature might be related to the use of human IL-11 in rodents in those previous studies (Obana et al., 2010, 2012; Stangou et al., 2011; Trepicchio and Dorner, 1998).

Figure 20F:
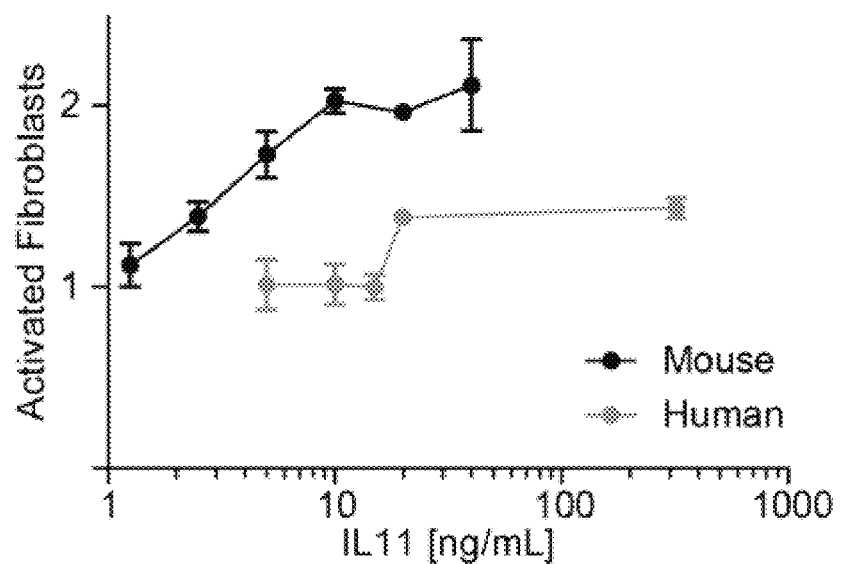

To investigate this hypothesis, serial dilutions of both human and mouse IL-11 were performed, and the activation of human atrial fibroblasts was monitored (FIG. 20F). No activation of fibroblasts was observed at low concentrations of human IL-11 on mouse cells, suggesting that previous insights into IL-11 function may in part be due to IL-11-non-specific observations.

5.3 IL-11 has a Profibrotic Role in Fibrosis of a Variety of Tissues

To test whether the profibrotic action of IL-11 was specific to atrial fibroblasts, human fibroblasts derived from several different tissues (heart, lung, skin, kidney and liver) were cultured in vitro, stimulated with human IL-11, and fibroblast activation and ECM production was analysed as described above. Increased fibroblast activation and production of ECM was observed as compared to non-stimulated cultures in fibroblasts derived from each of the tissues analysed.

5.3.1 Liver Fibrosis

To test whether IL-11 signalling is important in liver fibrosis, human primary liver fibroblasts (Cell Biologics, Cat #: H-6019) were cultured at low passage in wells of 96-well plates and either not stimulated, stimulated with TGFβ1 (5 ng/ml, 24 h), IL-11 (5 ng/ml, 24 h) or incubated with both TGFβ1 (5 ng/ml) and a neutralising IL-11 antibody (2 μg/ml), or TGFβ1 (5 ng/ml) and an Isotype control antibody. Fibroblast activation (αSMA positive cells), cell proliferation (EdU positive cells) and ECM production (periostin and collagen) was analysed using the Operetta platform.

The results of the experiments with primary human liver fibroblasts are shown in FIGS. 38A to 38D. IL-11 was found to activate liver fibroblasts, and IL-11 signalling was found to be necessary for the profibrotic action of TGFβ1 in liver fibroblasts. Both activation and proliferation of fibroblasts was inhibited by neutralising anti-IL-11 antibody.

5.3.2 Skin Fibrosis

To test whether IL-11 signalling is important in skin fibrosis, primary mouse skin fibroblasts were cultured at low passage in wells of 96-well plates and either not stimulated, stimulated with TGFβ1 (5 ng/ml, 24 h) or incubated for 24 h with both TGFβ1 (5 ng/ml) and a neutralising IL-11 antibody (2 μg/ml). Fibroblast activation (αSMA positive cells) was then analysed using the Operetta platform.

The results are shown in FIG. 39. TGFβ1-mediated activation of skin fibroblasts was inhibited by neutralising anti-IL-11 antibody.

5.3.3 Fibrosis in Multiple Organs

Next, mouse recombinant IL-11 was injected (100 μg/kg, 3 days/week, 28 days) into mice to test whether IL-11 can drive global tissue fibrosis in vivo.

Figure 21A:
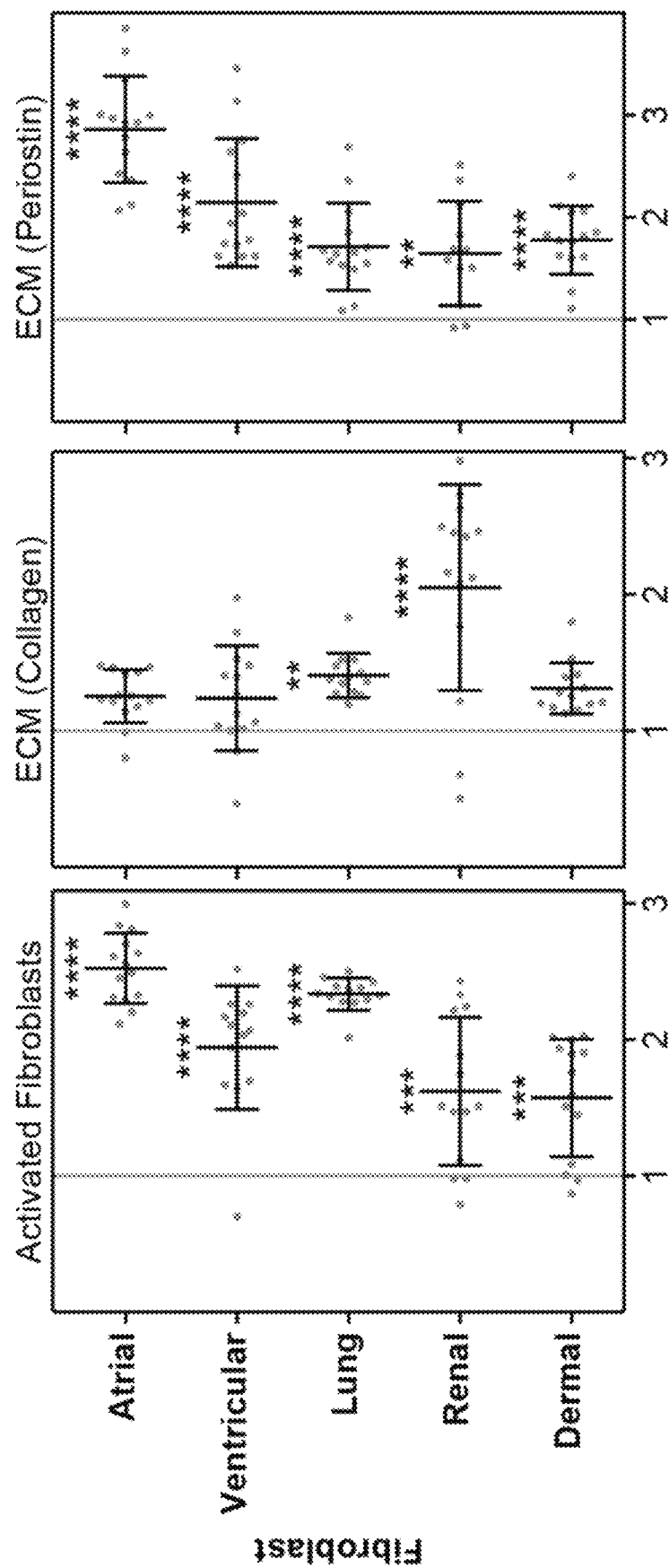
FIGS. 21A, 21B and 21C. Graphs showing the profibrotic effect of IL-11. (21A) Mouse fibroblasts from different tissues of origin can be activated by IL-11 and display increased ECM production. [Mean±SD, Dunnett]. Injection of mice with recombinant IL-11 or AngII results in (21B) an increase in organ weight [Mean±SEM], and (21C) an increase in collagen content (as determined by HPA assay). *P<0.05, P<0.01, *P<0.001, ****P<0.0001 [Mean±SD, Dunnett].
Figure 21B:
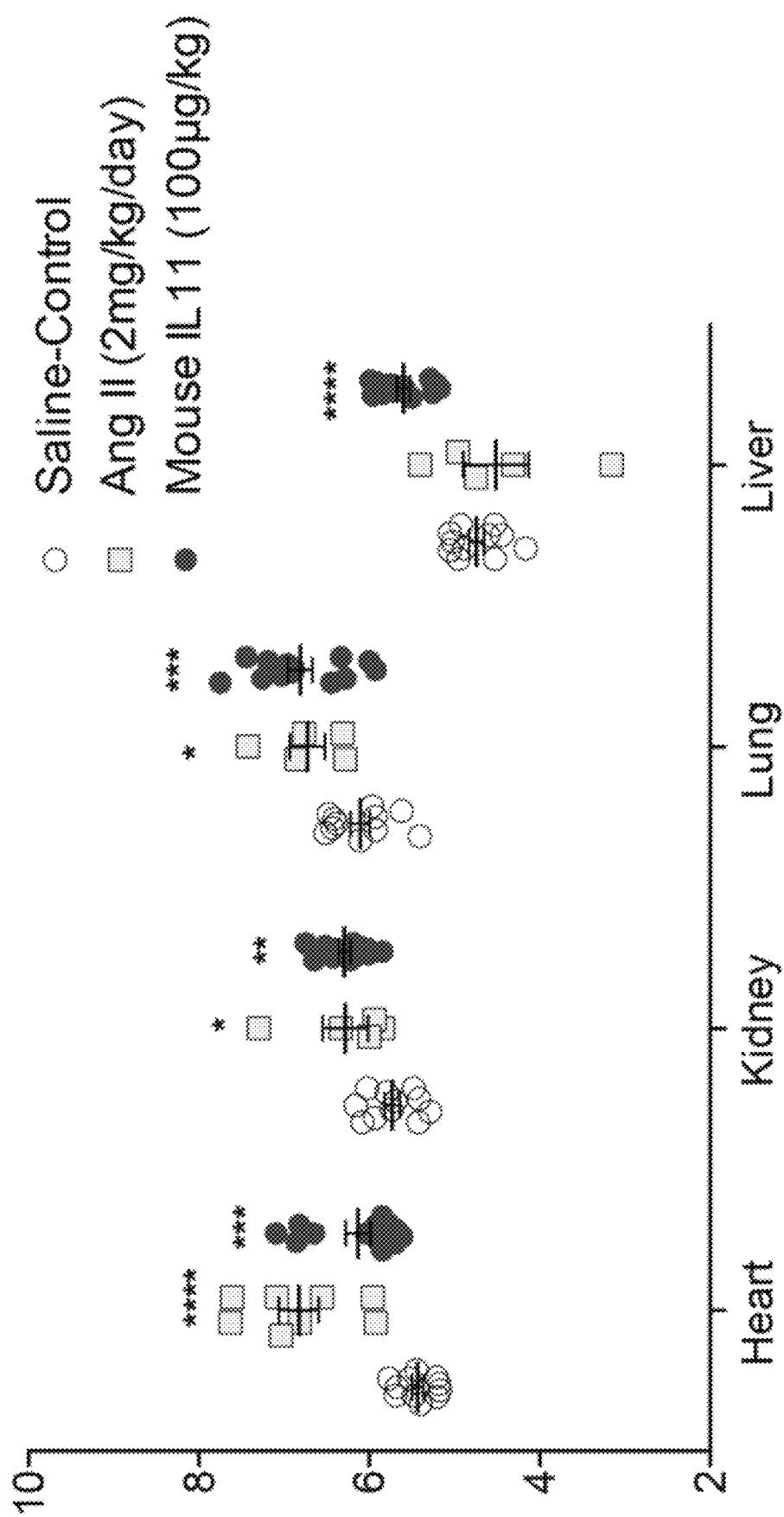
Figure 21C:
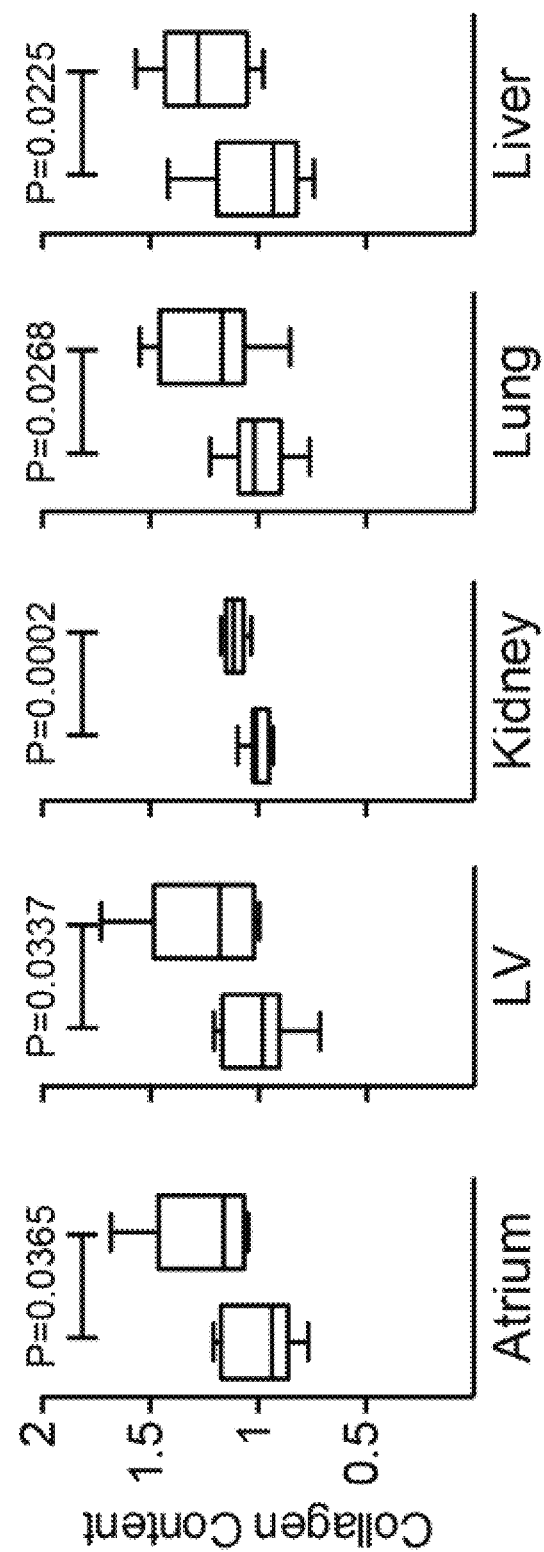
Figure 22A:
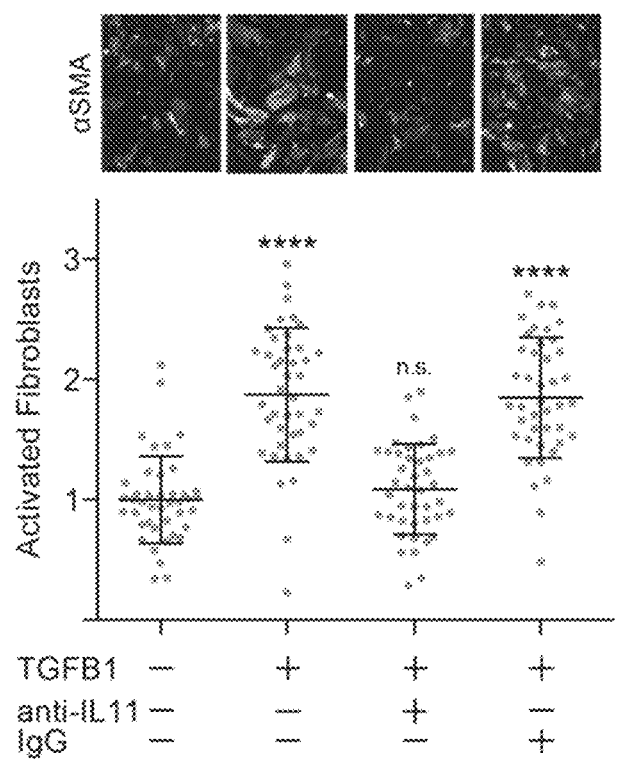
FIGS. 22A, 22B, 22C, 22D, 22E and 22F. Graphs and images showing that IL-11 is required the pro-fibrotic effects of TGFβ1 on fibroblasts. (22A) myofibroblast generation and ECM production by primary atrial fibroblasts, with or without stimulation with TGFβ1, and in the presence/absence of neutralising anti-IL-11 antibody or isotype control IgG, as measured by fluorescence microscopy following staining for (22A) α-SMA, (22B) EdU or (22C) Periostin. (22D to 22F) Secretion of the fibrosis markers (22D) IL-6, (22E) TIMP1, and (22F) MMP2 was analysed by ELISA.
Figure 22B:
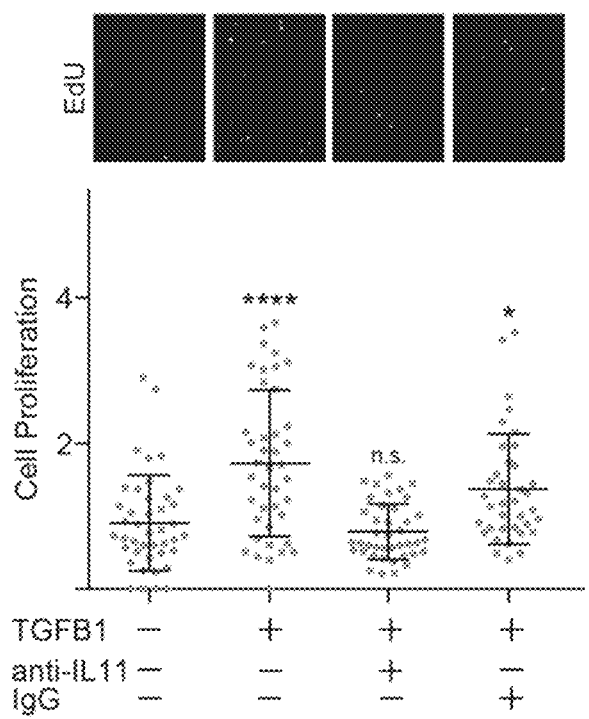
Figure 22C:
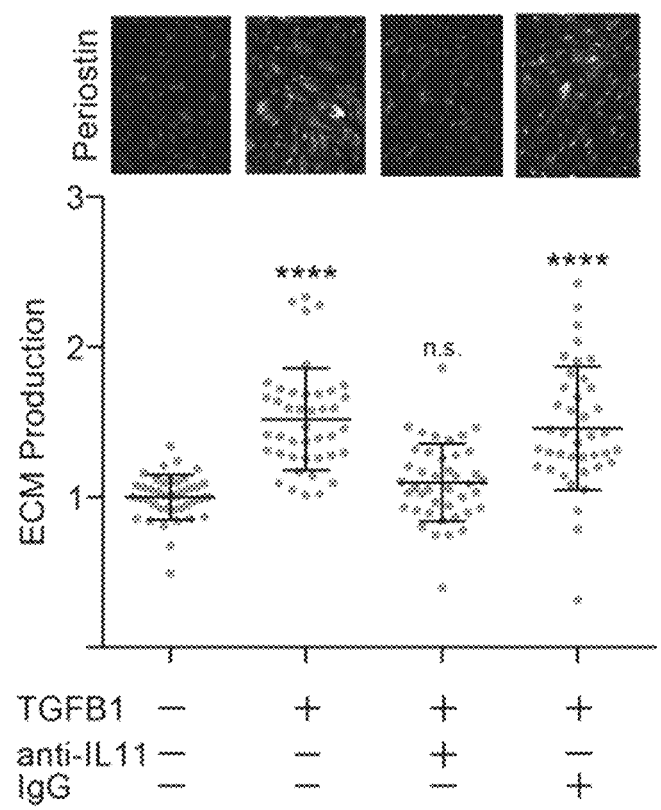
Figure 22D:
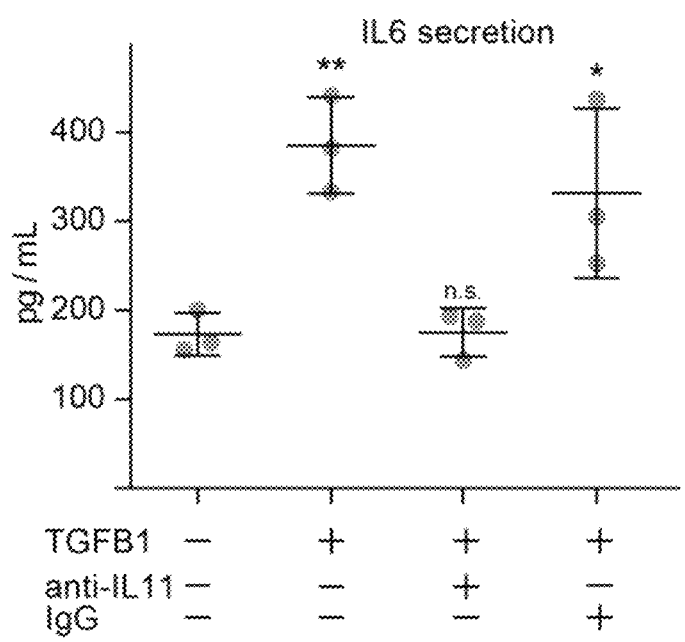
Figure 22E:
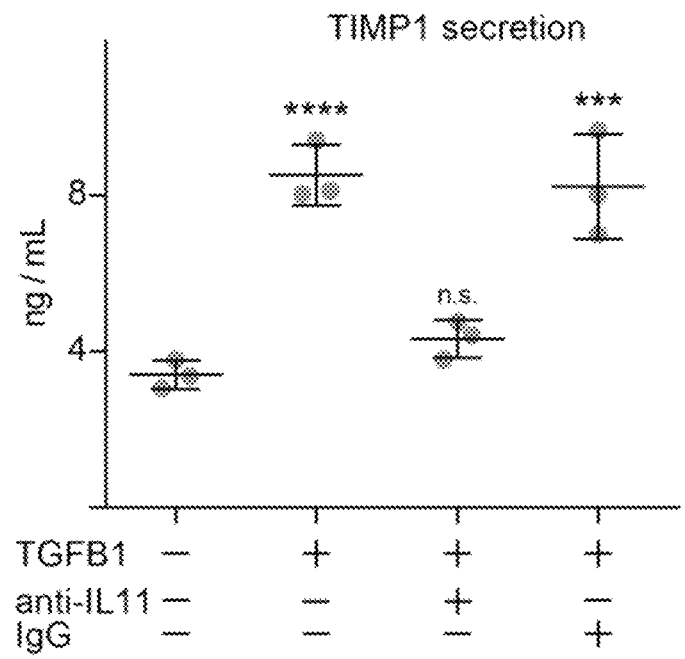
Figure 22F:
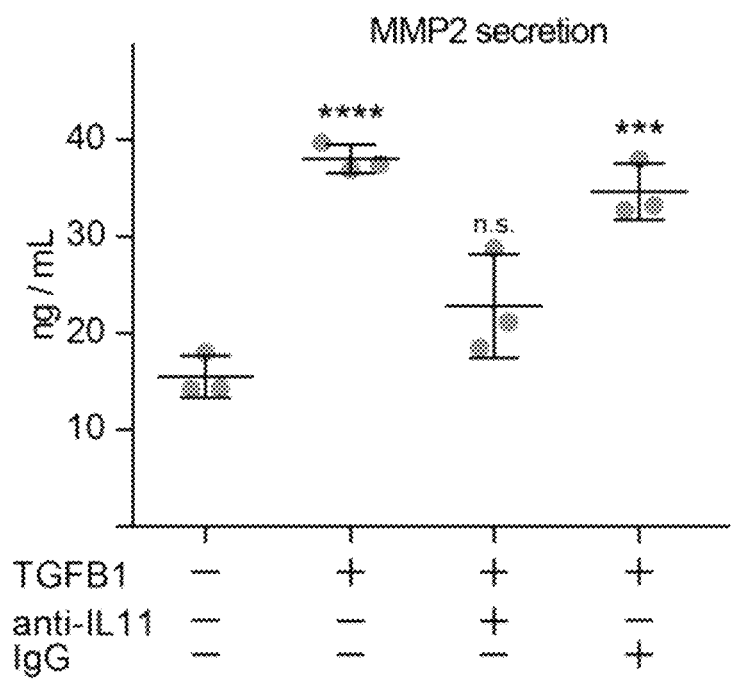

The results are shown in FIG. 21. Compared to injection of AngII (a cytokine that causes an elevation in blood pressure and hypertrophy of the heart), IL-11 also increased the heart weight but also kidney, lung and liver weight indexed to body weight (FIG. 21B). Assessing collagen content in these issues by hydroxyproline assay revealed an upregulation of collagen production in these tissues, indicating fibrosis as the likely cause for the increase in organ weight (FIG. 6C). Expression of fibrosis marker genes ACTA2 (=αSMA), Col1a1, Col3a1, Fn1, Mmp2 and Timp1 was also detected by qPCR analysis of RNA isolated from heart, kidney, lung and liver tissues of these animals.

Example 6: Therapeutic Potential of IL-11/IL-11R Antagonism 6.1 Inhibition of the Fibrotic Response Using Neutralising Antagonists of IL-11/IL-11R Next it was investigated whether the autocrine loop of IL-11 secretion was required for the pro-fibrotic effect of TGFβ1 on fibroblasts.

IL-11 was inhibited using a commercially available neutralizing antibody (Monoclonal Mouse IgG2A; Clone #22626; Catalog No. MAB218; R&D Systems, MN, USA). Fibroblasts were treated with TGFβ1 in the presence or absence of the antibody, and fibroblast activation, the proportion of proliferating cells and ECM production and markers of the fibrotic response were measured.

Briefly, atrial fibroblasts derived from 3 individuals were incubated for 24 h with TGFβ1 (5 ng/ml) or TGFβ1 in the presence of neutralising anti-IL-11 antibody or isotype control antibody. Following incubation, cells were stained for αSMA to determine the fraction of myofibroblasts, the proportion of proliferating cells was determined by analysing the cells for EdU incorporation, and periostin was measured to determine ECM production. Fluorescence was measured with the Operetta platform for 14 fields across 2 wells for each individual. Secretion of the fibrosis markers IL-6, TIMP1 and MMP2 was also analysed by ELISA. Fluorescence was normalized to the control group without stimulation.

The results are shown in FIGS. 22A to 22F. IL-11 inhibition was found to ameliorate TGFβ1-induced fibrosis, and it was shown that IL-11 is essential for the pro-fibrotic effect of TGFβ1. Inhibition of IL-11 was found to 'rescue' the TGFβ1 phenotype at the protein level.

Collagen production was also analysed. Cardiac fibroblasts derived from 3 individuals were incubated for 24 h with TGFβ1 (5 ng/ml) or TGFβ1 and a neutralizing IL-11 antibody. Following incubation the cells were stained for collagen using the Operetta assay and florescence was quantified as described above. Secreted collagen levels in the cell culture supernatant were assessed by Sirius Red staining.

The results are shown in FIGS. 23A and 23B, and confirm the anti-fibrotic effect of inhibition of IL-11 using a neutralising antibody.

Next, the ability of several other IL-11/IL-11R antagonists to inhibit fibrosis was analysed in vitro using the atrial fibroblast, TGFβ1-induced myofibroblast transition assay described herein above.

Briefly, human atrial fibroblasts cells were cultured in vitro, stimulated for 24 h with TGFβ1 (5 ng/ml) or left unstimulated, in the presence/absence of: (i) neutralising anti-IL-11 antibody, (ii) a IL-11RA-gp130 fusion protein (iii) neutralising anti-IL-11RA antibody, (iv) treatment with siRNA directed against IL-11 or (v) treatment with siRNA directed against IL-11RA. The proportion of activated fibroblasts (myofibroblasts) was analysed by evaluating αSMA content as described above.

The results are shown in FIG. 24. Each of the antagonists of IL-11/IL-11R signalling was found to be able to abrogate TGFβ1-mediated profibrotic response.

Example 7: In Vivo Confirmation of a Profibrotic Role for IL-11/IL-11R Signalling

7.1 In Vitro Studies Using Cells Derived from IL-11RA Gene Knock-Out Mice

All mice were bred and housed in the same room and provided food and water ad libitum. Mice lacking functional alleles for IL-11Rα (IL-11RA1 KO mice) were on C57Bl/6 genetic background. Mice were of 9-11 weeks of age and the weight of animals did not differ significantly.

To further confirm the anti-fibrotic effect of inhibition of IL-11/IL-11R signalling, primary fibroblasts were generated from IL-11RA gene knock-out mice and incubated with primary fibroblast cells harvested from IL-11RA+/+ (i.e. wildtype), IL-11RA+/− (i.e. heterozygous knockout) and IL-11RA−/− (i.e. homozygous knockout) animals with TGFβ1, IL-11 or AngII. Activation and proliferation of fibroblasts and ECM production was analysed.

Fibroblasts derived from IL-11RA+/+, IL-11RA+/− and IL-11RA−/− mice were incubated for 24 hours with TGFβ1, IL-11 or AngII (5 ng/ml). Following incubation, cells were stained for αSMA content to estimate the fraction of myofibroblasts, for EdU to identify the fraction of proliferating cells, and for collagen and periostin to estimate ECM production. Fluorescence was measured using the Operetta platform.

The results are shown in FIGS. 25A to 25D. IL-11RA−/− mice were found not to respond to pro-fibrotic stimuli. These results suggested that IL-11 signalling is also required for AngII-induced fibrosis.

Next, it was investigated whether this was also true for other pro-fibrotic cytokines. Briefly, fibroblasts were cultured in vitro in the presence/absence of various different pro-fibrotic factors (ANG2, ET-1 or PDGF), and in the presence/absence of neutralising anti-IL-11 antibody or pan anti-TGFβ antibody. After 24 hours, collagen production by the cells was determined by analysis using the Operetta system as described above, and myofibroblast generation was determined by analysis of αSMA expression as described above.

The results are shown in FIGS. 26A and 26B. IL-11 was found to be required for fibrosis downstream of various profibrotic stimuli, and was thus identified as a central mediator of fibrosis induced by a variety of different profibrotic factors.

In a further experiment, the role of IL-11 signalling was investigated in lung fibrosis, using an in vitro scratch assay of migration of lung fibroblasts. In response to pro-fibrotic stimuli, fibroblasts are activated and migrate within the fibrotic niche in the body. The migration rate of cells is a measure of cell-cell and cell-matrix interactions and a model for wound healing in vivo (Liang et al., 2007; Nat Protoc. 2(2):329-33).

Fibroblasts derived from lung tissue from both wild type (WT) and also homozygous IL-11RA (−/−) knockout mice were grown at low passage on a plastic surface until they formed a uniform cell monolayer. A scratch was then created in the cell layer, and cell migration close to the scratch was monitored, either in the absence of stimulation, or in the presence of TGFβ1 or IL-11. Images captured at images at the two time points of immediately after creating the scratch and at 24 h were used to determine the area covered by cells, and the rate of migration was compared between WT and KO fibroblasts. Cell migration (area in the scratch covered by cells after 24 h) was normalized to the migration rate of WT cells without stimulus.

The results are shown in FIG. 40. Lung fibroblasts derived from WT mice were shown to migrate faster in the presence of TGFβ1 and IL-11, indicating a pro-fibrotic effect of both cytokines in lung fibroblasts. Cells lacking IL-11 signalling derived from KO mice migrated more slowly as compared to WT cells. They also did not migrate faster in the presence of TGFβ1. The scratch assay revealed that lung fibroblasts lacking IL-11 signalling have a decrease cell migration rate both in the presence of TGFβ1 or IL-11, and at baseline. Thus, inhibition of IL-11 signalling is anti-fibrotic in the lung.

7.2 Heart Fibrosis

The efficacy of IL-11 inhibition to treat fibrotic disorders was investigated in vivo. A mouse model for cardiac fibrosis, in which fibrosis is induced by treatment with AngII, was used to investigate whether IL-11RA −/− mice were protected from cardiac fibrosis.

Briefly, a pump was implanted, and wildtype (WT) IL-11RA(+/+) and knockout (KO) IL-11RA(−/−) mice were treated with AngII (2 mg/kg/day) for 28 days. At the end of the experiment, collagen content was assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

The results are shown in FIGS. 27A to 27D. The IL-11RA−/− mice were found to be protected from the profibrotic effects of AngII.

7.3 Kidney Fibrosis

A mouse model for kidney fibrosis was established in wildtype (WT) IL-11RA(+/+) and knockout (KO) IL-11RA(−/−) mice by intraperitoneal injection of folic acid (180 mg/kg) in vehicle (0.3M $NaHCO_3$); control mice were administered vehicle alone. Kidneys were removed 28 days post-injection, weighed and either fixed in 10% neutral-buffered formalin for Masson's trichrome and Sirius staining or snap-frozen for collagen assay, RNA, and protein studies.

Total RNA was extracted from the snap-frozen kidney using Trizol reagent (Invitrogen) and Qiagen TissueLyzer method followed by RNeasy column (Qiagen) purification. The cDNA was prepared using iScript™ cDNA synthesis kit, in which each reaction contained 1 μg of total RNA, as per the manufacturer's instructions. Quantitative RT-PCR gene expression analysis was performed on triplicate samples with either TaqMan (Applied Biosystems) or fast SYBR green (Qiagen) technology using StepOnePlus™ (Applied Biosystem) over 40 cycles. Expression data were normalized to GAPDH mRNA expression level and we used the 2-ΔΔCt method to calculate the fold-change. The snap-frozen kidneys were subjected to acid hydrolysis by heating in 6M HCl at a concentration of 50 mg/ml (95° C., 20 hours). The amount of total collagen in the hydrolysate was quantified based on the colorimetric detection of hydroxyproline using Quickzyme Total Collagen assay kit (Quickzyme Biosciences) as per the manufacturer's instructions.

The results of the analysis are shown in FIG. 28. Folate-induced kidney fibrosis is shown to be dependent on IL-11 mediated signalling. A significant increase in collagen content in kidney tissue was observed in IL-11RA+/+ mice, indicative of kidney fibrosis. No significant increase in collagen content was observed in IL-11RA −/− mice. Animals deficient for IL-11 signalling had significantly less collagen deposition in kidneys after toxic injury as compared to wild type animals.

7.4 Lung Fibrosis

IL-11 is confirmed as a key mediator of fibrosis in the lung, skin and eye in further in vivo models using the IL-11RA −/− knockout mice. Schematics of the experiments are shown in FIGS. 29A to 29C.

To analyse pulmonary fibrosis, IL-11RA −/− mice and IL-11RA +/+ mice are treated by intratracheal administration of bleomycin on day 0 to establish a fibrotic response in the lung (pulmonary fibrosis). Fibrosis of the lung develops by 21 days, at which point animals are sacrificed and analysed for differences in fibrosis markers between animals with and without IL-11 signalling. IL-11RA −/− mice have a reduced fibrotic response in lung tissue as compared to IL-11RA +/+ mice, as evidenced by reduced expression of markers of fibrosis.

7.5 Skin Fibrosis

To analyse fibrosis of the skin, IL-11RA −/− mice and IL-11RA +/+ mice are treated by subcutaneous administration of bleomycin on day 0 to establish a fibrotic response in the skin. Fibrosis of the skin develops by 28 days, at which point animals are sacrificed and analysed for differences in fibrosis markers between animals with and without IL-11 signalling. IL-11RA −/− mice have a reduced fibrotic response in skin tissue as compared to IL-11RA +/+ mice, as evidenced by reduced expression of markers of fibrosis.

7.6 Eye Fibrosis

To analyse fibrosis in the eye, IL-11RA −/− mice and IL-11RA +/+ mice undergo trabeculectomy on day 0 to initiate a wound healing response in the eye. Fibrosis of the eye develops within 7 days. The fibrotic response is measured and compared between the IL-11RA −/− mice and IL-11RA +/+ mice. IL-11RA −/− mice have a reduced fibrotic response in eye tissue as compared to IL-11RA +/+ mice, as evidenced by reduced expression of markers of fibrosis.

7.7 Other Tissues

The effect of IL-11RA knockout on fibrosis is also analysed in mouse models of fibrosis for other tissues, such as the liver, bowel, and is also analysed in a model relevant to multiorgan (i.e. systemic) fibrosis. The fibrotic response is measured and compared between the IL-11RA −/− mice and IL-11RA +/+ mice. IL-11RA −/− mice have a reduced fibrotic response as compared to IL-11RA +/+ mice, as evidenced by reduced expression of markers of fibrosis.

Example 8: Analysis of the Molecular Mechanisms Underlying IL-11-Mediated Induction of Fibrosis The canonical mode of action of IL-11 is thought to be regulation of RNA expression via STATS-mediated transcription (Zhu et al., 2015 PLoS ONE 10, e0126296), and also through activation of ERK.

STAT3 activation is observed following stimulation with IL-11. However, when fibroblasts are incubated with TGFβ1, only activation of the canonical SMAD pathway and ERK pathways is seen, and activation of STAT3 is not observed, even in spite of the fact that IL-11 is secreted in response to TGFβ1. Only ERK activation is common to both TGFβ1 and IL-11 signal transduction.

Cross-talk between TGFβ1 and IL-6 signalling has previously been described, wherein TGFβ1 blocks the activation of STAT3 by IL-6 (Walia et al., 2003 FASEB J. 17, 2130-2132). Given the close relationship between IL-6 and IL-11, similar cross-talk may be observed for IL-11 mediated signalling.

The inventors investigated by RNA-seq analysis whether regulation of RNA abundance was the underlying mechanism for the increased expression of fibrosis marker proteins in response to IL-11, which would suggest STAT3 as the underlying signalling pathway for IL-11 mediated profibrotic processes. Fibroblasts were incubated for 24 hours either without stimulus, or in the presence of TGFβ1, IL-11 or TGFβ1 and IL-11.

The results are shown in FIG. 30A. TGFβ1 induced the expression of collagen, ACTA2 (αSMA) and other fibrosis marker at the RNA level. However, IL-11 did not regulate the expression of these genes, but a different set of genes.

Gene ontology analysis suggests that a pro-fibrotic effect in fibroblasts is driven by IL-11-regulated RNA expression. Both TGFβ1 and IL-11 regulate an almost completely different set of genes on the RNA level.

Whilst TGFβ1 increases IL-11 secretion, the target genes of IL-11 are not regulated when both TGFβ1 and IL-11 are present. This suggests that TGFβ1 upregulates IL-11 and simultaneously blocks the canonical IL-11-driven regulation of RNA expression via STAT3, similar to what is known about the interaction of TGFβ1 and IL-6 pathways (Walia et al., 2003 FASEB J. 17, 2130-2132).

We also analysed whether RNA expression differences induced by TGFβ1 are dependent on IL-11 signalling, by analysing changes in RNA expression in fibroblasts obtained from IL-11 RA −/− mice as compared to IL-11RA mice. RNA expression regulated by TGFβ1 is still observed when IL-11RA knockout cells were stimulated with TGFβ1, and RNA levels of αSMA, collagen etc. were still upregulated in the absence of IL-11 signalling (in IL-11RA −/− fibroblasts). When the pro-fibrotic effect of IL-11 and the anti-fibrotic effect of IL-11 inhibition was investigated in vitro, reduced expression of markers of fibrosis was only observed at the protein level, not at the transcriptional level as determined by qPCR.

The activation of non-canonical pathways (e.g. ERK signal transduction) is known to be crucial for the pro-fibrotic action of TGFβ1 (Guo and Wang, 2008 Cell Res 19, 71-88). It is likely that non-canonical pathways are likely to be important for signalling for all known pro-fibrotic cytokines, and that IL-11 is a post-transcriptional regulator which is essential for fibrosis.

Example 9: Human Anti-Human IL-11 Antibodies

Fully human anti-human IL-11 antibodies were developed via phage display.

Recombinant human IL-11 (Cat. No. Z03108-1) and recombinant murine IL-11 (Cat. No. Z03052-1) were obtained from GenScript (NJ, USA). Recombinant human IL-11 was expressed in CHO cells, both as an Fc-tagged version and a tag-free version. Tag-free murine IL-11 was expressed in HEK293 cells.

IL-11 bioactivity of recombinant human IL-11 and mouse IL-11 was confirmed by in vitro analysis using primary fibroblast cell cultures.

Recombinant, biotinylated human IL-11 and murine IL-11 were also prepared by biotinylation of the recombinant human IL-11 and murine IL-11 molecules, according to standard methods.

Antibodies capable of binding to both human IL-11 and murine IL-11 (i.e. cross-reactive antibodies) were identified by phage display using a human naïve library by panning using biotinylated and non-biotinylated recombinant human and murine IL-11, based on 16 different panning strategies.

The phage display identified 175 scFv binders, as 'first hits'. Sequence analysis of the CDR sequences from these 175 scFv identified 86 unique scFv.

The soluble scFv were produced by recombinant expression in *E. coli*, and analysed for their ability to bind to human IL-11 and murine IL-11 by ELISA. Briefly, the respective antigen was coated to wells of an ELISA plate, the cell culture supernatant containing the respective scFv was added at a 1:2 dilution, and binding was detected.

The results of the ELISA analysis revealed:
8 scFV capable of binding only to human IL-11;
6 scFv capable of binding to murine IL-11 only;
32 scFv displaying only weak binding to human/murine IL-11, with a high signal to noise ratio, and;
40 scFv having cross-reactivity for both human IL-11 and murine IL-11.

From these 86 scFV, 56 candidates were selected for further functional characterisation. For further analyses, the scFV were cloned into scFV-Fc format in E. coli.

The VH and VL sequences of the antibodies were cloned into expression vectors for the generation of scFv-Fc (human IgG1) antibodies. The vectors were transiently expressed in mammalian cells cultured in serum-free media, and isolated by protein A purification.

Example 10: Functional Characterisation of Human Anti-Human IL-11 Antibodies

The antibodies described in Example 9 were analysed in in vitro assays for their ability to (i) inhibit human IL-11-mediated signalling, and (ii) inhibit mouse IL-11-mediated signalling. The affinity of the antibodies for human IL-11 was also analysed by ELISA.

10.1 Ability to Inhibit Human IL-11 Mediated Signalling

To investigate ability to neutralise human IL-11-mediated signalling, cardiac atrial human fibroblasts were cultured in wells of 96-well plates in the presence of TGFβ1 (5 ng/ml) for 24 hours, in the presence or absence of the anti-IL-11 antibodies. TGFβ1 promotes the expression of IL-11, which in turn drives the transition of quiescent fibroblasts to activated, αSMA-positive fibroblasts. It has previously been shown that neutralising IL-11 prevents TGFβ1-induced transition to activated, αSMA-positive fibroblasts.

Expression of αSMA was analysed with the Operetta High-Content Imaging System in an automated high-throughput fashion.

In non-stimulated cultures, ~29.7% (=1) of the fibroblasts were αSMA-positive, activated fibroblasts at the end of the 24 hour culture period, whilst ~52% (=1.81) of fibroblasts were αSMA-positive in cultures that were stimulated with TGFβ1 in the absence of anti-IL-11 antibodies.

Anti-IL-11 antibodies (2 µg/ml) were added to fibroblast cultures that were stimulated with TGFβ1, and at the end of the 24 hour culture period, the percentage of αSMA-positive fibroblasts was determined. The percentages were normalised based on the percentage of αSMA-positive fibroblasts observed in cultures of fibroblasts which had not been stimulated with TGFβ1.

28 of the antibodies were demonstrated to be capable of neutralising signalling mediated by human IL-11.

A commercial monoclonal mouse anti-IL-11 antibody (Monoclonal Mouse IgG2A; Clone #22626; Catalog No. MAB218; R&D Systems, MN, USA) was also analysed for ability to inhibit signalling by human IL-11 in the experiments. This antibody was found to be able to reduce the percentage of activated fibroblasts to 28.3% (=0.99).

Several of the clones neutralised signalling by human IL-11 to a greater extent than the commercially available mouse anti-IL-11 antibody (industry standard).

10.2 Ability to Inhibit Mouse IL-11 Mediated Signalling

The ability of the human antibodies to inhibit mouse IL-11-mediated signalling was also investigated, following the same procedure as described in section 10.1 above, but using mouse dermal fibroblasts instead of human atrial fibroblasts.

After 24 hours in culture, about 31.8% (=1) of non-stimulated cells in culture were activated fibroblasts. Stimulation with TGFβ1 resulted in a ~2-fold increase in the percentage of activated fibroblasts (68.8%=2.16) as compared to non-stimulated cultures.

The antibodies were demonstrated to be capable of neutralising signalling mediated by mouse IL-11. Monoclonal Mouse IgG2A clone #22626, catalog No. MAB218 anti-IL-11 antibody was also analysed for ability to inhibit signalling by mouse IL-11. This antibody was found to be able to reduce the percentage of activated fibroblasts to 39.4% (=1.24).

Several of the clones neutralised signalling by mouse IL-11 to a greater extent than the commercially available mouse anti-IL-11 antibody (industry standard).

10.3 Analysis of Antibody Affinity for Human IL-11

The human anti-human IL-11 antibodies were analysed for their affinity of binding to human IL-11 by ELISA assay.

Recombinant human IL-11 was obtained from Genscript and Horseradish peroxidase (HRP)-conjugated anti-human IgG (Fc-specific) antibody was obtained from Sigma. Corning 96-well ELISA plates were obtained from Sigma. Pierce 3,3',5,5'-tetramethylbenzidine (TMB) ELISA substrate kit was obtained from Life Technologies (0.4 g/mL TMB solution, 0.02% hydrogen peroxide in citric acid buffer). Bovine serum albumin and sulphuric acid was obtained from Sigma. Wash buffer comprised 0.05% Tween-20 in phosphate buffered saline (PBS-T). ScFv-Fc antibodies were generated as described in above. Purified mouse and human IgG controls were purchased from Life Technologies. Tecan Infinite 200 PRO NanoQuant was used to measure absorbance.

Criss-cross serial dilution analysis was performed as described by Hornbeck et al., (2015) Curr Protoc Immunol 110, 2.1.1-23) to determine the optimal concentration of coating antigen, primary and secondary antibodies.

An indirect ELISA was performed to assess the binding affinity of primary ScFv-Fc antibodies at 50% of effective concentration ($EC_{50}$) as previously described (Unverdorben et al., (2016) MAbs 8, 120-128.). ELISA plates were coated with 1 µg/mL of recombinant human IL-11 overnight at 4° C. and remaining binding sites were blocked with 2% BSA in PBS. ScFv-Fc antibodies were diluted in 1% BSA in PBS, titrated to obtain working concentrations of 800, 200, 50, 12.5, 3.125, 0.78, 0.195, and 0.049 ng/mL, and incubated in duplicates for 2 hours at room temperature. Detection of antigen-antibody binding was performed with 15.625 ng/mL of HRP-conjugated anti-human IgG (Fc-specific) antibody. Following 2 hours of incubation with the detection antibody, 100 µl of TMB substrate was added for 15 mins and chromogenic reaction stopped with 100 µl of 2 M $H_2SO_4$. Absorbance reading was measured at 450 nm with reference wavelength correction at 570 nm. Data were fitted with GraphPad Prism software with log transformation of antibody concentrations followed by non-linear regression analysis with the asymmetrical (five-parameter) logistic dose-response curve to determine individual EC50 values.

The same materials and procedures as described above were performed to determine the affinity of binding for the murine monoclonal anti-IL-11 antibodies, with the exception that HRP-conjugated anti-mouse IgG (H&L) was used instead of HRP-conjugated anti-human IgG.

The same materials and procedures as described above were performed to determine the affinity of binding for the human monoclonal anti-IL-11 antibodies and murine monoclonal anti-IL-11 antibodies to recombinant murine IL-11 obtained from Genscript.

The results of the ELISA assays were used to determine $EC_{50}$ values for the antibodies.

10.4 Ability to Inhibit Human IL-11 Mediated Signalling in a Variety of Tissues

Ability of the antibodies to neutralise IL-11-mediated signalling in fibroblasts obtained from a variety of different tissues is investigated, essentially as described in section 10.1 except that instead of cardiac atrial human fibroblasts, human fibroblasts derived from liver, lung, kidney, eye, skin, pancreas, spleen, bowel, brain, and bone marrow are used for the experiments.

Anti-IL-11 antibodies are demonstrated to be capable of neutralising signalling in fibroblasts derived from the various different tissues, as determined by observation of a relative decrease in the proportion of αSMA-positive fibroblasts at the end of the 24 h culture period in the presence of the anti-IL-11 antibodies as compared to culture in the absence of the antibodies.

Example 11: Inhibition of Fibrosis In Vivo Using Anti-IL-11 Antibodies

The therapeutic utility of the anti-human IL-11 antibodies is demonstrated in in vivo mouse models of fibrosis for various different tissues.

11.1 Heart Fibrosis

A pump is implanted, and mice are treated with AngII (2 mg/kg/day) for 28 days.

Neutralising anti-IL-11 antibodies, or control antibodies, are administered to different groups of mice by intravenous injection. At the end of the experiment, collagen content is assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

Mice treated with neutralising anti-IL-11 antibodies have a reduced fibrotic response in heart tissue as compared to mice treated with control antibodies, as evidenced by reduced expression of markers of fibrosis.

11.2 Kidney Fibrosis

A mouse model for kidney fibrosis is established, in which fibrosis is induced by intraperitoneal injection of folic acid (180 mg/kg) in vehicle (0.3M $NaHCO_3$); control mice were administered vehicle alone.

Neutralising anti-IL-11 antibodies, or control antibodies, are administered to different groups of mice by intravenous injection. Kidneys are removed at day 28, weighed and either fixed in 10% neutral-buffered formalin for Masson's trichrome and Sirius staining or snap-frozen for collagen assay, RNA, and protein studies.

Total RNA is extracted from the snap-frozen kidney using Trizol reagent (Invitrogen) and Qiagen TissueLyzer method followed by RNeasy column (Qiagen) purification. The cDNA is prepared using iScript™ cDNA synthesis kit, in which each reaction contained 1 μg of total RNA, as per the manufacturer's instructions. Quantitative RT-PCR gene expression analysis is performed on triplicate samples with either TaqMan (Applied Biosystems) or fast SYBR green (Qiagen) technology using StepOnePlus™ (Applied Biosystem) over 40 cycles. Expression data are normalized to GAPDH mRNA expression level and the 2-ΔΔCt method is used to calculate the fold-change. The snap-frozen kidneys are subjected to acid hydrolysis by heating in 6M HCl at a concentration of 50 mg/ml (95° C., 20 hours). The amount of total collagen in the hydrolysate is quantified based on the colorimetric detection of hydroxyproline using Quickzyme Total Collagen assay kit (Quickzyme Biosciences) as per the manufacturer's instructions.

Mice treated with neutralising anti-IL-11 antibodies have a reduced fibrotic response in kidney tissue as compared to mice treated with control antibodies, as evidenced by reduced expression of markers of fibrosis.

11.3 Lung Fibrosis

Mice are treated by intratracheal administration of bleomycin on day 0 to establish a fibrotic response in the lung (pulmonary fibrosis).

Neutralising anti-IL-11 antibodies, or control antibodies, are administered to different groups of mice by intravenous injection. Mice are sacrificed at day 21, and analysed for differences in fibrosis markers.

Mice treated with neutralising anti-IL-11 antibodies have a reduced fibrotic response in lung tissue as compared to mice treated with control antibodies, as evidenced by reduced expression of markers of fibrosis.

11.4 Skin Fibrosis

Mice are treated by subcutaneous administration of bleomycin on day 0 to establish a fibrotic response in the skin.

Neutralising anti-IL-11 antibodies, or control antibodies, are administered to different groups of mice by intravenous injection. Mice are sacrificed at day 21, and analysed for differences in fibrosis markers.

Mice treated with neutralising anti-IL-11 antibodies have a reduced fibrotic response in skin tissue as compared to mice treated with control antibodies, as evidenced by reduced expression of markers of fibrosis.

11.5 Eye Fibrosis

Mice undergo trabeculectomy on day 0 to initiate a wound healing response in the eye.

Neutralising anti-IL-11 antibodies, or control antibodies, are administered to different groups of mice by intravenous injection, and fibrosis is monitored in the eye tissue.

Mice treated with neutralising anti-IL-11 antibodies have a reduced fibrotic response in eye tissue as compared to mice treated with control antibodies, as evidenced by reduced expression of markers of fibrosis.

11.6 Other Tissues

The effect of treatment with neutralising anti-IL-11 antibodies on fibrosis is also analysed in mouse models of fibrosis for other tissues, such as the liver, kidney, bowel, and is also analysed in a model relevant to multiorgan (i.e. systemic) fibrosis.

Mice treated with neutralising anti-IL-11 antibodies have a reduced fibrotic response as compared to mice treated with control antibodies, as evidenced by reduced expression of markers of fibrosis.

Example 12: Anti-Human IL-11Rα Antibodies

Mouse monoclonal antibodies directed against human IL-11Rα protein were generated as follows.

cDNA encoding the amino acid for human IL-11Rα was cloned into expression plasmids (Aldevron GmbH, Freiburg, Germany).

Mice were immunised by intradermal application of DNA-coated gold-particles using a hand-held device for particle-bombardment ("gene gun"). Serum samples were collected from mice after a series of immunisations, and tested in flow cytometry on HEK cells which had been transiently transfected with human IL-11Rα expression plasmids (cell surface expression of human IL-11Rα by transiently transfected HEK cells was confirmed with anti-tag antibodies recognising a tag added to the N-terminus of the IL-11Rα protein).

Antibody-producing cells were isolated from the mice and fused with mouse myeloma cells (Ag8) according to standard procedures.

Hybridomas producing antibodies specific for IL-11Rα were identified by screening for ability to bind to IL-11Rα expressing HEK cells by flow cytometry.

Cell pellets of positive hybridoma cells were prepared using an RNA protection agent (RNAlater, cat. #AM7020 by ThermoFisher Scientific) and further processed for sequencing of the variable domains of the antibodies.

Sequencing was performed using BigDye® Terminator v3.1 Cycle Sequencing kit (Life Technologies®) according to the manufacturer's instructions. All data was collected using a 3730xl DNA Analyzer system and Unified Data Collection software (Life Technologies®). Sequence assembly was performed using CodonCode Aligner (CodonCode Corporation). Mixed base calls were resolved by automatically assigning the most prevalent base call to the mixed base calls. Prevalence was determined by both frequency of a base call and the individual quality of the base calls.

In total, 17 mouse monoclonal anti-human IL-11Rα antibody clones were generated.

Example 13: Functional Characterisation of Anti-Human IL-11Rα Antibodies 13.1 Ability to Inhibit Human IL-11/IL-11R Mediated Signalling To investigate the ability of the anti-IL-11Rα antibodies to neutralise human IL-11/IL-11R mediated signalling, cardiac atrial human fibroblasts were cultured in wells of 96-well plates in the presence of TGFβ1 (5 ng/ml) for 24 hours, in the presence or absence of the anti-IL-11Rα antibodies. This profibrotic stimulus promotes the expression of IL-11, which in turn drives the transition of quiescent fibroblasts to activated, αSMA-positive fibroblasts. It has previously been shown that neutralising IL-11 prevents TGFβ1-induced transition to activated, αSMA-positive fibroblasts.

Anti-IL-11Rα antibodies (2 μg/ml) were added to fibroblast cultures that were stimulated with TGFβ1, and at the end of the 24 hour culture period, the percentage of αSMA-positive fibroblasts was determined. The percentages were normalised based on the percentage of αSMA-positive fibroblasts observed in cultures of fibroblasts which had not been stimulated with TGFβ1.

Expression of αSMA was analysed with the Operetta High-Content Imaging System in an automated high-throughput fashion.

Stimulation with TGFβ1 resulted in a 1.58 fold increase in the number of αSMA-positive, activated fibroblasts at the end of the 24 hour culture period in the absence of anti-IL-11Rα antibodies.

A commercial monoclonal mouse anti-IL-11 antibody (Monoclonal Mouse IgG2A; Clone #22626; Catalog No. MAB218; R&D Systems, MN, USA) was included as a control. This antibody was found to be able to reduce the percentage of activated fibroblasts to 0.89 fold of the percentage of activated fibroblasts in unstimulated cultures (i.e. in the absence of stimulation with TGFβ1).

The anti-IL-11Rα antibodies were found to be able to inhibit IL-11/IL-11R signalling in human fibroblasts, and several were able to inhibit IL-11/IL-11R signalling to a greater extent than the monoclonal mouse anti-IL-11 antibody.

13.2 Ability to Inhibit Mouse IL-11 Mediated Signalling

The ability of the anti-IL-11Rα antibodies to inhibit mouse IL-11-mediated signalling was also investigated, following the same procedure as described in section 13.1 above, but using mouse atrial fibroblasts instead of human atrial fibroblasts.

Stimulation with TGFβ1 resulted in a 2.24 fold increase in the number of αSMA-positive, activated fibroblasts at the end of the 24 hour culture period in the absence of anti-IL-11Rα antibodies.

The commercial monoclonal mouse anti-IL-11 antibody (Monoclonal Mouse IgG2A; Clone #22626; Catalog No. MAB218; R&D Systems, MN, USA) was included as a control. This antibody was found to be able to reduce the percentage of activated fibroblasts to 1.44 fold of the percentage of activated fibroblasts in unstimulated cultures (i.e. in the absence of stimulidine with TGFβ1).

The anti-IL-11Rα antibodies were found to be able to inhibit IL-11/IL-11R signalling in mouse fibroblasts, and several were able to inhibit IL-11/IL-11R signalling to a greater extent than the monoclonal mouse anti-IL-11 antibody.

13.3 Screening for Ability to Bind IL-11Rα

The mouse hybridomas producing anti-human IL-11Rα antibodies were sub-cloned, and cell culture supernatant from the subcloned hybridomas was analysed by "mix-and-measure" iQue assay for (i) ability to bind to human IL-11Rα, and (ii) cross reactivity for antigen other than IL-11Rα.

Briefly, labelled control cells (not expressing IL-11Rα at the cell surface) and unlabelled target cells expressing human IL-11Rα at their surface (following transient transfection with a plasmid encoding a FLAG-tagged human IL-11Rα) were mixed together with the cell culture supernatant (containing mouse-anti-IL-11Rα antibodies) and secondary detection antibodies (fluorescently-labelled anti-mouse IgG antibody).

The cells were then analysed using the HTFC Screening System (iQue) for the two labels (i.e. the cell label and the label on the secondary antibody). Detection of the secondary antibody on the unlabelled, IL-11Rα expressing cells indicated ability of the mouse-anti-IL-11Rα antibodies to bind to IL-11Rα. Detection of the secondary antibody on the labelled, control cells indicated cross-reactivity of the mouse-anti-IL-11Rα antibodies for target other than IL-11Rα.

As a positive control condition, labelled and unlabelled cells were incubated with a mouse anti-FLAG tag antibody as the primary antibody.

The majority of the subcloned hybridomas expressed antibody which was able to bind to human IL-11Rα, and which recognised this target with high specificity.

13.4 Analysis of Antibody Affinity for Human IL-11Rα

The anti-human IL-11Rα antibodies are analysed for their affinity of binding to human IL-11Rα by ELISA assay.

Recombinant human IL-11Rα is obtained from Genscript and Horseradish peroxidase (HRP)-conjugated anti-human IgG (Fc-specific) antibody is obtained from Sigma. Corning 96-well ELISA plates are obtained from Sigma. Pierce 3,3',5,5'-tetramethylbenzidine (TMB) ELISA substrate kit is obtained from Life Technologies (0.4 g/mL TMB solution, 0.02% hydrogen peroxide in citric acid buffer). Bovine serum albumin and sulphuric acid is obtained from Sigma. Wash buffer comprises 0.05% Tween-20 in phosphate buffered saline (PBS-T). Purified IgG controls are purchased from Life Technologies. Tecan Infinite 200 PRO NanoQuant is used to measure absorbance.

Criss-cross serial dilution analysis was performed as described by Hornbeck et al., (2015) Curr Protoc Immunol 110, 2.1.1-23) to determine the optimal concentration of coating antigen, primary and secondary antibodies.

An indirect ELISA is performed to assess the binding affinity of the mouse anti-IL-11Rα antibodies at 50% of effective concentration ($EC_{50}$) as previously described (Unverdorben et al., (2016) MAbs 8, 120-128.). ELISA plates are coated with 1 μg/mL of recombinant human IL-11Rα overnight at 4° C., and remaining binding sites are blocked with 2% BSA in PBS. The antibodies are diluted in 1% BSA in PBS, titrated to obtain working concentrations of 800, 200, 50, 12.5, 3.125, 0.78, 0.195, and 0.049 ng/mL, and incubated in duplicates for 2 hours at room temperature. Detection of antigen-antibody binding is performed with 15.625 ng/mL of HRP-conjugated anti-mouse IgG antibody. Following 2 hours of incubation with the detection antibody, 100 μl of TMB substrate is added for 15 mins and chromogenic reaction stopped with 100 μl of 2 M $H_2SO_4$. Absorbance reading is measured at 450 nm with reference wavelength correction at 570 nm. Data are fitted with GraphPad Prism software with log transformation of antibody concentrations followed by non-linear regression analysis with the asymmetrical (five-parameter) logistic dose-response curve to determine individual EC50 values.

13.5 Ability to Inhibit Human IL-11/IL-11R Signalling in a Variety of Tissues

Ability of the antibodies to neutralise IL-11/IL-11R signalling in fibroblasts obtained from a variety of different tissues is investigated, essentially as described in section 13.1 except that instead of cardiac atrial human fibroblasts, human fibroblasts derived from liver, lung, kidney, eye, skin, pancreas, spleen, bowel, brain, and bone marrow are used for the experiments.

Anti-IL-11Rα antibodies are demonstrated to be capable of neutralising IL-11/IL-11R signalling in fibroblasts derived from the various different tissues, as determined by observation of a relative decrease in the proportion of αSMA-positive fibroblasts at the end of the 24 h culture period in the presence of the anti-IL-11Rα antibodies as compared to culture in the absence of the antibodies.

Example 14: Inhibition of Fibrosis In Vivo Using Anti-IL-11Rα Antibodies

The therapeutic utility of the anti-human IL-11Rα antibodies is demonstrated in vivo in mouse models of fibrosis for various different tissues.

14.1 Heart Fibrosis

A pump is implanted, and mice are treated with AngII (2 mg/kg/day) for 28 days.

Neutralising anti-IL-11Rα antibodies, or control antibodies, are administered to different groups of mice by intravenous injection. At the end of the experiment, collagen content is assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

Mice treated with neutralising anti-IL-11Rα antibodies have a reduced fibrotic response in heart tissue as compared to mice treated with control antibodies, as evidenced by reduced expression of markers of fibrosis.

14.2 Kidney Fibrosis

A mouse model for kidney fibrosis is established, in which fibrosis is induced by intraperitoneal injection of folic acid (180 mg/kg) in vehicle (0.3M $NaHCO_3$); control mice were administered vehicle alone.

Neutralising anti-IL-11Rα antibodies, or control antibodies, are administered to different groups of mice by intravenous injection. Kidneys are removed at day 28, weighed and either fixed in 10% neutral-buffered formalin for Masson's trichrome and Sirius staining or snap-frozen for collagen assay, RNA, and protein studies.

Total RNA is extracted from the snap-frozen kidney using Trizol reagent (Invitrogen) and Qiagen TissueLyzer method followed by RNeasy column (Qiagen) purification. The cDNA is prepared using iScript™ cDNA synthesis kit, in which each reaction contained 1 μg of total RNA, as per the manufacturer's instructions. Quantitative RT-PCR gene expression analysis is performed on triplicate samples with either TaqMan (Applied Biosystems) or fast SYBR green (Qiagen) technology using StepOnePlus™ (Applied Biosystem) over 40 cycles. Expression data are normalized to GAPDH mRNA expression level and the 2-ΔΔCt method is used to calculate the fold-change. The snap-frozen kidneys are subjected to acid hydrolysis by heating in 6M HCl at a concentration of 50 mg/ml (95° C., 20 hours). The amount of total collagen in the hydrolysate is quantified based on the colorimetric detection of hydroxyproline using Quickzyme Total Collagen assay kit (Quickzyme Biosciences) as per the manufacturer's instructions.

Mice treated with neutralising anti-IL-11Rα antibodies have a reduced fibrotic response in kidney tissue as compared to mice treated with control antibodies, as evidenced by reduced expression of markers of fibrosis.

14.3 Lung Fibrosis

Mice are treated by intratracheal administration of bleomycin on day 0 to establish a fibrotic response in the lung (pulmonary fibrosis).

Neutralising anti-IL-11Rα antibodies, or control antibodies, are administered to different groups of mice by intravenous injection. Mice are sacrificed at day 21, and analysed for differences in fibrosis markers.

Mice treated with neutralising anti-IL-11Rα antibodies have a reduced fibrotic response in lung tissue as compared to mice treated with control antibodies, as evidenced by reduced expression of markers of fibrosis.

14.4 Skin Fibrosis

Mice are treated by subcutaneous administration of bleomycin on day 0 to establish a fibrotic response in the skin.

Neutralising anti-IL-11Rα antibodies, or control antibodies, are administered to different groups of mice by intravenous injection. Mice are sacrificed at day 21, and analysed for differences in fibrosis markers.

Mice treated with neutralising anti-IL-11Rα antibodies have a reduced fibrotic response in skin tissue as compared to mice treated with control antibodies, as evidenced by reduced expression of markers of fibrosis.

14.5 Eye Fibrosis

Mice undergo trabeculectomy on day 0 to initiate a wound healing response in the eye.

Neutralising anti-IL-11Rα antibodies, or control antibodies, are administered to different groups of mice by intravenous injection, and fibrosis is monitored in the eye tissue.

Mice treated with neutralising anti-IL-11Rα antibodies have a reduced fibrotic response in eye tissue as compared to mice treated with control antibodies, as evidenced by reduced expression of markers of fibrosis.

14.6 Other Tissues

The effect of treatment with neutralising anti-IL-11Rα antibodies on fibrosis is also analysed in mouse models of fibrosis for other tissues, such as the liver, kidney, bowel, and is also analysed in a model relevant to multiorgan (i.e. systemic) fibrosis.

Mice treated with neutralising anti-IL-11Rα antibodies have a reduced fibrotic response as compared to mice treated with control antibodies, as evidenced by reduced expression of markers of fibrosis.

Example 15: Decoy IL-11 Receptors 15.1 Decoy IL-11 Receptor Constructs

Decoy IL-11 Receptor molecules were designed and cloned into the pTT5 vector for recombinant expression in 293-6E cells.

Briefly, an insert for the plasmid comprising cDNA encoding the ligand binding domains D1, D2 and D3 of gp130 in-frame with cDNA encoding either a 50 amino acid or 33 amino acid linker region, followed by cDNA encoding the ligand binding domains D2 and D3 of human IL-11Rα, followed by cDNA encoding the FLAG tag. The cDNA insert incorporated a leader sequence, Kozak sequences at the 5' end, and included a 5' EcoRI restriction site and a 3' HindIII restriction site (downstream of a stop codon) for insertion into the pTT5 vector.

The two constructs encoding a decoy IL-11 receptor molecule having either a 50 amino acid or 33 amino acid sequence are respectively designated Decoy IL-11 Receptor 1 (D11R1) and Decoy IL-11 Receptor 2 (D11R2).

15.2 Decoy IL-11 Receptor Expression and Purification

The constructs were transfected into 293-6E cells for recombinant expression and purification.

293-6E cells were grown in serum-free FreeStyle™ 293 Expression Medium (Life Technologies, Carlsbad, Calif., USA). Cells were maintained in Erlenmeyer Flasks (Corning Inc., Acton, Mass.) at 37° C. with 5% $CO_2$ on an orbital shaker (VWR Scientific, Chester, Pa.).

One day before transfection, the cells were seeded at an appropriate density in Corning Erlenmeyer Flasks. On the day of transfection, DNA and transfection reagent were mixed at an optimal ratio and then added into the flask with cells ready for transfection. The recombinant plasmids encoding D11R1 and D11R2 were transiently transfected into suspension 293-6E cell cultures on two separate days.

Cell culture supernatants were collected on day 6 and used for purification. Briefly, cell culture broths were centrifuged and filtrated. 0.5 ml of resin was added to cell culture supernatants and incubated for 3-4 hours to capture the target protein.

After washing and elution with appropriate buffers, eluted fractions were analysed by SDS-PAGE and Western blot using Rabbit anti-FLAG polyclonal Ab (GenScript, Cat. No. A00170) to confirm expression of the FLAG-tagged decoy IL-11 receptor molecules.

The purified species were quantified and stored at −80° C.

Example 16: Functional Characterisation of Decoy IL-11 Receptors 16.1 Ability to Inhibit Human IL-11 Mediated Signalling To investigate ability to neutralise human IL-11-mediated signalling, cardiac atrial human fibroblasts were cultured in wells of 96-well plates in the presence of TGFβ1 (5 ng/ml) for 24 hours, in the presence or absence of various concentrations of D11R1 or D11R2.

TGFβ1 promotes the expression of IL-11, which in turn drives the transition of quiescent fibroblasts to activated, αSMA-positive fibroblasts. It has previously been shown that neutralising IL-11 prevents TGFβ1-induced transition to activated, αSMA-positive fibroblasts.

Expression of αSMA was analysed with the Operetta High-Content Imaging System in an automated high-throughput fashion.

D11R1 or D11R2 were added to fibroblast cultures that were stimulated with TGFβ1 at final concentrations of 5 ng/ml, 50 ng/ml and 500 ng/ml, and at the end of the 24 hour culture period, the percentage of αSMA-positive fibroblasts in the culture was determined.

Both D11R1 and D11R2 were demonstrated to be capable of neutralising signalling mediated by human IL-11 in a dose-dependent manner.

The results of the experiments are shown in FIGS. 32A and 32B. Both D11R1 and D11R2 were demonstrated to be capable of neutralising signalling mediated by human IL-11 in a dose-dependent manner.

The $IC_{50}$ for the D11R1 and D11R2 molecules was determined to be ~1 nM.

16.2 Ability to Inhibit Mouse IL-11 Mediated Signalling

The ability of D11R1 and D11R2 to inhibit mouse IL-11-mediated signalling is investigated, following the same procedure as described in section 16.1 above, but using mouse dermal fibroblasts instead of human atrial fibroblasts.

D11R1 and D11R2 are demonstrated to be capable of neutralising IL-11/IL-11R signalling in mouse dermal fibroblasts, as determined by observation of a relative decrease in the proportion of αSMA-positive fibroblasts at the end of the 24 h culture period in the presence of D11R1 or D11R2 as compared to culture in the absence of the decoy IL-11 receptors.

16.3 Analysis of Decoy IL-11 Receptor Affinity for IL-11

D11R1 and D11R2 are analysed for their affinity of binding to human IL-11 by ELISA assay.

Recombinant human IL-11 was obtained from Genscript and Horseradish peroxidase (HRP)-conjugated anti-FLAG antibody is obtained. Corning 96-well ELISA plates were obtained from Sigma. Pierce 3,3',5,5'-tetramethylbenzidine (TMB) ELISA substrate kit was obtained from Life Technologies (0.4 g/mL TMB solution, 0.02% hydrogen peroxide in citric acid buffer). Bovine serum albumin and sulphuric acid was obtained from Sigma. Wash buffer comprised 0.05% Tween-20 in phosphate buffered saline (PBS-T). Tecan Infinite 200 PRO NanoQuant is used to measure absorbance.

An indirect ELISA is performed to assess the binding affinity of D11R1 and D11R2 at 50% of effective concentration ($EC_{50}$) as previously described (Unverdorben et al., (2016) MAbs 8, 120-128.). ELISA plates are coated with 1 μg/mL of recombinant human IL-11 overnight at 4° C. and remaining binding sites were blocked with 2% BSA in PBS. D11R1 and D11R1 are diluted in 1% BSA in PBS, titrated to obtain working concentrations of 800, 200, 50, 12.5, 3.125, 0.78, 0.195, and 0.049 ng/mL, and incubated in duplicates for 2 hours at room temperature. Detection of antigen-decoy IL-11 receptor binding is performed with HRP-conjugated anti-FLAG antibody. Following 2 hours of incubation with the detection antibody, 100 μl of TMB substrate is added for 15 mins and chromogenic reaction stopped with 100 μl of 2 M $H_2SO_4$. Absorbance reading is measured at 450 nm with reference wavelength correction at 570 nm. Data are fitted with GraphPad Prism software with log transformation of decoy IL-11 receptor concentrations followed by non-linear regression analysis with the asymmetrical (five-parameter) logistic dose-response curve to determine EC50 values.

The same materials and procedures as described above were performed to determine the affinity of binding to recombinant murine IL-11 obtained from Genscript.

16.4 Ability to Inhibit Human IL-11 Mediated Signalling in a Variety of Tissues

Ability of the decoy IL-11 receptors D11R1 and D11R2 to neutralise IL-11-mediated signalling in fibroblasts obtained from a variety of different tissues is investigated, essentially as described in sections 18.1 except that instead of cardiac atrial human fibroblasts, human fibroblasts derived from liver, lung, kidney, eye, skin, pancreas, spleen, bowel, brain, and bone marrow are used for the experiments.

D11R1 and D11R2 are demonstrated to be capable of neutralising signalling in fibroblasts derived from the various different tissues, as determined by observation of a relative decrease in the proportion of αSMA-positive fibroblasts at the end of the 24 h culture period in the presence of the decoy IL-11 receptors as compared to culture in the absence of the decoy IL-11 receptors.

Example 17: Inhibition of Fibrosis In Vivo Using Decoy IL-11 Receptors

The therapeutic utility of the decoy IL-11 receptors is demonstrated in in vivo mouse models of fibrosis for various different tissues.

17.1 Heart Fibrosis

A pump is implanted, and mice are treated with AngII (2 mg/kg/day) for 28 days.

Decoy IL-11 receptors D11R1 or D11R2 are administered to different groups of mice by intravenous injection. At the end of the experiment, collagen content is assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

Mice treated with decoy IL-11 receptors have a reduced fibrotic response in heart tissue as compared to untreated/vehicle treated controls, as evidenced by reduced expression of markers of fibrosis.

17.2 Kidney Fibrosis

A mouse model for kidney fibrosis is established, in which fibrosis is induced by intraperitoneal injection of folic acid (180 mg/kg) in vehicle (0.3M $NaHCO_3$); control mice were administered vehicle alone.

Decoy IL-11 receptors D11R1 or D11R2 are administered to different groups of mice by intravenous injection. Kidneys are removed at day 28, weighed and either fixed in 10% neutral-buffered formalin for Masson's trichrome and Sirius staining or snap-frozen for collagen assay, RNA, and protein studies.

Total RNA is extracted from the snap-frozen kidney using Trizol reagent (Invitrogen) and Qiagen TissueLyzer method followed by RNeasy column (Qiagen) purification. The cDNA is prepared using iScript™ cDNA synthesis kit, in which each reaction contained 1 µg of total RNA, as per the manufacturer's instructions. Quantitative RT-PCR gene expression analysis is performed on triplicate samples with either TaqMan (Applied Biosystems) or fast SYBR green (Qiagen) technology using StepOnePlus™ (Applied Biosystem) over 40 cycles. Expression data are normalized to GAPDH mRNA expression level and the 2-ΔΔCt method is used to calculate the fold-change. The snap-frozen kidneys are subjected to acid hydrolysis by heating in 6M HCl at a concentration of 50 mg/ml (95° C., 20 hours). The amount of total collagen in the hydrolysate is quantified based on the colorimetric detection of hydroxyproline using Quickzyme Total Collagen assay kit (Quickzyme Biosciences) as per the manufacturer's instructions.

Mice treated with decoy IL-11 receptors have a reduced fibrotic response in kidney tissue as compared to untreated/vehicle treated controls, as evidenced by reduced expression of markers of fibrosis.

17.3 Lung Fibrosis

Mice are treated by intratracheal administration of bleomycin on day 0 to establish a fibrotic response in the lung (pulmonary fibrosis).

Decoy IL-11 receptors D11R1 or D11R2 are administered to different groups of mice by intravenous injection. Mice are sacrificed at day 21, and analysed for differences in fibrosis markers.

Mice treated with decoy IL-11 receptors have a reduced fibrotic response in lung tissue as compared to untreated/vehicle treated controls, as evidenced by reduced expression of markers of fibrosis.

17.4 Skin Fibrosis

Mice are treated by subcutaneous administration of bleomycin on day 0 to establish a fibrotic response in the skin.

Decoy IL-11 receptors D11R1 or D11R2 are administered to different groups of mice by intravenous injection. Mice are sacrificed at day 21, and analysed for differences in fibrosis markers.

Mice treated with decoy IL-11 receptors have a reduced fibrotic response in skin tissue as compared to untreated/vehicle treated controls, as evidenced by reduced expression of markers of fibrosis.

17.5 Eye Fibrosis

Mice undergo trabeculectomy procedure as described in Example 7.6 above to initiate a wound healing response in the eye.

Decoy IL-11 receptors D11R1 or D11R2 are administered to different groups of mice by intravenous injection, and fibrosis is monitored in the eye tissue.

Mice treated with decoy IL-11 receptors have a reduced fibrotic response in eye tissue as compared to untreated/vehicle treated controls, as evidenced by reduced expression of markers of fibrosis.

17.6 Other Tissues

The effect of treatment with decoy IL-11 receptors D11R1 or D11R2 on fibrosis is also analysed in mouse models of fibrosis for other tissues, such as the liver, kidney, bowel, and is also analysed in a model relevant to multiorgan (i.e. systemic) fibrosis.

The fibrotic response is measured and compared between mice treated with decoy IL-11 receptors and untreated mice, or vehicle treated controls. Mice treated with decoy IL-11 receptors have a reduced fibrotic response as compared to untreated/vehicle treated controls, as evidenced by reduced expression of markers of fibrosis.

Example 18: Genetic Biomarkers for IL-11 Response

In addition to measuring IL-11 protein as a potential biomarker for fibrosis, we developed an assay that can predict IL-11 secretion status in humans. This assay could be used as a companion diagnostic in IL-11-related clinical trials.

We first generated RNA-seq data (FIG. 16) and determined the genotype of 69 ethnically matched (Chinese)

individuals in the cohort using a SNP array based on fluorescent probe hybridization supplied by Illumina (HumanOmniExpress 24).

We then performed genome-wide linkage eQTL analysis to assess whether Single Nucleotide Polymorphisms (SNPs) affect RNA transcript levels of IL-11 or IL-11RA in unstimulated fibroblasts, in TGFB1 stimulated (5 ng/ml, 24 h) fibroblasts. We also tested if the increase in IL-11 upon TGFβ1 stimulation (=response) was dependent on the genotype.

At first we quantified the read count for both IL-11 and IL-11RA in all individuals and transformed these counts using the variance stabilization (VST) approach of the DESeq2 method (Love et al., Genome Biology 2014 15:550). We then considered IL-11 and IL-11RA expression in unstimulated ($VST_{unstim}$) and stimulated ($VST_{stim}$) cells. To assess the increase in IL-11, we also computed the delta in expression as $VST_{stim}-VST_{unstim}$. We corrected the expression values using covariates such as RNA sequencing library batch, RNA RIN quality score, library concentration, library fragment size, age, gender before analyses. SNP and transcript expression, or delta expression, pairs were analysed using the matrix eQTL approach (Andrey A. Shabalin., Bioinformatics 2012 May 15; 28(10): 1353-1358).

We did not observe variation in cis or trans that significantly affected IL-11 expression in unstimulated cells. However, we detected distant SNPs that regulated the expression in stimulated=fibrotic fibroblasts. These variants stratify the population between individuals that do express low levels of IL-11 and those that express high amounts of IL-11 in fibrosis. We also detected local and distal variants that predicted the increase in IL-11 expression in response to TGFβ1. These variants can be used to stratify individuals into high and low responders in fibrosis.

The SNPs identified are shown in FIGS. 33 to 35 and accompanying data is shown in FIGS. 36 and 37.

We claim:

1. A method of treating a disease or condition characterised by fibrosis of the liver in a human subject, the method comprising administering to the human subject in need of treatment a therapeutically effective amount of an Interleukin 11 (IL-11) antibody which is capable of inhibiting IL-11 mediated signaling.

2. The method according to claim 1, wherein the disease or condition is associated with liver cirrhosis.

3. The method according to claim 1, wherein the disease or condition is selected from the group consisting of: non-alcoholic steatohepatitis (NASH), primary biliary cirrhosis (PBC), and schistosomal liver disease.

4. The method according to claim 1, wherein the antibody is capable of inhibiting or reducing the binding of IL-11 to an IL-11 receptor.

5. The method according to claim 1, wherein the method comprises administering said antibody to a subject in which IL-11 or IL-11R expression is upregulated.

6. The method according to claim 1, wherein the method comprises administering said antibody to a subject in which IL-11 or IL-11R expression has been determined to be upregulated.

7. The method according to claim 1, wherein the method comprises determining whether IL-11 or IL-11R expression is upregulated in the subject and administering said antibody to a subject in which IL-11 or IL-11R expression is upregulated.

8. A method of treating a disease or condition characterised by fibrosis selected from the group consisting of: non-alcoholic steatohepatitis (NASH), primary biliary cirrhosis (PBC), schistosomal liver disease and liver cirrhosis in a human subject, the method comprising administering to the human subject in need of treatment a therapeutically effective amount of an Interleukin 11 (IL-11) antibody which is capable of inhibiting IL-11 mediated signaling.

9. The method according to claim 8, wherein the antibody is capable of inhibiting or reducing the binding of IL-11 to an IL-11 receptor.

10. The method according to claim 8, wherein the method comprises administering said antibody to a subject in which IL-11 or IL-11R expression is upregulated.

11. The method according to claim 8, wherein the method comprises administering said antibody to a subject in which IL-11 or IL-11R expression has been determined to be upregulated.

12. The method according to claim 8, wherein the method comprises determining whether IL-11 or IL-11R expression is upregulated in the subject and administering said antibody to a subject in which IL-11 or IL-11R expression is upregulated.

* * * * *

UNITED STATES PATENT AND TRADEMARK OFFICE
CERTIFICATE OF CORRECTION

PATENT NO. : 10,870,696 B2  
APPLICATION NO. : 16/055245  
DATED : December 22, 2020  
INVENTOR(S) : Stuart Alexander Cook et al.

Page 1 of 1

It is certified that error appears in the above-identified patent and that said Letters Patent is hereby corrected as shown below:

In the Specification

At Column 7, Line 53, the text:
"(3A) EdU,"
Should be replaced with:
--(3B) EdU,--.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*